US012612599B2

(12) United States Patent
Bennett et al.

(10) Patent No.: US 12,612,599 B2
(45) Date of Patent: Apr. 28, 2026

(54) COMPOSITIONS AND METHODS FOR MICROGLIA REPLACEMENT THERAPY

(71) Applicants:Savanna Biotherapeutics, Inc., Aliso Viejo, CA (US); The Board of Trustees of the Leland Stanford Junior University, Stanford, CA (US)

(72) Inventors: Frederick Christian Bennett, Philadelphia, PA (US); Peter A. Thompson, New York, NY (US); Mariko L. Bennett, Philadelphia, PA (US); Andy J. Jennings, San Diego, CA (US)

(73) Assignees: Savanna Biotherapeutics, Inc., Aliso Viejo, CA (US); The Board of Trustees of the Leland Stanford Junior University, Stanford, CA (US)

( * ) Notice: Subject to any disclaimer, the term of this patent is extended or adjusted under 35 U.S.C. 154(b) by 1752 days.

(21) Appl. No.: 16/566,675

(22) Filed: Sep. 10, 2019

(65) Prior Publication Data

US 2023/0081264 A1     Mar. 16, 2023

Related U.S. Application Data

(60) Provisional application No. 62/729,380, filed on Sep. 10, 2018.

(51) Int. Cl.
| | |
|---|---|
| *C12N 5/0787* | (2010.01) |
| *A61K 40/10* | (2025.01) |
| *A61K 40/41* | (2025.01) |
| *A61K 45/06* | (2006.01) |
| *C07K 14/715* | (2006.01) |
| *C12N 5/078* | (2010.01) |
| *C12N 5/079* | (2010.01) |
| *C12N 9/12* | (2006.01) |

(52) U.S. Cl.
CPC ............ *C12N 5/0642* (2013.01); *A61K 40/10* (2025.01); *A61K 40/414* (2025.01); *A61K 45/06* (2013.01); *C07K 14/7153* (2013.01); *C12N 5/0622* (2013.01); *C12N 5/0634* (2013.01); *C12N 9/12* (2013.01); *C12Y 207/10001* (2013.01); *A61K 2239/31* (2023.05); *C12N 2506/11* (2013.01)

(58) Field of Classification Search
None
See application file for complete search history.

(56) References Cited

U.S. PATENT DOCUMENTS

| | | |
|---|---|---|
| 2020/0038439 A1 | 2/2020 | Biffi et al. |
| 2020/0239844 A1 | 7/2020 | Blurton-Jones et al. |
| 2020/0316039 A1 | 10/2020 | Filiano et al. |
| 2020/0390857 A1 | 12/2020 | Kay et al. |
| 2021/0214681 A1 | 7/2021 | Studer et al. |
| 2022/0152115 A1 | 5/2022 | Zhang |
| 2022/0257600 A1 | 8/2022 | Jones et al. |
| 2022/0323503 A1 | 10/2022 | Biffi et al. |
| 2023/0165906 A1 | 6/2023 | Hebert et al. |
| 2023/0203500 A1 | 6/2023 | Blurton-Jones et al. |
| 2023/0248775 A1 | 8/2023 | Blurton-Jones et al. |

FOREIGN PATENT DOCUMENTS

| | | |
|---|---|---|
| CA | 3054730 A1 | 9/2018 |
| EP | 3589293 A1 | 1/2020 |
| EP | 4142745 A1 | 3/2023 |
| JP | 2020513794 A | 5/2020 |
| WO | WO-2018071898 A1 | 4/2018 |
| WO | WO-2018160496 A1 | 9/2018 |
| WO | WO-2019118951 A2 | 6/2019 |
| WO | WO-2020033791 A1 | 2/2020 |
| WO | WO-2020186237 A1 | 9/2020 |
| WO | WO-2021221879 A1 | 11/2021 |
| WO | WO-2022212897 A1 | 10/2022 |

OTHER PUBLICATIONS

Heidel et al. Clinical resistance to the kinase inhibitor PKC412 in acute myeloid leukemia by mutation of Asn-676 in the FLT3 tyrosine kinase domain Blood, 2006 vol. 107, No. 1) (Year: 2006).*
Etemad et al. A novel in vitro human microglia model: Characterization of human monocyte-derived microglia(Journal of Neuroscience Methods 209 (2012): 79-89) (Year: 2012).*
Tap et al. Structure-Guided Blockade of CSF1R Kinase in Tenosynovial Giant-Cell Tumor New England Journal of Medicine 2015;373:428-37 (Year: 2015).*
Stanley et al. CSF-1 Receptor Signaling in Myeloid Cells Cold Spring Harb Perspect Biol 2014;6 (Year: 2014).*
Yu et al. Macrophage Proliferation Is Regulated through CSF-1 Receptor Tyrosines 544, 559, and 807 (2012) Signal Transduction 287 (17): 13694-13704) (Year: 2012).*
Gupta Differentiation and Characterization of Myeloid Cells Dipti Curr Protoc Immunol. ; 104 (2015) (Year: 2015).*
Chitu et al. Emerging Roles for CSF-1 Receptor and its Ligands in the Nervous System Trends in Neurosciences, Jun. 2016, vol. 39, No. 6 : 378-393 (Year: 2016).*
Schubert et al. Crystal Structure of the Tyrosine Kinase Domain of Colony-stimulating Factor-1 Receptor (cFMS) in Complex with Two Inhibitors, 2007, The Journal of Biological Chemistry vol. 282, No. 6, pp. 4094-4101 (Year: 2007).*
Zhang et al. Design and pharmacology of a highly specific dual FMS and KIT kinase inhibitor 2012 PNAS 110 (14) 5689-5694 (Year: 2012).*

(Continued)

*Primary Examiner* — Maria G Leavitt
*Assistant Examiner* — Alexandra F Connors
(74) *Attorney, Agent, or Firm* — Wilson Sonsini Goodrich & Rosati

(57) ABSTRACT

The present disclosure provides methods and compositions for microglia replacement therapy in a subject in need thereof. In some cases, the method involves administering myeloid cells to the central nervous system of a subject. In some cases, the myeloid cells are derived from embryonic or extraembryonic tissue. In some cases, the myeloid cells are genetically modified. The genetic modification may include a colony stimulating factor 1 receptor (CSF1R) variant that is resistant to a CSF1R inhibitor, yet retains sensitivity to its ligand (e.g., CSF1, IL34).

17 Claims, 53 Drawing Sheets

Specification includes a Sequence Listing.

(56) References Cited

OTHER PUBLICATIONS

Elmore CSF1 receptor signaling is necessary for microglia viability, which unmasks a cell that rapidly repopulates the microgliadepleted adult brain Neuron. Apr. 16, 2014; 82(2): 380-397 (Year: 2014).*
Osman et al. Evaluating the Predictivity of Virtual Screening for Abl Kinase Inhibitors to Hinder Drug Resistance, Chem Biol Drug Des 2013; 82: 506-519 (Year: 2013).*
Bailey et al. The Resistance Tetrad: Amino Acid Hotspots for Kinome-Wide Exploitation of Drug-Resistant Protein Kinase Alleles Methods in Enzymology, vol. 548: 117-146 (Year: 2014).*
Krishnamurty et al. Biochemical Mechanisms of Resistance to Small-Molecule Protein Kinase Inhibitors ACS Chem. Biol. 2010, 5, 1 121-138 (Year: 2010).*
Cole et al. Mutation of a highly conserved aspartate residue in subdomain IX abolishes Fer protein-tyrosine kinase activity, Protein Engineering vol. 12 No. 2 pp. 155-162, 1999 (Year: 1999).*
A Public Health Approach To Alzheimer's and Other Dementias Module 1: Alzheimer's Disease as a Public Health Crisis. Alzheimer's Association—Centers for Disease Control and Prevention. Date unknown.
Abud, et al. iPSC-derived human microglia-like cells to study neurological diseases. Neuron. Apr. 19, 2017; 94(2): 278-293.e9.
Ajami, et al. Infiltrating monocytes trigger EAE progression, but do not contribute to the resident microglia pool. Nat Neurosci. Jul. 31, 2011;14(9):1142-9. doi: 10.1038/nn.2887.
Ajami, et al. Local self-renewal can sustain CNS microglia maintenance and function throughout adult life. Nat Neurosci. Dec. 2007;10(12):1538-43. Epub Nov. 18, 2007.
Bain, et al. Constant replenishment from circulating monocytes maintains the macrophage pool in adult intestine. Nat Immunol. Oct. 2014; 15(10): 929-937.
Barbato, Angelo. "Nations for mental health: Schizophrenia and public health." Geneva: World Health Organization Division of Mental Health and Prevention of Substance Abuse (MSA) (1998).
Bardou, et al. jvenn: an interactive Venn diagram viewer. BMC Bioinformatics. 2014; 15(1): 293.
Bennett, et al. A Combination of Ontogeny and CNS Environment Establishes Microglial Identity. Neuron. Jun. 27, 2018;98(6):1170-1183.e8. doi: 10.1016/j.neuron.2018.05.014. Epub May 31, 2018, with supplemental material.
Bennett, et al. New tools for studying microglia in the mouse and human CNS. Proc Natl Acad Sci U S A. Mar. 22, 2016; 113(12): E1738-E1746.
Berman, et al. The protein data bank. Nucleic acids research 28.1 (2000): 235-242.
Biffi, A. Hematopoietic Stem Cell Gene Therapy for Storage Disease: Current and New Indications. Mol Ther. May 3, 2017; 25(5): 1155-1162. Published online Apr. 4, 2017. doi: 10.1016/j.ymthe. 2017.03.025.
Biffi, et al. Lentiviral hematopoietic stem cell gene therapy benefits metachromatic leukodystrophy. Science. Aug. 23, 2013;341(6148):1233158. doi: 10.1126/science.1233158. Epub Jul. 11, 2013.
Bohlen, et al. Diverse requirements for microglial survival, specification, and function revealed by defined-medium cultures. Neuron. May 17, 2017; 94(4): 759-773.e8.
Bruttger, et al. Genetic Cell Ablation Reveals Clusters of Local Self-Renewing Microglia in the Mammalian Central Nervous System. Immunity. Jul. 21, 2015;43(1):92-106. doi: 10.1016/j.immuni. 2015.06.012. Epub Jul. 7, 2015.
Buttgereit, et al. Sall1 is a transcriptional regulator defining microglia identity and function. Nat Immunol. Dec. 2016;17(12):1397-1406. doi: 10.1038/ni.3585. Epub Oct. 24, 2016.
Cerami et al. The cBio cancer genomics portal: an open platform for exploring multidimensional cancer genomics data. Cancer Discov. 2:401-404 (2012).
Chiu, et al. (2013). A neuro-degeneration-specific gene-expression signature of acutely isolated microglia from an amyotrophic lateral sclerosis mouse model. Cell Rep. 4, 385-401.

Clarke, et al. (2018). Normal aging induces A1-like astrocyte reactivity. Proc. Natl. Acad. Sci. USA 115, E1896-E1905.
Cronk, et al. (2018). Peripherally derived mac-rophages can engraft the brain independent of irradiation and maintain an identity distinct from microglia. J. Exp. Med. 47, 1-10.
Dai, et al. (2002). Targeted disruption of the mouse col-ony-stimulating factor 1 receptor gene results in osteopetrosis, mononuclear phagocyte deficiency, increased primitive progenitor cell frequencies, and reproductive defects. Blood 99, 111-120.
Davalos, et al. ATP mediates rapid microglial response to local brain injury in vivo. Nat Neurosci. Jun. 2005;8(6):752-8. Epub May 15, 2005.
De Chaumont, et al. (2012). Icy: an open bioimage informatics platform for extended repro-ducible research. Nat. Methods 9, 690-696.
Dzenko, et al. (2001). The chemokine receptor CCR2 mediates the binding and internalization of mono-cyte chemoattractant protein-1 along brain microvessels. J. Neurosci. 21, 9214-9223.
Escolar, et al. Transplantation of umbilical-cord blood in babies with infantile Krabbe's disease. N Engl J Med. May 19, 2005;352(20):2069-81.
Filipello, et al. The Microglial Innate Immune Receptor TREM2 Is Required for Synapse Elimination and Normal Brain Connectivity. Immunity. May 15, 2018;48(5):979-991.e8. doi: 10.1016/j.immuni. 2018.04.016. Epub May 8, 2018.
Ginhoux, et al. (2010). Fate mapping analysis reveals that adult microglia derive from primitive macrophages. Science 330, 841-845.
Gomez Perdiguero, et al. (2015). Tissue-resident macrophages originate from yolk-sac-derived erythro-myeloid progenitors. Nature 518, 547-551.
Gosselin, et al. (2014). Environment drives selection and function of enhancers controlling tissue-specific macrophage identities. Cell 159, 1327-1340.
Gosselin, et al. (2017). An environment-dependent transcriptional network specifies human microglia identity. Science 356, 1-10.
Hagemeyer, et al. (2016). Transcriptome-based profiling of yolk sac-derived macrophages reveals a role for Irf8 in macrophage maturation. Embo J. 35, 1730-1744.
Hammond, et al. Complex cell-state changes revealed by single cell RNA sequencing of 76, 149 microglia throughout the mouse lifespan and in the injured brain. bioRxiv ( Aug. 31, 2018): 406140.
Haynes, et al. (2006). The P2Y12 receptor regulates microglial activation by extracellular nucleotides. Nat. Neurosci. 9, 1512-1519.
Heng, et al. Immunological Genome Project Consortium (2008). The Immunological Genome Project: networks of gene expression in immune cells. Nat. Immunol. 9, 1091-1094.
Hickman, et al. (2013). The microglial sensome revealed by direct RNA sequencing. Nat. Neurosci. 16, 1896-1905.
Hoeffel, et al. (2015). C-Myb(+) erythro-myeloid progenitor-derived fetal monocytes give rise to adult tissue-resident macrophages. Immunity 42, 665-678.
Hollingworth, et al. Alzheimer's Disease Neuroimaging Initiative; Charge consortium; EADI1 consortium (2011). Common variants at ABCA7, MS4A6A/MS4A4E, EPHA1 CD33 and CD2AP are associated with Alzheimer's disease. Nat. Genet. 43, 429-435.
Hong, et al. Complement and Microglia Mediate Early Synapse Loss in Alzheimer Mouse Models. Science. May 6, 2016; 352(6286): 712-716. Published online Mar. 31, 2016. doi: 10.1126/science. aad8373.
Horlbeck, et al. Compact and highly active next-generation libraries for CRISPR-mediated gene repression and activation. eLife. 2016; 5: e19760. Published online Sep. 23, 2016. doi: 10.7554/eLife. 19760.
Huang, et al. (2018). Repopulated microglia are solely derived from the proliferation of residual microglia after acute depletion. Nat. Neurosci. 21, 530-540.
Kierdorf, et al. (2013). Microglia emerge from erythromyeloid precursors via Pu.1- and Irf8-dependent path-ways. Nat. Neurosci. 16, 273-280.
Konno, et al. Clinical and genetic characterization of adult-onset leukoencephalopathy with axonal spheroids and pigmented glia

(56) References Cited

OTHER PUBLICATIONS associated with CSF1R mutation. Eur J Neurol. Jan. 2017; 24(1): 37-45. Published online Sep. 29, 2016. doi: 10.1111/ene.13125.

Krasemann, et al. (2017). The TREM2-APOE pathway drives the transcriptional phenotype of dysfunctional microglia in neurodegenerative diseases. Immunity 47, 566-581.e9.

Lavin, et al. (2014). Tissue-resident macrophage enhancer landscapes are shaped by the local microenvironment. Cell 159, 1312-1326.

Li, et al. (2006). Conditional deletion of the colony stimulating factor-1 receptor (c-fms proto-oncogene) in mice. Genesis 44, 328-335.

Li, et al. (2018). Microglia and macrophages in brain homeosta-sis and disease. Nat. Rev. Immunol. 18, 225-242.

Li, et al. Developmental heterogeneity of microglia and brain myeloid cells revealed by deep single-cell RNA sequencing. bioRxiv (2018): 406363.

Liddelow, et al. (2017). Neurotoxic reactive astrocytes are induced by activated micro-glia. Nature 541, 481-487.

Lovly, et al. Molecular Pathways: Resistance to Kinase Inhibitors and Implications for Therapeutic Strategies. Clin Cancer Res. May 1, 2014; 20(9): 2249-2256. doi: 10.1158/1078-0432.CCR-13-1610.

Maher, et al. Cellular Transplant Therapies for Globoid Cell Leukodystrophy: Preclinical and Clinical Observations. J Neurosci Res. Nov. 2016; 94(11): 1180-1188. doi: 10.1002/jnr.23782.

Maier, et al. ff14SB: Improving the accuracy of protein side chain and backbone parameters from ff99SB. J Chem Theory Comput. Aug. 11, 2015; 11(8): 3696-3713. Published online Jul. 23, 2015. doi: 10.1021/acs.jctc.5b00255.

Mass, et al. (2016). Specification of tissue-resident macrophages during organogenesis. Science 353, aaf4238.

Matcovitch-Natan, et al. (2016). Microglia development follows a stepwise program to regulate brain homeostasis. Science 353, aad8670.

Metsalu, et al. (2015). ClustVis: a web tool for visualizing clustering of multivariate data using principal component analysis and heatmap. Nucleic Acids Res. 43 (W1), W566-70.

Mildner, et al. (2007). Microglia in the adult brain arise from Ly-6ChiCCR2+ monocytes only under defined host con-ditions. Nat. Neurosci. 10, 1544-1553.

Miller, et al. MMPBSA.py: An Efficient Program for End-State Free Energy Calculations. J Chem Theory Comput. Sep. 11, 2012;8(9):3314-21.

Morgens, et al. Genome-scale measurement of off-target activity using Cas9 toxicity in high-throughput screens. Nat Commun. 2017; 8: 15178. Published online May 5, 2017. doi: 10.1038/ncomms15178.

Obermeier, et al. (2013). Development, main-tenance and disruption of the blood-brain barrier. Nat. Med. 19, 1584-1596.

Ohgidani, et al. (2014). Direct induction of ramified microglia-like cells from human monocytes: dynamic mi-croglial dysfunction in Nasu-Hakola disease. Sci. Rep. 4, 4957.

Phillips, et al. Scalable molecular dynamics with NAMD. J. Comp. Chem. 26.16 (2005): 1781-1802. doi: 10.1002/jcc.20289.

Priller, et al. (2001). Targeting gene-modified hematopoietic cells to the central nervous system: use of green fluorescent protein uncovers microglial engraftment. Nat. Med. 7, 1356-1361.

Qian, et al. Brain Region-specific Organoids using Mini-bioreactors for Modeling ZIKV Exposure. Cell. May 19, 2016; 165(5): 1238-1254. Published online Apr. 22, 2016. doi: 10.1016/j.cell.2016.04.032.

Rathinam, et al. (2011). Efficient differentiation and function of human macrophages in hu-manized CSF-1 mice. Blood 118, 3119-3128.

Robinson, et al. (2010). edgeR: a Bioconductor package for differential expression analysis of digital gene expression data. Bioinformatics 26, 139-140.

Saederup, et al. (2010). Selective chemokine receptor usage by central nervous system myeloid cells in CCR2-red fluorescent protein knock-in mice. PLoS ONE5, e13693.

Sagar, et al. (2017). Antibody blockade of CLEC12A delays EAE onset and attenuates disease severity by impairing myeloid cell CNS infiltration and restoring positive immu-nity. Sci. Rep. 7, 2707.

Salter, et al. (2017). Microglia emerge as central players in brain disease. Nat. Med. 23, 1018-1027.

Schafer, et al. Microglia Sculpt Postnatal Neural Circuits in an Activity and Complement-Dependent Manner. Neuron. May 24, 2012; 74(4): 691-705. doi: 10.1016/j.neuron.2012.03.026.

Schindelin, et al. (2012). Fiji: an open-source platform for biological-image analysis. Nat. Methods 9, 676-682.

Schneider, et al. (2012). NIH Image to ImageJ: 25 years of image analysis. Nat. Methods 9, 671-675.

Schulz, et al. (2012). A lineage of myeloid cells independent of Myb and hematopoietic stem cells. Science 336, 86-90.

Scott, et al. (2016). Bone marrow-derived monocytes give rise to self-renewing and fully differentiated Kupffer cells. Nat. Commun. 7, 10321.

Sekar, et al. Schizophrenia risk from complex variation of complement component 4. Nature. Feb. 11, 2016; 530(7589): 177-183. Published online Jan. 27, 2016. doi: 10.1038/nature16549.

Sellgren, et al. (2017). Patient-specific models of microglia-mediated engulfment of synapses and neural progenitors. Mol. Psychiatry 22, 170-177.

Shemer, et al. Engrafted parenchymal brain macrophages differ from microglia in transcriptome, chromatin landscape and response to challenge. Nat Commun. 2018; 9: 5206. Published online Dec. 6, 2018. doi: 10.1038/s41467-018-07548-5. bioRxiv (Jul. 16, 2018): 369942.

Shi, et al.; Alzheimer's Disease Neuroimaging Initiative (2017). ApoE4 markedly exacerbates tau-mediated neurodegenera-tion in a mouse model of tauopathy. Nature 549, 523-527.

Subramanian, et al. (2005). Gene set enrichment analysis: a knowledge-based approach for interpreting genome-wide expression profiles. Proc. Natl. Acad. Sci. USA 102, 15545-15550.

Suzuki, et al. (2014). pvclust: hierarchical clustering with p-values via multiscale Bootstrap resampling. R package version 1.2-2 https://cran.r-project.org/web/packages/pvclust/index.html.

Tap, et al. Structure-Guided Blockade of CSF1R Kinase in Tenosynovial Giant-Cell Tumor. N Engl J Med. Jul. 30, 2015;373(5):428-37. doi: 10.1056/NEJMoa1411366.

Thion, et al. Microbiome Influences Prenatal and Adult Microglia in a Sex-Specific Manner. Cell. Jan. 25, 2018; 172(3): 500-516.e16. doi: 10.1016/j.cell.2017.11.042.

Trapnell, et al. (2012). Differential gene and tran-script expression analysis of RNA-seq experiments with TopHat and Cufflinks. Nat. Protoc. 7, 562-578.

Trapnell, et al. Pseudo-temporal ordering of individual cells reveals dynamics and regulators of cell fate decisions. Nat Biotechnol. Apr. 2014; 32(4): 381-386. Published online Mar. 23, 2014. doi: 10.1038/nbt.2859.

Van De Laar, et al. (2016). Yolk sac macrophages, fetal liver, and adult monocytes can colonize an empty niche and develop into functional tissue-resident macrophages. Immunity 44, 755-768.

Varvel, et al. (2012). Microglial repopulation model reveals a robust homeostatic process for replacing CNS myeloid cells. Proc. Natl. Acad. Sci. USA 109, 18150-18155.

Villa, et al. Sex-specific features of microglia from adult mice. Cell reports 23.12 (2018): 3501-3511.

Waisman, et al. Homeostasis of Microglia in the Adult Brain: Review of Novel Microglia Depletion Systems. Trends Immunol. Oct. 2015;36(10):625-636. doi: 10.1016/j.it.2015.08.005.

Wang, et al. (2015). TREM2 lipid sensing sustains the microglial response in an Alzheimer's dis-ease model. Cell 160, 1061-1071.

Wenger, et al. Krabbe disease: One Hundred years from the bedside to the bench to the bedside. J Neurosci Res. Nov. 2016;94(11):982-9. doi: 10.1002/jnr.23743.

Wong, et al. (2017). Mice deficient in NRROS show abnormal microglial development and neurological disorders. Nat. Immunol. 18, 633-641.

Yang, et al. Perivascular, but not Parenchymal, Cerebral Engraftment of Donor Cells after Non-Myeloablative Bone Marrow Transplantation. Exp Mol Pathol. Aug. 2013; 95(1): 7-17. Published online Apr. 6, 2013. doi: 10.1016/j.yexmp.2013.03.010.

(56)         References Cited

OTHER PUBLICATIONS

Zhang, et al. (2014). An RNA-sequencing transcriptome and splic-
ing database of glia, neurons, and vascular cells of the cerebral
cortex. J. Neurosci. 34, 11929-11947.
Zhou, et al. In vivo simultaneous transcriptional activation of
multiple genes in the brain using CRISPR-dCas9-activator trans-
genic mice. Nat Neurosci. Mar. 2018;21(3):440-446. doi: 10.1038/
s41593-017-0060-6. Epub Jan. 15, 2018.
Anger, W.K.: Animal test systems to study behavioral dysfunctions
of neurodegenerative disorders. Neurotoxicology 12(3):403-413
(1991) Abstract.
Asai et al.: Depletion Of Microglia And Inhibition Of Exosome
Synthesis Halt Tau Propagation, Nature Neuroscience, vol. 18, pp.
1584-1593, 2015.
Bennett, M. et al.: The influence of environment and origin on brain
resident macrophages and implications for therapy. Nature Neuro-
science | vol. 23 | Feb. 2020 | 157-166 | www.nature.com/
natureneuroscience.
Blurton-Jones et al.: Neural stem cells improve cognition via BDNF
in a transgenic model of Alzheimer disease, Proc Natl Acad Sci U
S A., vol. 106, No. 32, pp. 13594-13599, 2009.
Capotondo, A. et al.: Brain conditioning is instrumental for suc-
cessful microglia reconstitution following hematopoietic stem cell
transplantation. PNAS, Sep. 11, 2012, vol. 109,No. 37; pp. 15018-
15023.
Capotondo, A. et al.: Intracerebroventricular delivery of hematopoietic
progenitors results in rapid and robust engraftment of microglia-like
cells. Sci. Adv. 2017;3: e1701211.
Castro-Poceiro, Jesús et al.: Mesenchymal stromal cells in the
treatment of perianal fistulas in Crohn's disease. Cell Report 24:1203-
1217 (2018). DOI: 10.2217/imt-2018-0099 (abstract).
Chadarevian, Jean Paul et al.: Engineering an inhibitor-resistant
human CSF1R variant for microglia replacement. J. Exp. Med. 6;
220(3):e20220857 (2023). doi: 10.1084/jem.20220857.
Etemad et al.: A novel in vitro human microglia model: Character-
ization of human monocyte-derived microglia. Journal of Neuro-
science Methods 209:79-89 (2012).
Han, Jinming et al.: Microglial replacement therapy: a potential
therapeutic strategy for incurable CSF1R-related leukoencephalopathy.
Acta Neuropathologica Communications 8:217 (2020).
Haney et al.: Genetically modified macrophages accomplish tar-
geted gene delivery to the inflamed brain in transgenic Parkin
Q311X (A) mice: importance of administration routes. Scientific
reports 10(1):1-13 (2020).
Heidel et al.: Clinical resistance to the kinase inhibitor PKC412 in
acute myeloid leukemia by mutation of Asn-676 in the FLT3
tyrosine kinase domain. BLOOD 107:1 (2006).
Hohsfield, L. A. et al.: Effects of long-term and brain-wide coloni-
zation of peripheral bone marrow-derived myeloid cells in the CNS.
J Neuroinflammation. Sep. 20, 2020;17(1):279. doi: 10.1186/s12974-
020-01931-0.
Lee et al.: Cytokines, Chemokines, and Cytokine Receptors in
Human Microglia, Journal of Neuroscience Research 69:94-103
(2002).

Machiraju, PK et al.: Identification, synthesis and evaluation of
CSF1R inhibitors using fragment based drug design. Computational
Biology and Chemistry 80:374-383 (2019). https://doi.org/10.1016/
j.compbiolchem.2019.04.015.
Mancuso, Renzo et al.: CSF1R inhibitor JNJ-40346527 attenuates
microglial proliferation and neurodegeneration in P301S mice.
Brain 142:3243-3264 (2019).
Marsh et al.: The Adaptive Immune System Restrains Alzheimer's
Disease Pathogenesis By Modulating Microglial Function, Proceed-
ings of the National Academy of Sciences of the United States of
America 113:E1316-1325 (2016).
Office Action dated Aug. 18, 2023 issued in U.S. Appl. No.
18/069,631.
Office Action dated Dec. 21, 2023 issued in U.S. Appl. No.
16/566,675.
Office Action dated Jan. 25, 2024 issued in U.S. Appl. No. 18/069,631.
Office Action dated Mar. 1, 2023 issued in U.S. Appl. No. 16/566,675.
Oosterhof, Nynke et al.: Colony-Stimulating Factor 1 Receptor
(CSF1R) Regulates Microglia Density and Distribution, but Not
Microglia Differentiation In Vivo. Cell Rep. 24(5):1203-1217.e6
(2018). doi: 10.1016/j.celrep.2018.06.113.
PCT/US2021/035454 International Search Report and Written Opin-
ion dated Dec. 21, 2021.
PCT/US2022/023139 International Search Report and Written Opin-
ion dated Aug. 30, 2022 (Publ. No. WO2022212897A1).
Rubino, Stephen J. et al.: Acute microglia ablation induces
neurodegeneration in the somatosensory system. Nature Commu-
nications 9:4578 (2018).
Sarter, Martin: Animal cognition: defining the issues. Neuroscience
& Biobehavioral Reviews 28(7):645-650 (2004). https://doi.org/10.
1016/j.neubiorev.2004.09.005 (abstract).
Shibuya, Y. et al.: Treatment of a genetic brain disease by CNS-wide
microglia replacement, Sci Transl Med. Mar. 16, 2022;14(636):eabl9945.
doi: 10.1126/scitranslmed.abl9945. Epub Mar. 16, 2022.
Spangenberg, Elizabeth et al.: Sustained microglial depletion with
CSF1R inhibitor impairs parenchymal plaque development in an
Alzheimer's disease model. Nature Communications 10: 3758
(2019).
Stalder et al.: Invasion Of Hematopoietic Cells Into The Brain Of
Amyloid Precursor Protein Transgenic Mice, The Journal of Neu-
roscience 25:11125-11132 (2005).
Tayebati, Seyed Khosrow: Animal models of cognitive dysfunction.
Mechanisms of Ageing and Development 127(2):100-108 (2006).
https://doi.org/10.1016/j.mad.2005.09.026 (abstract).
The gene summary of CSF1R from the website: bioinfo.uth.edu/
mutLBSgene_search_result.cgi?page=page&type=quick_search
&quick_search=1436 retrieved on Jul. 18, 2023.
U.S. Appl. No. 18/069,543 Office Action dated May 25, 2023.
U.S. Appl. No. 18/069,543 Office Action dated Oct. 25, 2024.
U.S. Appl. No. 18/069,631 Office Action dated Jan. 25, 2024.
Wang et al.: IL-34 Is A Tissue-Restricted Ligand Of CSF1 R
Required For The Development Of Langerhans Cells And Microglia,
Nature Immunology, vol. 13, pp. 753-760, 2012.

* cited by examiner

Figure 1D

PLX-3397 (Pexidartinib)
$IC_{50} = 13$ nM

Figure 1E

BLZ-945
$IC_{50} = 1.2$ nM

Figure 1F

BLZ-945 metabolite
$IC_{50} = 5.5$ nM

CFMS-IN-2

Figure 1I 6-chloro-3-(3-methyl-2H-1,2-
oxazol-5-ylidene)-4-
phenylquinolin-2-one

Figure 1J

Linifanib (ABT-869)

Figure 1K

OSI-930 log2(FC vs WT)

| Gene | WT MG | pICTMG | log2 (WT/ICT) | FDR | Gene | WT MG | pICTMG | log2 (WT/ICT) | FDR |
|---|---|---|---|---|---|---|---|---|---|
| Hlf | 30.0 | 2.0 | 3.93 | 0.000 | Gm14023 | 18.9 | 55.2 | -1.25 | 0.029 |
| Gpr165 | 389.1 | 32.3 | 3.69 | 0.000 | Icosl | 18.1 | 46.1 | -1.26 | 0.020 |
| Serpine2 | 91.1 | 10.9 | 3.16 | 0.000 | Apoe | 236.5 | 590.0 | -1.26 | 0.041 |
| Khdrbs3 | 33.6 | 5.0 | 2.49 | 0.000 | D10Wsu52e | 14.8 | 39.6 | -1.29 | 0.008 |
| Casc4 | 43.1 | 9.1 | 2.39 | 0.000 | Rnf150 | 9.4 | 23.9 | -1.29 | 0.001 |
| Rab6b | 32.3 | 7.3 | 2.21 | 0.000 | Cd84 | 62.0 | 162.1 | -1.32 | 0.001 |
| Snx9 | 25.7 | 16.8 | 2.10 | 0.001 | Rgs1 | 172.5 | 474.6 | -1.33 | 0.002 |
| Nav2 | 28.5 | 8.0 | 1.88 | 0.000 | Slc17a5 | 11.8 | 30.1 | -1.34 | 0.041 |
| F9 | 47.9 | 14.1 | 1.87 | 0.002 | Man2a1 | 10.2 | 25.8 | -1.37 | 0.000 |
| Lst1 | 45.4 | 19.5 | 1.82 | 0.001 | Hmox1 | 8.5 | 20.8 | -1.38 | 0.004 |
| Ccl9 | 93.4 | 29.5 | 1.78 | 0.000 | Myc | 12.6 | 35.1 | -1.39 | 0.010 |
| Ccl6 | 44.9 | 13.4 | 1.77 | 0.007 | Csf2ra | 41.2 | 117.6 | -1.45 | 0.001 |
| Tspan13 | 69.6 | 21.1 | 1.77 | 0.000 | Tank | 9.5 | 20.7 | -1.46 | 0.006 |
| Csmd3 | 41.9 | 13.0 | 1.73 | 0.001 | Ifi30 | 29.6 | 89.3 | -1.47 | 0.001 |
| Ngm | 25.9 | 8.0 | 1.68 | 0.001 | Syt6 | 13.2 | 36.6 | -1.49 | 0.001 |
| Hnmt | 31.7 | 10.1 | 1.67 | 0.004 | Osm | 6.6 | 21.6 | -1.53 | 0.017 |
| Tspan7 | 76.8 | 27.4 | 1.57 | 0.000 | Neat1 | 11.8 | 35.9 | -1.54 | 0.031 |
| Fam102b | 139.1 | 50.6 | 1.50 | 0.000 | 3200002M19Rik | 14.9 | 54.0 | -1.55 | 0.004 |
| DOH4S114 | 53.5 | 21.9 | 1.46 | 0.003 | Lilrb4 | 4.7 | 27.1 | -1.55 | 0.001 |
| Wrb | 25.3 | 9.9 | 1.43 | 0.025 | Cd52 | 17.9 | 54.9 | -1.56 | 0.030 |
| Znrf1 | 37.2 | 13.4 | 1.40 | 0.007 | Lrrc3 | 56.4 | 178.5 | -1.57 | 0.000 |
| Ets1 | 47.2 | 19.7 | 1.32 | 0.000 | C3ar1 | 42.8 | 134.0 | -1.57 | 0.000 |
| Ccr5 | 674.4 | 287.3 | 1.30 | 0.000 | Tlr2 | 8.1 | 24.7 | -1.61 | 0.001 |
| Gprasp1 | 26.7 | 11.8 | 1.28 | 0.001 | Smc4 | 10.5 | 34.7 | -1.70 | 0.011 |
| Cst3 | 20034.9 | 8776.6 | 1.28 | 0.020 | Ms4a6b | 20.1 | 62.7 | -1.77 | 0.000 |
| Jam2 | 67.9 | 28.8 | 1.27 | 0.001 | C030034L19Rik | 9.5 | 38.1 | -1.79 | 0.000 |
| Zbtb20 | 25.3 | 12.1 | 1.26 | 0.045 | H60b | 2.9 | 20.4 | -1.80 | 0.000 |
| Tuba1a | 73.8 | 44.3 | 1.23 | 0.003 | Ccrl2 | 5.6 | 23.2 | -1.88 | 0.001 |
| Zfp691 | 58.7 | 26.9 | 1.21 | 0.003 | Ccl2 | 31.5 | 182.9 | -1.90 | 0.001 |
| Basp1 | 162.0 | 76.4 | 1.19 | 0.002 | Gpr160 | 6.7 | 27.4 | -1.94 | 0.001 |
| Prkaca | 40.3 | 19.5 | 1.17 | 0.005 | Cdkn1a | 18.0 | 74.4 | -1.96 | 0.007 |
| 0610040J01Rik | 40.3 | 19.2 | 1.15 | 0.006 | Fmn1 | 6.1 | 25.6 | -2.02 | 0.000 |
| Idua | 24.6 | 12.6 | 1.13 | 0.045 | Dab2 | 7.3 | 35.0 | -2.09 | 0.000 |
| Gpr155 | 153.7 | 74.8 | 1.13 | 0.018 | Ccr1 | 13.0 | 63.1 | -2.17 | 0.000 |
| Cdk5r1 | 20.6 | 10.7 | 1.10 | 0.030 | Gm16907 | 3.8 | 22.7 | -2.24 | 0.000 |
| Sema4b | 29.2 | 15.3 | 1.06 | 0.010 | Ccl12 | 38.8 | 254.6 | -2.47 | 0.000 |
| Fscn1 | 109.4 | 56.2 | 1.04 | 0.023 | Ms4a6c | 5.9 | 30.7 | -2.47 | 0.000 |
| Crybb1 | 113.0 | 51.1 | 1.04 | 0.002 | H2-DMb1 | 3.8 | 23.5 | -2.48 | 0.000 |
| Tppp | 24.4 | 12.7 | 1.02 | 0.007 | Pvt1 | 3.3 | 21.3 | -2.58 | 0.000 |
| 1110004F10Rik | 40.2 | 20.8 | 1.01 | 0.035 | Myo5a | 4.7 | 29.3 | -2.60 | 0.000 |
| Bcl9l | 36.6 | 19.1 | 1.00 | 0.012 | Ctla2b | 5.3 | 33.2 | -2.62 | 0.000 |
| Stab1 | 16.2 | 34.7 | -1.00 | 0.044 | Ctse | 2.9 | 28.4 | -3.14 | 0.000 |
| P2rx4 | 12.3 | 22.5 | -1.03 | 0.032 | Lyz2 | 22.9 | 230.4 | -3.26 | 0.000 |
| Nfkbiz | 47.3 | 117.4 | -1.12 | 0.007 | Cd34 | 6.0 | 63.4 | -3.32 | 0.000 |
| Vps13c | 11.6 | 27.2 | -1.13 | 0.000 | 1810011010Rik | 2.8 | 41.4 | -3.44 | 0.000 |
| Fth1 | 313.3 | 781.4 | -1.13 | 0.001 | H2-DMa | 2.3 | 25.9 | -3.56 | 0.000 |
| Tpd52 | 10.2 | 22.3 | -1.14 | 0.006 | Mki67 | 2.4 | 36.5 | -3.84 | 0.002 |
| Rpl32 | 48.5 | 104.1 | -1.15 | 0.048 | Mrc1 | 4.8 | 60.8 | -3.85 | 0.000 |
| C5ar1 | 17.8 | 41.8 | -1.17 | 0.020 | Srgn | 7.0 | 106.6 | -3.92 | 0.000 |
| AU040972 | 8.8 | 20.8 | -1.20 | 0.041 | Niacr1 | 0.6 | 22.1 | -4.42 | 0.000 |
| Afap1l1 | 9.4 | 20.6 | -1.21 | 0.018 | 1300014I06Rik | 0.4 | 20.1 | -4.71 | 0.000 |
| Clec5a | 13.4 | 34.7 | -1.21 | 0.003 | Gpr65 | 1.8 | 65.3 | -5.16 | 0.000 |
| Il1a | 55.6 | 163.9 | -1.22 | 0.020 | Fxyd5 | 0.4 | 29.6 | -6.18 | 0.000 |
| Ctsh | 48.0 | 108.6 | -1.23 | 0.000 | Msr1 | 0.2 | 37.2 | -6.69 | 0.000 |
| Alox5 | 11.0 | 26.6 | -1.24 | 0.048 | Fn1 | 0.1 | 27.4 | -7.85 | 0.000 |
| Man2b1 | 136.4 | 340.0 | -1.25 | 0.000 | | | | | |

Figure 4

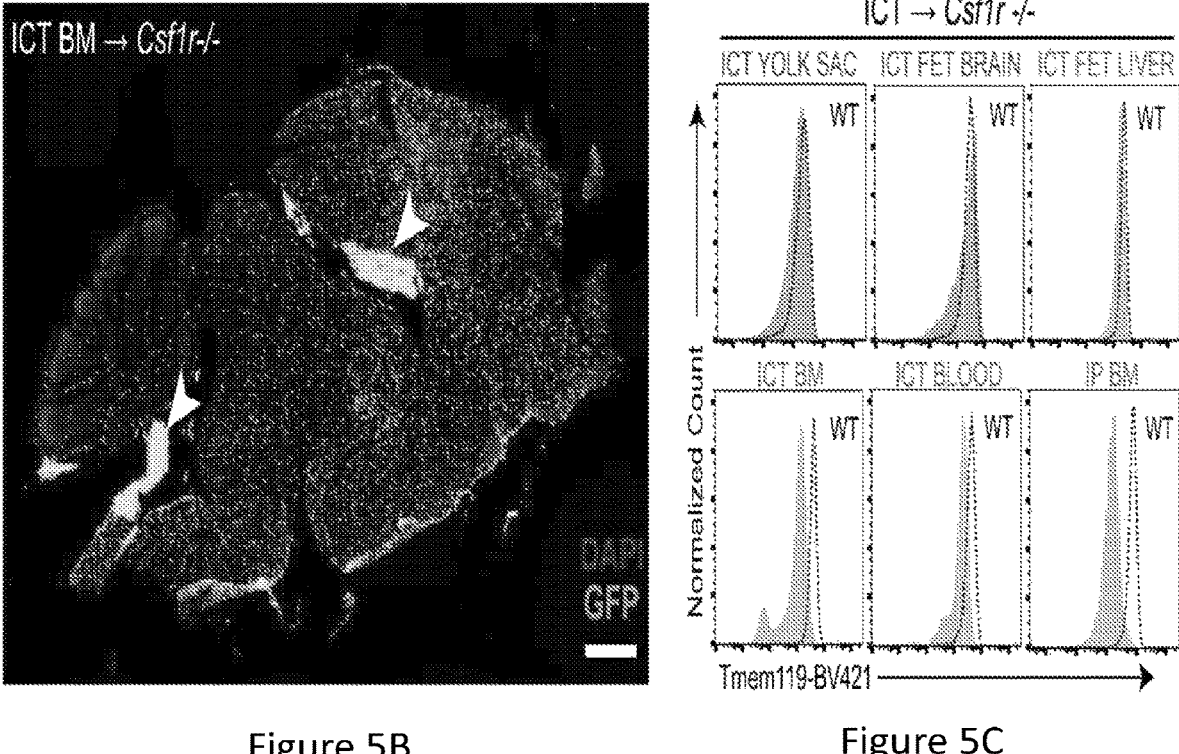
Figure 5B                    Figure 5C

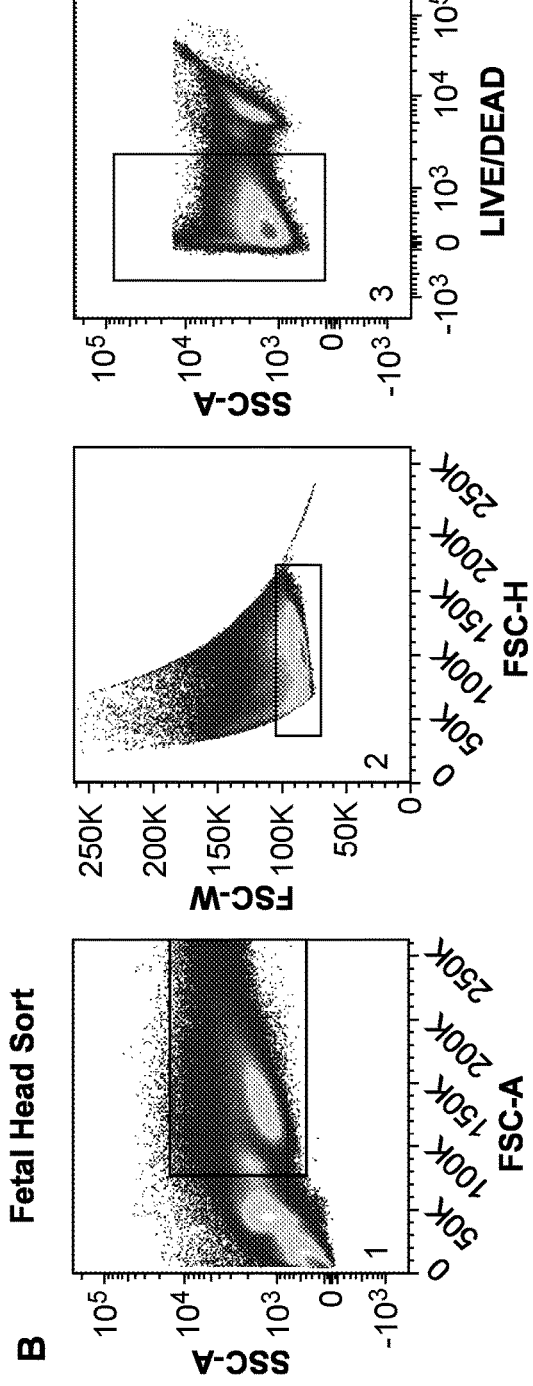
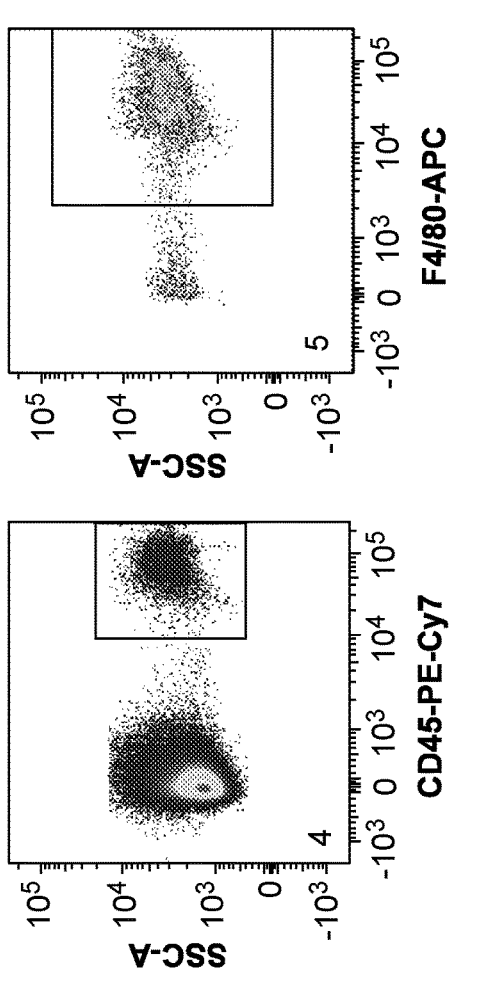
Figure 6B

| ICT Type | Sample | % Recovery (vs WT) | %Tmem119+ of Parenchymal Iba1+ | Yield, RIN>7 |
|---|---|---|---|---|
| BM | 1 | 11.3 | 100 | * |
|  | 2 | 9.1 | - | * |
|  | 3 | 11.0 | - | * |
|  | 4 | 8.2 | - | * |
|  | 5 | 10.1 | - | * |
|  | 6 | - | 100 |  |
|  | 7 | - | 100 |  |
|  | 8 | - | 100 |  |
|  | 9 | - | 100 |  |
| Blood | 1 | 1.9 | - | * |
|  | 2 | 13.8 | - | * |
|  | 3 | 15.2 | - |  |
|  | 4 | 12.2 | - |  |
|  | 5 | 4.4 | - |  |
|  | 6 | 2.7 | 100 | * |
|  | 7 | 3.6 | 100 | * |
|  | 8 | 8.3 | 100 | * |
|  | 9 | 2.8 | 100 |  |
|  | 10 | - | 100 |  |
|  | 11 | - | 100 |  |
|  | 12 | - | 100 |  |
|  | 13 | - | 100 |  |
|  | 14 | - | 100 |  |

| ICT Type | Sample | % Recovery (vs WT) | %Tmem119+ of Parenchymal Iba1+ | Yield, RIN>7 |
|---|---|---|---|---|
| Yol Sac | 1 | 4.8 | 100 |  |
|  | 2 | 12.2 | 100 | * |
|  | 3 | 32.5 | 100 | * |
|  | 4 | 44.3 | 100 | * |
|  | 5 | 18.7 | 100 | * |
|  | 6 | - | 100 |  |
| Fetal Brain | 1 | 10.4 | 100 | * |
|  | 2 | 9.3 | 100 | * |
|  | 3 | 11.0 | 100 | * |
|  | 4 | NA | - | * |
|  | 5 | NA | - | * |
| Fetal Liver | 1 | 31.4 | 100 | * |
|  | 2 | 35.6 | 100 | * |
|  | 3 | 11.7 | 100 |  |
|  | 4 | 35.1 | 100 | * |
|  | 5 | 29.5 | 100 | * |
|  | 6 | 2.9 | 100 |  |
|  | 7 | 1.3 | - |  |
|  | 8 | 74.1 | - | * |
|  | 9 | 69.1 | - | * |
|  | 10 | - | 100 |  |
|  | 11 | - | 100 |  |

| ICT Type | Sample | % Recovery (vs WT) | %Tmem119+ of Parenchymal Iba1+ | Yield, RIN>7 |
|---|---|---|---|---|
| Microglia | 1 | 4.8 | 100 |  |
|  | 2 | 12.2 | 100 | * |
|  | 3 | 24.8 | 100 | * |
|  | 4 | 3.6 | 100 |  |
|  | 5 | 0.0 | - |  |
| Cultured MG | 1 | 15.6 | 100 | * |
|  | 2 | 16.3 | 100 | * |
|  | 3 | 28.2 | 100 | * |
|  | 4 | 3.8 | - |  |
|  | 5 | 10.0 | - |  |
|  | 6 | 8.3 | - |  |
|  | 7 | 3.6 | - |  |
|  | 8 | 2.8 | - |  |
|  | 9 | 27.6 | 100 | * |
|  | 10 | 10.4 | 100 | * |
|  | 11 | 94.4 | - |  |
|  | 12 | - | 100 |  |
|  | 13 | - | 100 |  |
| P5 MG | 1 | 20.7 | 100 | * |
|  | 2 | 39.1 | 100 | * |
|  | 3 | 33.3 | 100 | * |
|  | 4 | 51.9 | 100 | * |
|  | 5 | 23.0 | 100 | * |
|  | 6 | - | 100 |  |
|  | 7 | - | 100 |  |

Figure 6G

Figure 7A                    Figure 7B
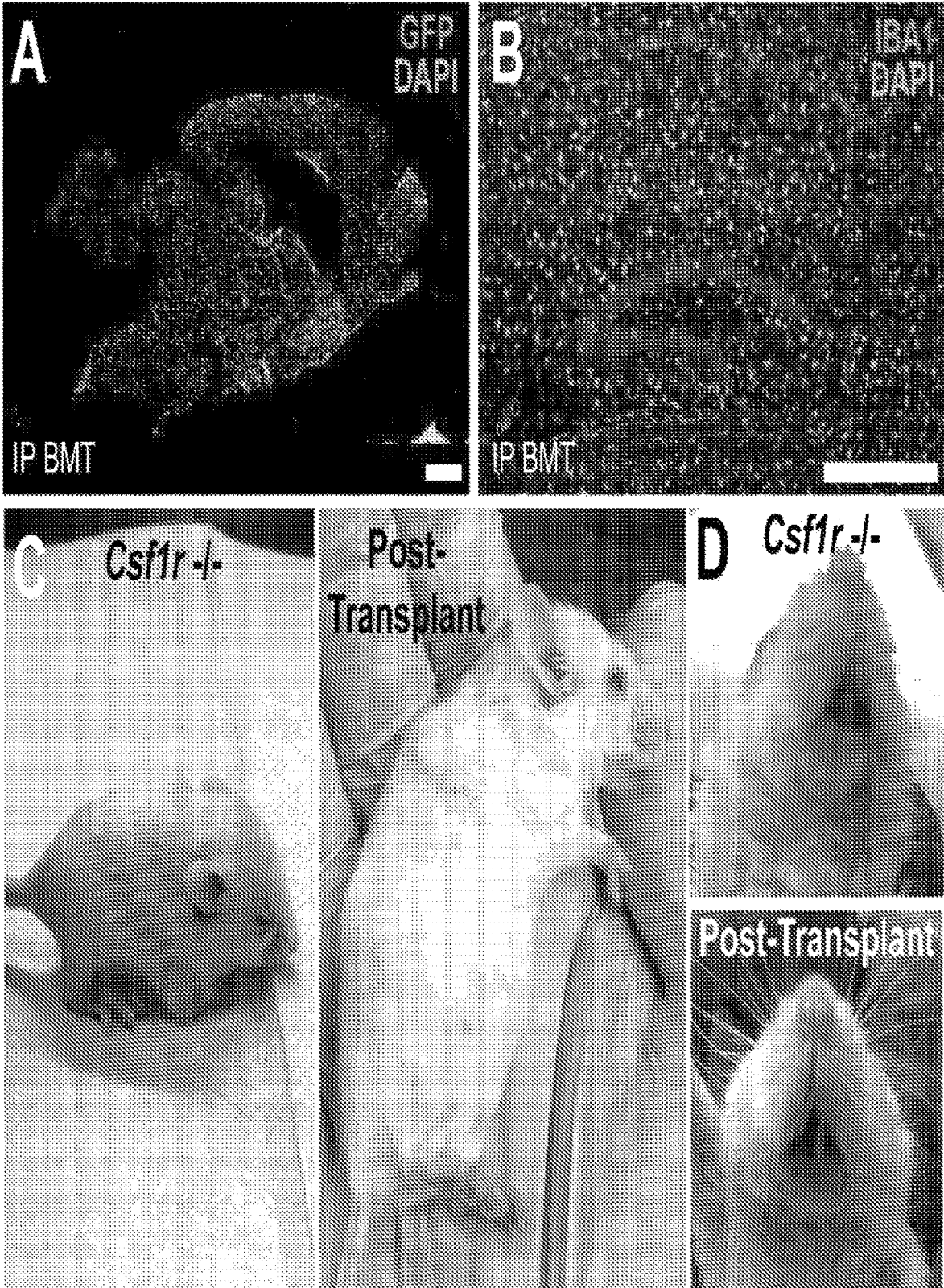
Figure 7C                              Figure 7D Figure 9A                                        Figure 9C

B

| Data | Citation |
| --- | --- |
| Neutrophils | Lavin et al |
| Monocytes | Lavin et al |
| Kupffer Cells | Lavin et al |
| Peritoneal Macrophages | Lavin et al |
| MG | Lavin et al |
| MG/M◆ | Zhang et al |
| MG | Bennett et al |
| Brain Myeloid | Bennett et al |

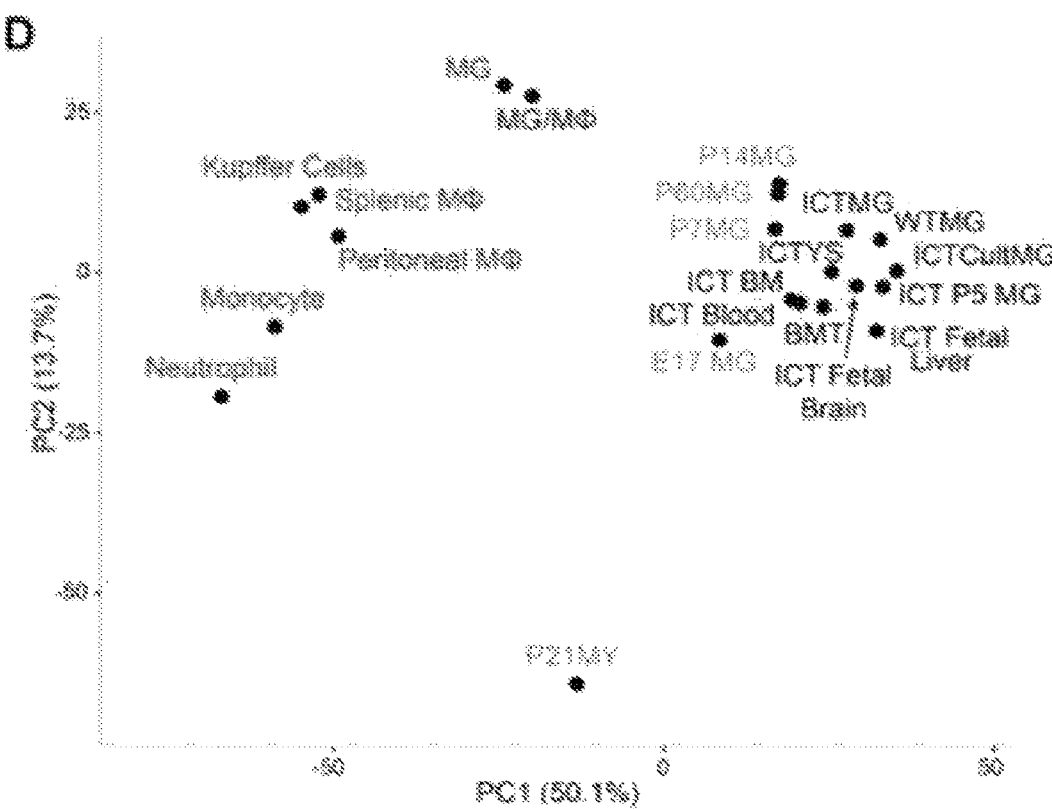

| Data | Citation |
|---|---|
| Neutrophils | Lavin et al |
| Monocytes | Lavin et al |
| Kupffer Cells | Lavin et al |
| Splenic MΦ | Lavin et al |
| Peritoneal MΦ | Lavin et al |
| MG | Lavin et al |
| MGMΦ | Zhang et al |
| P14MG | Bennett et al |
| P60MG | Bennett et al |
| P7MG | Bennett et al |
| E17MG | Bennett et al |
| P21MY | Bennett et al |
| ICT BM | current |
| ICT Blood | current |
| ICTMG | current |
| ICTYS | current |
| BMT | current |
| ICT Fetal Brain | current |
| WTMG | current |
| ICTCULT MG | current |
| ICT P5 MG | current |
| ICT Fetal Liver | current |

Figure 10D

Expression of microglia enriched genes in MLCs

| Gene | μCT MG | μCT YSs | μCT HSC | Log2 (YSs/MG) | p-value | Log2 (HSC/MG) | p-value | Log2 (YSs/HSC) | p-value |
|---|---|---|---|---|---|---|---|---|---|
| Slc2a5 | 37.1 | 271 | 3.2 | -0.58 | 0.19 | -3.63 | 0.00 | 3.08 | 0.00 |
| P2ry12 | 2097.3 | 1636.9 | 244.3 | -0.39 | 0.14 | -3.05 | 0.00 | 2.66 | 0.00 |
| Aspm | 953.4 | 124.1 | 27.3 | -0.60 | 0.04 | -2.91 | 0.00 | 2.33 | 0.00 |
| Gpr34 | 565.2 | 302.1 | 121.4 | -0.01 | 0.99 | -1.67 | 0.00 | 1.69 | 0.00 |
| Cers | 287.3 | 155.7 | 50.6 | 0.93 | 0.00 | -2.53 | 0.00 | 1.67 | 0.00 |
| Fam110a | 16.9 | 14.7 | 5.3 | 0.17 | 0.70 | -1.67 | 0.00 | 1.51 | 0.00 |
| Cd164 | 636.0 | 619.8 | 231.5 | -0.08 | 0.74 | -1.49 | 0.00 | 1.43 | 0.00 |
| Php | 96.9 | 87.9 | 37.6 | -0.35 | 0.15 | -1.49 | 0.00 | 1.16 | 0.00 |
| Epb4.1I2 | 574.2 | 551.2 | 262.8 | -0.18 | 0.42 | -1.28 | 0.00 | 1.11 | 0.00 |
| Grdm1 | 226.4 | 241.4 | 115.3 | 0.01 | 0.96 | -1.06 | 0.00 | 1.09 | 0.02 |
| 9330133O14Rik | 10.9 | 9.9 | 4.7 | -0.13 | 0.75 | -1.15 | 0.00 | 1.04 | 0.00 |
| P2ry13 | 1188.0 | 991.0 | 541.5 | -0.30 | 0.22 | -1.20 | 0.00 | 0.92 | 0.00 |
| Commd8 | 76.8 | 71.7 | 41.2 | -0.10 | 0.72 | -1.00 | 0.00 | 0.92 | 0.00 |
| Cfh | 280.0 | 238.8 | 124.6 | -0.10 | 0.32 | -1.15 | 0.00 | 0.91 | 0.00 |
| Fam102b | 60.6 | 32.4 | 17.8 | -0.10 | 0.03 | -1.60 | 0.00 | 0.89 | 0.00 |
| Cst3 | 155.5 | 141.9 | 77.1 | -0.10 | 0.54 | -1.02 | 0.00 | 0.82 | 0.00 |
| Cd3eap | 100.9 | 87.9 | 56.5 | -0.10 | 0.35 | -1.04 | 0.00 | 0.81 | 0.00 |
| Osrm3 | 459.7 | 352.2 | 203.0 | -0.10 | 0.04 | -1.27 | 0.00 | 0.90 | 0.00 |
| Rtn4rl1 | 56.1 | 42.4 | 25.6 | -0.10 | 0.06 | -1.25 | 0.00 | 0.75 | 0.01 |
| 6230427J02Rik | 17.9 | 32.6 | 21.2 | -0.10 | 0.01 | -0.35 | 0.30 | 0.75 | 0.03 |
| Tmem119 | 533.0 | 724.2 | 464.4 | -0.10 | 0.13 | -0.26 | 0.23 | 0.72 | 0.00 |
| 6610040J01Rik | 19.2 | 18.3 | 11.4 | -0.10 | 0.82 | -0.76 | 0.01 | 0.70 | 0.04 |
| Entpd1 | 266.5 | 219.0 | 141.9 | -0.10 | 0.15 | -1.01 | 0.00 | 0.69 | 0.02 |
| Zfp715 | 38.5 | 42.7 | 29.4 | -0.10 | 0.73 | -0.47 | 0.06 | 0.59 | 0.03 |
| Dhrsms12a | 136.5 | 97.6 | 58.9 | -0.10 | 0.11 | -0.92 | 0.00 | 0.58 | 0.01 |
| Cmtm6 | 210.6 | 99.7 | 72.7 | -0.10 | 0.51 | -0.67 | 0.00 | 0.50 | 0.03 |
| Ablim3 | 226.8 | 236.5 | 180.3 | -0.10 | 0.85 | -0.48 | 0.01 | 0.47 | 0.01 |
| Slfar1 | 319.8 | 341.2 | 261.4 | -0.10 | 0.82 | -0.36 | 0.10 | 0.43 | 0.00 |
| Serpb2 | 125.4 | 197.9 | 78.0 | -0.10 | 0.06 | -0.80 | 0.00 | 0.42 | 0.02 |
| Fkbn11 | 247.3 | 210.4 | 162.9 | -0.10 | 0.39 | -0.61 | 0.01 | 0.41 | 0.06 |
| Kremn173 | 91.8 | 84.4 | 65.6 | -0.10 | 0.52 | -0.57 | 0.01 | 0.40 | 0.06 |
| Rnase4 | 6530.4 | 1108.7 | 870.1 | -0.10 | 0.00 | -0.40 | 0.07 | 0.39 | 0.05 |
| Serinc3 | 1976.7 | 1984.5 | 1596.0 | -0.10 | 0.81 | -0.30 | 0.10 | 0.37 | 0.05 |
| Elmo1 | 146.4 | 117.1 | 95.1 | -0.10 | 0.06 | -0.63 | 0.20 | 0.36 | 0.06 |
| Slmap2 | 133.7 | 113.9 | 93.7 | -0.10 | 0.12 | -0.71 | 0.00 | 0.34 | 0.00 |
| Toffx1 | 969.2 | 913.8 | 416.1 | -0.10 | 0.45 | -0.51 | 0.00 | 0.34 | 0.10 |
| Tmem182 | 33.0 | 55.9 | 48.2 | -0.10 | 0.04 | -0.45 | 0.15 | 0.33 | 0.32 |
| Gns15 | 22.0 | 26.3 | 24.5 | -0.10 | 1.09 | -0.30 | 0.20 | 0.32 | 0.21 |
| B4galt4 | 16.9 | 12.6 | 8.9 | -0.10 | 0.19 | -0.60 | 0.02 | 0.30 | 0.45 |

Expression of TMEM119- myeloid cell enriched gene cassette in MLCs

Figure 12

| Gene | plCT MG | lCT YSs | lCT HSCs | Log2 (YSs/ MG) | p-value | Log2 (HSC /MG) | p-value | Log2 (YSs/ HSC) | p-value |
|---|---|---|---|---|---|---|---|---|---|
| Gm11419 | 9.9 | 6.1 | 17.4 | NA | NA | NA | NA | NA | NA |
| S100a11 | 5.7 | 8.1 | 7.4 | NA | NA | NA | NA | NA | NA |
| Lifr | 2.7 | 2.4 | 6.7 | NA | NA | NA | NA | NA | NA |
| S100a9 | 4.1 | 4.2 | 5.5 | NA | NA | NA | NA | NA | NA |
| Pygl | 2.3 | 3.3 | 4.9 | 0.44 | 0.44 | NA | NA | NA | NA |
| S100a8 | 1.8 | 1.0 | 4.1 | NA | NA | NA | NA | NA | NA |
| 2310036O11Rik | 0.2 | 0.6 | 3.6 | NA | NA | NA | NA | NA | NA |
| Fpr1 | 0.2 | 0.4 | 3.5 | NA | NA | NA | NA | NA | NA |
| Anxa1 | 0.6 | 7.6 | 3.4 | 3.18 | 0.00 | NA | NA | NA | NA |
| Prtn2 | 0.2 | 0.9 | 3.1 | NA | NA | NA | NA | NA | NA |
| H2-Eb1 | 0.2 | 0.2 | 2.7 | NA | NA | NA | NA | NA | NA |
| Fpr2 | 0.2 | 0.0 | 2.3 | NA | NA | NA | NA | NA | NA |
| Avp1 | 0.9 | 1.2 | 2.0 | NA | NA | NA | NA | NA | NA |
| Ngp | 0.2 | 0.9 | 1.7 | NA | NA | NA | NA | NA | NA |
| 1810055B17Rik | 0.4 | 1.8 | 1.7 | NA | NA | NA | NA | NA | NA |
| H2-Q10 | 0.1 | 0.1 | 1.6 | NA | NA | NA | NA | NA | NA |
| Gsr | 1.4 | 0.9 | 1.5 | NA | NA | NA | NA | NA | NA |
| S100a6 | 1.1 | 3.4 | 1.3 | NA | NA | NA | NA | NA | NA |
| Gda | 1.4 | 0.2 | 1.2 | NA | NA | NA | NA | NA | NA |
| Slfn2l1 | 1.4 | 0.2 | 1.1 | NA | NA | NA | NA | NA | NA |
| Wfm6 | 2.7 | 1.5 | 1.1 | NA | NA | NA | NA | NA | NA |
| Plac8 | 0.0 | 0.9 | 1.1 | NA | NA | NA | NA | NA | NA |
| Retnl | 0.0 | 1.9 | 1.0 | NA | NA | NA | NA | NA | NA |
| Lcn2 | 0.0 | 0.0 | 0.9 | NA | NA | NA | NA | NA | NA |
| Sell | 1.0 | 0.1 | 0.8 | NA | NA | NA | NA | NA | NA |
| Gm5483 | 1.8 | 0.7 | 0.7 | -0.47 | 0.62 | NA | NA | NA | NA |
| Gm16654 | 1.2 | 0.9 | 0.6 | NA | NA | NA | NA | NA | NA |
| Slfn4 | 0.5 | 0.5 | 0.6 | NA | NA | NA | NA | NA | NA |
| Atp6b4 | 0.4 | 0.6 | 0.5 | NA | NA | NA | NA | NA | NA |
| Camp | 0.4 | 0.2 | 0.5 | NA | NA | NA | NA | NA | NA |
| Dcn2 | 0.1 | 1.2 | 0.5 | NA | NA | NA | NA | NA | NA |
| Ear2 | 0.9 | 1.3 | 0.4 | NA | NA | NA | NA | NA | NA |
| Wfm1 | 0.0 | 0.4 | 0.4 | NA | NA | NA | NA | NA | NA |
| Cpd | 0.4 | 0.5 | 0.4 | NA | NA | NA | NA | NA | NA |
| Ch3l3 | 0.0 | 0.5 | 0.3 | NA | NA | NA | NA | NA | NA |
| Slpi1 | 0.0 | 0.3 | 0.2 | NA | NA | NA | NA | NA | NA |
| Mmp8 | 0.2 | 0.2 | 0.1 | NA | NA | NA | NA | NA | NA |
| Cxcr2 | 0.1 | 1.2 | 0.1 | NA | NA | NA | NA | NA | NA |
| Ltf | 0.8 | 0.3 | 0.1 | NA | NA | NA | NA | NA | NA |
| Trf3308 | 0.0 | 0.4 | 0.1 | NA | NA | NA | NA | NA | NA |
| Lyz2 | 0.0 | 0.0 | 0.0 | NA | NA | NA | NA | NA | NA |
| Hdc | 0.0 | 0.2 | 0.0 | NA | NA | NA | NA | NA | NA |
| Mmp9 | 0.0 | 0.0 | 0.0 | NA | NA | NA | NA | NA | NA |
| 1100001G20Rik | 0.0 | 0.0 | 0.0 | NA | NA | NA | NA | NA | NA |
| Elane | 0.0 | 0.0 | 0.0 | NA | NA | NA | NA | NA | NA |
| Fkbp1b1 | 0.1 | 0.0 | 0.0 | NA | NA | NA | NA | NA | NA |
| Mc2 | 0.0 | 0.0 | 0.0 | NA | NA | NA | NA | NA | NA |
| Padi4 | 0.0 | 0.0 | 0.0 | NA | NA | NA | NA | NA | NA |
| Sfpi | 1.7 | 1.7 | 0.0 | NA | NA | NA | NA | NA | NA |

Figure 12 (continued)

Figure 13     Genes decreased in IP BM MLCs (2-3 months brain residence) compared to ICT BM MLCs (2 weeks brain residence)

| Gene | ICT BM | IP BM | Log2 (ICT/ IP) | FDR |
|---|---|---|---|---|
| 4833417C18Rik | 20.51 | 0.82 | 4.06 | 0.000 |
| Ddit4 | 31.18 | 1.81 | 4.03 | 0.000 |
| Amica1 | 34.95 | 2.35 | 3.99 | 0.000 |
| 2810008O09Rik | 45.15 | 5.44 | 3.19 | 0.000 |
| Hist1h1e | 32.08 | 3.59 | 3.01 | 0.000 |
| Samd1 | 36.97 | 6.06 | 2.81 | 0.000 |
| Cbr2 | 20.64 | 4.64 | 2.76 | 0.010 |
| Adam19 | 68.65 | 10.3 | 2.78 | 0.000 |
| C030034L19Rik | 127.69 | 19 | 2.71 | 0.000 |
| U2af1l4 | 29.14 | 5.59 | 2.69 | 0.003 |
| Dok3 | 44.82 | 7.67 | 2.66 | 0.000 |
| Clec4a1 | 22.59 | 3.4 | 2.63 | 0.004 |
| Spp1 | 50.64 | 7.66 | 2.61 | 0.003 |
| Entrg3 | 80.39 | 15.4 | 2.52 | 0.001 |
| Ier2 | 209.03 | 37.5 | 2.50 | 0.000 |
| Arl10 | 41.57 | 7.63 | 2.48 | 0.004 |
| 2410004N09Rik | 35.35 | 5.05 | 2.48 | 0.024 |
| Samd1 | 43.99 | 7.81 | 2.45 | 0.008 |
| Pnpla2 | 45.86 | 9.17 | 2.37 | 0.000 |
| Per1 | 119.81 | 24.9 | 2.36 | 0.000 |
| Fkbp5 | 197.23 | 39.1 | 2.34 | 0.001 |
| Rps18 | 40.51 | 49.7 | 2.34 | 0.036 |
| Stab1 | 156.37 | 33.1 | 2.31 | 0.000 |
| Rps27a | 34.95 | 11.9 | 2.31 | 0.015 |
| Serpinf1 | 125.35 | 26.4 | 2.30 | 0.000 |
| Dctpp1 | 59.52 | 9.96 | 2.30 | 0.026 |
| Htra2 | 33.98 | 26.5 | 2.29 | 0.006 |
| Klf2 | 146.66 | 30.7 | 2.29 | 0.001 |
| Modu1 | 30.06 | 6.72 | 2.28 | 0.023 |
| C1qa | 1187.1 | 258 | 2.26 | 0.000 |
| Ppia | 154.48 | 142 | 2.23 | 0.012 |
| Lgr1 | 63.61 | 18 | 2.17 | 0.001 |
| Zfp414 | 31.63 | 6.01 | 2.17 | 0.002 |
| Slc38a7 | 22.27 | 4.27 | 2.14 | 0.002 |
| Fau | 76.92 | 56 | 2.13 | 0.050 |
| Rps29 | 285.31 | 218 | 2.13 | 0.017 |
| Sulfa1 | 184.48 | 37 | 2.13 | 0.003 |
| Sh3gl1 | 26.03 | 9.41 | 2.09 | 0.006 |
| Fcgrt | 25.74 | 6.22 | 2.07 | 0.016 |
| Exosc5 | 20.24 | 4.59 | 2.06 | 0.031 |
| Ardc1 | 62 | 16.1 | 2.05 | 0.000 |
| Olns4 | 33.61 | 8.82 | 2.05 | 0.029 |
| Mfd1 | 22.78 | 6.21 | 2.02 | 0.049 |
| Prkab1 | 65.28 | 19.2 | 2.00 | 0.008 |
| Neat3 | 225.68 | 56.9 | 1.98 | 0.008 |
| Ugt1a7c | 21.19 | 7.43 | 1.97 | 0.040 |
| Zfp512 | 23.22 | 5.76 | 1.97 | 0.008 |
| St3b4 | 22.66 | 7.6 | 1.97 | 0.012 |
| Asns1 | 32.26 | 6.18 | 1.92 | 0.014 |

| Gene | ICT BM | IP BM | Log2 (ICT/ IP) | FDR |
|---|---|---|---|---|
| Crybs4 | 48.54 | 10.16 | 1.92 | 0.011 |
| Dnase2a | 20.29 | 8.65 | 1.91 | 0.012 |
| Snrpa | 32.89 | 10.82 | 1.89 | 0.015 |
| Sfxs2 | 38.11 | 11.01 | 1.86 | 0.006 |
| Bc02l1 | 25.87 | 7.15 | 1.87 | 0.029 |
| Irf3 | 53.89 | 15.83 | 1.83 | 0.003 |
| Slc2a3 | 22.72 | 6.67 | 1.79 | 0.047 |
| Lyl1 | 151.1 | 63.34 | 1.77 | 0.000 |
| Ppp4c | 45.86 | 12.73 | 1.77 | 0.029 |
| Mfp | 21.75 | 8.19 | 1.74 | 0.028 |
| H2-DMa | 246.6 | 82.49 | 1.74 | 0.012 |
| H2-DMb2 | 77.86 | 32 | 1.69 | 0.049 |
| Polg | 24.62 | 7.23 | 1.69 | 0.015 |
| Atp13a1 | 23.52 | 9.18 | 1.69 | 0.006 |
| Ap1b1 | 44.13 | 13.47 | 1.67 | 0.004 |
| Sfrnt2 | 20.51 | 8.86 | 1.66 | 0.027 |
| Gtf25d1 | 85.77 | 20.3 | 1.64 | 0.002 |
| Ltc4s | 117.7 | 37.2 | 1.64 | 0.044 |
| Anapc16 | 74.34 | 21.78 | 1.63 | 0.012 |
| Isyna1 | 80.61 | 13.86 | 1.62 | 0.017 |
| Asal | 44.17 | 16.17 | 1.63 | 0.011 |
| Sdc4 | 50.53 | 15.86 | 1.61 | 0.004 |
| Rxgd | 142.9 | 52.51 | 1.60 | 0.012 |
| 1810031K17Rik | 52.81 | 17.67 | 1.56 | 0.047 |
| Slc35c2 | 56.31 | 20.12 | 1.56 | 0.036 |
| Ptms | 139.7 | 50.17 | 1.56 | 0.030 |
| Rnf188 | 71.47 | 23.1 | 1.54 | 0.002 |
| Trafdip3 | 30.69 | 10.03 | 1.52 | 0.029 |
| Scamp5 | 52.13 | 17.72 | 1.52 | 0.026 |
| Naga | 37.44 | 13.28 | 1.50 | 0.021 |
| Hk | 27.76 | 11.47 | 1.47 | 0.027 |
| Ggta1 | 80.25 | 29.43 | 1.45 | 0.027 |
| Gpr108 | 42.83 | 12.44 | 1.44 | 0.031 |
| B4galnt1 | 80.39 | 31.23 | 1.42 | 0.049 |
| Hist1h1c | 41.86 | 12.64 | 1.41 | 0.035 |
| Tsc22d3 | 252.6 | 96.9 | 1.40 | 0.036 |
| Ak2 | 134.5 | 91.24 | 1.38 | 0.028 |
| Tapyl2 | 39.75 | 14.85 | 1.38 | 0.037 |
| Zfp36l1 | 627.7 | 246.9 | 1.35 | 0.016 |
| P2ry6 | 222.2 | 88.71 | 1.35 | 0.003 |
| Tmem104 | 82.77 | 29.87 | 1.34 | 0.017 |
| Ptes | 69.87 | 30.98 | 1.32 | 0.030 |
| Cd14 | 550.6 | 226.4 | 1.32 | 0.026 |
| Kcsk6 | 94.49 | 37.25 | 1.30 | 0.022 |
| Atp8v0b | 283.4 | 128.7 | 1.29 | 0.048 |
| Hk3 | 24.35 | 10.92 | 1.28 | 0.049 |
| Kdm6b | 41.14 | 18.33 | 1.28 | 0.023 |
| Ppdc | 121.4 | 55.03 | 1.23 | 0.046 |
| Slc40a2 | 71.13 | 29.77 | 1.21 | 0.031 |

Genes increased in IP BM MLCs (2-3 months brain residence) compared to ICT BM MLCs (2 weeks brain residence)

| Gene | ICT BM | IP BM | log2 (ICT/IP) | FDR |
|---|---|---|---|---|
| Eif2s3y | 0.59 | 35.8 | -6.47 | 0.000 |
| Ddx3y | 0.31 | 21.53 | -6.17 | 0.000 |
| Lyz1 | 10.17 | 31.49 | -5.93 | 0.010 |
| St8sia6 | 0.99 | 30.67 | -5.30 | 0.000 |
| Atp1b1 | 1.54 | 50.09 | -5.01 | 0.015 |
| Rps23 | 85.35 | 112.7 | -4.55 | 0.000 |
| Cdr1 | 2.75 | 53.75 | -4.16 | 0.041 |
| Ndrg2 | 1.28 | 20.2 | -3.67 | 0.037 |
| 1810011O10Rik | 1.01 | 29.9 | -3.51 | 0.000 |
| G530011O06Rik | 3.19 | 29.62 | -3.46 | 0.000 |
| Qpct | 4.34 | 34.97 | -3.19 | 0.012 |
| Kcnj13 | 4.67 | 32.77 | -2.79 | 0.004 |
| Tgm2 | 4.26 | 38.35 | -2.76 | 0.002 |
| Galnt3 | 5.4 | 27.46 | -2.66 | 0.000 |
| Siglech | 45.59 | 229.05 | -2.34 | 0.000 |
| Cab39l | 5.19 | 23.24 | -2.33 | 0.023 |
| Ccnd2 | 8.37 | 37.82 | -2.22 | 0.003 |
| Inpp4b | 6.57 | 26.8 | -2.21 | 0.035 |
| Hmgb2 | 10.17 | 31.12 | -2.18 | 0.008 |
| AI504432 | 8.96 | 43.19 | -2.18 | 0.012 |
| H2-M3 | 11.55 | 44.83 | -2.12 | 0.009 |
| Cmpk1 | 14.61 | 61.48 | -2.12 | 0.000 |
| Tmed5 | 16.64 | 60.49 | -2.06 | 0.012 |
| Rab6b | 5.58 | 22.57 | -2.05 | 0.016 |
| Camk2n1 | 9.41 | 38.75 | -1.96 | 0.004 |
| Myo1b | 7.92 | 30.06 | -1.90 | 0.009 |
| Peli1 | 15.53 | 54.4 | -1.85 | 0.012 |
| Abcc9 | 8.87 | 31.52 | -1.85 | 0.006 |
| Niacr1 | 6.96 | 26.93 | -1.83 | 0.037 |
| Rtn1 | 24.9 | 91.44 | -1.79 | 0.030 |
| Pkib | 8.66 | 29.93 | -1.78 | 0.027 |
| Klra2 | 110.98 | 355.86 | -1.77 | 0.003 |
| Arhgap5 | 22.81 | 69.58 | -1.70 | 0.027 |
| Ids | 23.7 | 74.67 | -1.67 | 0.031 |
| B3gnt2 | 22.14 | 67.73 | -1.67 | 0.024 |
| Cfh | 70.15 | 176.16 | -1.67 | 0.020 |
| Plxna4 | 10.95 | 31.68 | -1.67 | 0.012 |
| Tex2 | 9.25 | 29.49 | -1.61 | 0.022 |
| Fam98b | 11.54 | 34.38 | -1.61 | 0.026 |
| Basp1 | 29.04 | 78.35 | -1.60 | 0.027 |
| Htra3 | 7.22 | 21.16 | -1.58 | 0.050 |
| Dnajc28 | 9.05 | 25.28 | -1.56 | 0.049 |
| Leprel1 | 8.84 | 23.64 | -1.56 | 0.048 |
| Ifi204 | 14.1 | 30.23 | -1.52 | 0.048 |
| Tlr3 | 13.16 | 34.91 | -1.50 | 0.037 |
| H2-K1 | 320.31 | 874.72 | -1.49 | 0.024 |
| Ier5 | 107.84 | 295.01 | -1.48 | 0.038 |
| Arhgap15 | 50.11 | 122.93 | -1.45 | 0.031 |
| Lrrc3 | 87.08 | 222.08 | -1.39 | 0.029 |
| Sgpp1 | 33.381 | 82.43 | -1.38 | 0.030 |

Figure 14

SEQUENCE LISTING

```
<160> NUMBER OF SEQ ID NOS: 17

<210> SEQ ID NO 1
<211> LENGTH: 513
<212> TYPE: PRT
<213> ORGANISM: Homo sapiens

<400> SEQUENCE: 1

Met Ile Gly Ser Gly His Leu Gln Ser Leu Gln Arg Leu Ile Asp Ser
1               5                   10                  15

Gln Met Glu Thr Ser Cys Gln Ile Thr Phe Glu Phe Val Asp Gln Glu
            20                  25                  30

Gln Leu Lys Asp Pro Val Cys Tyr Leu Lys Lys Ala Phe Leu Leu Val
        35                  40                  45

Gln Asp Ile Met Glu Asp Thr Met Arg Phe Arg Asp Asn Thr Pro Asn
    50                  55                  60

Ala Ile Ala Ile Val Gln Leu Gln Glu Leu Ser Leu Arg Leu Lys Ser
65                  70                  75                  80

Cys Phe Thr Lys Asp Tyr Glu Glu His Asp Lys Ala Cys Val Arg Thr
                85                  90                  95

Phe Tyr Glu Thr Pro Leu Gln Leu Leu Glu Lys Val Lys Asn Val Phe
            100                 105                 110

Asn Glu Thr Lys Asn Leu Leu Asp Lys Asp Trp Asn Ile Phe Ser Lys
            115                 120                 125

Asn Cys Asn Asn Ser Phe Ala Glu Cys Ser Ser Gln Asp Val Val Thr
        130                 135                 140

Lys Pro Asp Cys Asn Cys Leu Tyr Pro Lys Ala Ile Pro Ser Ser Asp
145                 150                 155                 160

Pro Ala Ser Val Ser Pro His Gln Pro Leu Ala Pro Ser Met Ala Pro
                165                 170                 175

Val Ala Gly Leu Thr Trp Glu Asp Ser Glu Gly Thr Glu Gly Ser Ser
            180                 185                 190

Leu Leu Pro Gly Glu Gln Pro Leu His Thr Val Asp Pro Gly Ser Ala
            195                 200                 205
```

```
Lys Gln Arg Pro Pro Arg Ser Thr Cys Gln Ser Phe Glu Pro Pro Glu
    210             215             220

Thr Pro Val Val Lys Asp Ser Thr Ile Gly Gly Ser Pro Gln Pro Arg
225             230             235             240

Pro Ser Val Gly Ala Phe Asn Pro Gly Met Glu Asp Ile Leu Asp Ser
            245             250             255

Ala Met Gly Thr Asn Trp Val Pro Glu Glu Ala Ser Gly Glu Ala Ser
            260             265             270

Glu Ile Pro Val Pro Gln Gly Thr Glu Leu Ser Pro Ser Arg Pro Gly
        275             280             285

Gly Gly Ser Met Gln Thr Glu Pro Ala Arg Pro Ser Asn Phe Leu Ser
    290             295             300

Ala Ser Ser Pro Leu Pro Ala Ser Ala Lys Gly Gln Gln Pro Ala Asp
305             310             315             320

Val Thr Gly Thr Ala Leu Pro Arg Val Gly Pro Val Arg Pro Thr Gly
            325             330             335

Gln Asp Trp Asn His Thr Pro Gln Lys Thr Asp His Pro Ser Ala Leu
            340             345             350

Leu Arg Asp Pro Pro Glu Pro Gly Ser Pro Arg Ile Ser Ser Leu Arg
        355             360             365

Pro Gln Gly Leu Ser Asn Pro Ser Thr Leu Ser Ala Gln Pro Gln Leu
    370             375             380

Ser Arg Ser His Ser Ser Gly Ser Val Leu Pro Leu Gly Glu Leu Glu
385             390             395             400

Gly Arg Arg Ser Thr Arg Asp Arg Arg Ser Pro Ala Glu Pro Glu Gly
            405             410             415

Gly Pro Ala Ser Glu Gly Ala Ala Arg Pro Leu Pro Arg Phe Asn Ser
            420             425             430

Val Pro Leu Thr Asp Thr Gly His Glu Arg Gln Ser Glu Gly Ser Phe
        435             440             445

Ser Pro Gln Leu Gln Glu Ser Val Phe His Leu Leu Val Pro Ser Val
    450             455             460

Ile Leu Val Leu Leu Ala Val Gly Gly Leu Leu Phe Tyr Arg Trp Arg
465             470             475             480

Arg Arg Ser His Gln Glu Pro Gln Arg Ala Asp Ser Pro Leu Glu Gln
            485             490             495

Pro Glu Gly Ser Pro Leu Thr Gln Asp Asp Arg Gln Val Glu Leu Pro
            500             505             510

Val
```

```
<210> SEQ ID NO 2
<211> LENGTH: 242
<212> TYPE: PRT
<213> ORGANISM: Homo sapiens

<400> SEQUENCE: 2

Met Pro Arg Gly Phe Thr Trp Leu Arg Tyr Leu Gly Ile Phe Leu Gly
1               5               10              15

Val Ala Leu Gly Asn Glu Pro Leu Glu Met Trp Pro Leu Thr Gln Asn
            20              25              30

Glu Glu Cys Thr Val Thr Gly Phe Leu Arg Asp Lys Leu Gln Tyr Arg
        35              40              45

Ser Arg Leu Gln Tyr Met Lys His Tyr Phe Pro Ile Asn Tyr Lys Ile
    50              55              60
```

-continued

```
Ser Val Pro Tyr Glu Gly Val Phe Arg Ile Ala Asn Val Thr Arg Leu
65              70                  75                  80

Gln Arg Ala Gln Val Ser Glu Arg Glu Leu Arg Tyr Leu Trp Val Leu
                85                  90                  95

Val Ser Leu Ser Ala Thr Glu Ser Val Gln Asp Val Leu Leu Glu Gly
            100                 105                 110

His Pro Ser Trp Lys Tyr Leu Gln Glu Val Glu Thr Leu Leu Leu Asn
            115                 120                 125

Val Gln Gln Gly Leu Thr Asp Val Glu Val Ser Pro Lys Val Glu Ser
        130                 135                 140

Val Leu Ser Leu Leu Asn Ala Pro Gly Pro Asn Leu Lys Leu Val Arg
145                 150                 155                 160

Pro Lys Ala Leu Leu Asp Asn Cys Phe Arg Val Met Glu Leu Leu Tyr
                165                 170                 175

Cys Ser Cys Cys Lys Gln Ser Ser Val Leu Asn Trp Gln Asp Cys Glu
            180                 185                 190

Val Pro Ser Pro Gln Ser Cys Ser Pro Glu Pro Ser Leu Gln Tyr Ala
            195                 200                 205

Ala Thr Gln Leu Tyr Pro Pro Pro Pro Trp Ser Pro Ser Ser Pro Pro
        210                 215                 220

His Ser Thr Gly Ser Val Arg Pro Val Arg Ala Gln Gly Glu Gly Leu
225                 230                 235                 240

Leu Pro
```

```
<210> SEQ ID NO 3
<211> LENGTH: 972
<212> TYPE: PRT
<213> ORGANISM: Homo sapiens

<400> SEQUENCE: 3
```

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
        50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
        130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190
```

-continued

```
Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
        210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
        515                 520                 525

Leu Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
```

-continued

```
        610                    615                    620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
                690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
                755                 760                 765

Leu Ala Ser Lys Asn Cys Ile His Arg Asp Val Ala Ala Arg Asn Val
770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
                835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
                915                 920                 925

Ser Ser Arg Ser Gly Gly Ser Gly Ser Ser Ser Ser Glu Leu Glu Glu
                930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 4
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

-continued

```
Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
        35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
            85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
        130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
            165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
            245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
    370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
            405                 410                 415

Leu Leu Cys Ala Ala Ser Gly Tyr Pro Gln Pro Asn Val Thr Trp Leu
```

-continued

```
                420                425                430

Gln Cys Ser Gly His Thr Asp Arg Cys Asp Glu Ala Gln Val Leu Gln
        435            440            445

Val Trp Asp Asp Pro Tyr Pro Glu Val Leu Ser Gln Glu Pro Phe His
    450            455            460

Lys Val Thr Val Gln Ser Leu Leu Thr Val Glu Thr Leu Glu His Asn
465                470            475                480

Gln Thr Tyr Glu Cys Arg Ala His Asn Ser Val Gly Ser Gly Ser Trp
            485            490            495

Ala Phe Ile Pro Ile Ser Ala Gly Ala His Thr His Pro Pro Asp Glu
            500            505            510

Phe Leu Phe Thr Pro Val Val Val Ala Cys Met Ser Ile Met Ala Leu
        515            520            525

Leu Leu Leu Leu Leu Leu Leu Leu Leu Tyr Lys Tyr Lys Gln Lys Pro
        530            535            540

Lys Tyr Gln Val Arg Trp Lys Ile Ile Glu Ser Tyr Glu Gly Asn Ser
545            550            555            560

Tyr Thr Phe Ile Asp Pro Thr Gln Leu Pro Tyr Asn Glu Lys Trp Glu
            565            570            575

Phe Pro Arg Asn Asn Leu Gln Phe Gly Lys Thr Leu Gly Ala Gly Ala
            580            585            590

Phe Gly Lys Val Val Glu Ala Thr Ala Phe Gly Leu Gly Lys Glu Asp
        595            600            605

Ala Val Leu Lys Val Ala Val Lys Met Leu Lys Ser Thr Ala His Ala
    610            615            620

Asp Glu Lys Glu Ala Leu Met Ser Glu Leu Lys Ile Met Ser His Leu
625            630            635            640

Gly Gln His Glu Asn Ile Ile Asn Leu Leu Gly Ala Cys Thr His Gly
            645            650            655

Gly Pro Val Leu Val Ile Thr Glu Tyr Cys Cys Tyr Gly Asp Leu Leu
        660            665            670

Asn Phe Leu Arg Arg Lys Ala Glu Ala Met Leu Gly Pro Ser Leu Ser
        675            680            685

Pro Gly Gln Asp Pro Glu Gly Gly Val Asp Tyr Lys Asn Ile His Leu
    690            695            700

Glu Lys Lys Tyr Val Arg Arg Asp Ser Gly Phe Ser Ser Gln Gly Val
705            710            715            720

Asp Thr Tyr Val Glu Met Arg Pro Val Ser Thr Ser Ser Asn Asp Ser
            725            730            735

Phe Ser Glu Gln Asp Leu Asp Lys Glu Asp Gly Arg Pro Leu Glu Leu
        740            745            750

Arg Asp Leu Leu His Phe Ser Ser Gln Val Ala Gln Gly Met Ala Phe
        755            760            765

Leu Ala Ser Lys Asn Cys Ile His Arg Asp Val Ala Ala Arg Asn Val
    770            775            780

Leu Leu Thr Asn Gly His Val Ala Lys Ile Gly Asp Phe Gly Leu Ala
785            790            795            800

Arg Asp Ile Met Asn Asp Ser Asn Tyr Ile Val Lys Gly Asn Ala Arg
            805            810            815

Leu Pro Val Lys Trp Met Ala Pro Glu Ser Ile Phe Asp Cys Val Tyr
            820            825            830

Thr Val Gln Ser Asp Val Trp Ser Tyr Gly Ile Leu Leu Trp Glu Ile
        835            840            845
```

-continued

```
Phe Ser Leu Gly Leu Asn Pro Tyr Pro Gly Ile Leu Val Asn Ser Lys
    850             855             860

Phe Tyr Lys Leu Val Lys Asp Gly Tyr Gln Met Ala Gln Pro Ala Phe
865             870             875             880

Ala Pro Lys Asn Ile Tyr Ser Ile Met Gln Ala Cys Trp Ala Leu Glu
            885             890             895

Pro Thr His Arg Pro Thr Phe Gln Gln Ile Cys Ser Phe Leu Gln Glu
            900             905             910

Gln Ala Gln Glu Asp Arg Arg Glu Arg Asp Tyr Thr Asn Leu Pro Ser
            915             920             925

Ser Ser Arg Ser Gly Gly Ser Gly Ser Ser Ser Ser Glu Leu Glu Glu
    930             935             940

Glu Ser Ser Ser Glu His Leu Thr Cys Cys Glu Gln Gly Asp Ile Ala
945             950             955             960

Gln Pro Leu Leu Gln Pro Asn Asn Tyr Gln Phe Cys
            965             970
```

```
<210> SEQ ID NO 5
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Met Gly Pro Gly Val Leu Leu Leu Leu Val Ala Thr Ala Trp His
1               5               10              15

Gly Gln Gly Ile Pro Val Ile Glu Pro Ser Val Pro Glu Leu Val Val
            20              25              30

Lys Pro Gly Ala Thr Val Thr Leu Arg Cys Val Gly Asn Gly Ser Val
        35              40              45

Glu Trp Asp Gly Pro Pro Ser Pro His Trp Thr Leu Tyr Ser Asp Gly
    50              55              60

Ser Ser Ser Ile Leu Ser Thr Asn Asn Ala Thr Phe Gln Asn Thr Gly
65              70              75              80

Thr Tyr Arg Cys Thr Glu Pro Gly Asp Pro Leu Gly Gly Ser Ala Ala
            85              90              95

Ile His Leu Tyr Val Lys Asp Pro Ala Arg Pro Trp Asn Val Leu Ala
            100             105             110

Gln Glu Val Val Val Phe Glu Asp Gln Asp Ala Leu Leu Pro Cys Leu
        115             120             125

Leu Thr Asp Pro Val Leu Glu Ala Gly Val Ser Leu Val Arg Val Arg
    130             135             140

Gly Arg Pro Leu Met Arg His Thr Asn Tyr Ser Phe Ser Pro Trp His
145             150             155             160

Gly Phe Thr Ile His Arg Ala Lys Phe Ile Gln Ser Gln Asp Tyr Gln
            165             170             175

Cys Ser Ala Leu Met Gly Gly Arg Lys Val Met Ser Ile Ser Ile Arg
            180             185             190

Leu Lys Val Gln Lys Val Ile Pro Gly Pro Pro Ala Leu Thr Leu Val
        195             200             205

Pro Ala Glu Leu Val Arg Ile Arg Gly Glu Ala Ala Gln Ile Val Cys
    210             215             220

Ser Ala Ser Ser Val Asp Val Asn Phe Asp Val Phe Leu Gln His Asn
```

-continued

```
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
                275                 280                 285

Thr Ser Met Phe Phe Arg Val Val Glu Ser Ala Tyr Leu Asn Leu Ser
                290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
                370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
                450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
                515                 520                 525

Leu Leu Leu Leu Leu Leu Leu Leu Leu Tyr Lys Tyr Lys Gln Lys Pro
                530                 535                 540

Lys Tyr Gln Val Arg Phe Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
                595                 600                 605

Ala Val Leu Lys Val Ala Val Lys Met Leu Lys Ser Thr Ala His Ala
                610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655
```

```
Gly Pro Val Leu Val Ile Thr Glu Tyr Cys Cys Tyr Gly Asp Leu Leu
        660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
        690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
        740                 745                 750

Arg Asp Leu Leu His Phe Ser Ser Gln Val Ala Gln Gly Met Ala Phe
        755                 760                 765

Leu Ala Ser Lys Asn Cys Ile His Arg Asp Val Ala Ala Arg Asn Val
        770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
        820                 825                 830

Thr Val Gln Ser Asp Val Trp Ser Tyr Gly Ile Leu Leu Trp Glu Ile
        835                 840                 845

Phe Ser Leu Gly Leu Asn Pro Tyr Pro Gly Ile Leu Val Asn Ser Lys
        850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
        900                 905                 910

Gln Ala Gln Glu Asp Arg Arg Glu Arg Asp Tyr Thr Asn Leu Pro Ser
        915                 920                 925

Ser Ser Arg Ser Gly Gly Ser Gly Ser Ser Ser Ser Glu Leu Glu Glu
        930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

```
<210> SEQ ID NO 6
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6
```

```
Met Gly Pro Gly Val Leu Leu Leu Leu Leu Val Ala Thr Ala Trp His
1                   5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
```

-continued

```
            35                    40                    45

Glu Trp Asp Gly Pro Pro Ser Pro His Trp Thr Leu Tyr Ser Asp Gly
    50                    55                    60

Ser Ser Ser Ile Leu Ser Thr Asn Asn Ala Thr Phe Gln Asn Thr Gly
65                    70                    75                    80

Thr Tyr Arg Cys Thr Glu Pro Gly Asp Pro Leu Gly Gly Ser Ala Ala
                85                    90                    95

Ile His Leu Tyr Val Lys Asp Pro Ala Arg Pro Trp Asn Val Leu Ala
                100                   105                   110

Gln Glu Val Val Val Phe Glu Asp Gln Asp Ala Leu Leu Pro Cys Leu
                115                   120                   125

Leu Thr Asp Pro Val Leu Glu Ala Gly Val Ser Leu Val Arg Val Arg
    130                   135                   140

Gly Arg Pro Leu Met Arg His Thr Asn Tyr Ser Phe Ser Pro Trp His
145                   150                   155                   160

Gly Phe Thr Ile His Arg Ala Lys Phe Ile Gln Ser Gln Asp Tyr Gln
                165                   170                   175

Cys Ser Ala Leu Met Gly Gly Arg Lys Val Met Ser Ile Ser Ile Arg
                180                   185                   190

Leu Lys Val Gln Lys Val Ile Pro Gly Pro Pro Ala Leu Thr Leu Val
                195                   200                   205

Pro Ala Glu Leu Val Arg Ile Arg Gly Glu Ala Ala Gln Ile Val Cys
    210                   215                   220

Ser Ala Ser Ser Val Asp Val Asn Phe Asp Val Phe Leu Gln His Asn
225                   230                   235                   240

Asn Thr Lys Leu Ala Ile Pro Gln Gln Ser Asp Phe His Asn Asn Arg
                245                   250                   255

Tyr Gln Lys Val Leu Thr Leu Asn Leu Asp Gln Val Asp Phe Gln His
                260                   265                   270

Ala Gly Asn Tyr Ser Cys Val Ala Ser Asn Val Gln Gly Lys His Ser
                275                   280                   285

Thr Ser Met Phe Phe Arg Val Val Glu Ser Ala Tyr Leu Asn Leu Ser
    290                   295                   300

Ser Glu Gln Asn Leu Ile Gln Glu Val Thr Val Gly Glu Gly Leu Asn
305                   310                   315                   320

Leu Lys Val Met Val Glu Ala Tyr Pro Gly Leu Gln Gly Phe Asn Trp
                325                   330                   335

Thr Tyr Leu Gly Pro Phe Ser Asp His Gln Pro Glu Pro Lys Leu Ala
                340                   345                   350

Asn Ala Thr Thr Lys Asp Thr Tyr Arg His Thr Phe Thr Leu Ser Leu
                355                   360                   365

Pro Arg Leu Lys Pro Ser Glu Ala Gly Arg Tyr Ser Phe Leu Ala Arg
    370                   375                   380

Asn Pro Gly Gly Trp Arg Ala Leu Thr Phe Glu Leu Thr Leu Arg Tyr
385                   390                   395                   400

Pro Pro Glu Val Ser Val Ile Trp Thr Phe Ile Asn Gly Ser Gly Thr
                405                   410                   415

Leu Leu Cys Ala Ala Ser Gly Tyr Pro Gln Pro Asn Val Thr Trp Leu
                420                   425                   430

Gln Cys Ser Gly His Thr Asp Arg Cys Asp Glu Ala Gln Val Leu Gln
                435                   440                   445

Val Trp Asp Asp Pro Tyr Pro Glu Val Leu Ser Gln Glu Pro Phe His
    450                   455                   460
```

-continued

```
Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
                515                 520                 525

Leu Leu Leu Leu Leu Leu Leu Leu Leu Tyr Lys Tyr Lys Gln Lys Pro
                530                 535                 540

Lys Tyr Gln Val Arg Leu Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
                595                 600                 605

Ala Val Leu Lys Val Ala Val Lys Met Leu Lys Ser Thr Ala His Ala
                610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
                690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
                755                 760                 765

Leu Ala Ser Lys Asn Cys Ile His Arg Asp Val Ala Ala Arg Asn Val
                770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
                820                 825                 830

Thr Val Gln Ser Asp Val Trp Ser Tyr Gly Ile Leu Leu Trp Glu Ile
                835                 840                 845

Phe Ser Leu Gly Leu Asn Pro Tyr Pro Gly Ile Leu Val Asn Ser Lys
                850                 855                 860

Phe Tyr Lys Leu Val Lys Asp Gly Tyr Gln Met Ala Gln Pro Ala Phe
865                 870                 875                 880
```

-continued

```
Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Glu Leu Glu Glu
            930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970
```

<210> SEQ ID NO 7
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
            50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
            130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
            210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270
```

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
        290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
                435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
                515                 520                 525

Leu Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
                595                 600                 605

Ala Val Leu Lys Val Ala Val Lys Met Leu Lys Ser Thr Ala His Ala
        610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Ala Asp Leu Leu
                660                 665                 670

Asn Phe Leu Arg Arg Lys Ala Glu Ala Met Leu Gly Pro Ser Leu Ser
        675                 680                 685

-continued

```
Pro Gly Gln Asp Pro Glu Gly Gly Val Asp Tyr Lys Asn Ile His Leu
    690             695                 700

Glu Lys Lys Tyr Val Arg Arg Asp Ser Gly Phe Ser Ser Gln Gly Val
705             710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
                755                 760                 765

Leu Ala Ser Lys Asn Cys Ile His Arg Asp Val Ala Ala Arg Asn Val
    770                 775                 780

Leu Leu Thr Asn Gly His Val Ala Lys Ile Gly Asp Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
    820                 825                 830

Thr Val Gln Ser Asp Val Trp Ser Tyr Gly Ile Leu Leu Trp Glu Ile
    835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
                900                 905                 910

Gln Ala Gln Glu Asp Arg Arg Glu Arg Asp Tyr Thr Asn Leu Pro Ser
    915                 920                 925

Ser Ser Arg Ser Gly Gly Ser Gly Ser Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

<210> SEQ ID NO 8
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80
```

```
Thr Tyr Arg Cys Thr Glu Pro Gly Asp Pro Leu Gly Gly Ser Ala Ala
             85              90              95

Ile His Leu Tyr Val Lys Asp Pro Ala Arg Pro Trp Asn Val Leu Ala
            100             105             110

Gln Glu Val Val Val Phe Glu Asp Gln Asp Ala Leu Leu Pro Cys Leu
            115             120             125

Leu Thr Asp Pro Val Leu Glu Ala Gly Val Ser Leu Val Arg Val Arg
        130             135             140

Gly Arg Pro Leu Met Arg His Thr Asn Tyr Ser Phe Ser Pro Trp His
145             150             155             160

Gly Phe Thr Ile His Arg Ala Lys Phe Ile Gln Ser Gln Asp Tyr Gln
                165             170             175

Cys Ser Ala Leu Met Gly Gly Arg Lys Val Met Ser Ile Ser Ile Arg
            180             185             190

Leu Lys Val Gln Lys Val Ile Pro Gly Pro Pro Ala Leu Thr Leu Val
            195             200             205

Pro Ala Glu Leu Val Arg Ile Arg Gly Glu Ala Ala Gln Ile Val Cys
        210             215             220

Ser Ala Ser Ser Val Asp Val Asn Phe Asp Val Phe Leu Gln His Asn
225             230             235             240

Asn Thr Lys Leu Ala Ile Pro Gln Gln Ser Asp Phe His Asn Asn Arg
            245             250             255

Tyr Gln Lys Val Leu Thr Leu Asn Leu Asp Gln Val Asp Phe Gln His
            260             265             270

Ala Gly Asn Tyr Ser Cys Val Ala Ser Asn Val Gln Gly Lys His Ser
            275             280             285

Thr Ser Met Phe Phe Arg Val Val Glu Ser Ala Tyr Leu Asn Leu Ser
        290             295             300

Ser Glu Gln Asn Leu Ile Gln Glu Val Thr Val Gly Glu Gly Leu Asn
305             310             315             320

Leu Lys Val Met Val Glu Ala Tyr Pro Gly Leu Gln Gly Phe Asn Trp
            325             330             335

Thr Tyr Leu Gly Pro Phe Ser Asp His Gln Pro Glu Pro Lys Leu Ala
            340             345             350

Asn Ala Thr Thr Lys Asp Thr Tyr Arg His Thr Phe Thr Leu Ser Leu
            355             360             365

Pro Arg Leu Lys Pro Ser Glu Ala Gly Arg Tyr Ser Phe Leu Ala Arg
        370             375             380

Asn Pro Gly Gly Trp Arg Ala Leu Thr Phe Glu Leu Thr Leu Arg Tyr
385             390             395             400

Pro Pro Glu Val Ser Val Ile Trp Thr Phe Ile Asn Gly Ser Gly Thr
            405             410             415

Leu Leu Cys Ala Ala Ser Gly Tyr Pro Gln Pro Asn Val Thr Trp Leu
            420             425             430

Gln Cys Ser Gly His Thr Asp Arg Cys Asp Glu Ala Gln Val Leu Gln
            435             440             445

Val Trp Asp Asp Pro Tyr Pro Glu Val Leu Ser Gln Glu Pro Phe His
        450             455             460

Lys Val Thr Val Gln Ser Leu Leu Thr Val Glu Thr Leu Glu His Asn
465             470             475             480

Gln Thr Tyr Glu Cys Arg Ala His Asn Ser Val Gly Ser Gly Ser Trp
            485             490             495
```

-continued

```
Ala Phe Ile Pro Ile Ser Ala Gly Ala His Thr His Pro Pro Asp Glu
            500             505             510

Phe Leu Phe Thr Pro Val Val Val Ala Cys Met Ser Ile Met Ala Leu
            515             520             525

Leu Leu Leu Leu Leu Leu Leu Leu Leu Tyr Lys Tyr Lys Gln Lys Pro
            530             535             540

Lys Tyr Gln Val Arg Trp Lys Ile Ile Glu Ser Tyr Glu Gly Asn Ser
545             550             555             560

Tyr Thr Phe Ile Asp Pro Thr Gln Leu Pro Tyr Asn Glu Lys Trp Glu
            565             570             575

Phe Pro Arg Asn Asn Leu Gln Phe Gly Lys Thr Leu Gly Ala Gly Ala
            580             585             590

Phe Gly Lys Val Val Glu Ala Thr Ala Phe Gly Leu Gly Lys Glu Asp
            595             600             605

Ala Val Leu Lys Val Ala Val Lys Met Leu Lys Ser Thr Ala His Ala
            610             615             620

Asp Glu Lys Glu Ala Leu Met Ser Glu Leu Lys Ile Met Ser His Leu
625             630             635             640

Gly Gln His Glu Asn Ile Val Asn Leu Leu Gly Ala Cys Thr His Gly
            645             650             655

Gly Pro Val Leu Val Ile Thr Glu Tyr Cys Cys Tyr Val Asp Leu Leu
            660             665             670

Asn Phe Leu Arg Arg Lys Ala Glu Ala Met Leu Gly Pro Ser Leu Ser
            675             680             685

Pro Gly Gln Asp Pro Glu Gly Gly Val Asp Tyr Lys Asn Ile His Leu
            690             695             700

Glu Lys Lys Tyr Val Arg Arg Asp Ser Gly Phe Ser Ser Gln Gly Val
705             710             715             720

Asp Thr Tyr Val Glu Met Arg Pro Val Ser Thr Ser Ser Asn Asp Ser
            725             730             735

Phe Ser Glu Gln Asp Leu Asp Lys Glu Asp Gly Arg Pro Leu Glu Leu
            740             745             750

Arg Asp Leu Leu His Phe Ser Ser Gln Val Ala Gln Gly Met Ala Phe
            755             760             765

Leu Ala Ser Lys Asn Cys Ile His Arg Asp Val Ala Ala Arg Asn Val
            770             775             780

Leu Leu Thr Asn Gly His Val Ala Lys Ile Gly Asp Phe Gly Leu Ala
785             790             795             800

Arg Asp Ile Met Asn Asp Ser Asn Tyr Ile Val Lys Gly Asn Ala Arg
            805             810             815

Leu Pro Val Lys Trp Met Ala Pro Glu Ser Ile Phe Asp Cys Val Tyr
            820             825             830

Thr Val Gln Ser Asp Val Trp Ser Tyr Gly Ile Leu Leu Trp Glu Ile
            835             840             845

Phe Ser Leu Gly Leu Asn Pro Tyr Pro Gly Ile Leu Val Asn Ser Lys
            850             855             860

Phe Tyr Lys Leu Val Lys Asp Gly Tyr Gln Met Ala Gln Pro Ala Phe
865             870             875             880

Ala Pro Lys Asn Ile Tyr Ser Ile Met Gln Ala Cys Trp Ala Leu Glu
            885             890             895

Pro Thr His Arg Pro Thr Phe Gln Gln Ile Cys Ser Phe Leu Gln Glu
            900             905             910

Gln Ala Gln Glu Asp Arg Arg Glu Arg Asp Tyr Thr Asn Leu Pro Ser
```

-continued

```
                915                    920                    925

Ser Ser Arg Ser Gly Gly Ser Gly Ser Ser Ser Glu Leu Glu Glu
    930                    935                    940

Glu Ser Ser Ser Glu His Leu Thr Cys Cys Glu Gln Gly Asp Ile Ala
945                    950                    955                    960

Gln Pro Leu Leu Gln Pro Asn Asn Tyr Gln Phe Cys
                965                    970

<210> SEQ ID NO 9
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Pro Gly Val Leu Leu Leu Leu Val Ala Thr Ala Trp His
1                   5                    10                    15

Gly Gln Gly Ile Pro Val Ile Glu Pro Ser Val Pro Glu Leu Val Val
                20                    25                    30

Lys Pro Gly Ala Thr Val Thr Leu Arg Cys Val Gly Asn Gly Ser Val
                35                    40                    45

Glu Trp Asp Gly Pro Pro Ser Pro His Trp Thr Leu Tyr Ser Asp Gly
    50                    55                    60

Ser Ser Ser Ile Leu Ser Thr Asn Asn Ala Thr Phe Gln Asn Thr Gly
65                    70                    75                    80

Thr Tyr Arg Cys Thr Glu Pro Gly Asp Pro Leu Gly Gly Ser Ala Ala
                85                    90                    95

Ile His Leu Tyr Val Lys Asp Pro Ala Arg Pro Trp Asn Val Leu Ala
                100                   105                   110

Gln Glu Val Val Val Phe Glu Asp Gln Asp Ala Leu Leu Pro Cys Leu
                115                   120                   125

Leu Thr Asp Pro Val Leu Glu Ala Gly Val Ser Leu Val Arg Val Arg
    130                   135                   140

Gly Arg Pro Leu Met Arg His Thr Asn Tyr Ser Phe Ser Pro Trp His
145                   150                   155                   160

Gly Phe Thr Ile His Arg Ala Lys Phe Ile Gln Ser Gln Asp Tyr Gln
                165                   170                   175

Cys Ser Ala Leu Met Gly Gly Arg Lys Val Met Ser Ile Ser Ile Arg
                180                   185                   190

Leu Lys Val Gln Lys Val Ile Pro Gly Pro Pro Ala Leu Thr Leu Val
                195                   200                   205

Pro Ala Glu Leu Val Arg Ile Arg Gly Glu Ala Ala Gln Ile Val Cys
    210                   215                   220

Ser Ala Ser Ser Val Asp Val Asn Phe Asp Val Phe Leu Gln His Asn
225                   230                   235                   240

Asn Thr Lys Leu Ala Ile Pro Gln Gln Ser Asp Phe His Asn Asn Arg
                245                   250                   255

Tyr Gln Lys Val Leu Thr Leu Asn Leu Asp Gln Val Asp Phe Gln His
                260                   265                   270

Ala Gly Asn Tyr Ser Cys Val Ala Ser Asn Val Gln Gly Lys His Ser
                275                   280                   285

Thr Ser Met Phe Phe Arg Val Val Glu Ser Ala Tyr Leu Asn Leu Ser
    290                   295                   300
```

-continued

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
                340                 345                 350

Asn Ala Thr Thr Lys Asp Thr Tyr Arg His Thr Phe Thr Leu Ser Leu
                355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                405                 410                 415

Leu Leu Cys Ala Ala Ser Gly Tyr Pro Gln Pro Asn Val Thr Trp Leu
                420                 425                 430

Gln Cys Ser Gly His Thr Asp Arg Cys Asp Glu Ala Gln Val Leu Gln
        435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                485                 490                 495

Ala Phe Ile Pro Ile Ser Ala Gly Ala His Thr His Pro Pro Asp Glu
                500                 505                 510

Phe Leu Phe Thr Pro Val Val Val Ala Cys Met Ser Ile Met Ala Leu
                515                 520                 525

Leu Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                565                 570                 575

Phe Pro Arg Asn Asn Leu Gln Phe Gly Lys Thr Leu Gly Ala Gly Ala
                580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
        610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Ile Glu Tyr Cys Cys Tyr Gly Asp Leu Leu
                660                 665                 670

Asn Phe Leu Arg Arg Lys Ala Glu Ala Met Leu Gly Pro Ser Leu Ser
                675                 680                 685

Pro Gly Gln Asp Pro Glu Gly Gly Val Asp Tyr Lys Asn Ile His Leu
        690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser

-continued

```
                    725                     730                     735

Phe Ser Glu Gln Asp Leu Asp Lys Glu Asp Gly Arg Pro Leu Glu Leu
                740                     745                     750

Arg Asp Leu Leu His Phe Ser Ser Gln Val Ala Gln Gly Met Ala Phe
                755                     760                     765

Leu Ala Ser Lys Asn Cys Ile His Arg Asp Val Ala Ala Arg Asn Val
        770                     775                     780

Leu Leu Thr Asn Gly His Val Ala Lys Ile Gly Asp Phe Gly Leu Ala
785                     790                     795                     800

Arg Asp Ile Met Asn Asp Ser Asn Tyr Ile Val Lys Gly Asn Ala Arg
                        805                     810                     815

Leu Pro Val Lys Trp Met Ala Pro Glu Ser Ile Phe Asp Cys Val Tyr
                820                     825                     830

Thr Val Gln Ser Asp Val Trp Ser Tyr Gly Ile Leu Leu Trp Glu Ile
                835                     840                     845

Phe Ser Leu Gly Leu Asn Pro Tyr Pro Gly Ile Leu Val Asn Ser Lys
        850                     855                     860

Phe Tyr Lys Leu Val Lys Asp Gly Tyr Gln Met Ala Gln Pro Ala Phe
865                     870                     875                     880

Ala Pro Lys Asn Ile Tyr Ser Ile Met Gln Ala Cys Trp Ala Leu Glu
                        885                     890                     895

Pro Thr His Arg Pro Thr Phe Gln Gln Ile Cys Ser Phe Leu Gln Glu
                900                     905                     910

Gln Ala Gln Glu Asp Arg Arg Glu Arg Asp Tyr Thr Asn Leu Pro Ser
                915                     920                     925

Ser Ser Arg Ser Gly Gly Ser Gly Ser Ser Ser Ser Glu Leu Glu Glu
        930                     935                     940

Glu Ser Ser Ser Glu His Leu Thr Cys Cys Glu Gln Gly Asp Ile Ala
945                     950                     955                     960

Gln Pro Leu Leu Gln Pro Asn Asn Tyr Gln Phe Cys
                965                     970
```

```
<210> SEQ ID NO 10
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Pro Gly Val Leu Leu Leu Leu Leu Val Ala Thr Ala Trp His
1                       5                       10                      15

Gly Gln Gly Ile Pro Val Ile Glu Pro Ser Val Pro Glu Leu Val Val
                20                      25                      30

Lys Pro Gly Ala Thr Val Thr Leu Arg Cys Val Gly Asn Gly Ser Val
        35                      40                      45

Glu Trp Asp Gly Pro Pro Ser Pro His Trp Thr Leu Tyr Ser Asp Gly
        50                      55                      60

Ser Ser Ser Ile Leu Ser Thr Asn Asn Ala Thr Phe Gln Asn Thr Gly
65                      70                      75                      80

Thr Tyr Arg Cys Thr Glu Pro Gly Asp Pro Leu Gly Gly Ser Ala Ala
                        85                      90                      95

Ile His Leu Tyr Val Lys Asp Pro Ala Arg Pro Trp Asn Val Leu Ala
                100                     105                     110
```

-continued

```
Gln Glu Val Val Val Phe Glu Asp Gln Asp Ala Leu Leu Pro Cys Leu
        115             120             125

Leu Thr Asp Pro Val Leu Glu Ala Gly Val Ser Leu Val Arg Val Arg
        130             135             140

Gly Arg Pro Leu Met Arg His Thr Asn Tyr Ser Phe Ser Pro Trp His
145             150             155             160

Gly Phe Thr Ile His Arg Ala Lys Phe Ile Gln Ser Gln Asp Tyr Gln
                165             170             175

Cys Ser Ala Leu Met Gly Gly Arg Lys Val Met Ser Ile Ser Ile Arg
                180             185             190

Leu Lys Val Gln Lys Val Ile Pro Gly Pro Pro Ala Leu Thr Leu Val
        195             200             205

Pro Ala Glu Leu Val Arg Ile Arg Gly Glu Ala Ala Gln Ile Val Cys
        210             215             220

Ser Ala Ser Ser Val Asp Val Asn Phe Asp Val Phe Leu Gln His Asn
225             230             235             240

Asn Thr Lys Leu Ala Ile Pro Gln Gln Ser Asp Phe His Asn Asn Arg
                245             250             255

Tyr Gln Lys Val Leu Thr Leu Asn Leu Asp Gln Val Asp Phe Gln His
                260             265             270

Ala Gly Asn Tyr Ser Cys Val Ala Ser Asn Val Gln Gly Lys His Ser
        275             280             285

Thr Ser Met Phe Phe Arg Val Val Glu Ser Ala Tyr Leu Asn Leu Ser
        290             295             300

Ser Glu Gln Asn Leu Ile Gln Glu Val Thr Val Gly Glu Gly Leu Asn
305             310             315             320

Leu Lys Val Met Val Glu Ala Tyr Pro Gly Leu Gln Gly Phe Asn Trp
                325             330             335

Thr Tyr Leu Gly Pro Phe Ser Asp His Gln Pro Glu Pro Lys Leu Ala
                340             345             350

Asn Ala Thr Thr Lys Asp Thr Tyr Arg His Thr Phe Thr Leu Ser Leu
        355             360             365

Pro Arg Leu Lys Pro Ser Glu Ala Gly Arg Tyr Ser Phe Leu Ala Arg
        370             375             380

Asn Pro Gly Gly Trp Arg Ala Leu Thr Phe Glu Leu Thr Leu Arg Tyr
385             390             395             400

Pro Pro Glu Val Ser Val Ile Trp Thr Phe Ile Asn Gly Ser Gly Thr
                405             410             415

Leu Leu Cys Ala Ala Ser Gly Tyr Pro Gln Pro Asn Val Thr Trp Leu
        420             425             430

Gln Cys Ser Gly His Thr Asp Arg Cys Asp Glu Ala Gln Val Leu Gln
        435             440             445

Val Trp Asp Asp Pro Tyr Pro Glu Val Leu Ser Gln Glu Pro Phe His
        450             455             460

Lys Val Thr Val Gln Ser Leu Leu Thr Val Glu Thr Leu Glu His Asn
465             470             475             480

Gln Thr Tyr Glu Cys Arg Ala His Asn Ser Val Gly Ser Gly Ser Trp
                485             490             495

Ala Phe Ile Pro Ile Ser Ala Gly Ala His Thr His Pro Pro Asp Glu
                500             505             510

Phe Leu Phe Thr Pro Val Val Val Ala Cys Met Ser Ile Met Ala Leu
        515             520             525

Leu Leu Leu Leu Leu Leu Leu Leu Leu Tyr Lys Tyr Lys Gln Lys Pro
```

```
          530                     535                     540

Lys Tyr Gln Val Arg Trp Lys Ile Ile Glu Ser Tyr Glu Gly Asn Ser
545                     550                     555                     560

Tyr Thr Phe Ile Asp Pro Thr Gln Leu Pro Tyr Asn Glu Lys Trp Glu
                    565                     570                     575

Phe Pro Arg Asn Asn Leu Gln Phe Gly Lys Thr Leu Gly Ala Gly Ala
                580                     585                     590

Phe Gly Lys Val Val Glu Ala Thr Ala Phe Gly Leu Gly Lys Glu Asp
                595                     600                     605

Ala Val Leu Lys Val Ala Val Lys Met Leu Lys Ser Thr Ala His Ala
            610                     615                     620

Asp Glu Lys Glu Ala Leu Met Ser Glu Leu Lys Ile Met Ser His Leu
625                     630                     635                     640

Gly Gln His Glu Asn Ile Val Asn Leu Leu Gly Ala Cys Thr His Gly
                645                     650                     655

Gly Pro Val Leu Val Ile Thr Glu Tyr Cys Cys Tyr Gly Asp Leu Leu
                660                     665                     670

Asn Phe Leu Arg Arg Lys Ala Glu Ala Met Leu Gly Pro Ser Leu Ser
            675                     680                     685

Pro Gly Gln Asp Pro Glu Gly Gly Val Asp Tyr Lys Asn Ile His Leu
        690                     695                     700

Glu Lys Lys Tyr Val Arg Arg Asp Ser Gly Phe Ser Ser Gln Gly Val
705                     710                     715                     720

Asp Thr Tyr Val Glu Met Arg Pro Val Ser Thr Ser Ser Asn Asp Ser
                725                     730                     735

Phe Ser Glu Gln Asp Leu Asp Lys Glu Asp Gly Arg Pro Leu Glu Leu
            740                     745                     750

Arg Asp Leu Leu His Phe Ser Ser Gln Val Ala Gln Gly Met Ala Phe
            755                     760                     765

Leu Ala Ser Lys Asn Cys Ile His Arg Asp Val Ala Ala Arg Asn Val
        770                     775                     780

Leu Leu Thr Asn Gly His Val Ala Lys Ile Ala Asp Phe Gly Leu Ala
785                     790                     795                     800

Arg Asp Ile Met Asn Asp Ser Asn Tyr Ile Val Lys Gly Asn Ala Arg
                805                     810                     815

Leu Pro Val Lys Trp Met Ala Pro Glu Ser Ile Phe Asp Cys Val Tyr
            820                     825                     830

Thr Val Gln Ser Asp Val Trp Ser Tyr Gly Ile Leu Leu Trp Glu Ile
            835                     840                     845

Phe Ser Leu Gly Leu Asn Pro Tyr Pro Gly Ile Leu Val Asn Ser Lys
        850                     855                     860

Phe Tyr Lys Leu Val Lys Asp Gly Tyr Gln Met Ala Gln Pro Ala Phe
865                     870                     875                     880

Ala Pro Lys Asn Ile Tyr Ser Ile Met Gln Ala Cys Trp Ala Leu Glu
                885                     890                     895

Pro Thr His Arg Pro Thr Phe Gln Gln Ile Cys Ser Phe Leu Gln Glu
                900                     905                     910

Gln Ala Gln Glu Asp Arg Arg Glu Arg Asp Tyr Thr Asn Leu Pro Ser
            915                     920                     925

Ser Ser Arg Ser Gly Gly Ser Gly Ser Ser Ser Ser Glu Leu Glu Glu
        930                     935                     940

Glu Ser Ser Ser Glu His Leu Thr Cys Cys Glu Gln Gly Asp Ile Ala
945                     950                     955                     960
```

-continued

```
Gln Pro Leu Leu Gln Pro Asn Asn Tyr Gln Phe Cys
                965                 970

<210> SEQ ID NO 11
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
```

-continued

```
              340              345              350

Asn Ala Thr Thr Lys Asp Thr Tyr Arg His Thr Phe Thr Leu Ser Leu
        355              360              365

Pro Arg Leu Lys Pro Ser Glu Ala Gly Arg Tyr Ser Phe Leu Ala Arg
        370              375              380

Asn Pro Gly Gly Trp Arg Ala Leu Thr Phe Glu Leu Thr Leu Arg Tyr
385              390              395              400

Pro Pro Glu Val Ser Val Ile Trp Thr Phe Ile Asn Gly Ser Gly Thr
                405              410              415

Leu Leu Cys Ala Ala Ser Gly Tyr Pro Gln Pro Asn Val Thr Trp Leu
                420              425              430

Gln Cys Ser Gly His Thr Asp Arg Cys Asp Glu Ala Gln Val Leu Gln
                435              440              445

Val Trp Asp Asp Pro Tyr Pro Glu Val Leu Ser Gln Glu Pro Phe His
        450              455              460

Lys Val Thr Val Gln Ser Leu Leu Thr Val Glu Thr Leu Glu His Asn
465              470              475              480

Gln Thr Tyr Glu Cys Arg Ala His Asn Ser Val Gly Ser Gly Ser Trp
                485              490              495

Ala Phe Ile Pro Ile Ser Ala Gly Ala His Thr His Pro Pro Asp Glu
                500              505              510

Phe Leu Phe Thr Pro Val Val Val Ala Cys Met Ser Ile Met Ala Leu
        515              520              525

Leu Leu Leu Leu Leu Leu Leu Leu Leu Tyr Lys Tyr Lys Gln Lys Pro
        530              535              540

Lys Tyr Gln Val Arg Trp Lys Ile Ile Glu Ser Tyr Glu Gly Asn Ser
545              550              555              560

Tyr Thr Phe Ile Asp Pro Thr Gln Leu Pro Tyr Asn Glu Lys Trp Glu
                565              570              575

Phe Pro Arg Asn Asn Leu Gln Phe Gly Lys Thr Leu Gly Ala Gly Ala
                580              585              590

Phe Gly Lys Val Val Glu Ala Thr Ala Phe Gly Leu Gly Lys Glu Asp
        595              600              605

Ala Val Leu Lys Val Ala Val Lys Met Leu Lys Ser Thr Ala His Ala
        610              615              620

Asp Glu Lys Glu Ala Leu Met Ser Glu Leu Lys Ile Leu Ser His Leu
625              630              635              640

Gly Gln His Glu Asn Ile Val Asn Leu Leu Gly Ala Cys Thr His Gly
                645              650              655

Gly Pro Val Leu Val Ile Thr Glu Tyr Cys Cys Tyr Gly Asp Leu Leu
                660              665              670

Asn Phe Leu Arg Arg Lys Ala Glu Ala Met Leu Gly Pro Ser Leu Ser
        675              680              685

Pro Gly Gln Asp Pro Glu Gly Gly Val Asp Tyr Lys Asn Ile His Leu
        690              695              700

Glu Lys Lys Tyr Val Arg Arg Asp Ser Gly Phe Ser Ser Gln Gly Val
705              710              715              720

Asp Thr Tyr Val Glu Met Arg Pro Val Ser Thr Ser Ser Asn Asp Ser
                725              730              735

Phe Ser Glu Gln Asp Leu Asp Lys Glu Asp Gly Arg Pro Leu Glu Leu
                740              745              750

Arg Asp Leu Leu His Phe Ser Ser Gln Val Ala Gln Gly Met Ala Phe
        755              760              765
```

```
Leu Ala Ser Lys Asn Cys Ile His Arg Asp Val Ala Ala Arg Asn Val
    770             775             780

Leu Leu Thr Asn Gly His Val Ala Lys Ile Gly Asp Phe Gly Leu Ala
785             790             795             800

Arg Asp Ile Met Asn Asp Ser Asn Tyr Ile Val Lys Gly Asn Ala Arg
            805             810             815

Leu Pro Val Lys Trp Met Ala Pro Glu Ser Ile Phe Asp Cys Val Tyr
        820             825             830

Thr Val Gln Ser Asp Val Trp Ser Tyr Gly Ile Leu Leu Trp Glu Ile
        835             840             845

Phe Ser Leu Gly Leu Asn Pro Tyr Pro Gly Ile Leu Val Asn Ser Lys
    850             855             860

Phe Tyr Lys Leu Val Lys Asp Gly Tyr Gln Met Ala Gln Pro Ala Phe
865             870             875             880

Ala Pro Lys Asn Ile Tyr Ser Ile Met Gln Ala Cys Trp Ala Leu Glu
            885             890             895

Pro Thr His Arg Pro Thr Phe Gln Gln Ile Cys Ser Phe Leu Gln Glu
        900             905             910

Gln Ala Gln Glu Asp Arg Arg Glu Arg Asp Tyr Thr Asn Leu Pro Ser
        915             920             925

Ser Ser Arg Ser Gly Gly Ser Gly Ser Ser Ser Glu Leu Glu Glu
    930             935             940

Glu Ser Ser Ser Glu His Leu Thr Cys Cys Glu Gln Gly Asp Ile Ala
945             950             955             960

Gln Pro Leu Leu Gln Pro Asn Asn Tyr Gln Phe Cys
            965             970
```

```
<210> SEQ ID NO 12
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

```
Met Gly Pro Gly Val Leu Leu Leu Leu Val Ala Thr Ala Trp His
1               5               10              15

Gly Gln Gly Ile Pro Val Ile Glu Pro Ser Val Pro Glu Leu Val Val
            20              25              30

Lys Pro Gly Ala Thr Val Thr Leu Arg Cys Val Gly Asn Gly Ser Val
        35              40              45

Glu Trp Asp Gly Pro Pro Ser Pro His Trp Thr Leu Tyr Ser Asp Gly
    50              55              60

Ser Ser Ser Ile Leu Ser Thr Asn Asn Ala Thr Phe Gln Asn Thr Gly
65              70              75              80

Thr Tyr Arg Cys Thr Glu Pro Gly Asp Pro Leu Gly Gly Ser Ala Ala
            85              90              95

Ile His Leu Tyr Val Lys Asp Pro Ala Arg Pro Trp Asn Val Leu Ala
            100             105             110

Gln Glu Val Val Val Phe Glu Asp Gln Asp Ala Leu Leu Pro Cys Leu
        115             120             125

Leu Thr Asp Pro Val Leu Glu Ala Gly Val Ser Leu Val Arg Val Arg
    130             135             140

Gly Arg Pro Leu Met Arg His Thr Asn Tyr Ser Phe Ser Pro Trp His
```

```
145              150              155              160

Gly Phe Thr Ile His Arg Ala Lys Phe Ile Gln Ser Gln Asp Tyr Gln
                165              170              175

Cys Ser Ala Leu Met Gly Gly Arg Lys Val Met Ser Ile Ser Ile Arg
                180              185              190

Leu Lys Val Gln Lys Val Ile Pro Gly Pro Pro Ala Leu Thr Leu Val
                195              200              205

Pro Ala Glu Leu Val Arg Ile Arg Gly Glu Ala Ala Gln Ile Val Cys
    210              215              220

Ser Ala Ser Ser Val Asp Val Asn Phe Asp Val Phe Leu Gln His Asn
225              230              235              240

Asn Thr Lys Leu Ala Ile Pro Gln Gln Ser Asp Phe His Asn Asn Arg
                245              250              255

Tyr Gln Lys Val Leu Thr Leu Asn Leu Asp Gln Val Asp Phe Gln His
                260              265              270

Ala Gly Asn Tyr Ser Cys Val Ala Ser Asn Val Gln Gly Lys His Ser
                275              280              285

Thr Ser Met Phe Phe Arg Val Val Glu Ser Ala Tyr Leu Asn Leu Ser
    290              295              300

Ser Glu Gln Asn Leu Ile Gln Glu Val Thr Val Gly Glu Gly Leu Asn
305              310              315              320

Leu Lys Val Met Val Glu Ala Tyr Pro Gly Leu Gln Gly Phe Asn Trp
                325              330              335

Thr Tyr Leu Gly Pro Phe Ser Asp His Gln Pro Glu Pro Lys Leu Ala
                340              345              350

Asn Ala Thr Thr Lys Asp Thr Tyr Arg His Thr Phe Thr Leu Ser Leu
                355              360              365

Pro Arg Leu Lys Pro Ser Glu Ala Gly Arg Tyr Ser Phe Leu Ala Arg
    370              375              380

Asn Pro Gly Gly Trp Arg Ala Leu Thr Phe Glu Leu Thr Leu Arg Tyr
385              390              395              400

Pro Pro Glu Val Ser Val Ile Trp Thr Phe Ile Asn Gly Ser Gly Thr
                405              410              415

Leu Leu Cys Ala Ala Ser Gly Tyr Pro Gln Pro Asn Val Thr Trp Leu
                420              425              430

Gln Cys Ser Gly His Thr Asp Arg Cys Asp Glu Ala Gln Val Leu Gln
                435              440              445

Val Trp Asp Asp Pro Tyr Pro Glu Val Leu Ser Gln Glu Pro Phe His
    450              455              460

Lys Val Thr Val Gln Ser Leu Leu Thr Val Glu Thr Leu Glu His Asn
465              470              475              480

Gln Thr Tyr Glu Cys Arg Ala His Asn Ser Val Gly Ser Gly Ser Trp
                485              490              495

Ala Phe Ile Pro Ile Ser Ala Gly Ala His Thr His Pro Pro Asp Glu
                500              505              510

Phe Leu Phe Thr Pro Val Val Val Ala Cys Met Ser Ile Met Ala Leu
                515              520              525

Leu Leu Leu Leu Leu Leu Leu Leu Tyr Lys Tyr Lys Gln Lys Pro
    530              535              540

Lys Tyr Gln Val Arg Trp Lys Ile Ile Glu Ser Tyr Glu Gly Asn Ser
545              550              555              560

Tyr Thr Phe Ile Asp Pro Thr Gln Leu Pro Tyr Asn Glu Lys Trp Glu
                565              570              575
```

-continued

```
Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
            595                 600                 605

Ala Val Leu Lys Val Ala Val Lys Met Leu Lys Ser Thr Ala His Ala
            610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
            675                 680                 685

Pro Gly Gln Asp Pro Glu Gly Gly Val Asp Tyr Lys Asn Ile His Leu
            690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                725                 730                 735

Phe Ser Glu Gln Asp Leu Asp Lys Glu Asp Gly Arg Pro Leu Glu Leu
                740                 745                 750

Arg Asp Leu Leu His Phe Ser Ser Gln Val Ala Gln Gly Met Ala Phe
            755                 760                 765

Leu Ala Ser Lys Asn Cys Ile His Arg Asp Val Ala Ala Arg Asn Val
            770                 775                 780

Leu Leu Thr Asn Gly His Val Ala Lys Ile Gly Ala Phe Gly Leu Ala
785                 790                 795                 800

Arg Asp Ile Met Asn Asp Ser Asn Tyr Ile Val Lys Gly Asn Ala Arg
                805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
                885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Ser Glu Leu Glu Glu
            930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
            965                 970
```

<210> SEQ ID NO 13
<211> LENGTH: 972

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Gly Pro Gly Val Leu Leu Leu Leu Val Ala Thr Ala Trp His
1               5                   10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
                100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
                180                 185                 190

Leu Lys Val Gln Lys Val Ile Pro Gly Pro Pro Ala Leu Thr Leu Val
            195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
                260                 265                 270

Ala Gly Asn Tyr Ser Cys Val Ala Ser Asn Val Gln Gly Lys His Ser
            275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
            325                 330                 335

Thr Tyr Leu Gly Pro Phe Ser Asp His Gln Pro Glu Pro Lys Leu Ala
            340                 345                 350

Asn Ala Thr Thr Lys Asp Thr Tyr Arg His Thr Phe Thr Leu Ser Leu
            355                 360                 365

Pro Arg Leu Lys Pro Ser Glu Ala Gly Arg Tyr Ser Phe Leu Ala Arg
    370                 375                 380
```

-continued

```
Asn Pro Gly Gly Trp Arg Ala Leu Thr Phe Glu Leu Thr Leu Arg Tyr
385                 390             395                 400

Pro Pro Glu Val Ser Val Ile Trp Thr Phe Ile Asn Gly Ser Gly Thr
                405             410             415

Leu Leu Cys Ala Ala Ser Gly Tyr Pro Gln Pro Asn Val Thr Trp Leu
            420             425             430

Gln Cys Ser Gly His Thr Asp Arg Cys Asp Glu Ala Gln Val Leu Gln
            435             440             445

Val Trp Asp Asp Pro Tyr Pro Glu Val Leu Ser Gln Glu Pro Phe His
        450             455             460

Lys Val Thr Val Gln Ser Leu Leu Thr Val Glu Thr Leu Glu His Asn
465             470             475                 480

Gln Thr Tyr Glu Cys Arg Ala His Asn Ser Val Gly Ser Gly Ser Trp
                485             490             495

Ala Phe Ile Pro Ile Ser Ala Gly Ala His Thr His Pro Pro Asp Glu
            500             505             510

Phe Leu Phe Thr Pro Val Val Ala Cys Met Ser Ile Met Ala Leu
            515             520             525

Leu Leu Leu Leu Leu Leu Leu Leu Leu Tyr Lys Tyr Lys Gln Lys Pro
        530             535             540

Lys Tyr Gln Val Arg Trp Lys Ile Ile Glu Ser Tyr Glu Gly Asn Ser
545             550             555                 560

Tyr Thr Phe Ile Asp Pro Thr Gln Leu Pro Tyr Asn Glu Lys Trp Glu
                565             570             575

Phe Pro Arg Asn Asn Leu Gln Phe Gly Lys Thr Leu Gly Ala Gly Ala
            580             585             590

Phe Gly Lys Val Val Glu Ala Thr Ala Phe Gly Leu Gly Lys Glu Asp
            595             600             605

Ala Val Leu Lys Val Ala Val Lys Met Leu Lys Ser Thr Ala His Ala
        610             615             620

Asp Glu Lys Glu Ala Leu Met Ser Glu Leu Lys Ile Met Ser His Leu
625             630             635                 640

Gly Gln His Glu Asn Ile Val Asn Leu Leu Gly Ala Cys Thr His Gly
                645             650             655

Gly Pro Val Leu Val Ile Thr Glu Tyr Ala Cys Tyr Gly Asp Leu Leu
            660             665             670

Asn Phe Leu Arg Arg Lys Ala Glu Ala Met Leu Gly Pro Ser Leu Ser
            675             680             685

Pro Gly Gln Asp Pro Glu Gly Gly Val Asp Tyr Lys Asn Ile His Leu
        690             695             700

Glu Lys Lys Tyr Val Arg Arg Asp Ser Gly Phe Ser Ser Gln Gly Val
705             710             715                 720

Asp Thr Tyr Val Glu Met Arg Pro Val Ser Thr Ser Ser Asn Asp Ser
                725             730             735

Phe Ser Glu Gln Asp Leu Asp Lys Glu Asp Gly Arg Pro Leu Glu Leu
            740             745             750

Arg Asp Leu Leu His Phe Ser Ser Gln Val Ala Gln Gly Met Ala Phe
            755             760             765

Leu Ala Ser Lys Asn Cys Ile His Arg Asp Val Ala Ala Arg Asn Val
        770             775             780

Leu Leu Thr Asn Gly His Val Ala Lys Ile Gly Asp Phe Gly Leu Ala
785             790             795                 800
```

-continued

```
Arg Asp Ile Met Asn Asp Ser Asn Tyr Ile Val Lys Gly Asn Ala Arg
            805                 810                 815

Leu Pro Val Lys Trp Met Ala Pro Glu Ser Ile Phe Asp Cys Val Tyr
            820                 825                 830

Thr Val Gln Ser Asp Val Trp Ser Tyr Gly Ile Leu Leu Trp Glu Ile
            835                 840                 845

Phe Ser Leu Gly Leu Asn Pro Tyr Pro Gly Ile Leu Val Asn Ser Lys
    850                 855                 860

Phe Tyr Lys Leu Val Lys Asp Gly Tyr Gln Met Ala Gln Pro Ala Phe
865                 870                 875                 880

Ala Pro Lys Asn Ile Tyr Ser Ile Met Gln Ala Cys Trp Ala Leu Glu
            885                 890                 895

Pro Thr His Arg Pro Thr Phe Gln Gln Ile Cys Ser Phe Leu Gln Glu
            900                 905                 910

Gln Ala Gln Glu Asp Arg Arg Glu Arg Asp Tyr Thr Asn Leu Pro Ser
            915                 920                 925

Ser Ser Arg Ser Gly Gly Ser Gly Ser Ser Ser Ser Glu Leu Glu Glu
    930                 935                 940

Glu Ser Ser Ser Glu His Leu Thr Cys Cys Glu Gln Gly Asp Ile Ala
945                 950                 955                 960

Gln Pro Leu Leu Gln Pro Asn Asn Tyr Gln Phe Cys
                965                 970
```

```
<210> SEQ ID NO 14
<211> LENGTH: 972
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Gly Pro Gly Val Leu Leu Leu Leu Leu Val Ala Thr Ala Trp His
1               5                   10                  15

Gly Gln Gly Ile Pro Val Ile Glu Pro Ser Val Pro Glu Leu Val Val
            20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Val Phe Glu Asp Gln Asp Ala Leu Leu Pro Cys Leu
            115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190
```

-continued

```
Leu Lys Val Gln Lys Val Ile Pro Gly Pro Ala Leu Thr Leu Val
        195             200             205

Pro Ala Glu Leu Val Arg Ile Arg Gly Glu Ala Ala Gln Ile Val Cys
    210             215             220

Ser Ala Ser Ser Val Asp Val Asn Phe Asp Val Phe Leu Gln His Asn
225             230             235             240

Asn Thr Lys Leu Ala Ile Pro Gln Gln Ser Asp Phe His Asn Asn Arg
            245             250             255

Tyr Gln Lys Val Leu Thr Leu Asn Leu Asp Gln Val Asp Phe Gln His
            260             265             270

Ala Gly Asn Tyr Ser Cys Val Ala Ser Asn Val Gln Gly Lys His Ser
            275             280             285

Thr Ser Met Phe Phe Arg Val Val Glu Ser Ala Tyr Leu Asn Leu Ser
    290             295             300

Ser Glu Gln Asn Leu Ile Gln Glu Val Thr Val Gly Glu Gly Leu Asn
305             310             315             320

Leu Lys Val Met Val Glu Ala Tyr Pro Gly Leu Gln Gly Phe Asn Trp
            325             330             335

Thr Tyr Leu Gly Pro Phe Ser Asp His Gln Pro Glu Pro Lys Leu Ala
            340             345             350

Asn Ala Thr Thr Lys Asp Thr Tyr Arg His Thr Phe Thr Leu Ser Leu
            355             360             365

Pro Arg Leu Lys Pro Ser Glu Ala Gly Arg Tyr Ser Phe Leu Ala Arg
    370             375             380

Asn Pro Gly Gly Trp Arg Ala Leu Thr Phe Glu Leu Thr Leu Arg Tyr
385             390             395             400

Pro Pro Glu Val Ser Val Ile Trp Thr Phe Ile Asn Gly Ser Gly Thr
            405             410             415

Leu Leu Cys Ala Ala Ser Gly Tyr Pro Gln Pro Asn Val Thr Trp Leu
            420             425             430

Gln Cys Ser Gly His Thr Asp Arg Cys Asp Glu Ala Gln Val Leu Gln
        435             440             445

Val Trp Asp Asp Pro Tyr Pro Glu Val Leu Ser Gln Glu Pro Phe His
    450             455             460

Lys Val Thr Val Gln Ser Leu Leu Thr Val Glu Thr Leu Glu His Asn
465             470             475             480

Gln Thr Tyr Glu Cys Arg Ala His Asn Ser Val Gly Ser Gly Ser Trp
            485             490             495

Ala Phe Ile Pro Ile Ser Ala Gly Ala His Thr His Pro Pro Asp Glu
            500             505             510

Phe Leu Phe Thr Pro Val Val Val Ala Cys Met Ser Ile Met Ala Leu
            515             520             525

Leu Leu Leu Leu Leu Leu Leu Leu Tyr Lys Tyr Lys Gln Lys Pro
    530             535             540

Lys Phe Gln Val Arg Trp Lys Ile Ile Glu Ser Tyr Glu Gly Asn Ser
545             550             555             560

Tyr Thr Phe Ile Asp Pro Thr Gln Leu Pro Tyr Asn Glu Lys Trp Glu
            565             570             575

Phe Pro Arg Asn Asn Leu Gln Phe Gly Lys Thr Leu Gly Ala Gly Ala
            580             585             590

Phe Gly Lys Val Val Glu Ala Thr Ala Phe Gly Leu Gly Lys Glu Asp
        595             600             605
```

```
Ala Val Leu Lys Val Ala Val Lys Met Leu Lys Ser Thr Ala His Ala
    610             615             620

Asp Glu Lys Glu Ala Leu Met Ser Glu Leu Lys Ile Met Ser His Leu
625             630             635             640

Gly Gln His Glu Asn Ile Val Asn Leu Leu Gly Ala Cys Thr His Gly
                645             650             655

Gly Pro Val Leu Val Ile Thr Glu Tyr Cys Cys Tyr Gly Asp Leu Leu
                660             665             670

Asn Phe Leu Arg Arg Lys Ala Glu Ala Met Leu Gly Pro Ser Leu Ser
            675             680             685

Pro Gly Gln Asp Pro Glu Gly Gly Val Asp Tyr Lys Asn Ile His Leu
    690             695             700

Glu Lys Lys Tyr Val Arg Arg Asp Ser Gly Phe Ser Ser Gln Gly Val
705             710             715             720

Asp Thr Tyr Val Glu Met Arg Pro Val Ser Thr Ser Ser Asn Asp Ser
                725             730             735

Phe Ser Glu Gln Asp Leu Asp Lys Glu Asp Gly Arg Pro Leu Glu Leu
            740             745             750

Arg Asp Leu Leu His Phe Ser Ser Gln Val Ala Gln Gly Met Ala Phe
            755             760             765

Leu Ala Ser Lys Asn Cys Ile His Arg Asp Val Ala Ala Arg Asn Val
    770             775             780

Leu Leu Thr Asn Gly His Val Ala Lys Ile Gly Asp Phe Gly Leu Ala
785             790             795             800

Arg Asp Ile Met Asn Asp Ser Asn Tyr Ile Val Lys Gly Asn Ala Arg
                805             810             815

Leu Pro Val Lys Trp Met Ala Pro Glu Ser Ile Phe Asp Cys Val Tyr
                820             825             830

Thr Val Gln Ser Asp Val Trp Ser Tyr Gly Ile Leu Leu Trp Glu Ile
            835             840             845

Phe Ser Leu Gly Leu Asn Pro Tyr Pro Gly Ile Leu Val Asn Ser Lys
    850             855             860

Phe Tyr Lys Leu Val Lys Asp Gly Tyr Gln Met Ala Gln Pro Ala Phe
865             870             875             880

Ala Pro Lys Asn Ile Tyr Ser Ile Met Gln Ala Cys Trp Ala Leu Glu
                885             890             895

Pro Thr His Arg Pro Thr Phe Gln Gln Ile Cys Ser Phe Leu Gln Glu
                900             905             910

Gln Ala Gln Glu Asp Arg Arg Glu Arg Asp Tyr Thr Asn Leu Pro Ser
            915             920             925

Ser Ser Arg Ser Gly Gly Ser Gly Ser Ser Ser Ser Glu Leu Glu Glu
    930             935             940

Glu Ser Ser Ser Glu His Leu Thr Cys Cys Glu Gln Gly Asp Ile Ala
945             950             955             960

Gln Pro Leu Leu Gln Pro Asn Asn Tyr Gln Phe Cys
                965             970
```

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer <400> SEQUENCE: 15

-continued

```
agactcattc cagaaccaga gc                                                     22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccggtagaat tcctcgagtc ta                                                     22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaatttggag tcctcacctt tg                                                     22
```

COMPOSITIONS AND METHODS FOR MICROGLIA REPLACEMENT THERAPY

CROSS-REFERENCE

This application claims the benefit of U.S. Provisional Application No. 62/729,380, filed Sep. 10, 2018, which application is incorporated herein by reference in its entirety.

SEQUENCE LISTING

The instant application contains a Sequence Listing which has been filed electronically in ASCII format and is hereby incorporated by reference in its entirety. Said ASCII copy, created on Dec. 17, 2019, is named 40116-713_201_SL.txt and is 108,497 bytes in size.

STATEMENT AS TO FEDERALLY SPONSORED RESEARCH

This invention was made with government support under contract number K08MH112120 awarded by the National Institute of Mental Health. The government has certain rights in the invention.

BACKGROUND

Homeostasis of the central nervous system (CNS) is vital to normal neurological activity within a subject. Disruption of CNS homeostasis is thought to be associated with the development and progression of neurological diseases and disorders. Microglia cells are a primary innate immune cell residing within the CNS and may be regulators of CNS homeostasis. Diseased microglia cells can sometimes play a role in neurological diseases or disorders. Generally, microglia cells are physically restricted to the CNS following neurodevelopment of the blood-brain barrier (BBB).

SUMMARY

In one aspect, a composition is provided comprising a myeloid cell, wherein the myeloid cell: a) comprises a receptor tyrosine kinase, wherein the receptor tyrosine kinase comprises a mutation that renders the receptor tyrosine kinase less sensitive to an inhibitor of the receptor tyrosine kinase; and b) has the potential to differentiate into a microglia-like cell. In some cases, the receptor tyrosine kinase is a class III RTK. In some cases, the receptor tyrosine kinase is selected from the group consisting of: platelet-derived growth factor alpha (PDGFRα), platelet-derived growth factor beta (PDGFRβ), C-kit protooncogene (C-KIT), receptor-type tyrosine-protein kinase FLT3 (FLT3), and macrophage colony-stimulating factor 1 receptor (CSF1R). In some cases, the receptor tyrosine kinase is macrophage colony-stimulating factor 1 receptor (CSF1R). In some cases, the mutation is an amino acid substitution, deletion, or insertion. In some cases, the amino acid substitution, deletion, or insertion is within the JM-domain, the N(P)-loop, the A-loop, the C-loop, the KID region, or the Hinge region of CSF1R. In some cases, the amino acid substitution, deletion, or insertion is at any one or more of positions corresponding to amino acids 546, 663, 795, or 796 of SEQ ID NO: 3. In some cases, the amino acid substitution, deletion, or insertion corresponds to any one or more of: a tyrosine to phenylalanine substitution at amino acid 546 of SEQ ID NO: 3; a threonine to isoleucine substitution at amino acid 663 of SEQ ID NO: 3; a glycine to alanine substitution at amino acid 795 of SEQ ID NO: 3; or an aspartic acid to alanine substitution at amino acid 796 of SEQ ID NO: 3. In some cases, the inhibitor of the receptor tyrosine kinase inhibits tyrosine kinase activity. In some cases, the inhibitor of the receptor tyrosine kinase is selected from the group consisting of: pexidartinib (PLX-3397), PLX-7486, PLX-5622, ARRY-382, BLZ945, DCC-3014, AMG-820, GW-2580, linifanib (ABT-869), OSI-930, and combinations thereof. In some cases, the myeloid cell is a myeloid precursor cell, a myeloid progenitor cell, an erythro-myeloid precursor cell, an erythro-myeloid progenitor cell, a myeloid-derived macrophage, a myeloid-derived monocyte, a myeloid-derived fetal macrophage, a non-hematopoietic stem cell (HSC)-derived myeloid cell, a hematopoietic stem cell (HSC)-derived myeloid cell, or a yolk-sac-derived myeloid cell. In some cases, the myeloid cell is a myeloid precursor cell or microglia-like cell. In some cases, the myeloid cell is derived from a natural myeloid cell. In some cases, the myeloid cell is derived from a non-natural myeloid cell. In some cases, the myeloid cell is generated or differentiated in vitro. In some cases, the myeloid cell is generated or differentiated ex vivo. In some cases, the myeloid cell is a human myeloid cell. In some cases, the human myeloid cell is from an individual that is healthy or afflicted with a neurological disease or disorder. In some cases, the human myeloid cell is from an individual that does not have a peripheral blood disorder or blood cancer.

In another aspect, a CSF1R polypeptide is provided comprising an amino acid substitution, deletion, or insertion wherein the amino acid substitution, deletion, or insertion is at any one or more of positions corresponding to amino acids 546, 663, 795, or 796 of SEQ ID NO: 3. In some cases, the CSF1R polypeptide lacks a signal sequence. In some cases, the amino acid substitution, deletion, or insertion corresponds to a tyrosine to phenylalanine substitution at amino acid 546 of SEQ ID NO: 3; a threonine to isoleucine substitution at amino acid 663 of SEQ ID NO: 3; a glycine to alanine substitution at amino acid 795 of SEQ ID NO: 3; an aspartic acid to alanine substitution at amino acid 796 of SEQ ID NO: 3; or any combination thereof.

In another aspect, a nucleic acid is provided encoding any one of the aforementioned CSF1R polypeptides.

In another aspect, an expression vector is provided comprising any one of the aforementioned nucleic acids. In some cases, the expression vector is a viral vector. In some cases, the expression vector is a non-viral vector.

In yet another aspect, a cell is provided comprising any one of the aforementioned nucleic acids.

In yet another aspect, a myeloid cell is provided comprising any one of the aforementioned expression vectors. In some cases, the myeloid cell is a human cell. In some cases, the myeloid cell is a myeloid precursor cell, a myeloid progenitor cell, an erythro-myeloid precursor cell, an erythro-myeloid progenitor cell, a myeloid-derived macrophage, a myeloid-derived monocyte, a myeloid-derived fetal macrophage, a non-hematopoietic stem cell (HSC)-derived myeloid cell, a hematopoietic stem cell (HSC)-derived myeloid cell, or a yolk-sac-derived myeloid cell. In some cases, the myeloid cell is a myeloid precursor cell or a microglia-like cell.

In another aspect, a method is provided comprising administering any one of the aforementioned myeloid cells to the central nervous system (CNS) of an individual in need thereof. In some cases, the myeloid cells differentiate in vivo into microglia-like cells that populate the CNS of the subject in need thereof. In some cases, the myeloid cells supplement or replace native microglia cells within the CNS of the subject in need thereof. In some cases, microglia cells native to the subject in need thereof are reduced in number or are completely absent. In some cases, the method further comprises inactivating, suppressing or depleting native microglia cells within the CNS of the subject in need thereof prior to or concurrently with the administering of the composition into the CNS of the subject in need thereof. In some cases, the method comprises administering to the individual in need thereof an inhibitor of CSF1R tyrosine kinase activity. In some cases, the inhibitor of CSF1R tyrosine kinase activity is selected from the group consisting of: pexidartinib (PLX-3397), PLX-7486, PLX-5622, ARRY-382, BLZ945, DCC-3014, AMG-820, GW-2580, linifanib (ABT-869), OSI-930, and combinations thereof.

In another aspect, a method is provided for microglia cell replacement therapy, wherein the method comprises: a) introducing a first microglia cell inhibitor into the central nervous system (CNS) of a subject in need thereof, thereby inactivating, suppressing, or depleting a native microglia cell population of the subject in need thereof; and b) introducing genetically-modified myeloid cells into the CNS of the subject in need thereof, wherein the genetically-modified myeloid cells comprise a nucleic acid encoding a receptor tyrosine kinase comprising a mutation that renders the receptor tyrosine kinase less sensitive to a first microglia cell inhibitor, wherein the genetically-modified myeloid cells replace the native microglia cell population by differentiating into microglia-like cells in vivo. In some cases, the genetically-modified myeloid cells have reduced sensitivity to a second microglia cell inhibitor. In some cases, the genetically-modified myeloid cells are sensitive to a second microglia cell inhibitor. In some cases, the method further comprises administering a second microglia cell inhibitor to the subject in need thereof in order to deplete or suppress the genetically-modified microglia-like cells. In some cases, the receptor tyrosine kinase is macrophage colony-stimulating factor 1 receptor (CSF1R). In some cases, the mutation is an amino acid substitution, deletion, or insertion. In some cases, the amino acid substitution, deletion, or insertion is within the JM-domain, the N(P)-loop, the A-loop, the C-loop, the KID region, or the Hinge region of CSF1R. In some cases, the amino acid substitution, deletion, or insertion is at any one or more of positions corresponding to amino acids 546, 663, 795, or 796 of SEQ ID NO: 3. In some cases, the amino acid substitution, deletion, or insertion corresponds to any one or more of: a tyrosine to phenylalanine substitution at amino acid 546 of SEQ ID NO: 3; a threonine to isoleucine substitution at amino acid 663 of SEQ ID NO: 3; a glycine to alanine substitution at amino acid 795 of SEQ ID NO: 3; and an aspartic acid to alanine substitution at amino acid 796 of SEQ ID NO: 3. In some cases, the inhibitor of the receptor tyrosine kinase inhibits tyrosine kinase activity. In some cases, the first microglia cell inhibitor is selected from the group consisting of: pexidartinib (PLX-3397), PLX-7486, PLX-5622, ARRY-382, BLZ945, DCC-3014, AMG-820, GW-2580, linifanib (ABT-869), OSI-930, and combinations thereof. In some cases, the second microglia cell inhibitor is selected from the group consisting of: pexidartinib (PLX-3397), PLX-7486, PLX-5622, ARRY-382, BLZ945, DCC-3014, AMG-820, GW-2580, linifanib (ABT-869), OSI-930, and combinations thereof.

In some cases, a genetically-modified CSF1R comprises one or more amino acid substitutions selected from the group consisting of: V647I, W550F, W550L, G669A, G669V, T663I, G795A, M637L, D796A, C666A, and Y546F; and has at least 70%, at least 75%, at least 80%, at least 85%, at least 90%, at least 95%, or at least 99% sequence identity to SEQ ID NO: 3.

In one aspect, a composition is provided comprising a myeloid cell, wherein the myeloid cell: a) comprises at least one genetic modification; and b) has the potential to differentiate into a microglia-like cell.

In another aspect, a composition is provided comprising a myeloid cell, wherein the myeloid cell comprises at least one genetic modification, the at least one genetic modification comprising a genetically-modified receptor tyrosine kinase (RTK).

In some cases, the myeloid cell is a myeloid precursor cell, a myeloid progenitor cell, an erythro-myeloid precursor cell, an erythro-myeloid progenitor cell, a myeloid-derived macrophage, a myeloid-derived monocyte, a myeloid-derived fetal macrophage, a non-hematopoietic stem cell (HSC)-derived myeloid cell, a hematopoietic stem cell (HSC)-derived myeloid cell, or a yolk-sac (YS)-derived myeloid cell. In some cases, the myeloid cell is a microglia-like cell. In some cases, the myeloid cell is derived from a natural myeloid cell or a non-natural myeloid cell. In some cases, the non-natural myeloid cell is generated in vitro, in vivo, or ex vivo. In some cases, the myeloid cell is derived from embryonic or extraembryonic tissues. In some cases, the myeloid cell is derived from postnatal tissues, a pluripotent stem cell, or an induced pluripotent stem cell. In some cases, the myeloid cell is derived from a human subject. In some cases, the human subject is healthy or afflicted with a neurological disease or disorder. In some cases, the human subject does not have a peripheral blood disorder or blood cancer. In some cases, the microglia-like cell is ramified or activated. In some cases, the activated microglia-like cell is a non-phagocytic cell, a phagocytic cell, an amoeboid cell, or a gitter cell. In some cases, the myeloid cell comprises a genetically-modified Receptor Tyrosine Kinase (RTK). In some cases, the genetically-modified RTK is a class III RTK. In some cases, the genetically-modified class III RTK is genetically-modified platelet-derived growth factor alpha (PDGFRα), platelet-derived growth factor beta (PDGFRβ), C-kit protooncogene (C-KIT), receptor-type tyrosine-protein kinase FLT3 (FLT3), or colony-stimulating factor 1 receptor (CSF1R). In some cases, the genetically-modified class III RTK is a genetically-modified CSF1R. In some cases, the genetically-modified RTK possesses normal ligand-dependent signaling or normal ligand-independent signaling. In some cases, the genetically-modified RTK is sensitive or insensitive to an endogenous RTK ligand. In some cases, the genetically-modified RTK has reduced sensitivity to an inhibitor. In some cases, the RTK inhibitor is a tyrosine kinase inhibitor (TKI) or an anti-RTK antibody. In some cases, the myeloid cell is genetically modified to express the genetically-modified RTK. In some cases, the genetically-modified RTK comprises one or more amino acid substitutions. In some cases, the genetically-modified RTK comprises one or more amino acid substitutions that increases or decreases binding to a TKI or anti-RTK antibody. In some cases, the genetically-modified RTK comprises one or more amino acid substitutions that increases or decreases binding to an endogenous or exogenous RTK ligand. In some cases, the genetically-modified RTK comprises one or more amino acid substitutions that increases or decreases ligand-dependent or ligand-independent signaling. In some cases, the myeloid cell comprising a genetically-modified RTK further comprises additional genetic modifications. In some cases, the additional genetic modifications increase or decrease myeloid cell viability, growth, or functional activity. In some cases, the additional genetic modifications are in a gene associated with neurological disease or disorder. In some cases, the additional genetic modifications reverse or reduce a phenotype associated with a neurological disease or disorder, or otherwise treat a neurological disease or disorder. In some cases, the endogenous or exogenous ligand is a CSF1R ligand. In some cases, the endogenous or exogenous ligand is colony stimulating factor (CSF1) or Interleukin-34 (IL-34). In some cases, the genetically-modified CSF1R is sensitive or insensitive to an exogenous CSF1R ligand. In some cases, the genetically-modified CSF1R is sensitive or insensitive to a CSF1R inhibitor. In some cases, the genetically-modified CSF1R is sensitive to a CSF1R ligand and is insensitive to a CSF1R inhibitor. In some cases, the genetically-modified CSF1R is sensitive or insensitive to a tyrosine kinase inhibitor (TKI) or to an anti-CSF1R antibody. In some cases, the CSF1R inhibitor is a TKI selected from the group consisting of: pexidartinib (PLX-3397), PLX-7486, PLX-5622, ARRY-382, BLZ945, DCC-3014, AMG-820, GW-2580, linifanib (ABT-869), and OSI-930. In some cases, the genetically-modified CSF1R is sensitive or insensitive to an anti-CSF1R antibody selected from the group consisting of: PD-0360324, RG-7455, IMC-CS4, and MCS110. In some cases, the genetically-modified CSF1R comprises one or more amino acid substitutions within the JM-domain, the N(P)-loop, the A-loop, the C-loop, the KID region, or the Hinge region of a CSF1R. In some cases, the genetically-modified CSF1R comprises a mutation at amino acid residue V647, W550, G669, T663, G795, M637, D796, C666, Y546, or any combination thereof. In some cases, the genetically-modified CSF1R comprises one or more amino acid substitutions selected from the group consisting of: V647I, W550F, W550L, G669A, G669V, T663I, G795A, M637L, D796A, C666A, and Y546F.

In another aspect, a composition is provided comprising genetically-modified myeloid cells that differentiate in vivo into microglia-like cells that repopulate a central nervous system (CNS) of a subject in need thereof, wherein the myeloid cells do not possess a gene expression profile associated with a neurological disease or disorder. In some cases, the genetically-modified myeloid cells have a gene expression profile of ApoE that is not associated with Alzheimer's disease. In some cases, the genetically-modified myeloid cells have a gene expression profile of alpha-synuclein, ubiquitin, neurofilament protein, Tau proteins, or alpha B crystalline that is not associated with Parkinson's disease. In some cases, the genetically-modified myeloid cell has a gene expression profile of mutant Huntingtin (mHTT) that is not associated with Huntington's disease. In some cases, the genetically-modified myeloid cell has a gene expression profile that is not associated with Multiple Sclerosis.

In yet another aspect, an isolated, non-naturally occurring oligonucleotide is provided comprising a nucleic acid sequence that encodes a polypeptide comprising a genetically-modified CSF1R, wherein the genetically-modified CSF1R is sensitive to a CSF1R ligand, and is insensitive to a CSF1R inhibitor.

In yet another aspect, a method is provided comprising administering any of the preceding compositions into the central nervous system (CNS) of a subject in need thereof. In some cases, the myeloid cells differentiate in vivo into microglia-like cells that populate the CNS of the subject in need thereof. In some cases, the myeloid cells supplement or replace native microglia cells within the CNS of the subject in need thereof. In some cases, microglia cells native to the subject in need thereof are reduced in number or are completely absent. In some cases, the method further comprises inactivating, suppressing, or depleting native microglia cells within the CNS of the subject in need thereof prior to or concurrently with the administering of the composition into the CNS of the subject in need thereof.

In another aspect, a method for microglia cell replacement therapy is provided, wherein the method comprises: a) introducing a first microglia cell inhibitor into the central nervous system (CNS) of a subject in need thereof, thereby inactivating, suppressing, or depleting a native microglia cell population of the subject in need thereof; and b) introducing genetically-modified myeloid cells into the CNS of the subject in need thereof, wherein the genetically-modified myeloid cells comprise a genetically-modified receptor that is insensitive to the first microglia cell inhibitor, wherein the genetically-modified myeloid cells replace the native microglia cell population by differentiating into microglia-like cells in vivo. In some cases, the genetically-modified receptor is a CSF1R. In some cases, the genetically-modified myeloid cells are insensitive to a second microglia cell inhibitor. In some cases, the genetically-modified myeloid cells are sensitive to a second microglia cell inhibitor. In some cases, the method further comprises administering a second microglia cell inhibitor to the subject in need thereof in order to deplete or suppress the genetically-modified microglia-like cells.

In yet another aspect, a method of treating a neurological disease or disorder associated with a genetic defect within a microglia cell of a subject in need thereof is provided, the method comprising: a) obtaining myeloid cells from the subject in need thereof, wherein the myeloid cells comprise the genetic defect; b) genetically engineering the myeloid cells to correct the genetic defect and to express a genetically-modified CSF1R, thereby producing genetically-modified myeloid cells; and c) transplanting the genetically-modified myeloid cells into the subject in need thereof, wherein the genetically-modified myeloid cells differentiate into microglia-like cells in vivo and correct the genetic defect, thereby treating the neurological disorder or disease. In some cases, the genetically-modified myeloid cells restore central nervous system (CNS) homeostasis within a subject in need thereof, thereby providing therapeutic efficacy to the subject in need thereof. In some cases, the genetically-modified myeloid cells restore CNS homeostasis within a subject in need thereof that resembles CNS homeostasis produced by microglia cells in a healthy subject. In some cases, the genetically-modified myeloid cells restore central nervous system (CNS) homeostasis within a subject in need thereof through ligand-dependent or ligand-independent activity of the microglia-like cells. In some cases, the genetically-modified myeloid cells possess a gene expression profile similar to microglia cells in a healthy subject. In some cases, the genetically-modified myeloid cell possesses a gene expression profile for ApoE that is not associated with Alzheimer's disease. In some cases, the genetically-modified myeloid cell possesses a gene expression profile that is not associated with Parkinson's disease, Huntington's disease, or Multiple Sclerosis. In some cases, the method further comprises monitoring the CNS of the subject in need thereof for signs of population of the microglia-like cells. In some cases, the method further comprises monitoring a central nervous system (CNS) of the subject in need thereof for signs of repopulation of the microglia-like cells or for signs of over-population of the microglia-like cells, or both. In some cases, the genetically-modified myeloid cells express a therapeutic gene or protein. In some cases, the expressed therapeutic gene or protein comprises a gene or protein that promotes the growth, survival, activity, or differentiation of the genetically-modified myeloid cells within a central nervous system (CNS) of the subject in need thereof. In some cases, the genetically-modified myeloid cells are administered as a heterogeneous mixture of cells. In some cases, the genetically-modified myeloid cells are derived from purified myeloid cells. In some cases, the genetically-modified myeloid cells are systemically administered to the subject in need thereof. In some cases, the genetically-modified myeloid cells are administered to the subject in need thereof via intravenous injection or intracerebroventricular injection (ICVI). In some cases, the genetically-modified myeloid cells are administered by introducing the genetically-modified myeloid cells into white or gray matter of a central nervous system (CNS) of the subject. In some cases, the genetically-modified myeloid cells are introduced into a brain or spinal cord of the subject in need thereof. In some cases, the method does not increase a risk of the subject in need thereof to a genetic disease or disorder of a central nervous system (CNS). In some cases, the genetically-modified microglia-like cells possess a gene expression profile similar to that expressed by microglia cells derived from hematopoietic stem cells. In some cases, the subject in need thereof has native microglia cells that are missing, inactive, or in a pathological state associated with a neurological disease or disorder. In some cases, the subject in need thereof has native microglia cells that have been partially or entirely inactivated, suppressed, or depleted. In some cases, population growth of the genetically-modified myeloid cells within a central nervous system (CNS) of the subject in need thereof is partial or complete. In some cases, population growth of the genetically-modified myeloid cells within a central nervous system (CNS) of the subject in need thereof is therapeutically effective. In some cases, the subject in need thereof has a neurological disease or disorder. In some cases, the subject in need thereof has a neurological disease or disorder selected from the group consisting of: Alzheimer's disease, Parkinson's disease, Huntington's disease, Multiple Sclerosis, a glioma, a viral infection, a microbial infection, and a neurological disease or disorder caused by diseased microglia cells.

In another aspect, a method of repopulating microglia cells in a subject in need thereof is provided, the method comprising administering myeloid cells to the subject in need thereof, wherein the myeloid cells generate or differentiate into microglia cells that repopulate a central nervous system (CNS) of the subject and the microglia cells do not express relatively high levels of a gene associated with a central nervous system (CNS) disorder or disease. In some cases, the gene associated with a CNS disorder or disease is ApoE. In some cases, the microglia cells do not express a level of ApoE associated with Alzheimer's disease or a level of ApoE that is greater than an ApoE level of a normal or non-diseased cell. In some cases, the CNS disorder or disease is Alzheimer's disease.

In another aspect, a method of repopulating microglia cells in a subject in need thereof is provided, the method comprising administering myeloid cells to the subject in need thereof, wherein the myeloid cells are genetically modified and wherein the myeloid cells differentiate into microglia cells in vivo.

In another aspect, a method is provided comprising administering myeloid cells to a central nervous system of a subject, wherein the myeloid cells are genetically modified and wherein the administering does not comprise reducing myeloid cells in the subject using a stem cell transplantation drug.

In another aspect, a method is provided comprising administering myeloid cells to a central nervous system of a subject, wherein the myeloid cells are genetically modified and wherein the subject does not have a peripheral blood disorder.

In another aspect, a method is provided comprising administering myeloid cells to a central nervous system of a subject, wherein the myeloid cells are genetically modified and wherein the subject does not have a blood cancer.

In another aspect, a method is provided comprising repopulating microglia cells in a subject in need thereof by administering myeloid cells to the subject in need thereof, wherein the myeloid cells are genetically modified.

In another aspect, a method of repopulating microglia cells in a subject in need thereof is provided, the method comprising administering myeloid cells to the subject in need thereof, wherein the myeloid cells generate or differentiate into microglia cells that repopulate a central nervous system of the subject and the microglia cells do not express relatively high levels of a gene associated with a central nervous system disorder or disease.

In another aspect, a method of repopulating microglia cells in a subject in need thereof is provided, the method comprising administering myeloid cells to the subject in need thereof, wherein the myeloid cells generate or differentiate into microglia cells that repopulate a central nervous system of the subject and the microglia cells do not express relatively high levels of ApoE.

In another aspect, a method of repopulating microglia cells in a subject in need thereof is provided, the method comprising administering myeloid cells to the subject in need thereof, wherein the myeloid cells generate or differentiate into microglia cells that repopulate a central nervous system of the subject and the microglia cells do not express a level of ApoE associated with Alzheimer's disease or a level of ApoE that is greater than an ApoE level of a normal or non-diseased cell.

In another aspect, a method of repopulating microglia cells in a subject in need thereof is provided, the method comprising administering myeloid cells to the subject in need thereof, wherein the myeloid cells generate or differentiate into microglia cells that repopulate a central nervous system of the subject and the microglia cells do not demonstrate a gene expression signature of Alzheimer's disease.

In some cases, the myeloid cells are myeloid precursor cells. In some cases, the myeloid cells are myeloid precursor cells derived from a non-hematopoietic stem cell lineage. In some cases, the myeloid cells are myeloid cells derived from a hematopoietic stem cell lineage. In some cases, the myeloid cells are erythro-myeloid progenitor cells or erythro-myeloid precursor cells. In some cases, the myeloid cells are derived from embryonic or extraembryonic tissue. In some cases, the myeloid cells are derived from embryonic or extraembryonic tissue from a subject or animal different from the subject. In some cases, the myeloid cells are derived from the subject. In some cases, the myeloid cells are myeloid precursor cells derived from a non-hematopoietic stem cell lineage. In some cases, the myeloid cells are macrophages or monocytes. In some cases, the myeloid cells are fetal macrophages. In some cases, the myeloid cells are derived from a yolk sac. In some cases, the myeloid cells are administered in a heterogeneous mixture of cells. In some cases, the myeloid cells are purified myeloid cells. In some cases, the administering comprises intravenous administration to the subject. In some cases, the myeloid cells comprise a genetically modified CSF1R. In some cases, the genetically-modified CSF1R possesses normal signaling capabilities. In some cases, the said genetically-modified CSF1R is resistant to a CSF1R inhibitor. In some cases, the genetically-modified CSF1R is resistant to a receptor tyrosine kinase inhibitor. In some cases, the method does not increase a risk of the subject to a genetic disease or disorder of a central nervous system. In some cases, the central nervous system is brain. In some cases, the microglia cells express genes or proteins or a combination thereof that are highly specific to microglia. In some cases, the microglia cells express genes or proteins or a combination thereof that are more specific to microglia genes or proteins than are genes or proteins expressed by microglia cells derived from hematopoietic stem cells. In some cases, the microglia cells express genes or proteins or a combination thereof that are more specific to microglia genes or proteins than are genes or proteins expressed by microglia cells derived from naturally-occurring or genetically-unmodified or unmodified hematopoietic stem cells. In some cases, the subject has microglia cells that have been partially or entirely depleted. In some cases, the repopulation is partial or complete repopulation. In some cases, the repopulation is therapeutically effective.

In another aspect, a composition is provided comprising a myeloid cell comprising a genetically modified CSF1R. In some cases, the genetically-modified CSF1R possesses normal signaling capabilities. In some cases, the genetically-modified CSF1R is resistant to a CSF1R inhibitor. In some cases, the genetically-modified CSF1R is resistant to a receptor tyrosine kinase inhibitor. In some cases, the myeloid cell is a myeloid precursor cell, a myeloid progenitor cell, a non-hematopoietic stem cell-derived myeloid cell, a HSC-derived myeloid cell, or a yolk-sac-derived myeloid cell. In some cases, the myeloid cell has one or more features of a myeloid cell described in any one of the preceding methods.

In another aspect, a composition is provided myeloid cells that are genetically modified and wherein the myeloid cells differentiate into microglia cells in vivo.

In another aspect, a composition is provided comprising myeloid cells wherein the myeloid cells are genetically-modified and generate or differentiate into microglia cells that repopulate a central nervous system of a subject and the microglia cells do not express relatively high levels of a gene associated with a central nervous system disorder or disease.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

FIG. 1D: Chemical structure of a non-limiting example of a CSF1R inhibitor (pexidartinib (PLX-3397)).

FIG. 1E: Chemical structure of a non-limiting example of a CSF1R inhibitor (BLZ-945).

FIG. 1F: Chemical structure of a non-limiting example of a CSF1R inhibitor (BLZ-945 metabolite).

FIG. 1G: Chemical structure of a non-limiting example of a CSF1R inhibitor (GW-2580).

FIG. 1H: Chemical structure of a non-limiting example of a CSF1R inhibitor (CFMS-IN-2).

FIG. 1I: Chemical structure of a non-limiting example of a CSF1R inhibitor (6-chloro-3-(3-methyl-2H-1,2-oxazol-5-ylidene)-4-phenylquinolin-2-one).

FIG. 1J: Chemical structure of a non-limiting example of a CSF1R inhibitor (Linifanib (ABT-869)).

FIG. 1K: Chemical structure of a non-limiting example of a CSF1R inhibitor (OSI-930).

FIG. 2A: Schematic of microglia transplantation system. FIG. 2B: Immunostaining showing ramified IBA1+(green)/TMEM119+(red) microglia in Csf1r+/+ (WT) and microglia-transplanted Csf1r−/− hosts, and untransplanted Csf1r−/− control. Scale bar=50 μm. FIG. 2C: Expression heat map ($\log_2$(FC/WT)) of microglia (blue), myeloid (orange) and reactivity (red) genes by microglia after culture or transplantation into Csf1r−/− CNS. Detailed inventory of experimental replicates is listed in methods. *=FDR<0.05 compared with WTD) Overlaid volcano plots show reduced differential gene expression of ICT-cells (blue) compared to non-transplanted cultured MGs (orange), represented by reduced spread of volcano.

FIG. 3A: IBA1 immunostained section of Csf1r−/− brain transplanted with adult microglia showing typical widespread engraftment with some unpopulated territories, encircled by white line. Scale bar=500 μm. FIG. 3B: In areas of cell engraftment, transplanted microglia in Csf1r−/− hosts reach same density as microglia in a WT brain, p>0.05 adjusted for multiple comparisons to WT by Student's t-test, N.S.=not significant. FIG. 3C: Sort strategy for MLC isolation showing FSC/SSC, single cell, live, CD45/11B, and TMEM119 gates. MLCs were sorted based on TMEM119 immunoreactivity. Numbers in lower left of plots shows gate hierarchy (1>2>3>4). Cells were sorted from gate 4. FIG. 3D: Transplantation into Csf1r−/− hosts, which lack microglia (left), leads to engraftment of CD45+CD11B+ cells (right) with similar profile to untransplanted microglia in a Csf1r+/+ (WT) control (middle) FIG. 3E: Transplanted microglia (blue distribution) express Tmem119 at normal levels (black dotted) by flow cytometric analysis. FIG. 3F: Genotyping gel demonstrating that transplanted, then sorted microglia ("ICT Cultured MG") are WT for the Csf1r gene. FIG. 3G: Venn diagram showing differentially expressed genes between transplanted and WT microglia (2-fold cutoff, FPKM>20, FDR<0.05). ICT=intracerebral transplantation, MG=microglia, MLC=microglia-like cell, WT=Csf1r+/+, Cult=Cultured, P5=postnatal day 5.

FIG. 4: Differentially expressed genes between ICT-MGs and WTMGs. Columns (left to right) show gene name, FPKM in WT MG and pooled ICT-MGs, log 2 (fold change), and false discovery rate (FDR) from edgeR comparison. Differential gene expression (DGE) was filtered for at least 2-fold change, FPKM>20 in at least 1 sample, and FDR<0.05.

FIGS. 5A-C: Diverse myeloid populations engraft in the Csf1r−/− brain, ramify, and are Tmem119+. FIG. 5A: IBA1+

(green) MLCs ramify and are TMEM119+ (red) in the brain parenchyma 14 days after ICT into Csf1r–/– hosts. Bottom row depicts TMEM119+ MLCs at high magnification. Scale bar=36.5 μm (top 3 rows), 25 μm (bottom row). FIG. 5B: Engrafted GFP+ MLCs 14 days after bone marrow ICT into P1 Csf1r–/– host. Arrowheads indicate non-parenchymal donor cells in the ventricles and choroid plexus, of which virtually all are IBA1 positive (see FIG. S2F). Scale bar=900 μm. FIG. 5C: Histograms show Tmem119 expression in MLCs 14 days after transplantation by flow cytometry, including reduced staining in HSC-derived MLCs.

FIGS. 6A-G: MLC transplantation system. FIG. 6A: Example FACS plots showing CD45/11B staining profile of MLCs across all donor types, with WT littermate control (CTL) to the right for comparison. FIG. 6B: Sort strategy for fetal head donor cell isolation showing FSC/SSC, single cell, live, CD45, and F4/80 gates. FIG. 6C: Sort strategy for fetal liver donor cell isolation showing FSC/SSC, single cell, live, CD45, and CD11B/F4/80 gates, and post-sort purity (large dots shown due to small number of cells collected for purity check). For B-C, numbers in lower left corner of plots shows gate hierarchy (1>2>3>4>5). Cells were sorted from gate 5. FIG. 6D: Lumbar spinal cord section from Csf1r–/– mouse transplanted by ICT at P3 with GFP-expressing WT bone marrow and harvested 14 days later. Scale bar=500 μm. FIG. 6E: MG and MLC density by Iba1 immunostaining across cortical and subcortical regions of engraftment normalized to area, p<0.0001 for effect of donor type on density by ANOVA, *p=0.0001 for pairwise difference between fetal liver and microglia, adjusted for multiple comparisons, p>0.05 for all other comparisons between MLCs and ICT MG control. FIG. 6F: Pertaining to FIG. 2B: IBA1 staining (red) of ventricular donor cells from GFP+ BM, showing that nearly all cells attach to the choroid plexus and are IBA1+. Scale bar=100 μm. FIG. 6G: Table showing relative engraftment levels for ICT experiments (expressed as % recovery of TMEM119+ cells in ICT compared to WT littermate), and percent of parenchymal IBA1+ cells that were also TMEM119+ for histological sections of same samples. Asterisks indicate samples with adequate RNA yield and RNA Integrity Number (RIN) (>7) for RNAseq. YS=yolk sac, Fet Br=fetal brain, Fet Liv=fetal liver, IP=intraperitoneal, BMT=bone marrow transplant, BM=bone marrow, P=brain parenchyma, V=ventricular space.

FIGS. 7A-F: Peripheral bone marrow injection leads to widespread engraftment of donor-derived cells and results in partial rescue of the Csf1r–/– phenotype; both purified monocytes and Ccr2–/– bone marrow cells engraft in the Csf1r–/– brain and express Tmem119. FIG. 7A: Engrafted MLCs 1 month after intraperitoneal (IP) bone marrow injection into P1 host. Scale bar=900 μm. FIG. 7B: Hippocampal section of Csf1r–/– brain stained for IBA1 8 months after IP BMT. Scale bar=400 μm. FIG. 7C: Typical Csf1r–/– mouse showing abnormal head shape, small size (left), compared to 3 months after intraperitoneal bone marrow injection at P2 (right). FIG. 7D: Untransplanted Csf1r–/– mouse lacks teeth (top), while transplanted Csf1r–/– mouse shows tooth growth (bottom). FIG. 7E: Both Ccr2 Rfp/Rfp BM and FIG. 7F: purified BM monocytes engraft in the Csf1r–/– brain and express TMEM119 at T=21 days. Scale bar=100 μm.

FIG. 8A: Csf1r genotyping gel for whole brain and TMEM119 sorted microglia and MLCs.

Green arrows indicate appearance of WT band in Csf1r–/– (KO) whole brain samples following WT donor cell engraftment. WT band has expected migration at 385 BP, KO band at 300 BP. FIG. 8B: Liver section from Csf1r–/– mouse following IP transplantation of GFP-labeled BM, scale bar=50 μm. FIG. 8C: Bar graph showing intensity of IgG and albumin (Alb) staining for Csf1r–/– (KO, n=2) compared to littermate control (CTL, n=3) animals at age P21, expressed as mean fluorescence intensity ratio between stain and control (no antibody for IgG, secondary only for albumin). FIG. 8D: Representative image of ramified IBA1+ (green) CCR2–/– (red) cells showing relatively low (arrowheads) and high RFP expressing cells engrafted in the Csf1r–/– parenchyma. Scale bar=25 μm. FIG. 8E: Representative image of ramified IBA1+(green) cells stained for RFP (red), demonstrating typical abundance of RFP+ cells in a periventricular distribution. V=ventricle. Scale bar=100 μm. FIG. 8F: Pertaining to FIG. 3F: purification strategy for BM monocyte transplantation, showing FSC/SSC, single cell gates, followed by c-kit/CD45 and Lytic/lineage plots before bead enrichment, before FACS, and post-sort. The lineage cocktail included antibodies against CD3, B220, NK1.1, Il7Ra, SiglecF, and GR1. Numbers in lower left corner of plots show gate hierarchy (1>2>3>4). Cells were sorted from gate 4.

FIGS. 9A-G: Ontogeny shapes adoption of microglia transcriptional identity; BM-derived cells show highly similar transcriptomes at 2 weeks compared to 2-3 months of brain residence. FIG. 9A: Heatmap showing log 2 (FC versus WT) expression of microglia (blue), myeloid (orange) and reactivity (red) genes across MLC types. *=FDR<0.05 compared to WT. Grey box indicates that edgeR algorithm could not compute log 2 (FC) due to low read abundance. FIG. 9B: Plot of largest principal components for cultured microglia (purple), WT microglia (dark blue), pooled ICT MG (blue), YS-MLCs (ICT yolk sac, fetal brain; lighter shades of blue), fetal liver MLCs (light orange), and HSC-MLCs (ICT Blood, BM, and BMT; orange/red), using top 2500 most variant genes. Ellipses demarcate 95% confidence interval for assigned clusters. FIG. 9C: Unsupervised hierarchical clustering of microglia, pooled ICT microglia and MLCs by Spearman coefficients using 1000 most variant genes, AU=approximately unbiased p-value using PVclust package, bootstrap n=10000 FIG. 9D: Venn diagram showing differential gene expression between pooled YS- and HSC-MLCs, both compared to pooled ICT-MGs (2-fold cutoff, FPKM>20, FDR<0.05). See also FIG. S5A. FIG. 9E: Volcano plot overlay showing differential gene expression of YS- and HSC-MLCs types compared to ICT-MGs, measured as log 2 (pMLC/pMG). FIG. 9F: Volcano plot overlay comparing MLCs derived from ICT BM at 14 days (red), to MLCs from IP BM at 2-3 months (orange) showing no gross shift in transcriptome difference from MGs. FIG. 9G: MG identity genes do not change between ICT BM (red) and IP BM (orange), see also FIG. S5C. MG=microglia, MLC=microglia-like cell, ICT=intracerebral transplant, HSC=hematopoietic stem cells, YS=Yolk Sac, pYS=pooled YS, Fetal Br=fetal brain, Fetal Liv=fetal liver, IP BM=intraperitoneal bone marrow transplant.

FIGS. 10A-D: Transcriptomic profiling of highly pure myeloid cells reveals similarities and differences between microglia and MLCs in the CNS environment. FIG. 10A: Sorted cell purity heatmap showing expression of brain cell-type specific markers. FIG. 10B: Principal component analysis (PCA) coded by library prep batch (colors) and sequencing run lane (symbols). Ellipses demarcate 95% confidence intervals for samples grouped by batch. FIG. 10C: Correlation heatmap depicting Spearman coefficients between microglia, MLCs from all sources, and myeloid cell types from published datasets. Table identifies source of datasets. FIG. 10D: Scatterplot showing 2 largest principle components for diverse myeloid cells from current and other studies (PCA performed on 2500 most variant genes). Table identifies source of datasets. ICT=Intracerebral transplant, MG=microglia, fetal br=fetal brain donor tissue, fetal liv=fetal liver donor tissue, BM=bone marrow, MG (Cult CTL)=WT microglia purified in parallel to MGs used for culture ICTs, BMT=MLCs derived from peripheral bone marrow transplantation.

FIG. 11: Expression of microglia-enriched gene cassette from Bennett et al 2016 in ICT-MGs, HSC- and YS-MLCs. Columns (left to right) show gene name, FPKM values, Log 2 (fold change) for 3 relevant comparisons, and associated p-values. Colored genes indicate DGE between YS- and HSC-MLCs (2 fold cutoff, FDR<0.05, FPKM>20). Genes colored blue were closer to MG levels in YS-MLCs, while genes colored orange were closer in HSC-MLCs.

FIG. 12: Expression of non-microglia myeloid cell-enriched gene cassette from Bennett et al 2016 in ICT-MGs, HSC- and YS-MLCs. Columns (left to right) show gene name, FPKM values, Log 2 (fold change values) for 3 relevant comparisons, and associated p-values. Colored genes indicate DGE between YS- and HSC-MLCs (2 fold cutoff, FDR<0.05, FPKM>20). Genes colored blue were closer to MG levels in YS-MLCs, while genes colored orange were closer in HSC-MLCs. NA=unable to achieve meaningful statistical comparison based on read counts by edgeR.

FIG. 13: Genes more highly expressed in MLCs from BM ICT at 2 weeks than MLCs from BM IP at 2-3 months. Columns (left to right) show gene name, FPKM values, Log 2 (fold change), and associated FDRs, for all genes with FPKM>20 in at least 1 sample, and Log 2 (FC) of 1 or higher.

FIG. 14: Genes more highly expressed in MLCs from BM IP at 2-3 months than MLCs from BM ICT at 2 weeks. Columns (left to right) show gene name, FPKM values, Log 2 (fold change), and associated FDRs, for all genes with FPKM>20 in at least 1 sample, and Log 2 (FC) of −1 or lower.

FIG. 15A: Normalized Enrichment Scores (NES) from GSEA comparing YS- to HSC-MLCs for enrichment in genes upregulated in Sall1−/− (Sall1 KO UP), Nrros−/− (Nrros KO UP), Amyotrophic Lateral Sclerosis (ALS UP from), AD (AD UP), after LPS treatment (LPS UP1, 2), changed in during development (DEV UP 1, 2 or DEV DOWN1, 2), in culture (CULT DOWN) and WWII genes. *=FDR<0.05. FIG. 15B: Expression plot comparing HSC-MLCs and Sall1−/− microglia, both expressed as log 2 (FC/WT). Red dots highlight genes of interest. r=correlation coefficient, p=p-value for linear regression analysis. FIG. 15C: Apoe gene expression in MGs/MLCs. *=FDR<0.05. FIG. 15D: RNA in situ hybridization for Apoe (red) with IBA1 counterstain in Csf1r−/− brains 14D post-transplantation with BM or MGs. Arrows indicate Apoe+ MLCs. Scale bar=100 µm.

FIG. 16A: Signature gene expression in microglia, HSC- and YS-MLCs. *=FDR<0.05. Error bars depict SEM. FIG. 16B: Sall1 expression (in FPKM) by microglia and MLCs of YS (blue) and HSC (orange) origin. *=FDR<0.05, NS=not significant. Error bars represent SEM. FIG. 16C: Relative expression of myeloid genes in ICT microglia (blue), ICT BM (red, 14 day brain residence), and IP BMT (orange, 2-3 month brain residence). NS indicates no statistical difference between any pairwise comparison. *, FDR<0.05 comparing ICT BM to IP BMT. #, FDR<0.05 comparing ICT BM to pICT MG. %, FDR<0.05 comparing IP BMT to pICT MG. Error bars depict SEM. FIG. 16D: Ingenuity Pathway Analysis® comparing YS- to HSC-MLCs for pathways with −log(p)>5 cutoff (red line). Orange line shows fraction of genes in pathway that are differentially expressed. Orange bars show positive association of pathway with YS-MLCs, blue bars with HSC-MLCs, gray bars represent indeterminate direction of association.

FIG. 17A: FPKM values for HSC- and YS-MLC/MG enriched genes (red-orange and blue bars, respectively). Error bars represent SEM, FDR<0.005 for all genes between YS/MG and HSC groups. FIG. 17B: RNA in situ hybridization showing expression of Ms4a7 or Clec12a (red) in ICT BM- but not YS-MLCs nor ICT MGs. Arrowheads highlight BM-MLCs. Scale bar=50 µm. FIG. 17C: Fluorescent RNA in situ hybridization showing expression of Ms4a7 or Clec12a (red) in ICT BM- but not YS-MLCs nor ICT MGs, co-stained for IBA1 (green). Scale bar=50 µm. FIG. 17D: RNA in situs show persistent expression of Ms4a7 (red) in IBA1+ cells (green) six months after transplantation in HSC-MLCs, but no expression in WT microglia. Scale bar=50 µm.

FIG. 18A: RNA In situ hybridization for Gpr56 (blue) and Ms4a7 (red) in BM-MLCs, ICT MGs. Scale bar=100 µm, arrowheads highlight Ms4a7+ cells. FIG. 18B: Immunostaining shows persistent residence and expression of TMEM119 (red) and IBA1 (green) by MLCs 6 months after transplantation. FIG. 18C: RNA In situ hybridization for Ms4a7 (red) and Cx3cr1 (green) shows absence of Ms4a7+ cells in the brain parenchyma of WT animals at 3 days, 2 months, and 2 years. Arrowheads depict Cx3cr1+/Ms4a7-macrophages in 2 year-old animals, to distinguish from vast autofluorescence. Scale bar=100 µm. (FIG. 18D, FIG. 18F) TMEM119 (red) and donor cell marker (green) expression 2 months after BM ICT into tamoxifen-injected Cx3cr1-CreER; Csf1r fl/fl neonates (FIG. 18D) or adults (FIG. 18F), showing that donor cells intermix with host, ramify and express TMEM119. (FIG. 18E, FIG. 18G) RNA In situ hybridization and protein staining of the same tissue for Ms4a7 (red) and IBA1 protein (green) shows Ms4a7+ macrophages in the same pattern as donor cells from nearby immunostained sections, intermixed with Ms4a7− cells 2 months after neonatal (FIG. 18E) or adult (FIG. 18G) transplantation. Scale bars=100 µm (D, F), 50 µm (FIG. 18E, FIG. 18G).

FIG. 19A: Pervasively engrafted TMEM119+(red) cells from human blood in the Rag2−/-Il2rg−/− hMCSF+/+Csf1r−/− brain parenchyma, co-stained with human cytoplasm marker (hCyto, green). Arrowhead indicates TMEM119− cells at edge of engraftment territory. Scale bar=200 µm. (FIGS. 19B-D) Representative images of MLCs from human blood (FIG. 19B), adult microglia (FIG. 19C), and cultured fetal brain (FIG. 19D), immunostained for human TMEM119 (red), IBA1 (yellow) and human cytoplasmic marker (green). Arrowheads in (FIG. 19B) identify human TMEM119 low/− cells. Scale bar=50 μm. (FIG. 19E) A custom anti-human TMEM119 antibody identifies CD45+/CD11B+ fetal human MLCs 14 days after transplantation into the mouse CNS. Tmem119 staining (blue) is shown compared to isotype control (red). (FIGS. 19F-H) Representative images of MLCs from blood (FIG. 19F), fetal brain (FIG. 19G) and primary human microglia (FIG. 19H) immunostained for human MS4A7 (red) and IBA1 (green). Arrowheads (FIG. 19B, FIGS. 19F-H) mark location IBA1+ cell bodies. Scale bar=100 μm. (FIGS. 19I-K) Representative images from RNA in situ hybridization of post-mortem Alzheimer's disease brain samples, showing (FIG. 19I) rare MS4A 7+(red)/TMEM119+ (green)/IBA1 protein+ (white) macrophages, (FIG. 19J) abundant MS4A7-ITMEM119+/IBA1+ macrophages, and (FIG. 19K) MS4A7+/TMEM119–/ IBA1+ perivascular macrophages. Arrowheads show examples of positive puncta, given abundant autofluorescent signal (puncta in perfect registration) Scale bars=12.5 μm.

FIG. 20A: Mouse anti-hTMEM119 monoclonal clone A16075D does not stain human blood (blue) above isotype control (red) but FIG. 20B does stain most CD45/11B double positive cells from the brain, resolving a mixed double positive population into two otherwise inseparable groups. Numbers in lower left corner of plots shows gate hierarchy (1>2>3>4>5>6). (FIG. 20C) Gating strategy related to FIG. 7E, numbers in lower left corner of plots shows gate hierarchy (1>2>3>4). Histogram in main Figure depicts cells in gate 4 from TMEM119 stained vs isotype control stain. FIG. 20D: Engrafted human blood cells immunostained with antibodies against IBA1 (green) and MS4A7 (red). FIG. 20E: Engrafted human blood cells stained with antibodies against IBA1 (green) and MS4A7 preincubated with molar excess of immunizing peptide (red) FIG. 20F: Human surgical sample stained with antibodies against IBA1 and MS4A7, and overlaid with signal from unstained channel to identify tissue autofluorescence (light yellow in left panel, white in right panel). Scale bar=50 μm. FIGS. 20G-I: Full images of cells shown in FIGS. 71-7K, with area of cropping designated by a white square. Scale bars=25 μm.

DETAILED DESCRIPTION

Overview

Figure 1A:
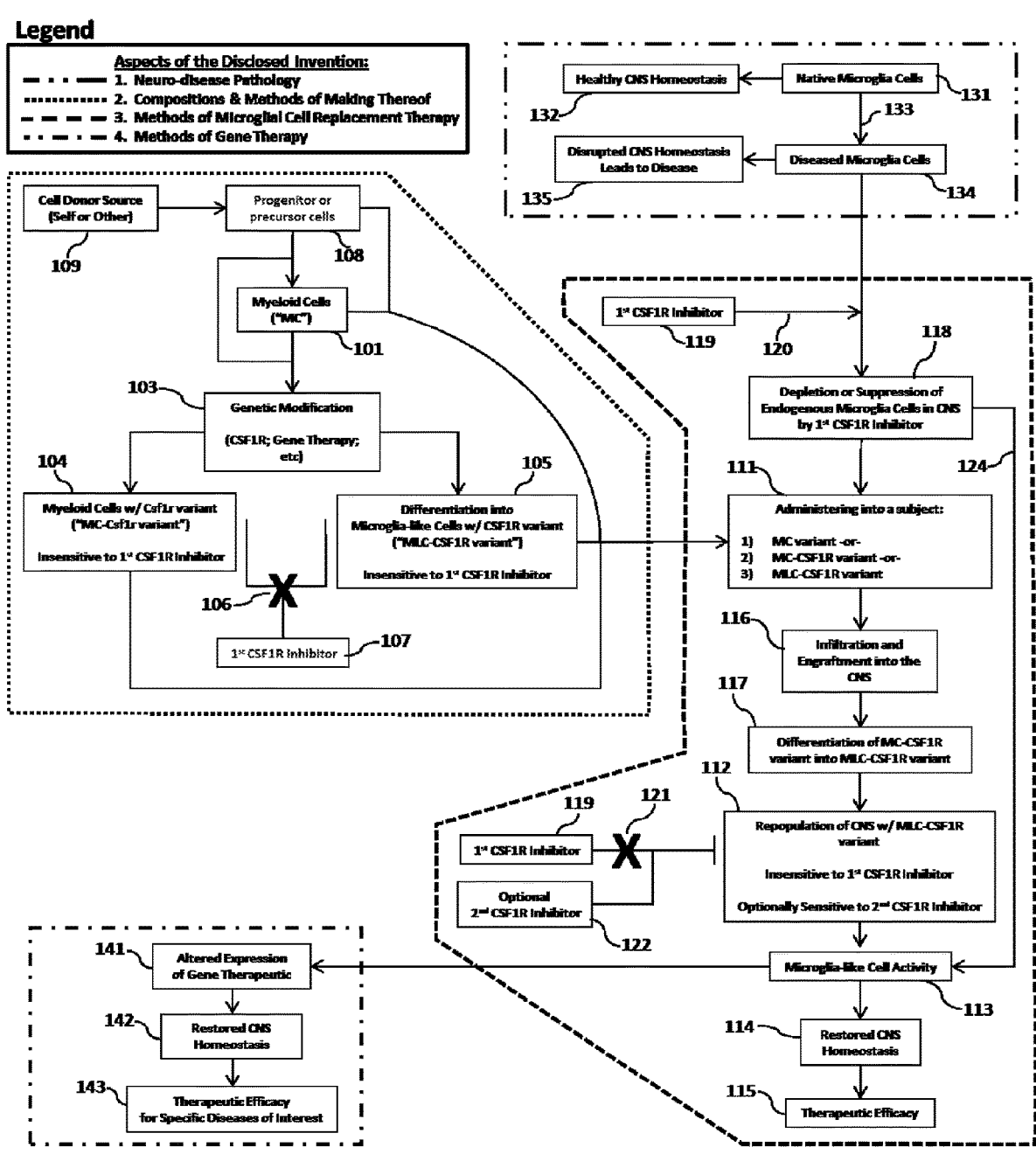
FIG. 1A: Schematic flowchart illustrating various aspects of the disclosure.

Compositions and methods of the disclosure provided herein include myeloid cells (MCs), particularly genetically-modified MCs, which can be used in microglia cell replacement therapy in a subject in need thereof (FIG. 1A, 101). MCs provided herein may differentiate into microglia-like cells (MLCs) in vitro, in vivo, or ex vivo. MCs or MLCs of the disclosure may be genetically modified; in some cases, a certain genetic modification may make the MCs or MLCs resistant to an inhibitor (FIG. 1A, 103) or may reduce the sensitivity of the MCs or MLCs to the inhibitor. In some aspects, the MCs or MLCs may possess a genetically-modified colony stimulating factor 1 receptor (CSF1R; also known as macrophage colony-stimulating factor receptor (M-CSFR) or CD115) variant (FIG. 1A, 104, 105) that is insensitive to a specific CSF1R inhibitor (FIG. 1A, 106) or to all CSF1R inhibitors, or to one or more receptor tyrosine kinase inhibitors. In some cases, the CSF1R variant may be insensitive to a CSF1R inhibitor, yet remains capable of interacting with its corresponding ligands (e.g., colony stimulating factor 1 (CSF1), interleukin-34 (IL-34)) and thus retains at least some functionality. In some instances, the genetically-modified MCs and MLCs provided herein do not have an undue risk of eliciting an immune reaction in the subject.

In some cases, MCs or MLCs may include, but are not limited to, one or more myeloid lineages derived from a myeloid progenitor cell or a myeloid precursor cell (FIG. 1A, 108) obtained from a donor source (FIG. 1A, 109). The donor source may be an autologous source such as the subject in need thereof. In some cases, the donor source may be a different subject or animal. In some cases, the donor source may be an induced pluripotent stem cell, such as an induced pluripotent stem cell derived from a somatic cell (e.g., a blood cell, a fibroblast) of the subject.

Figure 1B:
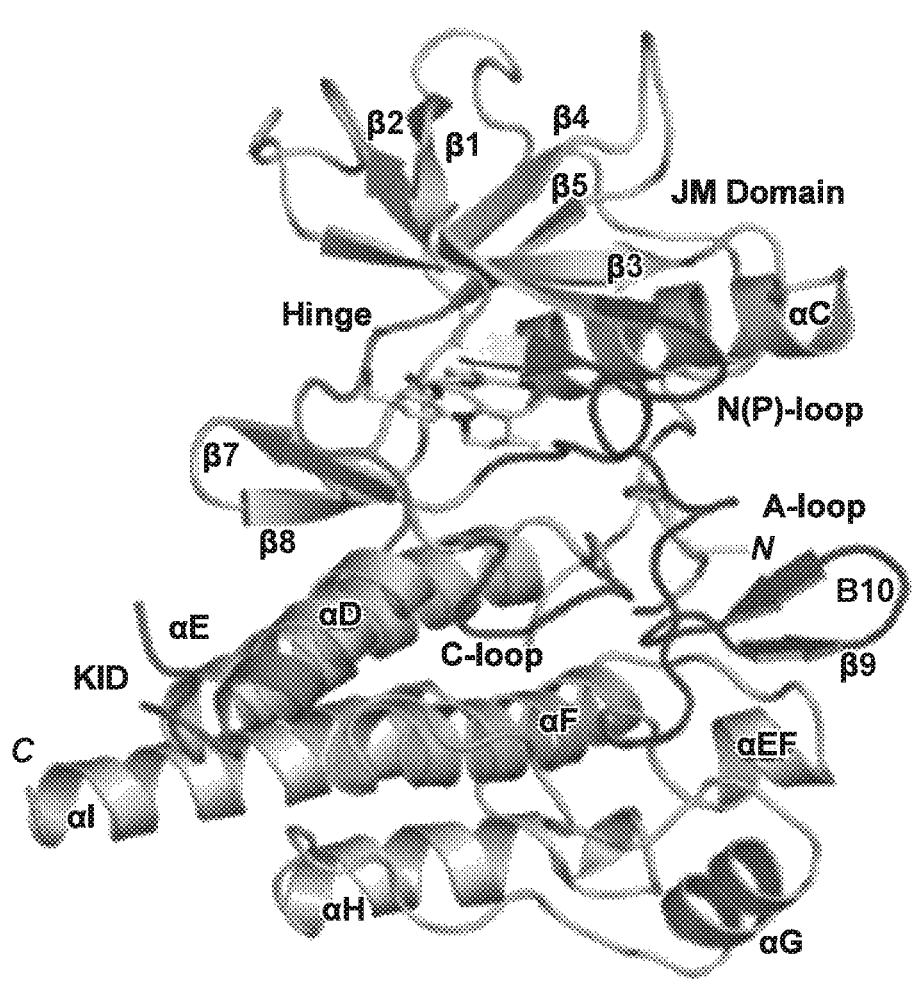
FIG. 1B: Crystallographic structure of CSF1R (Protein Data Bank (PDB): 4R7H) bound to PLX-3397 (Pexidartinib) inhibitor with various structural regions notated.
Figure 1C:
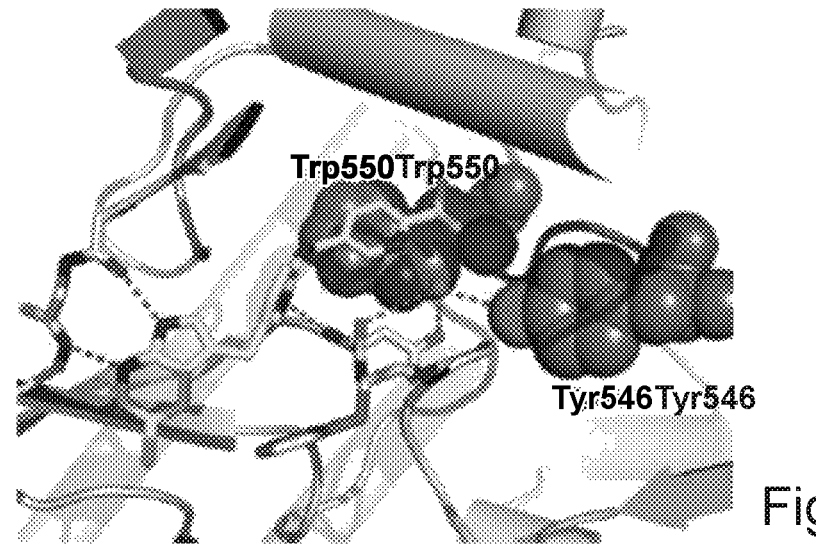
FIG. 1C: Expanded crystallographic structural view of CSF1R residues Tyr456 and Trp550 binding interactions with PLX-3397 (Pexidartinib) inhibitor.
Figures 1D, 1E, 1F:
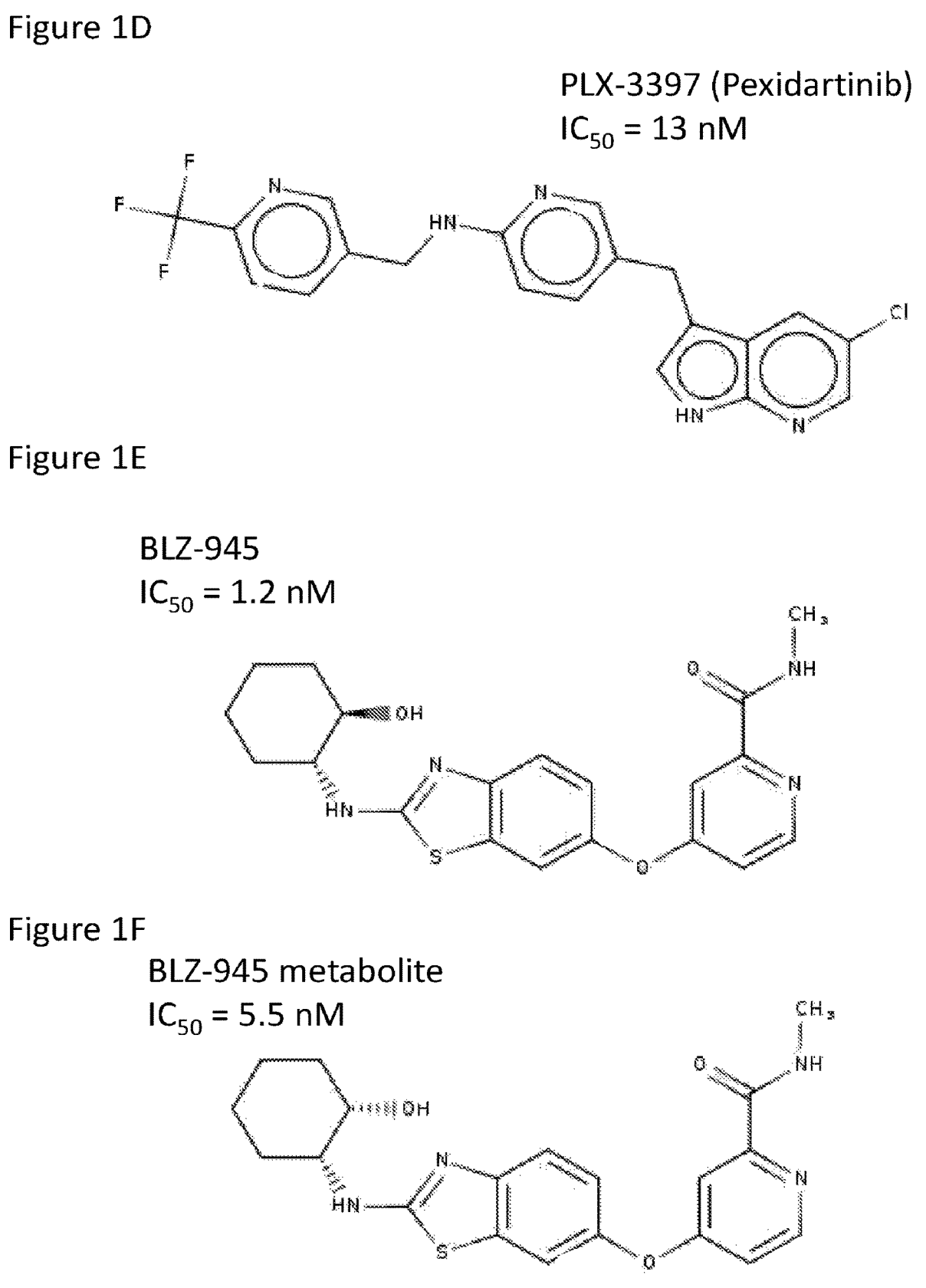
Figures 1G, 1H:
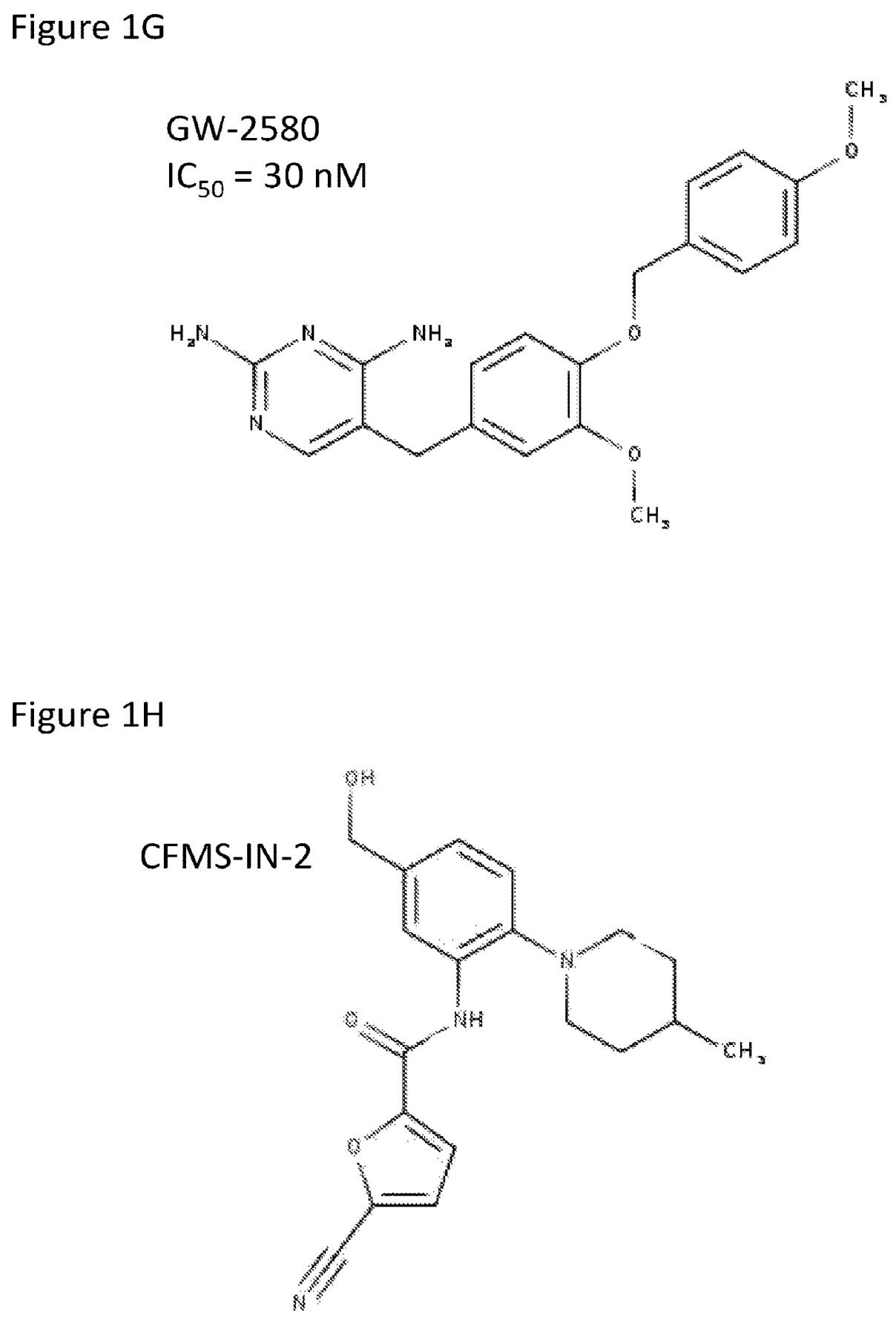
Figures 1I, 1J, 1K:
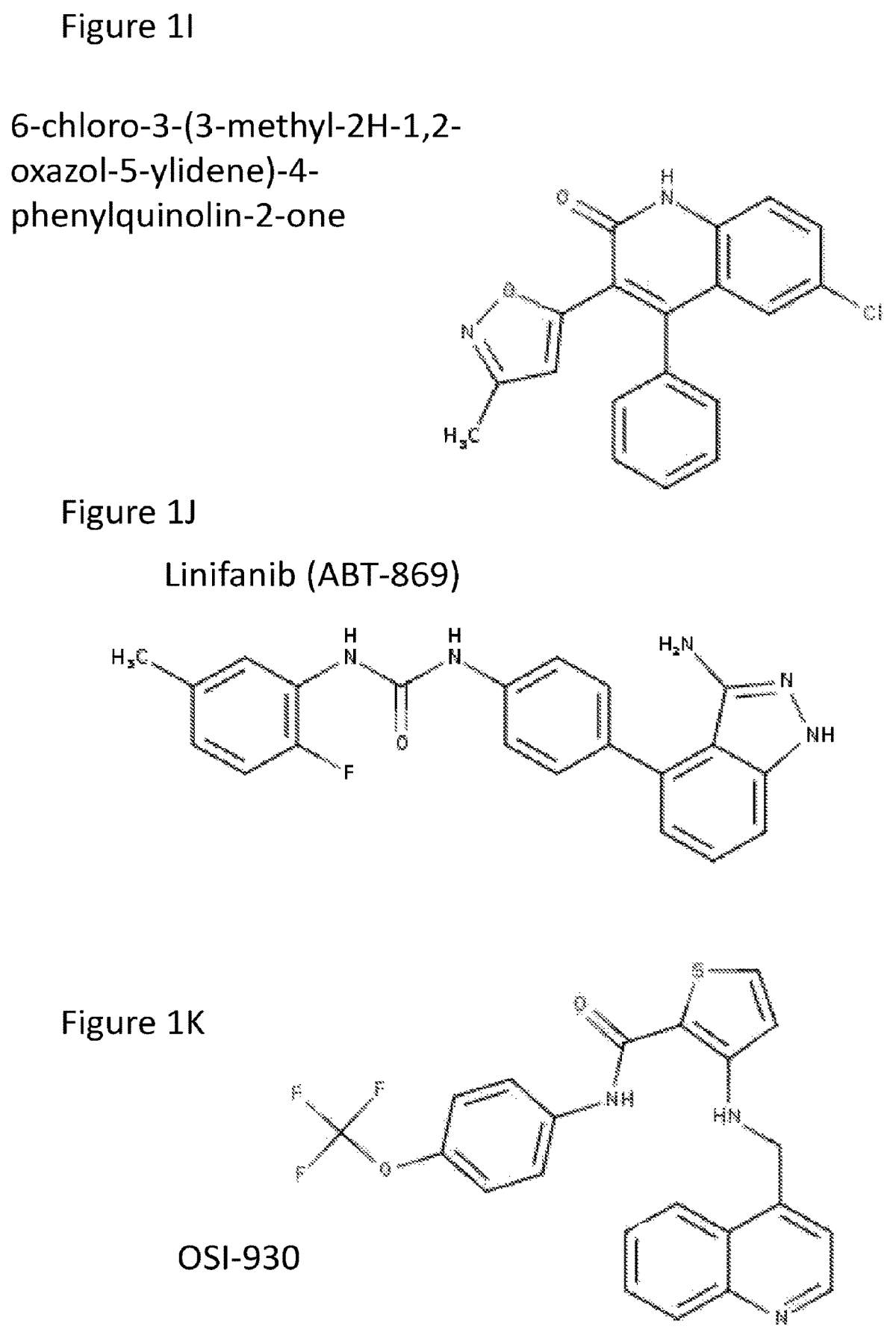

In some cases, crystallographic structures of CSF1R bound to known inhibitors can be used to identify key residues involved in inhibitor binding (FIGS. 1B, 1C). In some cases, exemplary CSF1R inhibitors may include pexidartinib (PLX-3397), PLX-7486, PLX-5622, ARRY-382, BLZ945, DCC-3014, AMG-820, GW-2580, linifanib (ABT-869), OSI-930, or any metabolites thereof. FIGS. 1D-1K depict chemical structures of exemplary CSF1R inhibitors (e.g., FIG. 1D depicts pexidartinib (PLX-3397); FIG. 1E depicts BLZ-945; FIG. 1F depicts BLZ-945 metabolite; FIG. 1G depicts GW-2580; FIG. 1H depicts CFMS-IN-2; FIG. 1I depicts 6-chloro-3-(3-methyl-2H-1,2-oxazol-5-ylidene)-4-phenylquinolin-2-one; FIG. 1J depicts linifanib (ABT-869); and FIG. 1K depicts OSI-930).

In some cases, the MCs or MLCs, genetically modified or unmodified, may be administered to a subject (FIG. 1A, 111) for the treatment of a neurological disease or disorder. In some cases, the MCs or MLCs can be introduced into the CNS of a subject in need thereof. In some cases, the MCs or MLCs may be administered systemically to the subject in need thereof, such as by introduction into the bloodstream of the subject in need thereof. In some instances, MCs or MLCs may be transplanted into the CNS of a subject, such as by transplantation into the brain of the subject. In some cases, the MCs or MLCs may be introduced into the subject via intracerebroventricular injection (ICVI).

In healthy CNS tissue, native microglia cells generally maintain proper CNS homeostasis (FIG. 1A, 132). Conversion (FIG. 1A, 133) of healthy microglia cells into a diseased state (FIG. 1A, 134) disrupts CNS homeostasis and may lead to a neurological disease or disorder (FIG. 1A, 135). In some aspects of the disclosure, following administration, the MCs or MLCs may populate within the CNS (FIG. 1A, 112), whereby they may restore normal, healthy microglia cell activity (FIG. 1A, 113). In such cases, restored microglia cell activity may repair CNS homeostasis (FIG. 1A, 114) which may provide therapeutic efficacy (FIG. 1A, 115) in the treatment of a neurological disease or disorder of interest.

In some aspects, MCs or MLCs as described herein may be used to replace or supplement host microglia cells upon administration to a subject in need thereof. In some cases, transplanted MCs can replace or offset host endogenous microglia cells by differentiating into MLCs. In some cases, host endogenous microglia cells may be missing, inactive, or in a pathological state associated with a neurological disease or disorder. In some cases, MCs or MLCs introduced into a subject in need thereof can prevent, reduce, or eliminate symptoms and signs of a neurological disease or disorder by replacing or offsetting the activity or lack of activity associated with host diseased microglia cells.

In some cases, the introduced MCs or MLCs can infiltrate and engraft into host CNS tissues (FIG. 1A, 116). In some instances, engrafted MCs may differentiate into MLCs within the host CNS tissues (FIG. 1A, 117). In some cases, engraftment of MCs or MLCs into host tissues may lead to repopulation of the host CNS by the MCs or MLCs (FIG. 1A, 112). To facilitate MC or MLC engraftment, host endogenous microglia cells may, in some instances, be depleted, suppressed, or modulated (FIG. 1A, 118).

In some cases, a microglia cell inhibitor or antagonist may be used to deplete, suppress or modulate the host endogenous microglia cells. In some cases, the microglia cell inhibitor or antagonist may be a receptor tyrosine kinase inhibitor that is able to deplete, suppress, or modulate the host endogenous microglia cells. In particular cases, the microglia cell inhibitor or antagonist may be a CSF1R inhibitor or antagonist (FIG. 1A, 119) that is able to deplete, suppress or modulate the host endogenous microglia cells, as such cells are generally sensitive to CSF1R inhibitors or antagonists (FIG. 1A, 120). In some instances, the genetically-modified MCs or MLCs introduced into the subject possess a genetic variant that is insensitive to the microglia cell inhibitor or antagonist (FIG. 1A, 121) that is used to deplete, suppress, or modulate the host endogenous microglia cells. In some instances, the genetically modified MCs or MLCs introduced into the subject possess a CSF1R variant that is insensitive to a CSF1R inhibitor (FIG. 1A, 121) that is used to deplete, suppress, or modulate host endogenous microglia cells. In some cases, the genetically-modified MCs or MLCs are resistant, or have reduced sensitivity to, a plurality of different CSF1R inhibitors, a plurality of different receptor tyrosine kinase inhibitors, all CSF1R inhibitors, or all receptor tyrosine kinase inhibitors.

In some cases, the genetically-modified MCs or MLCs may possess a first genetic variant that makes them insensitive to a first inhibitor and a second genetic variant that makes them sensitive to a second inhibitor. In such cases, the first inhibitor may be used to deplete endogenous microglia cells, with minimal impact on the genetically-modified MCs or MLCs introduced into the subject; and, the second inhibitor may be used to regulate the levels of MCs or MLCs in the subject, such as by depleting, suppressing, or inactivating them if needed. For example, the genetically modified MCs or MLCs possessing a CSF1R variant may be insensitive to a first CSF1R inhibitor (FIG. 1A, 119) but not to a second CSF1R inhibitor (FIG. 1A, 122). In such cases, the first CSF1R inhibitor may have little or no effect on the genetically-modified MCs or MLCs; and the second CSF1R inhibitor may be used to deplete, suppress, or modulate the genetically-modified MCs or MLCs introduced into the subject. As such, the second CSF1R inhibitor may be used to deplete the population of genetically-modified MCs or MLCs in the subject if the introduced MCs or MLCs are not therapeutically effective in the subject or cause an adverse reaction in the subject. In some cases, the second CSF1R inhibitor may be used to maintain microglia homeostasis or prevent overgrowth of the genetically-modified microglia cells.

In some cases, the MCs or MLCs, as described herein, may be further genetically-modified in addition to, or separate from, the genetically-modified CSF1R variant (FIG. 1A, 103). In some cases, the MCs or MLCs may possess additional genetic modifications to microglia genes or other genes of interest that enhance cell viability, growth, or activity. These genetically modified genes may be endogenous to or exogenously introduced into the MCs or MLCs.

In some cases, the MCs or MLCs may be further genetically-modified to be sensitive or insensitive to endogenous or exogenous stimuli within the CNS of a subject. Such genetic modification may enable the growth or activity of the MCs or MLCs to be selectively controlled.

In some cases, the MCs or MLCs of the disclosure can be genetically modified to modulate the expression of a gene or protein associated with a neurological disease or disorder (FIG. 1A, 141), particularly to correct a phenotype caused by a genetic defect. In some cases, the modulated gene or protein expression can restore CNS homeostasis (FIG. 1A, 142) which may provide therapeutic relief (FIG. 1A, 143). In some instances, the gene or protein expression can be increased to provide therapeutic relief associated with the gene or protein. In some cases, the gene or protein expression can be repressed to decrease detrimental effects associated with the gene or protein. As a non-limiting example, MCs or MLCs may be genetically modified to decrease the expression of Apolipoprotein E (ApoE) associated with Alzheimer's disease. In some instances, decreased ApoE expression may provide therapeutic benefits to a subject with Alzheimer's disease. In some cases, the gene may be associated with a different neurological disease or disorder such as Huntington's disease, Parkinson's disease, or any other neurological disorder.

Definitions

The term "about" generally refers to a range which encompasses up to 10% greater than or less than a stated numerical value. Therefore, for example, a statement of "about 10" is to be read as a range encompassing from 9 to 11, for instance.

The term "or", as used herein, is intended to signify "and/or". The use of "or" throughout the disclosure is interpreted as having a meaning that encompasses multiple variations of any grouping of a stated composition or method. For example, the phrase "MC or MLC" may be nonexclusively read as meant to include "MC but not MLC", "MLC but not MC", and "MC and MLC" unless otherwise specified or indicated by context.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, *Proc. Natl. Acad. Sci. USA,* 87:2264-2268 (1990) and as discussed in Altschul, et al., *J. Mol. Biol.,* 215:403-410 (1990); Karlin And Altschul, *Proc. Natl. Acad. Sci. USA,* 90:5873-5877 (1993); and Altschul et al., *Nucleic Acids Res.,* 25:3389-3402 (1997). The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, *Computers and Chemistry* 17:149-163 (1993).

The terms "administer", "introduce", or "transplant" are generally used herein to encompass any technical means or methodologies of placing compositions of the disclosure (e.g., myeloid cells, microglia cells, or CSF1R inhibitors) into the body of a subject in need thereof. For example, myeloid cells may be administered into the CNS by intravenous injection into the blood of a subject. In some cases, the method involves administering myeloid cells to the CNS of a subject. In some cases, the cells are directly injected into the CNS (e.g., brain, spinal cord) or the bloodstream of the subject. In some cases, administered MCs provided herein may differentiate into MLCs in vitro, in vivo, or ex vivo. Alternatively, for example, myeloid cells may be injected intracerebroventricularly into the brain parenchyma of a subject. As a further, non-limiting example, compositions, formulations, and methods of the disclosure may be inserted into the CNS of a subject as a liquid solution, as a semi-solid biomaterial, or as a solid biomaterial.

The term "microglia-like cells" and "MLCs" are used interchangeably and refer specifically to myeloid cell progeny that resemble natural microglia cells, but differ from natural microglia cells in at least one aspect. For example, the microglia-like cells may be genetically-modified. The microglia-like cells may also have gene expression signatures that are distinguishable from that of natural microglia cells. In some instances, the microglia-like cells are ramified or actively phagocytic in nature. In some cases, MLCs express CD45 and/or CD11B at a higher level than a non-immune cell. In some cases, MLCs are capable of phagocytosis.

The terms "subject", "host", or "patient" are used interchangeably herein to refer to a vertebrate, preferably a mammal, and more preferably a human. Mammals include, but are not limited to, rodents (e.g., mice, rats, rabbits, etc.), simians, humans, non-human animals, non-human primates, primates, research animals (e.g., beagles, etc.), livestock animals, farm animals (e.g., pigs, horses, cows, etc.), sport animals, veterinary animals, and pets.

Generally, the terms "populate" or "repopulate" as used herein encompass the population growth of myeloid cells or microglia cells following transplantation into a subject in need thereof. Both terms may be used interchangeably where appropriate. For example, where host endogenous microglia cells are not missing or depleted, the growth of introduced myeloid cells may be described in terms of "populating". Conversely, where host endogenous microglia cells are missing or depleted, the growth of introduced myeloid cells may be described in terms of "repopulating".

The terms "treat", "treating", and "treatment" as used within this disclosure are meant to encompass any improvement in the signs or symptoms of a subject and also may encompass prophylactic or preventative or protective benefits. Improvement may cover any range of change from a measured numerical value indicative of the severity of signs and symptoms for a neurological disease. For example, the improvement may be measured as a percentile change or a fold-change from a stated numerical value prior to treatment or as compared to a subject treated with a placebo.

The terms "therapeutically effective amount" generally refers to any amount or range of a therapeutic agent which elicits a therapeutic response in a subject with a neurological disease or disorder. In some cases, the therapeutic response can be the alleviation of one or more symptoms. In some cases, a therapeutic response may be a preventative treatment of a disease or a disorder. In some cases, the "effective amount or dose" may be that which is necessary or sufficient to produce a therapeutic response within the subject. Such an amount or dose may vary depending on the therapeutic agent used within the subject, as well as subject factors including, but not limited to age, weight, height or general health of the subject in need of treatment.

The terms "formulated", "prepared", or "mixed" generally refer to a formulation containing a composition as described and provided within the disclosure which contains a technical element or limitation that renders said composition suitable for use in a subject in need thereof. Such formulations contain additional elements or limitations that further distinguish the composition over other compositions that lack such technical elements or limitations. In some non-limiting examples, the formulation may comprise a CSF1R inhibitor used for the depletion, suppression, or modulation of host microglia.

The term "unit dose" when used in reference to a therapeutic composition or method of using a therapeutic composition generally refers to physically discrete units suitable as unitary dosage for humans. Each unit dose contains a predetermined quantity of active material calculated to produce the desired therapeutic effect in association with the required diluent; e.g., carrier, or vehicle.

The term "sensitive" and "sensitivity" as used herein means that an entity is capable of responding to a signal. For example, a receptor may be sensitive to its natural ligand, meaning that the receptor is capable of responding to an interaction with a ligand.

The term "insensitive" and "resistant" are used interchangeably herein and, when used in relation to a receptor variant of the disclosure, refers to the variant having a reduced sensitivity to an agonist or an antagonist as compared to a receptor not having the variant. For example, a CSF1R variant of the disclosure may be insensitive to a CSF1R inhibitor, meaning that the CSF1R variant has reduced sensitivity to the CSF1R inhibitor as compared to a CSF1R receptor without the variant (e.g., a wild-type CSF1R). Similarly, the term "insensitive", when used in relation to a genetically-modified cell of the disclosure, refers to the genetically-modified cell having a reduced sensitivity to an agonist or an antagonist as compared to a cell not comprising the genetic modification. "Insensitivity" can encompass both complete insensitivity and partial insensitivity.

Myeloid Cells and Microglia-Like Cells

The myeloid cells (MCs) and microglia-like cells (MLCs) provided herein may be used for the treatment of a neurological disease or disorder in a subject in need thereof, particularly by replacing microglia cells in a subject in need thereof. In some cases, the myeloid cells are genetically modified. The genetic modification may include a CSF1R variant that is resistant to a CSF1R inhibitor, yet retains sensitivity to its ligand (e.g., CSF1, IL-34). In some cases, the MCs are not genetically modified. For example, in some cases, the MCs or MLCs may be generated in vitro, prior to administration to the patient.

In some cases, MLCs may be derived from yolk-stem cells (e.g., fetal brain) and may possess a gene expression profile that more closely resembles microglia cells than that seen for MLCs derived from HSCs (e.g., from blood or bone marrow) or MLCs derived from a mixed origin (e.g., fetal liver). In some cases, the myeloid cells may be derived from embryonic or extraembryonic tissue. In some cases, the myeloid cells may be derived from postnatal tissue.

The MCs (or cells of a myeloid lineage) provided herein may include microglia, monocytes, bone marrow cells, blood cells, yolk sac cells, fetal brain macrophages, fetal liver macrophages, or any other myeloid-lineage cells. In some cases, MCs may be one or more lineages of blood cells arising from multipotent hematopoietic stem cells (HSCs) that are involved in dendritic cell formation. During hematopoiesis, a common myeloid progenitor cell arises along with a common lymphoid progenitor cell that differentiates into the lymphoid cell lineage comprising of T cells, B cells, and natural killer (NK) cells. In some cases, myeloid progenitor cells can differentiate into multiple cell types and lines including monocytes, macrophages, neutrophils, basophils, eosinophils, erythrocytes, megakaryocytes which produce thrombocytes, and mast cells. Differentiation and proliferation of myeloid progenitor-derived cells can be influenced by a variety of growth factors and cytokines. In some cases, specific combinations of growth factors and cytokines may help control the differentiation pathway potential for myeloid progenitor cells.

In general, this disclosure provides MCs that are myeloid progenitor cells capable of differentiating into microglia or microglia-like cells in vitro, ex vivo, or in vivo. As described herein, in some aspects, the MCs may be myeloid progenitor cells that can differentiate into microglia or MLC cells after administration to a subject in need thereof.

In some cases, the MCs or MLCs may possess a gene expression profile similar to those of normal, healthy, or natural microglia cells (e.g., the microglia sensome/phenotype). In some cases, MCs or MLCs may express genes or proteins that are specific to microglia. For example, MCs or MLCs may express the following microglia specific gene biomarkers: Tmem119, P2ry12, Olfml3, Sall1, Gpr34, Gpr56, and Gpr84, or any subset thereof. In another example, MCs or MLCs may express the following microglia specific protein biomarkers: transmembrane protein 119 (TMEM119), P2Y purinoceptor 12 (P2RY12), olfactomedin-like protein 3 (OLFML3), Sal-like protein 1 (SALL1), G protein-coupled receptor 34 (GPR34), G protein-coupled receptor 56 (GPR56), and G protein-coupled receptor 84 (GPR84), or any subset thereof. In some cases, MCs or MLCs may express one or more additional gene biomarkers including, but not limited to, Cd45, Cd11b, Iba1, Clec12a, Ms4a7, Lilra5, Klra2, or any combination thereof. In some cases, MCs or MLCs may express one or more additional protein biomarkers including, but not limited to, cluster of differentiation 45 (CD45), cluster of differentiation 11B (CD11B), ionized calcium binding adapter molecule 1 (IBA1), C-type lectin domain family 12 member A (CLEC12A), membrane-spanning 4-domains subfamily A (MS4A7), leukocyte immunoglobulin-like receptor subfamily A member 5 (LILRA5), killer cell lectin-like receptor 2 (KLRA2), or any combination thereof. In some cases, the cells may express genes or proteins that are more specific to microglia cells than those expressed in microglia cells derived from HSCs. In some cases, the MCs or MLCs introduced into a subject may be conditioned by the CNS to express microglia specific genes or proteins.

Unlike native microglia cells, the MCs or MLCs of this disclosure, may, in some instances, relocate and infiltrate into the CNS by passing through a blood-brain barrier (BBB) of a host subject (e.g., a human subject). Thus, in some instances, a method provided herein may involve administering the MCs or MLCs outside of the CNS and allowing the MCs or MLCs to pass through the BBB and relocate to the CNS.

An open niche for brain macrophages may enable transplanted cells to engraft in the brain parenchyma. In some cases, inhibiting a function of CSF1R in a population of microglia cells may lead to depletion of the population of microglia cells. For example, Csf1r−/− (knock-out (KO)) mice as described herein lack microglia and therefore may have an open macrophage niche in the brain. It is generally not possible to genetically modify humans, however, CSF1R small molecule inhibitors (e.g., receptor tyrosine kinase inhibitors) may be used to deplete microglia from the brain (e.g., in a human subject), thereby opening the appropriate niche for transplanted cells. In one aspect of the disclosure, a host microglia population may be depleted from a subject by administration of a CSF1R inhibitor, thereby opening a niche for transplanted cells to engraft and repopulate the niche. Upon cessation of treatment with CSF1R inhibitors, microglia may rapidly repopulate from internal pools of host microglia, and in some cases, these repopulating cells may out-compete transplanted cells injected into the brain. Furthermore, neonatal pups treated with CSF1R inhibitor in utero develop what appears to be massive neuroinflammation after transplantation.

In some cases, donor cells (e.g., MCs or MLCs) may be introduced into a mouse (e.g., a Csf1r−/− (KO) mouse). In some cases, the donor cells can engraft in the mouse brain, attain a morphology similar to microglia, and express genes and proteins thought to be highly specific to microglia (and not expressed by other macrophages). In some cases, a Csf1r−/− CNS can be sufficient to sustain, induce, or re-induce microglia identity, and that microglia identity potential persists despite dramatic transcriptional perturbations induced ex vivo. This shows that the brain environment can induce a microglia phenotype in many kinds of macrophages. Furthermore, transplanted cells may fill the entire brain, demonstrating that transplanted macrophages may replace host microglia. In diseases where microglia contribute to pathology, diseased microglia may be replaced with healthy donor cells to treat disease. Thus, some aspects of the disclosure may involve replacing diseased microglia with healthy donor cells to treat disease. In another aspect of the disclosure, modified donor cells (e.g., over-expressing a deficient enzyme, or an immune modulator) may be transplanted into a subject in order to deliver therapeutics directly to the brain using cell therapy.

MCs or MLCs may be genetically modified or engineered with nucleic acid or protein sequences of interest. Alternatively, in some cases, MCs or MLCs may be genetically unmodified. In some cases, MCs or MLCs may be genetically engineered to express one or more endogenous or exogenous genes or proteins which may be specific or non-specific to microglia cells. In some cases, the expression of genetically modified genes or proteins may aid in the therapeutic efficacy. In some cases, these modified genes or proteins may enhance activity, proliferation, and/or survival. In some cases, these modified genes or proteins may confer new therapeutic properties useful in treating a neurological disease or disorder in a subject in need thereof. The expressed genes or proteins of the genetically modified MCs or MLCs may be further specific to HSCs or non-HSCs. Modified MCs or MLCs provided herein may comprise MCs or MLCs that have genetically modified receptors.

In one aspect of the invention, MCs or MLCs, as described herein, may possess a genetically modified receptor tyrosine kinase (RTK) which may include, but is not limited to, CSF1R. In some cases, this disclosure provides methods of engineering custom CSF1 receptors that signal normally, but are resistant to one or more CSF1R inhibitors. In some cases, this disclosure provides custom or genetically-modified CSF1 receptors that signal normally, but are resistant to CSF1R inhibitors. Genetically, modified residues may be identified based on a crystal structure for an inhibitor bound to CSF1R. The genetically modified residues may also be identified from or present in the genomic sequences for RTK resistant tumors.

When introduced into donor cells, the custom receptors provided herein may allow donor microglia to preferentially survive in the brain during treatment with CSF1R inhibitors, while host cells expressing wild-type CSF1R may be affected by the inhibitor and therefore depleted, thereby allowing the donor cells to colonize the brain without interference from the host cells. In some aspects, this disclosure provides myeloid cell-based therapies for brain disease. In some cases, the methods involve replacing host microglia (e.g., human microglia) with donor cells. In some cases, the donor cells may be cells isolated from the subject and modified ex vivo to correct a genetic mutation. Additionally or alternatively, the donor cells may be cells engineered to overexpress one or more therapeutic molecules. In some cases, the crystal structure for a CSF1R inhibitor complexed with CSF1R may be used to identify candidate residues that may be mutated in CSF1R in order to confer resistance to the inhibitor.

In some cases, diseased MCs may be obtained from a subject with a neurological disease or disorder, wherein the obtained MCs may be genetically modified to correct the causative factor of said neurological disease or disorder. In some instances, these genetically modified cells may be further modified. In some cases, these genetically modified cells may be administered back into the host subject. Repopulation of the host CNS with these corrected MCs or MLCs may provide therapeutic efficacy in treating the neurological disease or disorder of the host subject.

Receptor Tyrosine Kinases

In some aspects, MCs and subsequently differentiated MLCs, as described herein, may contain a genetically modified receptor tyrosine kinase (RTK). RTKs are a diverse collection of high affinity cell surface receptors involved in regulating cellular processes. Expressed RTKs are sensitive to growth factors, cytokines, and hormones. As described herein, in one aspect of the disclosure, MCs or MLCs may contain one or more genetically modified RTKs. MCs or MLCs containing a genetically modified RTK may be useful, e.g., in the treatment of a neurological disease or disorder in a subject in need thereof. MCs or MLCs may be genetically modified to express a genetically modified RTK. In some cases, the genetically modified RTK may be a class III RTK. In some instances, the class III RTK may include, but is not limited to, platelet-derived growth factor receptor a (PDGFRα), platelet-derived growth factor receptor 0 (PDGFRβ), C-KIT proto-oncogene (C-KIT), receptor-type tyrosine-protein kinase FLT3 (FLT3), CSF1R, or any combination thereof. In some instances, the MCs or MLCs may contain one or more specific genetically modified variants of CSF1R.

In some cases, the genetically modified RTK possesses normal ligand-dependent signaling. In some cases, the genetically modified RTK possesses normal ligand-independent signaling. In some cases, the genetically modified RTK may be sensitive to one or more endogenous RTK ligands. In some cases, the genetically modified RTK may be insensitive to one or more endogenous RTK ligands. In some cases, the genetically modified RTK may be sensitive to one or more RTK inhibitors or antagonists. In some cases, the genetically modified RTK may be insensitive to one or more RTK inhibitors or antagonists. In some instances, the genetically modified RTK may be sensitive to one or more tyrosine kinase inhibitors (TKI). In some instances, the genetically modified RTK may be insensitive to one or more tyrosine kinase inhibitors (TKI). In some instances, the genetically modified RTK may be sensitive to one or more anti-RTK antibodies. In some instances, the genetically modified RTK may be insensitive to one or more anti-RTK antibodies.

In some cases, the RTK may be genetically modified with one or more amino acid substitutions that increases or decreases sensitivity to an RTK inhibitor. Similarly, in some cases, the RTK may be genetically modified with one or more amino acid substitutions that increases or decreases binding to an endogenous or exogenous RTK ligand. In some cases, the one or more amino acid substitutions within the genetically modified RTK can increase or decrease ligand-dependent or ligand-independent signaling. In some cases, the one or more amino acid substitutions within the genetically modified RTK may decrease the signaling activity associated with a neurological disease or disorder. In addition to or separately from the genetically modified RTK, MCs or MLCs, as provided herein, can contain additional genetic modifications. In some cases, these additional genetic modifications may be independent of the modified RTK (e.g., a genetic modification in a gene or protein other than the RTK). In some cases, the additional modifications may increase or decrease MC or MLC viability, growth, or functional activity. Additionally, in some aspects, the additional genetic modifications can correct for a neurological disease or disorder. For example, the additional genetic modifications can include the inactivation or removal of a causative factor for a neurological disease or disorder. In another example, the additional genetic modifications can include the introduction of a therapeutic factor against a neurological disease or disorder.

Colony-Stimulating Factor 1 Receptor (CSF1R)

As described in the disclosure, MCs or MLCs can contain one or more genetically modified CSF1R variants. Microglia cells may be dependent upon signaling from ligand binding to CSF1R. In some cases, loss of ligand binding to CSF1R can cause rapid depletion of microglia cells within the CNS which can affect CNS homeostasis. However, subsequent gain of ligand binding to CSF1R may allow for microglia cell repopulation which may restore CNS homeostasis.

Therefore, in some cases, disruption of endogenous ligand-CSF1R binding can be used to control the levels of host endogenous microglia cells within the CNS of a subject. Depletion of host endogenous microglia cells may be useful for the treatment of neurological diseases and disorders associated with absent, inactive, senescent, and/or pathologically abnormal host endogenous microglia cells. Furthermore, depletion of endogenous microglia cells may provide a niche environment opening in which introduced MCs or MLCs can engraft and repopulate within the CNS of a subject. In some cases, the introduced MCs or MLCs may be modified to possess properties of interest. Replacement of host endogenous microglia cells with the introduced exogenous MCs or MLCs may be useful in the treatment of neurological diseases and disorders wherein abnormal CNS homeostasis is stabilized into a normal, healthy homeostatic condition.

CSF1R, also known as macrophage colony-stimulating factor receptor (M-CSFR) or cluster of differentiation 115

(CD115), is encoded by the CSFR1 gene. CSF1R is a 108 kDa tyrosine kinase transmembrane receptor comprising 972 amino acids which may be expressed in a variety of cells and tissues including, but not limited to, whole blood, monocytes, myeloid cells, natural killer (NK) cells, dendritic cells, various CNS tissues, heart tissue, lung tissue, and placental tissue. As a single pass type I transmembrane protein, CSF1R may act as the receptor for cytokine colony-stimulating factor 1 (CSF1) ligand. CSF1 is a 56 kDa extracellular hematopoietic growth factor which may control the production, differentiation, survival, and functional activity of macrophages, monocytes, and bone marrow progenitor cells. In some cases, CSF1 binding to CSF1R may lead to receptor oligomerization and trans-phosphorylation. CSF1 ligand binding may, in some cases, cause an increased phagocytic, chemotactic, and/or tumor cytotoxic activity in receptor associated cells. In some cases, CSF1 may also modulate the proliferation of hematopoietic progenitor cells.

CSF1-CSF1R binding and subsequent signaling events may be important to microglia cell survival and activity. In some cases, CSF1R activation by CSF1 can lead to phosphorylation of targets including, but not limited to, phosphatidylinositol 3-kinase regulatory subunit alpha (PIK3R1), 1-phosphatidylinositol 4,5-bisphosphate phosphodiesterase gamma-2 (PLCG2), growth factor receptor-bound protein 2 (GRB2), src-like-adapter 2 (SLA2), and E3 ubiquitin-protein ligase CBL (CBL). In some instances, PLCG2 activation may lead to production of the cellular signaling molecules diacylglycerol and inositol 1,4,5-trisphosphate. In some instances, these signaling molecules in turn may lead to the activation of protein kinase C (PKC) family members, particularly protein kinase C delta type (PRKCD). For example, PIK3R1 is a regulatory subunit of phosphatidylinositol 3-kinase and when phosphorylated by CSF1R activity, may activate the RAC-alpha serine/threonine-protein kinase (AKT1) signaling pathway. CSF1R can also activate mitogen-activated protein (MAP) kinases, such as MAPK1/ERK2 or MAPK3/ERK1. Similarly, CSF1R can also activate SRC family kinases, such as proto-oncogene tyrosine-protein kinase SRC (SRC), tyrosine-protein kinase FYN (FYN), and tyrosine-protein kinase YES (YES1). Activated CSF1R may transmit signals to proteins that directly interact with the phosphorylated tyrosine residues of the tyrosine kinase domain (TKD) of CSF1R. Additionally, CSF1R may transmit signaling via adapter proteins, such as GRB2. Additionally, in some instances, CSF1R can activate signal transducer and activator of transcription (STAT) family members, such as STAT3, STAT5A and STAT5B. In some cases, tyrosine phosphorylation of SHC-transforming protein-1 (SHC1) and phosphatidylinositol 3,4,5-trisphosphate 5-phosphatase 1 (INPP5D/SHIP-1) may also be mediated by CSF1R activity. Additionally, CSF1R signaling itself can down-regulate protein phosphatases, such as INPP5D/SHIP-1. Dephosphorylation of CSF1R and its downstream effectors, along with rapid internalization of the activated CSF1R, can regulate ligand-dependent activation.

Disruption of CSF1-CSF1R binding may cause rapid loss of microglia cells within CNS tissues. In some cases, changes to the microglia cell population may drastically alter CNS homeostasis. However, restoration of CSF1-CSF1R binding may lead to repopulation of endogenous microglia cells within CNS tissues. In some cases, repopulation of microglia cells may restore CNS homeostasis.

Therefore, in some aspects of the disclosure, known CSF1 or CSF1R inhibitors or antagonists may be used to deplete, suppress, and/or modulate host endogenous microglia cells within the CNS of a subject in need thereof. In some instances, CSF1-CSF1R binding inhibitors or antagonists may include, but are not limited to, small molecule inhibitors, antibodies, or competitive ligands. In some cases, disruption of CSF1-CSF1R binding by an administered inhibitor or antagonist may be temporary or permanent. In some cases, disruption of CSF1-CSF1R binding by an inhibitor or antagonist may be spatially controlled by the route or site of administration into the CNS of a subject. In some instances, one or more inhibitors or antagonists may be administered at one or more locations within a subject or within the CNS of a subject. In some cases, disruption of CSF1-CSF1R binding by an inhibitor or antagonist may be temporally controlled by the duration or frequency of administration into the CNS of a subject. In some cases, one or more types of inhibitors or antagonists may be used to modulate endogenous microglia cells.

Non-limiting examples of inhibitors that may be used to modulate CSF1R activity include: tyrosine kinase inhibitors (TKIs) and anti-CSF1R antibodies that include, but are not limited to, pexidartinib (PLX-3397) ($IC_{50}$=13 nM), PLX-7486, and PLX-5622 (Daiichi Sankyo); ARRY-382 (ARRY Biopharma); BLZ945 (Novartis, $IC_{50}$=1.2 nM); BLZ945 metabolite (Novartis, $IC_{50}$=5.5 nM); DCC-3014 (Deciphera Pharmaceuticals); AMG-820 (AMGEN); GW-2580 (Sigma-Aldrich, $IC_{50}$=30 nM); linifanib (ABT-869) (Abbott Laboratories), OSI-930 (OSI Pharmaceuticals), or any known metabolites thereof. In some cases, the binding poses of TKIs may fall into different structural groups. Non-limiting examples of CSF1R antagonists may also include anti-CSF1R antibodies including: PD-0360324 (Pfizer), RG-7455 (e.g., Emactuzumab, Genentech/Roche), IMC-CS4 (Lilly), and MCS110 (Novartis). In some cases, introduction of such CSF1R inhibitors or antagonists into a subject may be used to disrupt endogenous CSF1-CSF1R binding interactions. In some cases, such CSF1R inhibitors and antagonists may be used to deplete, suppress, or modulate host endogenous microglia cells within the CNS of a subject. In some cases, the CSF1R inhibitors or antagonists may be used as irreversible competitive ligands. In some cases, an irreversible competitive CSF1R ligand may be used to block the binding, and therefore inhibit the functional activity, of endogenous CSF1. In such instances, the irreversible CSF1R competitive ligand may lead to depletion of host endogenous microglia cells.

In some aspects, CSF1 variants or fragments thereof that retain binding to CSF1R but which do not elicit or trigger a functional response may be used as a competitive ligand. In some cases, competitive CSF1 ligands may be used to disrupt endogenous CSF1-CSF1R binding interactions (e.g., by competing with endogenous CSF1 for binding to CSF1R). In some cases, the disruption of endogenous CSF1-CSF1R binding by such CSF1 competitive ligands may be used to deplete, suppress, or modulate host endogenous microglia cells within the CNS of a subject. In some cases, the CSF1 competitive ligand may be an irreversible competitive ligand. In some cases, an irreversible competitive CSF1 ligand can be used to block the functional activity of endogenous CSF1. In such instances, the irreversible CSF1 competitive ligand may lead to depletion of host endogenous microglia cells. In some cases, a competitive CSF1 ligand may be a genetically modified CSF1 variant.

In some cases, the sequence of CSF1 or any homolog or functional fragment thereof may be obtained from human or non-human CSF1. In some cases, a genetically modified CSF1 variant may be from a sequence of CSF1 including, but not limited to, GenBank Gene ID No. 1435 and NCBI accession number XP_0168558581 The protein sequence for human for CSF1 is listed below in FASTA format:

```
                                    (SEQ ID NO: 1)
MIGSGHLQSLQRLIDSQMETSCQITFEFVDQEQLKDPVCYLKKAFLLVQ

DIMEDTMRFRDNTPNAIAIVQLQELSLRLKSCFTKDYEEHDKACVRTFY

ETPLQLLEKVKNVFNETKNLLDKDWNIFSKNCNNSFAECSSQDVVTKPD

CNCLYPKAIPSSDPASVSPHQPLAPSMAPVAGLTWEDSEGTEGSSLLPG

EQPLHTVDPGSAKQRPPRSTCQSFEPPETPVVKDSTIGGSPQPRPSVGA

FNPGMEDILDSAMGTNWVPEEASGEASEIPVPQGTELSPSRPGGGSMQT

EPARPSNFLSASSPLPASAKGQQPADVTGTALPRVGPVRPTGQDWNHTP

QKTDHPSALLRDPPEPGSPRISSLRPQGLSNPSTLSAQPQLSRSHSSGS

VLPLGELEGRRSTRDRRSPAEPEGGPASEGAARPLPRFNSVPLTDTGHE

RQSEGSFSPQLQESVFHLLVPSVILVLLAVGGLLFYRWRRRSHQEPQRA

DSPLEQPEGSPLTQDDRQVELPV.
```

In addition to CSF1 binding, CSF1R may also act as a receptor for Interleukin-34 (IL-34). IL-34 is a 39 kDa cytokine. Similarly to CSF1, IL-34 can bind to CSF1R to cause activation of similar signaling pathways. In some cases, the expression profile of IL-34 can differ spatially and temporally from that of CSF1. In some cases, IL-34 can supplement the activity of CSF1. Within the CNS, IL-34 may be produced by neuronal cells. Deficiency of IL-34 may impair microglia cell population numbers. In some cases, absence of IL-34 may not impair the ability of microglia cells to produce inflammatory cytokines. In some instances, IL-34 deficiency may lead to dysfunctional anti-viral activity of microglia cells. In some cases, restoration of IL-34-CSF1R binding may allow for repopulation of endogenous microglia cells within CNS tissues which can restore CNS homeostasis. Therefore, in some aspects of the disclosure, IL-34 inhibitors or antagonists may be used to deplete, suppress, or modulate host endogenous microglia cells within the CNS of a subject. In some instances, IL-34-CSF1R binding inhibitors or antagonists may include, but are not limited to, small molecule inhibitors, antibodies, and competitive ligands. In some cases, disruption of IL-34-CSF1R binding may be temporary or permanent. In some cases, disruption of IL-34-CSF1R binding by an inhibitor or antagonist may be spatially controlled by the route or site of administration into the CNS of a subject. In some cases, disruption of IL34-CSF1R binding by an inhibitor or antagonist may be temporally controlled by the duration or frequency of administration into the CNS of a subject. In some cases, one or more types of inhibitors or antagonists may be used to modulate endogenous microglia cells.

In some aspects, IL-34 variants or fragments thereof that retain binding to CSF1R but which do not elicit or trigger a functional response may be used as a competitive ligand. In some cases, competitive IL-34 ligands may be used to disrupt endogenous IL-34-CSF1R binding interactions. In some cases, competitive IL-34 ligands may be used to deplete, suppress, or modulate host endogenous microglia cells within the CNS of a subject. In some cases, a competitive IL-34 ligand may be an irreversible competitive ligand. In some cases, an irreversible competitive IL-34 ligand can be used to inhibit the functional activity of endogenous IL-34. In such instances, the irreversible IL-34 competitive ligand may lead to depletion of host endogenous microglia cells. In some cases, a competitive IL-34 ligand is a genetically modified IL-34 variant.

In some cases, the sequence of IL-34 or any homolog or functional fragment thereof may be obtained from human or non-human IL-34. In some cases, a genetically modified IL-34 variant may be from a sequence of IL-34 that includes, but is not limited to, GenBank Gene ID No. 146433 and NCBI accession number NP_001166243.1. The protein sequence for human IL-34 is listed below in FASTA format:

```
                                    (SEQ ID NO: 2)
MPRGFTWLRYLGIFLGVALGNEPLEMWPLTQNEECTVTGFLRDKLQYRS

RLQYMKHYFPINYKISVPYEGVFRIANVTRLQRAQVSERELRYLWVLVS

LSATESVQDVLLEGHPSWKYLQEVETLLLNVQQGLTDVEVSPKVESVLS

LLNAPGPNLKLVRPKALLDNCFRVMELLYCSCCKQSSVLNWQDCEVPSP

QSCSPEPSLQYAATQLYPPPPWSPSSPPHSTGSVRPVRAQGEGLLP
```

Genetically-Modified CSF1R

MCs or MLCs of the disclosure as described herein may contain one or more genetically modified CSF1R variants. In some cases, the genetically modified CSF1R variants may possess insensitivity against one or more CSF1R inhibitors or antagonists, e.g., a CSF1R inhibitor or antagonist that is able to deplete, modulate, or suppress endogenous microglia cells. In some cases, the genetically modified CSF1R variants are insensitive to one or more different CSF1R inhibitors, to one or more different RTK inhibitors, to all CSF1R inhibitors, or to all RTK inhibitors.

The genetically-modified CSF1R variants may be insensitive to a certain type of inhibitor (e.g., CSF1R inhibitor), while being sensitive to a different type of inhibitor. In some cases, the genetically-modified CSF1R variant is insensitive to a first CSF1R inhibitor and sensitive to a second CSF1R inhibitor. In some instances, the second CSF1R inhibitor may be used to remove, reduce the number of, eliminate, modulate, or suppress the genetically-modified MCs or MLCs after the MCs or MLCs are introduced into the subject. The second CSF1R inhibitor may be used, for example, to remove the MCs or MLCs if the MCs or MLCs appear to lack therapeutic efficacy in the subject or if they cause an adverse reaction in the subject.

In some cases, the genetically-modified CSF1R variants may possess normal ligand binding or ligand-dependent signaling activity. In some cases, the genetically modified CSF1R variants may possess normal ligand-independent signaling activity, or no adverse ligand-independent activity. In some cases, the genetically modified CSF1R variants may possess insensitivity against one or more CSF1R inhibitors or antagonists while retaining normal ligand binding or ligand-dependent signaling. In some cases, the genetically modified CSF1R variants may possess sensitivity against one or more CSF1R inhibitors or antagonists while retaining normal ligand binding or ligand-dependent signaling activity. In some cases, the genetically modified CSF1R variants may possess insensitivity against one or more CSF1R inhibitors or antagonists while retaining normal ligand-independent signaling activity. In some cases, the genetically modified CSF1R variants may possess sensitivity against one or more CSF1R inhibitors or antagonists while retaining normal ligand-independent signaling activity. In some cases, the genetically modified CSF1R variants may have a loss in functional activity. In some cases, the genetically modified CSF1R variants may no longer contribute to a neurological disease or disorder.

In some cases, the sequence of CSF1R or any homolog or functional fragment thereof may be obtained from human or non-human CSF1R. In some cases, a genetically modified CSF1R variant may be from a sequence of CSF1R that includes, but is not limited to, GenBank Gene ID No. 1436 and NCBI accession number NP_001336665.1. The protein sequence for human CSF1R is listed below in FASTA format:

```
                                          (SEQ ID NO: 3)
MGPGVLLLLLVATAWHGQGIPVIEPSVPELVVKPGATVTLRCVGNGSVE

WDGPPSPHWTLYSDGSSSILSTNNATFQNTGTYRCTEPGDPLGGSAAIH

LYVKDPARPWNVLAQEVVVFEDQDALLPCLLTDPVLEAGVSLVRVRGRP

LMRHTNYSFSPWHGFTIHRAKFIQSQDYQCSALMGGRKVMSISIRLKVQ

KVIPGPPALTLVPAELVRIRGEAAQIVCSASSVDVNFDVFLQHNNTKLA

IPQQSDFHNNRYQKVLTLNLDQVDFQHAGNYSCVASNVQGKHSTSMFFR

VVESAYLNLSSEQNLIQEVTVGEGLNLKVMVEAYPGLQGFNWTYLGPFS

DHQPEPKLANATTKDTYRHTFTLSLPRLKPSEAGRYSFLARNPGGWRAL

TFELTLRYPPEVSVIWTFINGSGTLLCAASGYPQPNVTWLQCSGHTDRC

DEAQVLQVWDDPYPEVLSQEPFHKVTVQSLLTVETLEHNQTYECRAHNS

VGSGSWAFIPISAGAHTHPPDEFLFTPVVVACMSIMALLLLLLLLLLYK

YKQKPKYQVRWKIIESYEGNSYTFIDPTQLPYNEKWEFPRNNLQFGKTL

GAGAFGKVVEATAFGLGKEDAVLKVAVKMLKSTAHADEKEALMSELKIM

SHLGQHENIVNLLGACTHGGPVLVITEYCCYGDLLNFLRRKAEAMLGPS

LSPGQDPEGGVDYKNIHLEKKYVRRDSGFSSQGVDTYVEMRPVSTSSND

SFSEQDLDKEDGRPLELRDLLHFSSQVAQGMAFLASKNCIHRDVAARNV

LLTNGHVAKIGDFGLARDIMNDSNYIVKGNARLPVKWMAPESIFDCVYT

VQSDVWSYGILLWEIFSLGLNPYPGILVNSKFYKLVKDGYQMAQPAFAP

KNIYSIMQACWALEPTHRPTFQQICSFLQEQAQEDRRERDYTNLPSSSR

SGGSGSSSSELEEESSSEHLTCCEQGDIAQPLLQPNNYQFC.
```

MCs or MLCs may be genetically modified to inactivate or delete endogenous CSF1R. In some cases, MCs or MLCs may be genetically modified to introduce a genetically modified exogenous CSF1R variant. In some instances, the introduced exogenous CSF1R variant replaces or supplements endogenous CSF1R. In some cases, MCs or MLCs may be genetically modified to produce progeny containing one or more endogenously modified or exogenously introduced CSF1R variants.

In some cases, the genetically modified CSF1R variants may possess either or both 1) insensitivity against one or more CSF1R inhibitors or antagonists and 2) sensitivity against one or more CSF1R inhibitors or antagonists. In some cases, the genetically modified CSF1R variants may possess insensitivity against a first known CSF1R inhibitor or antagonist that retains inhibitory activity against host endogenous microglia cells. In some cases, the genetically modified CSF1R variants may possess sensitivity against a second known CSF1R inhibitor or antagonist that retains inhibitory activity against host endogenous microglia cells and/or the introduced MCs or MLCs. For example, a first known CSF1R inhibitor, such as Pexidartinib (PLX-3397), may be used to deplete or suppress host endogenous microglia cells in a subject. Meanwhile, MCs or MLCs containing a genetically modified CSF1R variant that is rendered insensitive to Pexidartinib (PLX-3397) may be introduced to replace the depleted host microglia cells, thereby allowing for the introduced MCs or MLCs to engraft and repopulate within the host CNS. As a further example, the genetically modified CSF1R variant may also be sensitive or rendered to be sensitive to a second different known CSF1R inhibitor, such as PLX-7486. In such examples, the second CSF1R inhibitor may be used to deplete, suppress, or modulate the transplanted MCs or MLCs used to repopulate the host CNS following depletion of the endogenous microglia cells resulting from the first CSF1R inhibitor. Further examples of MCs or MLCs containing CSF1R variants that are sensitive or insensitive to a plurality of CSF1R inhibitors can be used for achieving multi-faceted control over both host endogenous microglia cells and exogenously introduced MCs or MLCs within the CNS of a subject.

Genetically modified CSF1R variants possessing altered sensitivity towards known inhibitors or antagonists may be achieved by changes to the protein sequence of CSF1R. In some cases, a CSF1R variant may be generated through mutations, truncations, additions, or any combination thereof. Importantly, CSF1R may be genetically modified to produce such inhibitor sensitive or insensitive variants while retaining or enhancing all other wild-type functional activity related to ligand-dependent or ligand-independent signaling. For example, a MC or MLC containing a CSF1R variant which is insensitive to one or more CSF1R inhibitors or antagonists may be used to replace depleted endogenous microglia cells or to supplement endogenous microglia cells but with the CSF1R variant capable of interacting with endogenous or exogenously introduced CSF1 or IL-34 or any variants thereof, so as to restore and maintain critical microglia cell functions necessary for CNS homeostasis.

Structural and functional studies of CSF1R may be used in designing genetically engineered CSF1R variants. Insight into the structure and activity of CSF1R can be seen from mutations seen in Hereditary Diffuse Leukoencephalopathy with spheroids (HDLS), mutagenesis studies, drug resistance studies, and X-ray crystallography/NMR studies. In some cases, MCs or MLCs, as described herein, may comprise a CSF1R variant comprising substitutions to key residues that may convey inhibitor insensitivity while preserving wild-type functional activity. Known Protein Data Bank (PDB) CSF1R structures and related structures include, but are not limited to, PDB 4R7H, PDB 4R71, PDB 4WRL, PDB 4WRM, PDB 4LIQ, PDB 4HW7, PDB 4DKD, PDB 3KRJ, PDB 3KRL, PDB 3LCO, PDB 3LCO, PDB 3DPK, PDB 3BEA, PDB 2OGV, PDB 2I0V, PDB 2I0Y, and PDB 2I1M. Future CSF1R structures and related structures may also be used in designing CSF1R variants. Additionally, in some cases, known and future structures of CSF1 or IL-34 may also be used in designing genetically modified CSF1R, CSF1, or IL-34 variants. Known PDB structures of CSF1 include, but are not limited to, PDB 5LXF, PDB 3UF2, PDB 3UF5, PDB 3EJJ, PDB 3UEZ, and PDB 4FA8. Known PDB structures of IL-34 include, but are not limited to, PDB 4DKC, PDB 4DKD, PDB 4DKE, and PDB 4DKF.

CSF1R is a 108 kDa transmembrane receptor protein. Structurally, CSF1R is organized into an N-terminal extracellular domain, a transmembrane domain, and a C-terminal intracellular domain. The N-terminal extracellular domain comprises a ligand binding domain. A hydrophobic transmembrane domain connects the N-terminal extracellular ligand binding domain to the C-terminal intracellular domain. The intracellular domain comprises a catalytically active tyrosine kinase domain (TKD). Key TKD residues, e.g., sites of phosphorylation, may include Y699, Y708, and Y809. Native CSF1R is post-translationally modified with N-linked oligosaccharides. The final size of CSF1R can vary depending upon the degree and type of glycosylation specific to each species, tissue, and cell type. Structurally, CSF1R is primarily α-helical in nature with regions of β-sheets and unstructured loops. Key regions of CSF1R may include the JM-domain, the N(P)-loop, the A-loop, the C-loop, the KID region, and the Hinge region. In some cases, the binding of a CSF1R inhibitor may cause structural or conformational changes to CSF1R. In some cases, binding of a CSF1R inhibitor to CSF1R may induce an inactive confirmation. In some cases, the binding of a CSF1R inhibitor may not cause displacement of the JM-domain. In some instances, PLX-3397 (Pexidartinib) binding to CSF1R may stabilize an inactive confirmation of CSF1R by not disrupting the JM-domain.

In some cases, structural and functional studies of CSF1R can be used to reveal mutational substitutions that can modulate the activity of CSF1R. In some cases, mutagenesis of key CSF1R residues can confer insensitivity or enhanced sensitivity to known inhibitors or antagonists, result in increased or decreased ligand-dependent activity, result in increased or decreased ligand-independent activity, result in loss of functional activity, or contribute to known neurological diseases and disorders. In some cases, the residues for substitution may be residues which contribute to the Gibbs free energy state of CSF1R. In some cases, the residues for substitution may be residues which do not contribute to the Gibbs free energy state of CSF1R.

MCs or MLCs of the disclosure as described herein may contain genetically modified CSF1R variants wherein one or more residues are substituted. In some cases, substituted residues may produce CSF1R variants that may be insensitive to one or more inhibitors or antagonists. In some cases, substituted residues may produce CSF1R variants that may possess enhanced sensitivity to one or more inhibitors or antagonists. In some cases, substituted residues may produce CSF1R variants that may retain normal ligand binding or ligand-dependent signaling. In some cases, substituted residues may produce CSF1R variants that may retain normal ligand-independent signaling activity. In some cases, substituted residues may produce CSF1R variants that may possess increased or decreased ligand binding or ligand-dependent signaling. In some cases, substituted residues may produce CSF1R variants that may possess increased or decreased ligand-independent signaling activity. In some cases, substituted residues may produce CSF1R variants that may have a loss in functional activity. In some cases, substituted residues may produce CSF1R variants that may no longer contribute to a neurological disease or disorder.

As provided herein, MCs or MLCs of the disclosure may contain genetically modified CSF1R variants wherein one or more residues are substituted. In some cases, the substitution may be within the JM-domain of CSF1R. In some cases, the substitution may be within the N(P)-loop of CSF1R. In some cases, the substitution may be within the C-loop of CSF1R. In some cases, the substitution may be within the A-loop of CSF1R. In some cases, the substitution may be within the KID region of CSF1R. In some cases, the substitution may be within the Hinge region of CSF1R. In some cases, the substitution may cause structural or conformational changes to CSF1R. In some cases, the substitution may induce an inactive confirmation. In some cases, the substation may or may not cause displacement of the JM-domain.

In some cases, the genetically-modified CSF1R may be a genetically-modified human CSF1R. In some cases, the genetically-modified CSF1R may comprise a mutation at one or more amino acid residues selected from the group consisting of: (numbering based on human CSF1R disclosed as SEQ ID NO: 3) V647, W550, G669, T663, G795, M637, D796, C666, Y546, or any combination thereof. In some cases, the genetically-modified CSF1R may comprise one or more amino acid substitutions (numbering based on human CSF1R disclosed as SEQ ID NO: 3) selected from the group consisting of: V647I, W550F, W550L, G669A, G669V, T663I, G795A, M637L, D796A, C666A, and Y546F. In some cases, the genetically-modified CSF1R may comprise an amino acid sequence according to any CSF1R variant disclosed in Table 1 or any one of SEQ ID NOs: 4-14. In some cases, the genetically-modified CSF1R does not comprise a loss-of-function mutation. In some cases, the genetically-modified CSF1R does not comprise a mutation that confers ligand-independent activity on CSF1R. In some cases, the genetically-modified CSF1R does not comprise a mutation that is causative of a neurological disease or disorder.

In some cases, the genetically-modified CSF1R may comprise one or more amino acid substitutions (numbering based on human CSF1R disclosed as SEQ ID NO: 3) selected from the group consisting of: V647I, W550F, W550L, G669A, G669V, T663I, G795A, M637L, D796A, C666A, and Y546F; and may further comprise one or more additional mutations relative to SEQ ID NO: 3. In some cases, a genetically-modified CSF1R may comprise one or more amino acid substitutions selected from the group consisting of: V647I, W550F, W550L, G669A, G669V, T663I, G795A, M637L, D796A, C666A, and Y546F; and may further comprise one or more additional genetic modifications, such as, but not limited to, a truncation, a deletion, an inversion, an addition, a substitution, or a fusion. Any additional mutation, insertion, deletion, truncation, or other genetic variation to a CSF1R variant described herein (e.g., V647I, W550F, W550L, G669A, G669V, T663I, G795A, M637L, D796A, C666A, and Y546F) is contemplated. In particular, this disclosure encompasses any additional mutation, insertion, deletion, truncation, or other genetic variation that does not significantly impact the function of the CSF1R variant as described herein (e.g., sensitive to CSF1, and insensitive to a CSF1R inhibitor). In some cases, a genetically-modified CSF1R comprises one or more amino acid substitutions selected from the group consisting of: V647I, W550F, W550L, G669A, G669V, T663I, G795A, M637L, D796A, C666A, and Y546F; and has at least 70%, at least 75%, at least 80%, at least 85%, at least 90%, at least 95%, or at least 99% sequence identity to SEQ ID NO: 3.

In some aspects, the disclosure further provides expression vectors. A "vector" or "expression vector" as used herein refers to a macromolecule or association of macromolecules that comprises or associates with a polynucleotide and which can be used to mediate delivery of the polynucleotide to a cell. Examples of vectors include plasmids, viral vectors, liposomes, and other gene delivery vehicles. The vector generally comprises genetic elements, e.g., regulatory elements, operatively linked to a gene to facilitate expression of the gene in a target. In some cases, an expression vector of the disclosure may comprise a polynucleotide having a nucleic acid sequence encoding a CSF1R variant. In some cases, an expression vector of the disclosure may comprise a polynucleotide having a nucleic acid sequence encoding a CSF1R variant having an amino acid mutation at one or more of V647, W550, G669, T663, G795, M637, D796, C666, and Y546. In some cases, an expression vector of the disclosure may comprise a polynucleotide having a nucleic acid sequence encoding a CSF1R variant selected from the group consisting of: V647I, W550F, W550L, G669A, G669V, T663I, G795A, M637L, D796A, C666A, and Y546F. In some cases, an expression vector of the disclosure may comprise a polynucleotide encoding an amino acid sequence according to any one of SEQ ID NOs: 4-14.

In some aspects, the disclosure further provides polynucleotides comprising a nucleic acid sequence that encodes one or more CSF1R variants. In some cases, a polynucleotide of the disclosure may comprise a nucleic acid sequence encoding a CSF1R variant having an amino acid mutation at one or more of V647, W550, G669, T663, G795, M637, D796, C666, and Y546. In some cases, a polynucleotide of the disclosure may comprise a nucleic acid sequence encoding a CSF1R variant selected from the group consisting of: V647I, W550F, W550L, G669A, G669V, T663I, G795A, M637L, D796A, C666A, and Y546F. In some cases, a polynucleotide of the disclosure may comprise an amino acid sequence according to any one of SEQ ID NOs: 4-14. In some cases, a polynucleotide of the disclosure may be isolated or purified.

TABLE 1

CSF1R Variants

| CSF1R variant | Amino Acid Sequence |
|---|---|
| V647I | MGPGVLLLLLLVATAWHGQGIPVIEPSVPELVVKPGATVTLRCVGNGSVEWDGPPSPHWTL YSDGSSSILSTNNATFQNTGTYRCTEPGDPLGGSAAIHLYVKDPARPWNVLAQEVVVFED QDALLPCLLTDPVLEAGVSLVRVRGRPLMRHTNYSFSPWHGFTIHRAKFIQSQDYQCSAL MGGRKVMSISIRLKVQKVIPGPPALTLVPAELVRIRGEAAQIVCSASSVDVNFDVFLQHN NTKLAIPQQSDFHNNRYQKVLTLNLDQVDFQHAGNYSCVASNVQGKHSTSMFFRVVESAY LNLSSEQNLIQEVTVGEGLNLKVMVEAYPGLQGFNWTYLGPFSDHQPEPKLANATTKDTY RHTFTLSLPRLKPSEAGRYSFLARNPGGWRALTFELTLRYPPEVSVIWTFINGSGTLLCA ASGYPQPNVTWLQCSGHTDRCDEAQVLQVWDDPYPEVLSQEPFHKVTVQSLLTVETLEHN QTYECRAHNSVGSGSWAFIPISAGAHTHPPDEFLFTPVVVACMSIMALLLLLLLLLLYKY KQKPKYQVRWKIIESYEGNSYTFIDPTQLPYNEKWEFPRNNLQFGKTLGAGAFGKVVEAT AFGLGKEDAVLKVAVKMLKSTAHADEKEALMSELKIMSHLGQHENIVNLLGACTHGGPVL VITEYCCYGDLLNFLRRKAEAMLGPSLSPGQDPEGGVDYKNIHLEKKYVRRDSGFSSQGV DTYVEMRPVSTSSNDSFSEQDLDKEDGRPLELRDLLHFSSQVAQGMAFLASKNCIHRDVA ARNVLLTNGHVAKIGDFGLARDIMNDSNYIVKGNARLPVKWMAPESIFDCVYTVQSDVWS YGILLWEIFSLGLNPYPGILVNSKFYKLVKDGYQMAQPAFAPKNIYSIMQACWALEPTHR PTFQQICSFLQEQAQEDRRERDYTNLPSSSRSGGSGSSSSELEEESSSEHLTCCEQGDIA QPLLQPNNYQFC (SEQ ID NO: 4) |
| W550F | MGPGVLLLLLLVATAWHGQGIPVIEPSVPELVVKPGATVTLRCVGNGSVEWDGPPSPHWTL YSDGSSSILSTNNATFQNTGTYRCTEPGDPLGGSAAIHLYVKDPARPWNVLAQEVVVFED QDALLPCLLTDPVLEAGVSLVRVRGRPLMRHTNYSFSPWHGFTIHRAKFIQSQDYQCSAL MGGRKVMSISIRLKVQKVIPGPPALTLVPAELVRIRGEAAQIVCSASSVDVNFDVFLQHN NTKLAIPQQSDFHNNRYQKVLTLNLDQVDFQHAGNYSCVASNVQGKHSTSMFFRVVESAY LNLSSEQNLIQEVTVGEGLNLKVMVEAYPGLQGFNWTYLGPFSDHQPEPKLANATTKDTY RHTFTLSLPRLKPSEAGRYSFLARNPGGWRALTFELTLRYPPEVSVIWTFINGSGTLLCA ASGYPQPNVTWLQCSGHTDRCDEAQVLQVWDDPYPEVLSQEPFHKVTVQSLLTVETLEHN QTYECRAHNSVGSGSWAFIPISAGAHTHPPDEFLFTPVVVACMSIMALLLLLLLLLLYKY KQKPKYQVRFKIIESYEGNSYTFIDPTQLPYNEKWEFPRNNLQFGKTLGAGAFGKVVEAT AFGLGKEDAVLKVAVKMLKSTAHADEKEALMSELKIMSHLGQHENIVNLLGACTHGGPVL VITEYCCYGDLLNFLRRKAEAMLGPSLSPGQDPEGGVDYKNIHLEKKYVRRDSGFSSQGV DTYVEMRPVSTSSNDSFSEQDLDKEDGRPLELRDLLHFSSQVAQGMAFLASKNCIHRDVA ARNVLLTNGHVAKIGDFGLARDIMNDSNYIVKGNARLPVKWMAPESIFDCVYTVQSDVWS YGILLWEIFSLGLNPYPGILVNSKFYKLVKDGYQMAQPAFAPKNIYSIMQACWALEPTHR PTFQQICSFLQEQAQEDRRERDYTNLPSSSRSGGSGSSSSELEEESSSEHLTCCEQGDIA QPLLQPNNYQFC (SEQ ID NO: 5) |
| W550L | MGPGVLLLLLLVATAWHGQGIPVIEPSVPELVVKPGATVTLRCVGNGSVEWDGPPSPHWTL YSDGSSSILSTNNATFQNTGTYRCTEPGDPLGGSAAIHLYVKDPARPWNVLAQEVVVFED QDALLPCLLTDPVLEAGVSLVRVRGRPLMRHTNYSFSPWHGFTIHRAKFIQSQDYQCSAL MGGRKVMSISIRLKVQKVIPGPPALTLVPAELVRIRGEAAQIVCSASSVDVNFDVFLQHN NTKLAIPQQSDFHNNRYQKVLTLNLDQVDFQHAGNYSCVASNVQGKHSTSMFFRVVESAY LNLSSEQNLIQEVTVGEGLNLKVMVEAYPGLQGFNWTYLGPFSDHQPEPKLANATTKDTY RHTFTLSLPRLKPSEAGRYSFLARNPGGWRALTFELTLRYPPEVSVIWTFINGSGTLLCA ASGYPQPNVTWLQCSGHTDRCDEAQVLQVWDDPYPEVLSQEPFHKVTVQSLLTVETLEHN QTYECRAHNSVGSGSWAFIPISAGAHTHPPDEFLFTPVVVACMSIMALLLLLLLLLLYKY KQKPKYQVRLKIIESYEGNSYTFIDPTQLPYNEKWEFPRNNLQFGKTLGAGAFGKVVEAT AFGLGKEDAVLKVAVKMLKSTAHADEKEALMSELKIMSHLGQHENIVNLLGACTHGGPVL VITEYCCYGDLLNFLRRKAEAMLGPSLSPGQDPEGGVDYKNIHLEKKYVRRDSGFSSQGV DTYVEMRPVSTSSNDSFSEQDLDKEDGRPLELRDLLHFSSQVAQGMAFLASKNCIHRDVA ARNVLLTNGHVAKIGDFGLARDIMNDSNYIVKGNARLPVKWMAPESIFDCVYTVQSDVWS YGILLWEIFSLGLNPYPGILVNSKFYKLVKDGYQMAQPAFAPKNIYSIMQACWALEPTHR PTFQQICSFLQEQAQEDRRERDYTNLPSSSRSGGSGSSSSELEEESSSEHLTCCEQGDIA QPLLQPNNYQFC (SEQ ID NO: 6) |
| G669A | MGPGVLLLLLLVATAWHGQGIPVIEPSVPELVVKPGATVTLRCVGNGSVEWDGPPSPHWTL YSDGSSSILSTNNATFQNTGTYRCTEPGDPLGGSAAIHLYVKDPARPWNVLAQEVVVFED QDALLPCLLTDPVLEAGVSLVRVRGRPLMRHTNYSFSPWHGFTIHRAKFIQSQDYQCSAL MGGRKVMSISIRLKVQKVIPGPPALTLVPAELVRIRGEAAQIVCSASSVDVNFDVFLQHN NTKLAIPQQSDFHNNRYQKVLTLNLDQVDFQHAGNYSCVASNVQGKHSTSMFFRVVESAY LNLSSEQNLIQEVTVGEGLNLKVMVEAYPGLQGFNWTYLGPFSDHQPEPKLANATTKDTY |

TABLE 1-continued

<div align="center">CSF1R Variants</div>

| CSF1R variant | Amino Acid Sequence |
|---|---|
| | RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLLYKY<br>KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VITEYCCYADLLNFLRRKAEAMLGPSLSPGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGDFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 7) |
| G669V | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLLYKY<br>KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VITEYCCYVDLLNFLRRKAEAMLGPSLSPGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGDFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 8) |
| T663I | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLLYKY<br>KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VIIEYCCYGDLLNFLRRKAEAMLGPSLSPGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGDFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 9) |
| G795A | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLLYKY<br>KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VITEYCCYGDLLNFLRRKAEAMLGPSLSPGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIADFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 10) |
| M637L | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLLYKY |

TABLE 1-continued

CSF1R Variants

| CSF1R variant | Amino Acid Sequence |
|---|---|
| | KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKILSHLGQHENIVNLLGACTHGGPVL<br>VITEYCCYGDLLNFLRRKAEAMLGPSLSPGGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGDFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 11) |
| D796A | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLYKY<br>KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VITEYCCYGDLLNFLRRKAEAMLGPSLSPGGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGAFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 12) |
| C666A | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLYKY<br>KQKPKYQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VITEYACYGDLLNFLRRKAEAMLGPSLSPGGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGDFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 13) |
| Y546F | MGPGVLLLLLVATAWHGQGIPVIEPSVPELVVKPGATVTLRCVGNGSVEWDGPPSPHWTL<br>YSDGSSSILSTNNATFQNTGTYRCTEPGDPLGGSAAIHLYVKDPARPWNVLAQEVVVFED<br>QDALLPCLLTDPVLEAGVSLVRVRGRPLMRHTNYSFSPWHGFTIHRAKFIQSQDYQCSAL<br>MGGRKVMSISIRLKVQKVIPGPPALTLVPAELVRIRGEAAQIVCSASSVDVNFDVFLQHN<br>NTKLAIPQQSDFHNNRYQKVLTLNLDQVDFQHAGNYSCVASNVQGKHSTSMFFRVVESAY<br>LNLSSEQNLIQEVTVGEGLNLKVMVEAYPGLQGFNWTYLGPFSDHQPEPKLANATTKDTY<br>RHTFTLSLPRLKPSEAGRYSFLARNPGGWRALTFELTLRYPPEVSVIWTFINGSGTLLCA<br>ASGYPQPNVTWLQCSGHTDRCDEAQVLQVWDDPYPEVLSQEPFHKVTVQSLLTVETLEHN<br>QTYECRAHNSVGSGSWAFIPISAGAHTHPPDEFLFTPVVVACMSIMALLLLLLLLLLYKY<br>KQKPKFQVRWKIIESYEGNSYTFIDPTQLPYNEKWEFPRNNLQFGKTLGAGAFGKVVEAT<br>AFGLGKEDAVLKVAVKMLKSTAHADEKEALMSELKIMSHLGQHENIVNLLGACTHGGPVL<br>VITEYCCYGDLLNFLRRKAEAMLGPSLSPGGQDPEGGVDYKNIHLEKKYVRRDSGFSSQGV<br>DTYVEMRPVSTSSNDSFSEQDLDKEDGRPLELRDLLHFSSQVAQGMAFLASKNCIHRDVA<br>ARNVLLTNGHVAKIGDFGLARDIMNDSNYIVKGNARLPVKWMAPESIFDCVYTVQSDVWS<br>YGILLWEIFSLGLNPYPGILVNSKFYKLVKDGYQMAQPAFAPKNIYSIMQACWALEPTHR<br>PTFQQICSFLQEQAQEDRRERDYTNLPSSSRSGGSGSSSSELEEESSSEHLTCCEQGDIA<br>QPLLQPNNYQFC (SEQ ID NO: 14) |

Subjects

In some aspects, the methods and compositions provided herein may be used to treat a subject in need thereof. In some cases, the subject may suffer from a neurological disease or disorder. In some cases, the subject may be a human or an animal. In some cases, the human may be a patient at a hospital or a clinic.

In some cases, the methods described herein may be used on tissues or cells derived from a subject and the progeny of such tissues or cells. For example, compositions described herein may be used to achieve some functional activity within tissues or cells of a subject. The tissues or cells may be obtained from a subject in vivo. In some cases, the tissues or cells are cultured in vitro and contacted with a composition provided herein.

In some cases, the methods and compositions provided herein are used to treat a subject having, suspected of having, or at risk of developing a neurological disease or disorder. In some instances, the methods and compositions provided herein are used to treat a subject having, suspected of having, or at risk of developing symptoms associated with a neurological disease or disorder. In some cases, the methods and compositions provided herein are used to treat a subject having, suspected of having, or at risk of developing Adult onset leukoencephalopathy with axonal spheroids and pigmented glia (ALSP) (also known as Pigmented ortho-chromatic leukodystrophy (POLD) and/or Hereditary diffuse leukoencephalopathy with axonal spheroids (HDLS)); Leukodystrophies including, but not limited to: Globoid cell leukodystrophy (Krabbe disease), Metachromatic leukodystrophy, Mucopolysaccharidosis IIIA/B (Sanfilippo syndrome), Mucopolysaccharidosis IIA (Hunter syndrome), Gaucher disease Type II/III, Niemann-Pick Cerebrotendinous xanthomatosis (CTX), Canavan disease, or Alexander disease; Neuroinflammatory diseases including, but not limited to: Multiple sclerosis (any subtype), Neuromyelitis optica, Optic neuritis, or Transverse myelitis; Tauopathies/ Synucleinopathies including, but not limited to: Progressive supranuclear palsy, Corticobasal degeneration, Dementia with Lewy Bodies, or Multiple System Atrophy; Neurodegenerative diseases including, but not limited to: Alzheimer's disease, Frontotemporal dementia, Parkinson's disease (including GBA and LRRK2 variants), Huntington's disease; Rett syndrome; or any other known neurological disease or disorder or any other known diseases or disorders associated therein. In some cases, the methods and compositions provided herein are used to treat a subject having, suspected of having, or at risk of developing any form of dementia, any movement disorder condition, spinal cord injury, traumatic brain injury, stroke, or cerebral amyloid angiopathy.

Cell Sources

MCs or MLCs of the disclosure, as described herein, may be derived from a donor. In some cases, MCs or MLCs can be isolated from a donor. In some instances, the donor may be a human host, a human donor, or an animal. In some instances, the donor may be autologous, allogeneic, or heterologous in nature. In some cases, the donor may be healthy or afflicted with a neurological disease or disorder. In some cases, the donor may not be afflicted with a peripheral blood disorder or a blood cancer. In some cases, MCs or MLCs may be derived from embryonic or extraembryonic tissue. In some cases, the MCs may be derived from postnatal tissue. In some cases, MCs may include myeloid precursor cells, myeloid progenitor cells, erythro-myeloid precursor cells, erythro-myeloid progenitor cells, myeloid-derived macrophages, myeloid-derived monocytes, myeloid-derived fetal macrophages, non-hematopoietic stem cell (HSC)-derived myeloid cells, hematopoietic stem cell (HSC)-derived myeloid cells, yolk-sac-derived myeloid cells, or any combination thereof.

In some aspects, the MCs or MLCs may be derived from a pluripotent stem cell. In some cases, the pluripotent stem cell may be an embryonic stem cell. In some cases, the pluripotent stem cell may be an induced pluripotent stem cell. In some cases, a somatic cell (e.g., blood cell, fibroblast) of a subject may be used to produce an induced pluripotent stem cell. The induced pluripotent stem cell may be differentiated into a MC or MLC; in some cases, the MC or MLC is then introduced into the subject who was the original source of the somatic cell used to produce the induced pluripotent stem cell. In some cases, the pluripotent stem cell is genetically modified, such that the resulting MC or MLC is genetically-modified. In some cases, the MC or MLC derived from the induced pluripotent stem cell is genetically modified.

In some cases, MCs or MLCs may be purified. In some cases, MCs or MLCs can be a mixture of one or more different types of MCs or MLCs. In some cases, differentiated MLCs may more closely resemble microglia than other tissue macrophages, monocytes, or neutrophils. In some cases, MLCs derived from yolk-stem cells (e.g., fetal brain) may possess a gene expression profile that more closely resembles microglia cells than that seen for MLCs derived from HSCs (e.g., from blood or bone marrow) or MLCs derived from a mixed origin (e.g., fetal liver).

In some cases, MCs or MLCs may possess gene expression profiles associated with healthy or diseased microglia cells. For example, in some cases, MLCs derived from HSCs, as compared to MLCs derived from yolk sac, can be significantly enriched in gene sets associated with specific neurological diseases or disorders, immaturity, and in vitro culture from prior studies, along with major histocompatibility complex class II genes. In some instances, MLCs derived from yolk sac may be relatively enriched in gene sets associated with CNS homeostasis. In some cases, MLCs may possess dysregulated gene expression. In one non limiting example, MCs or MLCs may possess dysregulated expression of ApoE. In some instances, dysregulated gene expression associated with MCs or MLCs may have expression profiles similar to that seen for microglia cells associated with a neurological disease or disorder.

In some cases, the subsequently differentiated MLCs can be ramified or activated. In some instances, activated MLCs may include a non-phagocytic cell, a phagocytic cell, an amoeboid, or a gitter cell. In some cases, MCs or MLCs may express genes or proteins similar to those of normal, healthy microglia cells (e.g., the microglia sensome/phenotype). In some cases, MCs or MLCs may express genes or proteins that are specific to microglia cells. In some cases, MCs or MLCs may express genes or proteins that are more specific to microglia cells than those seen expressed in microglia cells derived from HSCs.

Culture Medium

In some cases, isolated MCs or MLCs can be cultured in vitro. In some cases, MCs may be differentiated into MLCs in vitro or in vivo. In some cases, the MCs or MLCs may be obtained from a host subject for culturing or differentiation ex vivo. The growth medium, salt concentrations, nutrient levels, culture pH, and temperature may all be optimized for culturing MCs or MLCs. In some cases, MCs or MLCs may be cultured in the presence of one or more growth factors. In some cases, MCs or MLCs may be cultured in the presence of one or more CSF1R inhibitors or antagonists. In some cases, MCs or MLCs may be cultured in the presence of one or more ligand inhibitors or antagonists. In some cases, MCs or MLCs may be cultured in the presence of one or more supplemental cell types. In some instances, the one or more supplemental cells may modulate the growth, survival, activity, or differentiation of MCs into MLCs. Examples of supplemental cells include, but are not limited to, astrocytes, oligodendrocytes, ependymal cells, Schwann cells, satellite cells, enteric glia cells, or any other known cell within the CNS or known to associate or regulate microglia cells.

In some cases, MCs or MLCs may be cultured in the presence of natural or synthetic polymers. In some instances, polymers within the culture may provide a three-dimensional matrix that promotes MC or MLC growth, differentiation, and activity.

In some cases, MCs or MLCs may be cultured to a different passage number. In some instances, MCs or MLCs may be cultured to P0, P1, P2, P3, P4, P5, or greater before administration into a subject. In some cases, the passage number for deriving MCs of MLCs may vary depending on the cell course used for deriving said MCs or MLCs. In some instances, the passage number can vary for MCs or MLCs derived from embryonic or extraembryonic tissue. In some cases, the myeloid cells may be derived from postnatal tissue. In some instances, the passage number can vary for MCs or MLCs derived from a myeloid precursor cell, a myeloid progenitor cell, an erythro-myeloid precursor cell, an erythro-myeloid progenitor cell, a myeloid-derived macrophage, a myeloid-derived monocyte, a myeloid-derived fetal macrophage, a non-hematopoietic stem cell (HSC)-derived myeloid cell, a hematopoietic stem cell (HSC)-derived myeloid cell, or a yolk-sac-derived myeloid cell. For example, the passage number can vary for MCs or MLCs derived from yolk sac and/or fetal brain as compared with MCs or MLCs derived from blood and/or bone marrow (BM), and monocytes from the fetal liver which, at E13-14, contain a mixture of HSC- or YS-derived cells.

Genetic Modification of MCs and MLCs

The MCs or MLCs may be genetically modified at one or more genetic loci. As described herein, the genetic modification may cause the MCs or MLCs to be sensitive or insensitive to a particular inhibitor. In some cases, the MCs or MLCs may be genetically modified so that they are sensitive to one type of inhibitor and insensitive to another type of inhibitor. In some instances, genetic modifications to MCs or MLCs may include one or more genetic modifications that increase or decrease cellular properties such as, but not limited to, viability, growth, metabolism, activity in response to stimuli of interest, or therapeutic efficacy within the CNS of a subject in need thereof. For example, MCs or MLCs may contain separate cellular modifications such as the upregulation or downregulation of sequences of interest unrelated to the activity of CSF1-CSF1R or IL-34-CSF1R. In another example, MCs or MLCs may contain one or more introduced gene or protein sequences of interest which provide therapeutic efficacy against a neurological disease or disorder unrelated to the activity of CSF1-CSF1R, e.g., sequences for use in gene/protein therapy.

In some cases, diseased MCs or MLCs may be obtained from a subject with a neurological disease or disorder, wherein the obtained MCs or MLCs may be genetically modified to correct the causative factor of said neurological disease or disorder. In some instances, these genetically modified cells may be further modified. In some cases, these genetically modified cells may be administered back into the host subject. Repopulation of the host CNS with these corrected MCs or MLCs may provide therapeutic efficacy in treating the neurological disease or disorder of the host subject. In some cases, these types of genetically-modified MCs or MLCs may be further genetically-modified to render them insensitive to a particular inhibitor (e.g., CSF1R inhibitor).

Genetic modification of MCs or MLCs may be achieved through, but not limited to, site-directed mutagenesis, recombinant engineering, homologous recombination, genomic editing, and so forth. In some cases, MCs or MLCs may be transfected or transformed with a nucleic acid, preferably an expression vector, containing a nucleic acid encoding an exogenous genetically modified CSF1R sequence. Non-limiting examples of expression vectors may include (a) non-viral vectors such as nucleic acid vectors including linear oligonucleotides and circular plasmids; artificial chromosomes such as human artificial chromosomes (HACs), yeast artificial chromosomes (YACs), and bacterial artificial chromosomes (BACs or PACs); episomal vectors; transposons (e.g., PiggyBac); and (b) viral vectors such as retroviral vectors, lentiviral vectors, adenoviral vectors, and AAV vectors. In some cases, an expression vector comprises a polynucleotide encoding a CSF1R variant comprising an amino acid mutation at one or more of: V647, W550, G669, T663, G795, M637, D796, C666, and Y546. In some cases, an expression vector comprises a polynucleotide encoding a CSF1R variant selected from the group consisting of: V647I, W550F, W550L, G669A, G669V, T663I, G795A, M637L, D796A, C666A, and Y546F. In some cases, an expression vector comprises a polynucleotide encoding a CSF1R variant having an amino acid sequence according to any one of SEQ ID NOs: 4-14.

In some cases, the introduced exogenous CSF1R sequence is a CSF1R variant as described throughout the disclosure, wherein the CSF1R variant replaces or supplements endogenous CSF1R. For example, an expression construct encoding a wild-type CSF1R sequence may be genetically modified by site-specific mutagenesis to produce a CSF1R variant comprising substitutions that confer insensitivity to a known CSF1R inhibitor or antagonist. This CSF1R variant construct may then be introduced into a MC or MLC that has been previously modified to inactivate or delete the endogenous CSF1R, for example, using a CRISPR-Cas system.

In some cases, MCs or MLCs may be transfected or transformed with a nucleic acid, preferably an expression vector, encoding a nucleic acid for a type-I or type-II CRISPR-Cas system. The CRISPR/Cas system is an RNA-mediated bacterial immune system that provides a form of acquired immunity against viruses and plasmids. Clustered regularly interspaced short palindromic repeats (CRISPR) are short repetitions of bacterial DNA followed by short repetitions of spacer DNA from viruses or plasmids. In some cases, CRISPR systems can recognize these short repetitions of foreign DNA to produce DNA strand breakages. Type-I CRISPR-Cas systems comprise multiple components including: a Cas3 (CASCADE associated protein 3), a crRNA (CRISPR RNA), and a CASCADE (CRISPR-associated complex for antiviral defense) complex. The Cas3 endonuclease in association with the CASCADE complex is programmed by a crRNA to cleave the target sequence through a single-strand DNA break. Type-II CRISPR-Cas systems comprise three components: a Cas9 (CRISPR associated protein 9) endonuclease, a crRNA (CRISPR RNA), and a tracrRNA (transactivating crRNA). The Cas9 endonuclease contains two nuclease domains and is programmed by a crRNA and tracrRNA hybrid to cleave the target sequence through double strand DNA breaks. In some cases, the crRNA sequence can be genetically modified to be substantially homologous to a portion of a nucleic acid sequence of interest to introduce DNA strand breaks. In some cases, endogenous CSF1R in MCs or MLCs, as described herein, may be inactivated, deleted, or otherwise modified by use of an appropriate crRNA and CRISPR-Cas system.

MC and MLC Administration and Repopulation

MCs or MLCs of the disclosure, as described herein, may be used for the treatment of a neurological disease or disorder in a subject in need thereof. MCs provided herein may be administered to a subject wherein they can differentiate into MLCs. MCs or MLCs described herein may be used to replace or supplement host microglia cells upon administration to a subject in need thereof.

MCs or MLCs, as provided herein, may be administered to a subject by any known route of administration. In some cases, MCs can be introduced into the CNS of a subject in need thereof. In some cases, MCs or MLCs can be transplanted or injected into the CNS. In some cases, MCs or MLCs can be introduced into the blood of a subject in need thereof. In some instances, MCs or MLCs may be injected into the bloodstream. In some cases, MCs or MLCs introduced into the blood of a subject can relocate into the CNS of the subject. In some cases, relocation into the CNS may be facilitated by CCR2. MC or MLC introduction into or relocation to host CNS tissue may allow for MC or MLC engraftment within the subject. MCs or MLCs residing within the CNS of a subject may undergo phenotypic changes. In some cases, changes in MC or MLC phenotype may be influenced or directed by environmental stimuli present in, administered into, or applied to host tissues. In some instances, MCs or MLCs may undergo morphological and phenotypic changes to resemble host microglia cells. In some cases, phenotypic changes may include changes in the expression of microglia specific biomarkers. The degree of phenotypic changes by MCs or MLCs may be directed by the developmental lineage of the MCs or MLCs administered.

For administered MCs or MLCs to engraft into host tissues for residency, an open niche may be necessary. In some cases, an open niche for MC or MLC engraftment can be created within host tissues of a subject. In some cases, host endogenous microglia cells can be depleted prior to or concurrently with the introduction of MCs or MLCs. In some cases, depletion of host microglia cells allows for introduced MCs or MLCs to repopulate host tissues. In some cases, the open niche CNS environment may allow for engraftment of MCs or MLCs derived from multiple donor tissues, cell types, or cell lineages. In some cases, MC or MLC repopulation of host tissue may be partial or complete. In some cases, MC or MLC repopulation of host tissue may be transient or permanent in nature. In some cases, MC or MLC repopulation of host tissue may be spatially specific within host tissues. In some cases, MC or MLC repopulation of host tissue may be specific to sub-tissues or sub-regions. In some instances, CSF1R inhibitors or antagonists may be used to selectively control the growth and activity of MCs or MLCs introduced into the CNS of a subject in need thereof. For example, a first known CSF1R inhibitor may be used to deplete and suppress endogenous microglia cells in a patient in need thereof. Depletion of the cells then allows for repopulation of host CNS tissues with introduced MCs or MLCs, wherein the introduced MCs or MLCs comprise a CSF1R variant that is insensitive to the first known CSF1R inhibitor. In a further example, the introduced MCs or MLCs comprising the CSF1R variant may be controlled by the use of a second known CSF1R inhibitor for which the CSF1R variant is sensitive to.

Depletion or suppression of host microglia cells may allow for repopulation of host CNS tissues with MCs or MLCs by engraftment. In some cases, MCs or MLCs may repopulate within grey matter of the CNS. Grey matter generally comprises unmyelinated neurons and other cells of the CNS. Grey matter is found throughout the cerebrum, brainstem, and cerebellum of the brain. Grey matter is also present throughout the spinal cord. Grey matter is generally present at the surfaces of the cerebral hemispheres and the cerebellum as well as within deeper anatomical parts of the brain including, but not limited to, the thalamus, the hypothalamus, the subthalamus, the putamen of the basal ganglia, the deep cerebellar nuclei, and the brainstem, which may be surrounded by white matter. Grey matter present in the spinal cord includes the grey column which is further sub-divided into the anterior, posterior, and later grey columns. Grey matter of the CNS comprises neuropil, neuroglia, and capillaries. Neuropil further comprises mostly unmyelinated axons, dendrites, and glial cells. Neuroglia further comprises macroglia, microglia, and other minor accessory cells such as pituicytes and tanycytes. Macroglia comprises astrocytes, oligodendrocytes, ependymal, radial glia, Schwann cells, satellite glia, and enteric glia cells. Microglia comprises specialized macrophages that derive from mononuclear cells originating in the yolk sac during a defined embryonal period before populating the brain mesenchyme.

Depletion or suppression of host microglia cells may allow for repopulation of host CNS tissues with MCs or MLCs by engraftment. In some cases, MCs or MLCs may repopulate within white matter of the CNS. White matter generally comprises myelinated neurons and other cells of the CNS. White matter is found throughout the cerebrum, brainstem, and cerebellum of the brain. White matter forms the bulk of the cerebrum and cerebellum. White matter is also present throughout the superficial parts of the spinal cord. White matter is generally present below the surfaces of the cerebral hemispheres and the cerebellum. In the brain stem, white matter is found superficially, while grey matter is present in the depth of the brainstem. White matter also forms the arbor vitae sub-region of the cerebellum.

MCs or MLCs provided herein may repopulate into the brain parenchyma of a host subject. In some cases, repopulation within the brain may be partial or complete. In some cases, MC or MLC repopulation of the brain may be transient or permanent. In some cases, MC or MLC repopulation of the brain may be spatially specific. In some cases, MC or MLC repopulation of the brain may be to specific sub-tissues or sub-regions of the brain. For example, MCs or MLCs may repopulate within specific regions of the human brain including, but not limited to, the cerebrum, the brainstem, or the cerebellum.

MCs or MLCs provided herein may repopulate within the cerebrum of a subject. In some cases, MCs or MLCs may repopulate within the cerebral cortex, the hippocampus, the basal ganglia, the olfactory bulb, or any combination thereof, of the cerebrum. Sub-regions of the basal ganglia include the putamen, the globus pallidus, the nucleus accumbens, and the septal nuclei. In some instances, MCs or MLCs may repopulate in either cerebral hemispheres of the cerebral cortex. In some instances, MCs or MLCs may repopulate within the corpus callosum connecting the two cerebral hemispheres. In some instances, MCs or MLCs may repopulate within the frontal lobe, the parietal lobe, the occipital lobe, or the temporal lobe of the cerebral cortex in any combination thereof. In some instances, MCs or MLCs may repopulate within different cortical layers of the cerebral cortex. The cerebral cortex comprises six main cortical layers including: 1) the molecular layer, 2) the external granular layer, 3) the external pyramidal layer, 4) the internal granular layer, 5) the internal pyramidal layer or ganglionic layer, and 6) the polymorphic or multiform layer.

MCs or MLCs provided herein may repopulate within the brainstem of a subject. In some cases, MCs or MLCs may repopulate within regions of the brainstem including the midbrain, the pons, the medulla oblongata, the diencephalon of the forebrain, or in any combination thereof. In some cases, MCs or MLCs may repopulate within the regions of the midbrain such as the tectum, the tegmentum, or the ventral tegmentum. Other sub-regions of the midbrain include, but are not limited to, the periaqueductal gray, the oculomotor nerve, the trochlear nerve, the red nucleus, the substantia nigra pars compacta, the reticular formation, the central tegmental tract, the ventral tegmental area, and the rostromedial tegmental nucleus. In some cases, MCs or MLCs may repopulate within the regions of the pons including the basilar part of the pons (e.g., the ventral part of the pons) and the pontine tegmentum (e.g., the dorsal part of the pons). In some cases, MCs or MLCs may repopulate within the regions of the medulla oblongata including the upper and lower parts. In some cases, MCs or MLCs may repopulate within the regions of the diencephalon of the forebrain including the thalamus, the hypothalamus, the epithalamus, the subthalamus, or any combination thereof. The epithalamus further comprises the habenula, the habenular nuclei, the habenular commissure, the habenular trigone, the stria medullaris, and the pineal gland.

MCs or MLCs provided herein may repopulate within the cerebellum of a subject. In some cases, MCs or MLCs may repopulate within regions of the cerebellum including the flocculonodular lobe, the anterior lobe, the posterior lobe, the arbor vitae or any combination thereof. The posterior lobe may be further separated into the midline cerebellar vermis, and two lateral cerebellar hemispheres. In some cases, MCs or MLCs may repopulate within sub-regions of the cerebellum including the four deep cerebellar nuclei: 1) dentate nucleus, 2) the emboliform nucleus, 3) the globose nucleus, and 4) the fastigii nucleus. In some cases, MCs or MLCs may repopulate within sub-regions of the cerebellum including the three cerebellar cortex layers: 1) the molecular layer, 2) the Purkinje layer, and 3) the granular layer. In some cases, MCs or MLCs may repopulate within sub-regions of the cerebellum including the superior (brachium conjunctivium), the middle (brachium pontis), and the inferior (resitform and juxtarestiform bodies) cerebellar peduncles connecting the cerebellum to the midbrain.

MCs or MLCs provided herein may repopulate into the spinal cord of a host subject. In some cases, repopulation within the spinal cord may be partial or complete. In some cases, MC or MLC repopulation of the spinal cord may be transient or permanent. In some cases, MC or MLC repopulation of the spinal cord may be spatially specific. In some cases, MC or MLC repopulation of the spinal cord may be to specific sub-tissues or sub-regions of the spinal. For example, MCs or MLCs may repopulate the cervical, thoracic, lumbar, conus medullaris, or cauda equine regions of the spinal cord, or any combination thereof.

Dosing of MLCs and MCs

As described herein, one or more MCs or MLCs may be used to replace depleted, suppressed, or modulated host endogenous microglia cell population within the CNS of a subject. In some cases, MCs or MLCs may be formulated for administration into a subject in need thereof. In some cases, the MCs or MLCs may be administered in a dosage range of about $10^1$ to about $10^{10}$ cells/per mL or $10^1$ to about $10^{10}$ cells/kg of body weight.

MCs or MLCs may be administered once or more than once a day. In some cases, administration may occur as a single dose or multiple doses. In some instances, the single dose may provide sufficient repopulation of MLCs to replace or supplement host endogenous microglia cells so as to restore normal, healthy CNS homeostasis to the subject. In some instances, multiple doses may be needed to provide sufficient repopulation of MLCs to replace or supplement host endogenous microglia cells so as to restore normal, healthy CNS homeostasis to the subject. In some cases, MCs or MLCs may be administered to the subject once, repeatedly, or continuously indefinitely.

In some cases, a subject in need thereof may be given a therapeutically effective amount of MCs or MLCs that can be administered at least every hour, at least every 2 hours, at least every 3 hours, at least every 4 hours, at least every 5 hours, at least every 6 hours, at least every 7 hours, at least every 8 hours, at least every 9 hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day. In some cases, MCs or MLCs may be administered once, every day, once every two days, once every three days, once every four days, once every five days, once every six days, once every week, and so forth. In some cases, treatment of a subject in need thereof with a therapeutically effective amount of MCs or MLCs may be for at least 1 week, for at least 2 weeks, for at least 3 weeks, for at least 4 weeks, for at least 1 month, for at least 2 months, for at least 3 month, for at least 4 months, for at least 5 months, for at least 6 months, for at least 7 months, for at least 8 months, for at least 9 months, for at least 10 months, for at least 11 months, for at least 12 months, or for more than 1 year.

MC and MLC Repopulation Efficacy

Administration of MCs or differentiated MLCs may be used to repopulate the CNS of a subject in need thereof. In some cases, MCs or MLCs repopulation within the CNS of a subject may occur during or after depletion, suppression, or modulation of host endogenous microglia cells. In some cases, MCs or MLCs repopulation within the CNS of a subject may occur without depletion, suppression, or modulation of host endogenous microglia cells. In some cases, MCs or MLCs repopulation levels may be less than, approximately similar to, or greater than the levels of host endogenous cells prior to depletion, suppression, or modulation. In some cases, the level of repopulation may be assessed by the change in microglia cell concentration as compared to levels seen prior to MC or MLC administration. In some cases, the level of repopulation may be assessed by the change in microglia cell concentration as compared to levels seen prior to MC or MLC administration but following depletion of host endogenous microglia cells using one or more CSF1R inhibitors or antagonists. Population levels of introduced MCs or MLCs within a given CNS tissue may be assessed by any method known in the art. In some cases, MCs or MLCs repopulation levels may be assessed by the presence of or the quantity of specific gene biomarkers including, but not limited to Cd45, Cd11b, Tmem119, P2ry12, Olfml3, Sall1, Fcrls, Hexb, Iba1, Gpr34, Gpr56, Gpr84, or any other microglia cell biomarker. In some cases, MCs or MLCs repopulation levels may be assessed by the presence of or the quantity of specific protein biomarkers including, but not limited to CD45, CD11B, TMEM119, P2RY12, OLFML3, SALL1, FCRLS, HEXB, IBA1, GPR34, GPR56, GPR84, or any other microglia cell biomarker.

In some cases, when MCs or MLCs engraft within the CNS of a subject, they may develop expression gene profiles similar to healthy endogenous microglia cells. In some instances, this gene profile resemblance may occur within days, weeks, or months following introduction. In some cases, when MLCs derived from HSCs engraft in the brain, they may become similar to microglia by about 14 days, but may not further increase expression of microglia identity genes when incubated in the brain for at least four times longer. In contrast, in some cases, YS-derived macrophages, which share a common ancestor with microglia, may have the intrinsic potential to become highly similar to transplanted microglia by about 14 days.

In some cases, the level of MC and/or MLC repopulation may be greater than about 1%, greater than about 2%, greater than about 3%, greater than about 4%, greater than about 5%, greater than about 10%, greater than about 14%, greater than about 20%, greater than about 25%, greater than about 30%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, greater than about 99%, or about 100%. In some cases, the level of MC and/or MLC repopulation may be less than about 1%, less than about 2%, less than about 3%, less than about 4%, less than about 5%, less than about 10%, less than about 14%, less than about 20%, less than about 25%, less than about 30%, less than about 40%, less than about 45%, less than about 50%, less than about 55%, less than about 60%, less than about 65%, less than about 70%, less than about 75%, less than about 80%, less than about 85%, less than about 90%, less than about 95%, less than about 96%, less than about 97%, less than about 98%, less than about 99%, or about 100%.

Repopulation by introduced MCs or MLCs may be permanent or temporary. In some cases, repopulation can be measured as the presence of MCs or MLCs at any given time following administration of one or more unmodified or modified MCs or MLCs. In some cases, MC or MLC repopulation can be assessed at 1 hour, 2 hours, 3 hours, 4 hours, 5 hours, 6 hours, 8 hours, 10, hours, 12 hours, 24 hours, 2 days, 3 days, 4 days, 5 days, 6 days, 1 week, 2 weeks, 3 weeks, 4 weeks, 1 month or longer.

Microglia-Like Cell Activity

MCs or MLCs, as described herein, may be used to replace or supplement the host endogenous microglia cell population within the CNS of a subject. Microglia cells represent a distinct CNS cell population with an important role in CNS homeostasis. In some cases, host endogenous microglia cells may be associated with a neurological disease or disorder. Therefore, the introduction of MCs or MLCs into the CNS of a subject in need thereof can be used to restore normal, healthy microglia activity in CNS homeostasis.

In some cases, MCs or MLCs may demonstrate rapid, high fidelity repopulation of the CNS upon introduction therein. In some cases, MCs or MLCs may be highly plastic in both morphology and functionality. Localized conditions and chemical stimuli present within the CNS can influence the phenotypic plasticity of MCs or MLCs.

In some cases, MCs or MLCs of the disclosure may express a gene or protein profile similar to that seen for normal, healthy microglia cells, e.g., the microglia sensome. The microglia sensome is the unique phenotypic patterning of gene and protein transcripts used by microglia cells for sensing ligands and pathogens. In some cases, the microglia sensome may play a role in neurodevelopment and neurodegeneration. In some cases, genes of interest within the microglia sensome are those for receptors and transmembrane proteins that are highly expressed relative to that seen on neuronal cells within the CNS or other macrophage cell types not associated with the CNS. In some instances, these expressed genes code for pattern recognition receptors for endogenous CNS ligands. The expression profile of the microglia sensome can be used as a phenotypic biomarker profile unique to different microglia cells. In some cases, MCs or MLCs may express genes or proteins that are specific to microglia. For example, MCs or MLCs may express the following microglia specific gene biomarkers: Tmem119, P2ry12, Olfml3, Sall1, Gpr34, Gpr56, and Gpr84, or any subset thereof. In another example, MCs or MLCs may express the following microglia specific protein biomarkers: transmembrane protein 119 (TMEM119), P2Y purinoceptor 12 (P2RY12), olfactomedin-like protein 3 (OLFML3), Sal-like protein 1 (SALL1), G protein-coupled receptor 34 (GPR34), G protein-coupled receptor 56 (GPR56), and G protein-coupled receptor 84 (GPR84), or any subset thereof. In some cases, MCs or MLCs may express one or more additional gene biomarkers including, but not limited to, Cd45, Cd11b, Iba1, Clec12a, Ms4a7, Lilra5, Klra2, or any combination thereof. In some cases, MCs or MLCs may express one or more additional protein biomarkers including, but not limited to, cluster of differentiation 45 (CD45), cluster of differentiation 11B (CD11B), ionized calcium binding adapter molecule 1 (IBA1), C-type lectin domain family 12 member A (CLEC12A), membrane-spanning 4-domains subfamily A (MS4A7), leukocyte immunoglobulin-like receptor subfamily A member 5 (LILRA5), killer cell lectin-like receptor 2 (KLRA2), or any combination thereof. In some cases, differentiated MLCs may more closely resemble microglia than other tissue macrophages, monocytes, or neutrophils. In some cases, MLCs derived from yolk-stem cells (e.g., fetal brain) may possess a gene expression profile that more closely resembles microglia cells than that seen for MLCs derived from HSCs (e.g., from blood or bone marrow) or MLCs derived from a mixed origin (e.g., fetal liver). In some cases, MCs or MLCs may possess gene expression profiles associated with healthy or diseased microglia cells. For example, in some cases, HSC- compared to YS-MLCs can be significantly enriched in gene sets associated with ALS, AD, LPS treatment, immaturity, and in vitro culture from prior studies, along with major histocompatibility complex class II genes. In some instances, YS-MLCs may be relatively enriched in gene sets associated with CNS homeostasis. In some cases, MLCs may possess dysregulated gene expression. In one non limiting example, MCs or MLCs may possess dysregulated expression of ApoE. In some instances, dysregulated gene expression associated with MCs or MLCs may share expression profiles similar to that seen for microglia cells associated with a neurological disease or disorder.

In some cases, introduced MCs or MLCs may mimic the functional activity of normal healthy microglia cells. In some cases, MCs or MLCs may directly or indirectly regulate CNS homeostasis. In some cases, MCs or MLCs may possess functional activities including scavenging, phagocytosis, antigen presentation, extracellular signaling, release of cytotoxic molecules (e.g., hydrogen peroxide and nitic oxide), synaptic stripping, and promotion of neuronal regrowth. In some instances, MCs or MLCs introduced into the CNS of a subject may function primarily through the phagocytosis of foreign materials. In some instances, MCs or MLCs introduced into the CNS of a subject may function primarily through the regulation of extracellular signaling pathways.

MCs or MLCs, as described herein, may possess signaling pathway activity similar to healthy, normal endogenous microglia cells once introduced into the CNS of a subject. In some cases, MCs or MLCs may possess normal CSF1-CSF1R binding and subsequent signaling events that regulate cell survival and activity. In some cases, MCs or MLCs may express CSF1R that can be activated by CSF1. In some cases, activation of CSF1R on MCs or MLCs can lead to phosphorylation of targets including, but not limited to, PIK3R1, PLCG2, GRB2, SLA2 and CBL. In some instances, PLCG2 activation leads to production of the cellular signaling molecules diacylglycerol and inositol 1,4, 5-trisphosphate. In some instances, these signaling molecules in turn lead to the activation of protein kinase C (PKC) family members, particularly PRKCD. For example, PIK3R1 is a regulatory subunit of phosphatidylinositol 3-kinase and when phosphorylated by CSF1R activity can activate the AKT1 signaling pathway. In some instances, CSF1R can also activate MAP kinases, such as MAPK1/ ERK2 or MAPK3/ERK1. Similarly, CSF1R can also activate SRC family kinases, such as SRC, FYN, and YES1. Activated CSF1R transmits signals to proteins that directly interact with the phosphorylated tyrosine residues of the tyrosine kinase domain (TKD) of CSF1R. Additionally, in some instances, MCs or MLCs may possess CSF1R that can transmit signaling via adapter proteins, such as GRB2. Additionally, in some instances, MCs or MLCs may possess CSF1R capable of activating STAT family members, such as STAT3, STAT5A and STAT5B. In some cases, tyrosine phosphorylation of SHC1 and INPP5D/SHIP-1 may also be mediated by CSF1R activity within the MCs or MLCs. Lastly, CSF1R signaling within MCs or MLCs can down-regulate protein phosphatases, such as INPP5D/SHIP-1. Dephosphorylation of CSF1R and its downstream effectors, along with rapid internalization of the activated CSF1R, can regulate ligand-dependent activation within the MCs or MLCs.

In some cases, upon introduction into the CNS of a subject, MLCs may exist as two general types: ramified or activated. Ramified MLCs may be found throughout the brain and spinal cord of the CNS. In the absence of foreign material, these cells may exist in a "resting" state where the cell is composed of highly sensitive long cellular branches extending from a small cellular body. While the cellular body remains fixed, the long cellular branches are in a constant state of movement that surveys the surrounding environment for stimuli. In some cases, ramified MLCs may be non-phagocytic but highly sensitive through chemical monitoring of the nearby microenvironment of the CNS. While "resting" ramified MLCs can be highly active in their fixed location, they can also be further transformed into activated MLCs at any time in response to various stimuli. In some cases, ramified MLCs are directly transformed into active MLCs upon the introduction of an appropriate signal. In some instances, this transformation can be spatially or temporally controlled.

Activated, also known as "reactive", MLCs may exist as different sub-types that include: 1) non-phagocytic, 2) phagocytic, 3) amoeboid, and 4) gitter cell types. In some cases, activation of ramified MLCs into non-phagocytic MLCs can be induced by a variety of stimuli such as pro-inflammatory cytokines, cell necrosis factors, lipopoly-saccharides, or extracellular potassium (e.g., indicative of nearby ruptured apoptotic or necrosed cells). In some instances, activation causes the cellular branches to retract and thicken. In other instances, phenotypic changes upon activation may include uptake of MHC class I/II proteins, expression of immunomolecules, secretion of cytotoxic factors, secretion of recruitment molecules, and secretion of pro-inflammatory signaling molecules, which can result in a pro-inflammatory signal cascade. In some cases, activated MLCs can undergo rapid proliferation. Activation of MLCs may continue into the formation of phagocytic MLCs.

In some cases, phagocytic MLCs may be highly immuno-responsive. In some instances, the morphology of phago-cytic MLCs can vary. In response to phagocytosing foreign materials, these MLCs may be capable of antigen presentation and secreting molecules for mediating cytotoxic and inflammatory signaling pathways for activating T-cells. In some cases, phagocytic MLCs may interact with astrocytes and neuronal cells to fight off infections within the CNS.

MLCs can continue their activation into an amoeboid shape. In some cases, an amoeboid shaped activated MLC cane move freely throughout the CNS as a scavenger. While retaining phagocytosing capabilities, amoeboid MLCs may not antigen present or regulate inflammatory signaling pathways similar to that seen by earlier stage activated MLCs. In some cases, amoeboid MLCs can be prevalent in perinatal white matter areas such as in the corpus callosum and are highly active during the development and rewiring of the brains when large amounts of extracellular debris needs to be removed. Finally, in some cases, amoeboid MLCs can advance into a gitter-stage MLC once they are unable to phagocytize any further materials. Gitter-shaped MLCs may present as a granular morphological cell type.

Alternatively to phagocytic activity, MLCs can, in some aspects of the disclosure, be involved in the regulation of extracellular signaling pathways involved in maintaining CNS homeostasis. In some cases, MLCs may be capable of communicating with other cells such as astrocytes, neurons, T-cells, or myeloid progenitor cells. In some cases, MLCs can be activated by the presence of cytokine IFN-γ, thereby causing more stimulated release of IFN-γ into the extracellular space. In some instances, a cytokine induced cascade can rapidly activate nearby MLCs. In some instances, activated MLCs can produce signaling molecules such as TNF-α, IL-8, IL-1, MDC, MIP-3β, and prostanoids for regulating B-cell activation, dendritic cell antigen presentation, T-cell recruitment, and $T_H1$ response for instance.

Depletion of Endogenous Microglia Cells

For administered MCs or MLCs to engraft into host tissues for residency, an open niche may be advantageous. In some cases, an open niche for engraftment can be created within host tissues of a subject. Formation of a niche environment opening within the CNS of a subject in need thereof may be achieved through the use of stimuli that modulate the activity or survival of endogenous host micro-glia cells. In some cases, host endogenous microglia cells can be depleted prior to or concurrently with the introduction of MCs or MLCs.

Host endogenous microglia cells may be modulated or depleted through the use of exogenous stimuli administered into or applied to the CNS of a subject in need thereof. Stimuli may include, but are not limited to, ions, physiological pH, molecules, inorganic compounds, organic compounds, biomolecules, temperature, light, or any combination thereof within or applied to the CNS of a subject. For example, in some cases, irradiation of the CNS may be used to deplete, suppress, or modulate host endogenous microglia cells. Similarly, in some cases, chemotherapies may be used to deplete, suppress, or modulate host endogenous microglia cells. In some cases, the stimulus is a microglia cell inhibitor or antagonist for CSF1R. In some cases, the CSF1R inhibitor or antagonist may be used to deplete, suppress, or modulate host endogenous microglia cells that are sensitive to the inhibitor. In some cases, the use of a CSF1R inhibitor or antagonist is advantageous over the use of other stimuli, such as, but not limited to, irradiation or chemotherapy.

Known inhibitors that modulate CSF1R activity comprise tyrosine kinase inhibitors (TKIs) and anti-CSF1R antibodies that include, but are not limited to, pexidartinib (PLX-3397) ($IC_{50}$=13 nM), PLX-7486, and PLX-5622 (Daiichi Sankyo); ARRY-382 (ARRY Biopharma); BLZ945 (Novartis, $IC_{50}$=1.2 nM); BLZ945 metabolite (Novartis, $IC_{50}$=5.5 nM); DCC-3014 (Deciphera Pharmaceuticals); AMG-820 (AMGEN); GW-2580 (Sigma-Aldrich, $IC_{50}$=30 nM); linifanib (ABT-869) (Abbott Laboratories), OSI-930 (OSI Pharmaceuticals), or any known metabolites thereof. In some cases, the binding poses of known TKIs may fall into different structural groups. Known CSF1R antagonists also include anti-CSF1R antibodies such as, but not limited to, PD-0360324 (Pfizer), RG-7455 (e.g., Emactuzumab, Genentech/Roche), IMC-CS4 (Lilly), and MCS110 (Novartis). In some cases, administration of such CSF1R inhibitors and antagonists into a subject in need thereof may be used to disrupt endogenous ligand binding interactions. In some cases, such CSF1R inhibitors and antagonists may be used to deplete, suppress, or modulate host endogenous microglia cells within the CNS of a subject. In some cases, the CSF1R inhibitors and antagonists may be used as irreversible competitive ligands. In some cases, an irreversible competitive CSF1R ligand may be used to block the binding, and therefore inhibit the functional activity, of endogenous ligands. In such instances, the irreversible CSF1R competitive ligand may lead to depletion of host endogenous microglia cells.

In addition to known CSF1R inhibitory molecules and anti-ligand antibodies, ligand variants or fragments thereof which retain binding to CSF1R but which do not elicit or trigger a functional response may be used as a competitive ligand. In some cases, introduction of such competitive ligands into a subject in need thereof may be used to disrupt endogenous ligand binding interactions. In some cases, the disruption of endogenous ligand binding by such competitive ligands may be used to inactivate, suppress, or deplete host endogenous microglia cells within the CNS of a subject. In some cases, the ligand variants may comprise genetically modified CSF1 or IL-34 and any fragments thereof. In some cases, the genetically modified CSF1 or IL-34 and fragments thereof may be an irreversible competitive ligand. In some cases, an irreversible competitive CSF1 or IL-34 ligand may be used to block the binding, and therefore the functional activity, of endogenous CSF1 or IL-34. In such instances, the irreversible CSF1 or IL-34 competitive ligand may lead to depletion of host endogenous microglia cells.

The depletion of host microglia cells may allow for the introduced MCs or MLCs to repopulate host tissues. In some cases, MC or MLC repopulation of host tissue may be partial or complete. In some cases, MC or MLC repopulation of host tissue may be transient or permanent in nature. In some cases, MC or MLC repopulation of host tissue may be spatially specific within host tissues. In some cases, MC or MLC repopulation of host tissue may be to specific sub-tissues or sub-regions. In some cases, a CNS depleted of host endogenous microglia cells and thus rendered as a CSF1R–/– environment, may be sufficient to sustain, induce, or re-induce microglia identity. In some cases, such a CSF1R–/– environment can allow for engraftment of introduced MCs or MLCs.

Administration of CSF1R Inhibitors

CSF1R inhibitors and antagonists, as provided herein, may be administered to a subject by any known route of administration. In some cases, CSF1R inhibitors and antagonists can be introduced into the CNS of a subject in need. In some cases, the CSF1R inhibitors or antagonists may be injected into the CNS. In some cases, the CSF1R inhibitors or antagonists may be injected into the bloodstream. In some cases, CSF1R inhibitors or antagonists introduced into the blood of a subject can relocate into the CNS of the subject. Introduction of CSF1R inhibitors or antagonists into or relocation to host CNS tissue may allow for depletion, suppression, or modulation of host endogenous microglia cells within the subject. In some instances, host endogenous microglia cells may undergo morphological and phenotypic changes upon interaction with the introduced CSF1R inhibitors or antagonists. In some cases, phenotypic changes may include cellular death. In some cases, phenotypic changes may include changes in the expression of microglia specific biomarkers. The degree of phenotypic changes seen by host endogenous microglia cells upon interaction with the introduced CSF1R inhibitors or antagonists may be influenced by their developmental lineage.

In some cases, CSF1R inhibitors and antagonists may be used to deplete, suppress, or modulate host endogenous microglia cells within grey matter of the CNS. Grey matter generally comprises unmyelinated neurons and other cells of the CNS. Grey matter is found throughout the cerebrum, brainstem, and cerebellum of the brain. Grey matter is also present throughout the spinal cord. Grey matter is generally present at the surfaces of the cerebral hemispheres and the cerebellum as well as within deeper anatomical parts of the brain including, but not limited to, the thalamus, the hypothalamus, the subthalamus, the putamen of the basal ganglia, the deep cerebellar nuclei, and the brainstem, which may be surrounded by white matter. Grey matter present in the spinal cord includes the grey column which is further sub-divided into the anterior, posterior, and later grey columns. Grey matter of the CNS comprises neuropil, neuroglia, and capillaries. Neuropil further comprises mostly unmyelinated axons, dendrites, and glial cells. Neuroglia further comprises macroglia, microglia, and other minor accessory cells such as pituicytes and tanycytes. Macroglia comprises astrocytes, oligodendrocytes, ependymal, radial glia, Schwann, satellite glia, and enteric glia cells. Microglia comprises specialized macrophages that derive from mononuclear cells originating in the yolk sac during a defined embryonal period before populating the brain mesenchyme.

In some cases, CSF1R inhibitors or antagonists may be used to deplete, suppress, or modulate host endogenous microglia cells within white matter of the CNS. White matter generally comprises myelinated neurons and other cells of the CNS. White matter is found throughout the cerebrum, brainstem, and cerebellum of the brain. White matter forms the bulk of the cerebrum and cerebellum. White matter is also present throughout the superficial parts of the spinal cord. White matter is generally present below the surfaces of the cerebral hemispheres and the cerebellum. In the brain stem, white matter is found superficially, while grey matter is present in the depth of the brainstem. White matter forms the arbor vitae sub-region of the cerebellum.

CSF1R inhibitors and antagonists provided herein may be used to deplete, suppress, or modulate host endogenous microglia cells within the brain parenchyma of a host subject. In some cases, depletion, suppression, or modulation of host endogenous microglia cells within the brain may be partial or complete. In some cases, depletion, suppression, or modulation of host endogenous microglia cells within the brain may be transient or permanent. In some cases, depletion, suppression, or modulation of host endogenous microglia cells within the brain may be spatially specific. In some cases, depletion, suppression, or modulation of host endogenous microglia cells within the brain may be to specific sub-tissues or sub-regions of the brain. For example, CSF1R inhibitors and antagonists may deplete, suppress, or modulate host endogenous microglia cells within specific regions of the human brain including, but not limited to, the cerebrum, the brainstem, or the cerebellum.

CSF1R inhibitors or antagonists, provided herein, may be used to deplete, suppress, or modulate host endogenous microglia cells within the cerebrum of a subject. In some cases, CSF1R inhibitors and antagonists may be used to deplete, suppress, or modulate host endogenous microglia cells within the cerebral cortex, the hippocampus, the basal ganglia, the olfactory bulb, or any combination thereof, of the cerebrum. Sub-regions of the basal ganglia include the putamen, the globus pallidus, the nucleus accumbens, and the septal nuclei. In some cases, CSF1R inhibitors or antagonists may be used to deplete, suppress, or modulate host endogenous microglia cells in either cerebral hemispheres of the cerebral cortex. In some cases, CSF1R inhibitors or antagonists may be used to deplete, suppress, or modulate host endogenous microglia cells within the corpus callosum connecting the two cerebral hemispheres. In some cases, CSF1R inhibitors or antagonists may be used to deplete, suppress, or modulate host endogenous microglia cells within the frontal lobe, the parietal lobe, the occipital lobe, or the temporal lobe of the cerebral cortex in any combination thereof. In some cases, CSF1R inhibitors or antagonists may be used to deplete, suppress, or modulate host endogenous microglia cells within different cortical layers of the cerebral cortex. The cerebral cortex comprises six main cortical layers including: 1) the molecular layer, 2) the external granular layer, 3) the external pyramidal layer, 4) the internal granular layer, 5) the internal pyramidal layer or ganglionic layer, and 6) the polymorphic or multiform layer.

CSF1R inhibitors or antagonists, provided herein, may be used to deplete, suppress, or modulate host endogenous microglia cells within the brainstem of a subject. In some cases, CSF1R inhibitors or antagonists may be used to deplete, suppress, or modulate host endogenous microglia cells within regions of the brainstem including the midbrain, the pons, the medulla oblongata, the diencephalon of the forebrain, or any combination thereof. In some cases, CSF1R inhibitors or antagonists may be used to deplete, suppress, or modulate host endogenous microglia cells within the regions of the midbrain such as the tectum, the tegmentum, or the ventral tegmentum. Other sub-regions of the midbrain include, but are not limited to, the periaqueductal gray, the oculomotor nerve, the trochlear nerve, the red nucleus, the substantia nigra pars compacta, the reticular formation, the central tegmental tract, the ventral tegmental area, and the rostromedial tegmental nucleus. In some cases, CSF1R inhibitors or antagonists may be used to deplete, suppress, or modulate host endogenous microglia cells within the regions of the pons including the basilar part of the pons (e.g., the ventral part of the pons) and the pontine tegmentum (e.g., the dorsal part of the pons). In some cases, CSF1R inhibitors or antagonists may be used to deplete, suppress, or modulate host endogenous microglia cells within the regions of the medulla oblongata including the upper and lower parts. In some cases, CSF1R inhibitors or antagonists may be used to deplete, suppress, or modulate host endogenous microglia cells within the regions of the diencephalon of the forebrain including the thalamus, the hypothalamus, the epithalamus, the subthalamus, or any combination thereof. The epithalamus further comprises the habenula, the habenular nuclei, the habenular commissure, the habenular trigone, the stria medullaris, and the pineal gland.

CSF1R inhibitors or antagonists provided herein may be used to deplete, suppress, or modulate host endogenous microglia cells within the cerebellum of a subject. In some cases, CSF1R inhibitors or antagonists may be used to deplete, suppress, or modulate host endogenous microglia cells within regions of the cerebellum including the flocculonodular lobe, the anterior lobe, the posterior lobe, the arbor vitae, or any combination thereof. The posterior lobe may be further separated into the midline cerebellar vermis, and two lateral cerebellar hemispheres. In some cases, CSF1R inhibitors or antagonists may be used to deplete, suppress, or modulate host endogenous microglia cells within sub-regions of the cerebellum including the four deep cerebellar nuclei: 1) dentate nucleus, 2) the emboliform nucleus, 3) the globose nucleus, and 4) the fastigii nucleus. In some cases, CSF1R inhibitors or antagonists may be used to deplete, suppress, or modulate host endogenous microglia cells within sub-regions of the cerebellum including the three cerebellar cortex layers: 1) the molecular layer, 2) the Purkinje layer, and 3) the granular layer. In some cases, CSF1R inhibitors or antagonists may be used to deplete, suppress, or modulate host endogenous microglia cells within sub-regions of the cerebellum including the superior (brachium conjunctivium), the middle (brachium pontis), and the inferior (restiform and juxtarestiform bodies) cerebellar peduncles connecting the cerebellum to the midbrain.

CSF1R inhibitors or antagonists provided herein may be used to deplete, suppress, or modulate host endogenous microglia cells within the spinal cord of a host subject. In some cases, depletion, suppression, or modulation of host endogenous microglia cells within the spinal cord may be partial or complete. In some cases, depletion, suppression, or modulation of host endogenous microglia cells with the spinal cord may be transient or permanent. In some cases, depletion, suppression, or modulation of host endogenous microglia cells within the spinal cord may be spatially specific. In some cases, depletion, suppression, or modulation of host endogenous microglia cells of the spinal cord may be to specific sub-tissues or sub-regions of the spinal. For example, CSF1R inhibitors or antagonists may be used to deplete, suppress, or modulate host endogenous microglia cells within the cervical, thoracic, lumbar, conus medullaris, or cauda equine regions of the spinal cord, or any combination thereof.

CSF1R Inhibitor Dosage

As described herein, one or more CSF1R inhibitors or antagonists may be used to deplete, suppress, or modulate the population of host endogenous microglia cells within the CNS of a subject. In some cases, the CSF1R inhibitors or antagonists may be formulated for administration into a subject in need thereof. In some cases, the CSF1R inhibitor or antagonist may be administered in a dose greater than about 0.05 mg, greater than about 0.1 mg, greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 4.5 mg, greater than about 5 mg, greater than about 5.5 mg, greater than about 6 mg, greater than about 6.5 mg, greater than about 7 mg, greater than about 7.5 mg, greater than about 8 mg, greater than about 8.5 mg, greater than about 9 mg, greater than about 9.5 mg, greater than about 10 mg, greater than about 15 mg, greater than about 20 mg, greater than about 25 mg, greater than about 30 mg, greater than about 35 mg, greater than about 40 mg, greater than about 45 mg, greater than about 50 mg, greater than about 75 mg, greater than about 100 mg, greater than about 125 mg, greater than about 150 mg, greater than about 175 mg, greater than about 200 mg, greater than about 250 mg, greater than about 300 mg, greater than about 350 mg, greater than about 400 mg, greater than about 450 mg, greater than about 500 mg, greater than about 750 mg, greater than about 1,000 mg, greater than about 2,000 mg, greater than about 3,000 mg, greater than about 4,000 mg, or greater than about 5,000 mg. In some cases, the CSF1R inhibitor or antagonist may be administered in a dose of less than about 0.05 mg, less than about 0.1 mg, less than about 0.5 mg, less than about 1 mg, less than about 1.5 mg, less than about 2 mg, less than about 2.5 mg, less than about 3 mg, less than about 3.5 mg, less than about 4 mg, less than about 4.5 mg, less than about 5 mg, less than about 5.5 mg, less than about 6 mg, less than about 6.5 mg, less than about 7 mg, less than about 7.5 mg, less than about 8 mg, less than about 8.5 mg, less than about 9 mg, less than about 9.5 mg, less than about 10 mg, less than about 15 mg, less than about 20 mg, less than about 25 mg, less than about 30 mg, less than about 35 mg, less than about 40 mg, less than about 45 mg, less than about 50 mg, less than about 75 mg, less than about 100 mg, less than about 125 mg, less than about 150 mg, less than about 175 mg, less than about 200 mg, less than about 250 mg, less than about 300 mg, less than about 350 mg, less than about 400 mg, less than about 450 mg, less than about 500 mg, less than about 750 mg, less than about 1,000 mg, less than about 2,000 mg, less than about 3,000 mg, less than about 4,000 mg, or less than about 5,000 mg.

CSF1R inhibitors or antagonists may be administered once or more than once a day. In some cases, administration may occur as a single dose or multiple doses. In some instances, the single dose may provide sufficient depletion, suppression, or modulation of the host endogenous microglia cells. In some instances, multiple doses may be needed to provide sufficient depletion, suppression, or modulation of the host endogenous microglia cells. In some cases, CSF1R inhibitors or antagonists may be administered to the subject once, repeatedly, or continuously indefinitely.

In some cases, a subject in need thereof may be given a therapeutically effective amount that can be administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day. In some cases, CSF1R inhibitors or antagonists may be administered once, every day, once every two days, once every three days, once every four days, once every five days, once every six days, once every week, and so forth. In some cases, treatment of a subject in need thereof with a therapeutically effective amount of CSF1R inhibitors or antagonists may be for at least 1 week, for at least 2 weeks, for at least 3 weeks, for at least 4 weeks, for at least 1 month, for at least 2 months, for at least 3 month, for at least 4 months, for at least 5 months, for at least 6 months, for at least 7 months, for at least 8 months, for at least 9 months, for at least 10 months, for at least 11 months, for at least 12 months, or for more than 1 year.

CSF1R Inhibitor Efficacy

Administration of one or more CSF1R inhibitors or antagonists may be used to deplete, suppress, or modulate the population of host endogenous microglia cells within the CNS of a subject in need thereof. The level of depletion may be assessed by the change in microglia cell concentration as compared to that seen prior to CSF1R inhibitor or antagonist administration. Levels of host endogenous microglia cell population within a given CNS tissue may be assessed by any method known in the art. In some cases, the level of host endogenous microglia cell depletion may be greater than about 1%, greater than about 2%, greater than about 3%, greater than about 4%, greater than about 5%, greater than about 10%, greater than about 14%, greater than about 20%, greater than about 25%, greater than about 30%, greater than about 40%, greater than about 45%, greater than about 50%, greater than about 55%, greater than about 60%, greater than about 65%, greater than about 70%, greater than about 75%, greater than about 80%, greater than about 85%, greater than about 90%, greater than about 95%, greater than about 96%, greater than about 97%, greater than about 98%, greater than about 99%, or about 100%. In some cases, the level of host endogenous microglia cell depletion may be less than about 1%, less than about 2%, less than about 3%, less than about 4%, less than about 5%, less than about 10%, less than about 14%, less than about 20%, less than about 25%, less than about 30%, less than about 40%, less than about 45%, less than about 50%, less than about 55%, less than about 60%, less than about 65%, less than about 70%, less than about 75%, less than about 80%, less than about 85%, less than about 90%, less than about 95%, less than about 96%, less than about 97%, less than about 98%, less than about 99%, or about 100%.

Depletion of host endogenous microglia cells may be permanent or temporary. In some cases, depletion can be measured as the loss of host endogenous microglia cells at any given time following administration of one or more CSF1R inhibitors or antagonists. In some cases, host endogenous microglia cell depletion can be assessed at 1 hour, 2 hours, 3 hours, 4 hours, 5 hours, 6 hours, 8 hours, 10, hours, 12 hours, 24 hours, 2 days, 3 days, 4 days, 5 days, 6 days, 1 week, 2 weeks, 3 weeks, 4 weeks, 1 month, or longer post-administration.

Neurological Diseases or Disorders

MCs or MLCs described and provided herein, which may further comprise genetically modified CSF1R variants, may be used as a microglia cell replacement therapy for treating one or more neurological diseases or disorders in a subject in need thereof. In some cases, administration of MCs or MLCs into a subject may lead to their relocation into the CNS whereby they may engraft and repopulate within the CNS. Engraftment and population may be further aided by the depletion suppression, or modulation of host endogenous microglia cells through the use of CSF1R inhibitors or antagonists. In some cases, repopulation of MCs or MLCs within the CNS of a subject in need thereof may be used to restore normal, healthy CNS homeostasis. Restoration of CNS homeostasis may be used to therapeutically treat a neurological disease or disorder.

Neurological diseases and disorders may be broadly separated into neurodevelopmental or neurodegenerative in nature. In some cases, neurodevelopmental diseases and disorders can be characterized by the impairment in the proper growth and development of the CNS of a subject during their early and middle lifetime development. Such impairments generally affect emotional regulation, cognitive abilities such as self-control and learning capability, and memory of an affected subject. Therefore, in some cases, neurodevelopmental diseases and disorders may be broadly categorized into sub-groups including, but not limited to: 1)

intellectual disabilities, 2) Autism spectrum disorders, 3) neuromuscular disorders, 4) traumatic brain injury, 5) language and communication disorders, 6) genetic disorders, and 7) neurotoxicant induced disorders. Given the highly complex nature of CNS development, alterations to CNS homeostasis early with the human life cycle can have profound lasting effects. In some cases, such effects may not become apparent until much later in the human life cycle. In some instances, neurodevelopmental diseases and disorders can stem from a variety of genetic or environmental factors and agents.

In contrast to neurodevelopmental diseases and disorders, neurodegenerative diseases and disorders are generally associated with the onset of advanced age. In some cases, neurodegenerative diseases and disorders can be characterized by the progressive loss in structural integrity and functional activity of neurons within the CNS that ultimately leads to neuronal cell death. In some cases, neurodegenerative diseases and disorders may be heavily influenced by genetic and environmental factors. In some instances, misfolding or aggregation of neuronal proteins can characterize many neurodegenerative diseases and disorders. Such protein aggregates can lead to membrane damage that can contribute to cell death.

Neurological diseases and disorders may be any which directly or indirectly involve microglia cells. In some cases, MCs or MLCs of the disclosure may be used to treat neurological diseases or disorders associated with missing, inactive, or diseased host endogenous microglia cells. In some cases, MCs or MLCs of the disclosure may be used to treat neurological diseases or disorders not associated with missing, inactive, or diseased host endogenous microglia cells. In some cases, MCs or MLCs of the disclosure may be used to treat any secondary neurological diseases or disorders which arise subsequently to any first neurological disease or disorder. In some cases, MCs or MLCs of the disclosure may be used to treat neurological diseases or disorders which arise subsequently to any non-neurological disease or disorder.

Neurological diseases and disorders or diseases associated with a neurological disease or disorder may include those within the CNS of the nervous system. Examples of neurological diseases or disorders that may be treated by the methods and compositions provided herein may include, but are not limited to, Adult onset leukoencephalopathy with axonal spheroids and pigmented glia (ALSP) (also known as Pigmented orthochromatic leukodystrophy (POLD) and/or Hereditary diffuse leukoencephalopathy with axonal spheroids (HDLS)); Leukodystrophies including, but not limited to: Globoid cell leukodystrophy (Krabbe disease), Metachromatic leukodystrophy, Mucopolysaccharidosis IIIA/B (Sanfilippo syndrome), Mucopolysaccharidosis IIA (Hunter syndrome), Gaucher disease Type II/III, Niemann-Pick C1, Cerebrotendinous xanthomatosis (CTX), Canavan disease, or Alexander disease; Neuroinflammatory diseases including, but not limited to: Multiple sclerosis (any subtype), Neuromyelitis optica, Optic neuritis, or Transverse myelitis; Tauopathis/Synucleinopathies including, but not limited to: Progressive supranuclear palsy, Corticobasal degeneration, Dementia with Lewy Bodies, or Multiple System Atrophy; Neurodegenerative diseases including, but not limited to: Alzheimer's disease, Frontotemporal dementia, Parkinson's disease (including GBA and LRRK2 variants), Huntington's disease; Rett syndrome; or any other known neurological disease or disorder or any other known diseases or disorders associated therein. Additional examples of diseases or disorders that may be treated by the methods and compositions provided herein may include, but are not limited to, any form of dementia, any movement disorder condition, spinal cord injury, traumatic brain injury, stroke, or cerebral amyloid angiopathy.

In some cases, MCs or MLCs of the disclosure may be used to treat tumors associated with the CNS. In some cases, the tumor may be a primary brain tumor. In some cases, the tumor may be a metastatic or secondary brain tumor which infiltrates the CNS of a subject. In some cases, infiltration into the CNS may be facilitated by CCR2. In some instances, the tumor may be a brain or a spinal cord tumor. Brain and spinal cord tumors may be categorized into four distinct grades. Grade I are slow growing tumors that do not infiltrate into nearby tissues which can be generally treated by surgical means. Grade II are also slow growing but capable of infiltrating surrounding tissues. Grade II are likely to increase growth rate over time and are more likely to reappear after surgery. Grade III tumors are fast growing and more likely to invade nearby tissues. Grade III are less treatable by surgical means alone. Lastly, grade IV tumors are aggressively growing tumors which require corresponding aggressive therapeutic treatment. Examples of CNS associated tumors may include, but are not limited to, Gliomas, Meningiomas, Medulloblastomas, Ganglioglio-mas, Schwannomas (e.g., neurilemmomas), and Cranio-pharyngiomas. Gliomas may further comprise Astrocytomas, Oligodendrogliomas, and Ependymomas of various grade levels. Likewise, Meningiomas comprises multiple grade levels. Other CNS related tumors include Chordomas or Non-Hodgkin lymphomas (e.g., primary CNS lymphomas).

Alzheimer's Disease

Alzheimer's disease (AD) is a progressive neurodegenerative disease characterized by the formation of amyloid plaques and neurofibrillary tangles within the brain of a subject. The cause of AD is poorly understood, but microglia cells have been found to associate with amyloid deposits wherein they produce an inflammatory response. Interaction with amyloid fibers stimulates microglia cells into the active state whereby they produce and secret cytokines to induce a neurotoxic response. In some cases, subjects with AD display altered levels of Apolipoprotein E (ApoE) and associated variants. ApoE is a class of proteins involved in metabolic processing of fats and contributes to the formation of chylomicrons and intermediate-density lipoprotein (IDL) particles. In the CNS, ApoE is produced primarily by astrocytes and is involved in cholesterol transport to neuronal cells. In some cases, ApoE is implicated in enhancing proteolytic degradation of β-amyloid intracellularly and extracellularly. In other cases, ApoE variants demonstrate decreased functional activity that may allow for the build-up of β-amyloid plaques within the CNS.

Compositions and methods of using MCs or MLCs, as described herein, may be used for the treatment of AD in a subject in need thereof. MCs or MLCs may be used as a microglia replacement therapy for AD in a subject in need thereof. In some cases, MCs or MLCs may be used to replace or supplement the activity of host endogenous microglia cells within an AD subject. In some cases, the host endogenous microglia cells of an AD subject are missing, inactive, or in a pathological state associated with AD. In some cases, one or more CSF1R inhibitors or antagonists may be administered into an AD subject. The introduction of one or more CSF1R inhibitors or antagonists may be used to deplete, suppress, or modulate host endogenous microglia cells in an AD subject. In some instances, the introduction of one or more CSF1R inhibitors or antagonists may be transient or permanent in nature. In some instances, the introduction of one or more CSF1R inhibitors or antagonists may be to a specific region of the CNS for an AD subject. In some cases, MCs or MLCs which repopulate the CNS of an AD subject may demonstrate a gene expression signature (e.g., the microglia sensome/phenotypic profile) associated with healthy, normal microglia cells of a non-AD subject. In some cases, MCs or MLCs which repopulate the CNS of an AD subject may not demonstrate a gene expression signature (e.g., the microglia sensome/phenotypic profile) associated with diseased or unhealthy microglia cells of an AD subject.

Administration of one or more CSF1R inhibitors or antagonists may be used to open a niche environment within the CNS of an AD subject. In some cases, the opening of a niche environment within the CNS may allow for engraftment and residency of introduced MCs or MLCs. In some cases, MCs or MLCs are administered into an AD subject. Introduction of MCs or MLCs may lead to their relocation into the CNS of an AD subject. MC or MLC introduction into or relocation into the CNS of an AD subject may lead to their repopulation of the host CNS with MCs or MLCs. In some cases, repopulation of the CNS of an AD subject with MCs or MLCs may restore normal, healthy CNS homeostasis. In some cases, restoration of normal, healthy CNS homeostasis by introduced MCs or MLCs can provide therapeutic benefits in treating AD within a subject in need thereof. In some instances, the introduction of MCs or MLCs may be transient or permanent in nature. In some instances, the introduction of MCs or MLCs may be to a specific region of the CNS for an AD subject.

MCs or MLCs administered into an AD subject may be genetically modified. In some cases, genetically modified MC or MLCs may possess alterations that confer enhanced growth, survival, or activity. MCs or MLCs may contain a genetically modified CSF1R variant. In some cases, the genetically modified CSF1R variant may possess increased or decreased sensitivity to one or more CSF1R inhibitors or antagonists. In some cases, the genetically modified CSF1R variant may be insensitive to one or more CSF1R inhibitors or antagonists used to deplete, suppress, or modulate host endogenous microglia cells within an AD subject. In some cases, the CSF1R variant may comprise a mutation at one or more of V647, W550, G669, T663, G795, M637, D796, C666, Y546. In some cases, the CSF1R variant may be selected from the group consisting of: V647I, W550F, W550L, G669A, G669V, T663I, G795A, M637L, D796A, C666A, and Y546F. In some cases, MCs or MLCs containing a genetically modified CSF1R variant may be introduced into an AD subject with or after introduction of one or more CSF1R inhibitors or antagonists. In some cases, MCs or MLCs containing a genetically modified CSF1R variant may repopulate the CNS of an AD subject in need thereof. Repopulation of the CNS by MCs or MLCs may be aided by the use of one or more CSF1R inhibitors or antagonists to deplete, suppress, or modulate host endogenous microglia cells, wherein the introduced MCs or MLCs containing a CSF1R variant are insensitive to the administered CSF1R inhibitors or antagonists. Similarly, control over the introduced MCs or MLCs repopulating the CNS of an AD subject may be achieved through the administration of one or more CSF1R inhibitors or antagonists for which the CSF1R variant is sensitive to.

MCs or MLCs administered into an AD subject may be further genetically modified beyond CSF1R. In some cases, MCs or MLCs may be further genetically modified for gene therapy against AD. In some cases, MCs or MLCs may be genetically modified to express endogenous or exogenous genes or proteins that provide therapeutic efficacy against AD. For example, MCs or MLCs may be modified to express and secrete anti-Tau or anti-amyloid-β agents, e.g., antibodies, for instance. In some cases, genetically modified MCs or MLCs can contain decreased expression of ApoE. In some cases, MCs or MLCs genetically modified with decreased expression levels of ApoE may be useful in the treatment of AD in a subject.

Parkinson's Disease

Parkinson's disease (PD) is a neurological disease affecting the motor system of a subject with Dementia commonly associated with the later stages of the disease. The primary symptoms associated with PD are reduced activity of dopamine-secreting cells caused by cell death in the substantia nigra, a region within the midbrain. In addition to the substantia nigra, other brain regions exhibit neuronal loss and formation of Lewy bodies. Lewy bodies are abnormal protein aggregates that develop inside nerve cells and are comprised of multiple proteins such as alpha-synuclein, ubiquitin, neurofilament protein, Tau proteins, and alpha B crystallin.

Compositions and methods of using MCs or MLCs, as described herein, may be used for the treatment of PD in a subject in need thereof. MCs or MLCs may be used as a microglia replacement therapy for PD in a subject in need thereof. In some cases, MCs or MLCs may be used to replace or supplement the activity of host endogenous microglia cells within a PD subject. In some cases, the host endogenous microglia cells of a PD subject are missing, inactive, or in a pathological state associated with PD. In some cases, one or more CSF1R inhibitors or antagonists may be administered into a PD subject. The introduction of one or more CSF1R inhibitors or antagonists may be used to deplete, suppress, or modulate host endogenous microglia cells in a PD subject. In some instances, the introduction of one or more CSF1R inhibitors or antagonists may be transient or permanent in nature. In some instances, the introduction of one or more CSF1R inhibitors or antagonists may be to a specific region of the CNS for a PD subject. In some cases, MCs or MLCs which repopulate the CNS of a PD subject may demonstrate a gene expression signature (e.g., the microglia sensome/phenotypic profile) associated with healthy, normal microglia cells of a non-PD subject. In some cases, MCs or MLCs which repopulate the CNS of a PD subject may not demonstrate a gene expression signature (e.g., the microglia sensome/phenotypic profile) associated with diseased or unhealthy microglia cells of a PD subject.

Administration of one or more CSF1R inhibitors or antagonists may be used to open a niche environment within the CNS of a PD subject. In some cases, the opening of a niche environment within the CNS may allow for engraftment and residency of introduced MCs or MLCs. In some cases, MCs or MLCs are administered into a PD subject. Introduction of MCs or MLCs may lead to their relocation into the CNS of a PD subject. MC or MLC introduction into or relocation into the CNS of a PD subject may lead to their repopulation of the host CNS with MCs or MLCs. In some cases, repopulation of the CNS of a PD subject with MCs or MLCs may restore normal, healthy CNS homeostasis. In some cases, restoration of normal, healthy CNS homeostasis by introduced MCs or MLCs can provide therapeutic benefits in treating PD within a subject in need thereof. In some instances, the introduction of MCs or MLCs may be transient or permanent in nature. In some instances, the introduction of MCs or MLCs may be to a specific region of the CNS for a PD subject.

MCs or MLCs administered into a PD subject may be genetically modified. In some cases, genetically modified MC or MLCs may possess alterations that confer enhanced growth, survival, or activity. MCs or MLCs may contain a genetically modified CSF1R variant. In some cases, the genetically modified CSF1R variant may comprise increased or decreased sensitivity to one or more CSF1R inhibitors or antagonists. In some cases, the genetically modified CSF1R variant may be insensitive to one or more CSF1R inhibitors or antagonists used to deplete, suppress, or modulate host endogenous microglia cells within a PD subject. In some cases, the CSF1R variant may comprise a mutation at one or more of V647, W550, G669, T663, G795, M637, D796, C666, Y546. In some cases, the CSF1R variant may be selected from the group consisting of: V647I, W550F, W550L, G669A, G669V, T663I, G795A, M637L, D796A, C666A, and Y546F. In some cases, MCs or MLCs containing a genetically modified CSF1R variant may be introduced into a PD subject with or after introduction of one or more CSF1R inhibitors or antagonists. In some cases, MCs or MLCs containing a genetically modified CSF1R variant may repopulate the CNS of a PD subject in need thereof. Repopulation of the CNS by MCs or MLCs may be aided by the use of one or more CSF1R inhibitors or antagonists to deplete, suppress, or modulate host endogenous microglia cells, wherein the introduced MCs or MLCs containing a CSF1R variant are insensitive to the administered CSF1R inhibitors or antagonists. Similarly, control over the introduced MCs or MLCs repopulating the CNS of a PD subject may be achieved through the administration of one or more CSF1R inhibitors or antagonists for which the CSF1R variant is sensitive to.

MCs or MLCs administered into a PD subject may be further genetically modified beyond CSF1R. In some cases, MCs or MLCs may be further genetically modified for gene therapy against PD. In some cases, MCs or MLCs may be genetically modified to express endogenous or exogenous genes or proteins that provide therapeutic efficacy against PD. For example, MCs or MLCs may be modified to express and secrete aromatic amino acid decarboxylase (AADC), glutamic acid decarboxylase (GAD) or growth factors such as glial cell line-derived neurotrophic factor (GDNF). In some cases, MC s or MLCs may be modified to decrease expression of alpha-synuclein, ubiquitin, neurofilament protein, Tau proteins, alpha B crystalline, or any combination thereof.

Huntington's Disease

Huntington's disease (HD) is a neurological disease that is marked by the progressive loss of brain cells leading to dysregulation of psychomotor and cognitive capabilities. Progression of HD is often accompanied by dementia. HD is a hereditary genetic disease wherein huntingtin (HTT) protein is mutated. HTT functionality is poorly understood but appears to be involved in a wide range of cellular activities including cell signaling, transcriptional activity, and intracellular transport, particularly that related to vesicular transport and synaptic transmission. Loss of HTT is not directly the causative agent of HD. Instead, the production of a mutant HTT (mHTT) resulting from alterations in the HTT gene (HD) is believed to be a primary causative factor. mHTT is believed to be neurotoxic and its increased presence correlates with HD symptoms and disease progression. HD is also associated with increased activation of microglia cells.

Compositions and methods of using MCs or MLCs, as described herein, may be used for the treatment of HD in a subject in need thereof. MCs or MLCs may be used as a microglia replacement therapy for HD in a subject in need thereof. In some cases, MCs or MLCs may be used to replace or supplement the activity of host endogenous microglia cells within a HD subject. In some cases, the host endogenous microglia cells of a HD subject are missing, inactive, or in a pathological state associated with HD. In some cases, one or more CSF1R inhibitors or antagonists may be administered into a HD subject. The introduction of one or more CSF1R inhibitors or antagonists may be used to deplete, suppress, or modulate host endogenous microglia cells in a HD subject. In some instances, the introduction of one or more CSF1R inhibitors or antagonists may be transient or permanent in nature. In some instances, the introduction of one or more CSF1R inhibitors or antagonists may be to a specific region of the CNS for a HD subject. In some cases, MCs or MLCs which repopulate the CNS of a HD subject may demonstrate a gene expression signature (e.g., the microglia sensome/phenotypic profile) associated with healthy, normal microglia cells of a non-HD subject. In some cases, MCs or MLCs which repopulate the CNS of a HD subject may not demonstrate a gene expression signature (e.g., the microglia sensome/phenotypic profile) associated with diseased or unhealthy microglia cells of a HD subject.

Administration of one or more CSF1R inhibitors or antagonists may be used to open a niche environment within the CNS of a HD subject. In some cases, the opening of a niche environment within the CNS may allow for engraftment and residency of introduced MCs or MLCs. In some cases, MCs or MLCs are administered into a HD subject. Introduction of MCs or MLCs may lead to their relocation into the CNS of a HD subject. MC or MLC introduction into or relocation into the CNS of a HD subject may lead to their repopulation of the host CNS with MCs or MLCs. In some cases, repopulation of the CNS of a HD subject with MCs or MLCs may restore normal, healthy CNS homeostasis. In some cases, restoration of normal, healthy CNS homeostasis by introduced MCs or MLCs can provide therapeutic benefits in treating HD within a subject in need thereof. In some instances, the introduction of MCs or MLCs may be transient or permanent in nature. In some instances, the introduction of MCs or MLCs may be to a specific region of the CNS for a HD subject.

MCs or MLCs administered into a HD subject may be genetically modified. In some cases, genetically modified MC or MLCs may possess alterations that confer enhanced growth, survival or activity. MCs or MLCs may contain a genetically modified CSF1R variant. In some cases, the genetically modified CSF1R variant may contain increased or decreased sensitivity to one or more CSF1R inhibitors or antagonists. In some cases, the genetically modified CSF1R variant may be insensitive to one or more CSF1R inhibitors or antagonists used to deplete, suppress, or modulate host endogenous microglia cells within a HD subject. In some cases, the CSF1R variant may comprise a mutation at one or more of V647, W550, G669, T663, G795, M637, D796, C666, Y546. In some cases, the CSF1R variant may be selected from the group consisting of: V647I, W550F, W550L, G669A, G669V, T663I, G795A, M637L, D796A, C666A, and Y546F. In some cases, MCs or MLCs containing a genetically modified CSF1R variant may be introduced into a HD subject with or after introduction of one or more CSF1R inhibitors or antagonists. In some cases, MCs or MLCs containing a genetically modified CSF1R variant may repopulate the CNS of a HD subject in need thereof. Repopulation of the CNS by MCs or MLCs may be aided by the use of one or more CSF1R inhibitors or antagonists to deplete, suppress, or modulate host endogenous microglia cells, wherein the introduced MCs or MLCs containing a CSF1R variant are insensitive to the administered CSF1R inhibitors or antagonists. Similarly, control over the introduced MCs or MLCs repopulating the CNS of a HD subject may be achieved through the administration of one or more CSF1R inhibitors or antagonists for which the CSF1R variant is sensitive to.

MCs or MLCs administered into a HD subject may be further genetically modified beyond CSF1R. In some cases, MCs or MLCs may be further genetically modified for gene therapy against HD. In some cases, MCs or MLCs may be genetically modified to express endogenous or exogenous genes or proteins that provide therapeutic efficacy against HD.

Multiple Sclerosis

Multiple sclerosis (MS) is a chronic inflammatory and neurodegenerative disease in which the myelin sheaths of the nerve cells within the CNS are damaged. MS is characterized by protein aggregates, such as sclerae, lesions, or plaques; focal lesions of inflammation; axonal loss; gliosis; and neuronal demyelination. Damage of myelinated neurons within MS subjects is associated with activation of macrophages and microglia cells, along with release of cytokines and antibodies. Demyelination of neuronal cells in MS subjects leads to disruption of normal communicative and psychomotor functions. Although the pathophysiology underlying MS remains poorly understood, genetic factors, exposure to infectious agents, and environmental stimuli are believed to be contributing factors. Activation of microglia cells, along with their cytokine expression, is believed to be an additional contributing factor.

Compositions and methods of using MCs or MLCs, as described herein, may be used for the treatment of MS in a subject in need thereof. MCs or MLCs may be used as a microglia replacement therapy for MS in a subject in need thereof. In some cases, MCs or MLCs may be used to replace or supplement the activity of host endogenous microglia cells within a MS subject. In some cases, the host endogenous microglia cells of a MS subject are missing, inactive, or in a pathological state associated with MS. In some cases, one or more CSF1R inhibitors or antagonists may be administered into a MS subject. The introduction of one or more CSF1R inhibitors or antagonists may be used to deplete, suppress, or modulate host endogenous microglia cells in a MS subject. In some instances, the introduction of one or more CSF1R inhibitors or antagonists may be transient or permanent in nature. In some instances, the introduction of one or more CSF1R inhibitors or antagonists may be to a specific region of the CNS for a MS subject. In some cases, MCs or MLCs which repopulate the CNS of a MS subject may demonstrate a gene expression signature (e.g., the microglia sensome/phenotypic profile) associated with healthy, normal microglia cells of a non-MS subject. In some cases, MCs or MLCs which repopulate the CNS of a MS subject may not demonstrate a gene expression signature (e.g., the microglia sensome/phenotypic profile) associated with diseased or unhealthy microglia cells of a MS subject.

Administration of one or more CSF1R inhibitors or antagonists may be used to open a niche environment within the CNS of a MS subject. In some cases, the opening of a niche environment within the CNS may allow for engraftment and residency of introduced MCs or MLCs. In some cases, MCs or MLCs are administered into a MS subject. Introduction of MCs or MLCs may lead to their relocation into the CNS of a MS subject. MC or MLC introduction into or relocation into the CNS of a MS subject may lead to their repopulation of the host CNS with MCs or MLCs. In some cases, repopulation of the CNS of a MS subject with MCs or MLCs may restore normal, healthy CNS homeostasis. In some cases, restoration of normal, healthy CNS homeostasis by introduced MCs or MLCs can provide therapeutic benefits in treating MS within a subject in need thereof. In some instances, the introduction of MCs or MLCs may be transient or permanent in nature. In some instances, the introduction of MCs or MLCs may be to a specific region of the CNS for a MS subject.

MCs or MLCs administered into a MS subject may be genetically modified. In some cases, genetically modified MC or MLCs may possess alterations that confer enhanced growth, survival or activity. MCs or MLCs may contain a genetically modified CSF1R variant. In some cases, the genetically modified CSF1R variant may contain increased or decreased sensitivity to one or more CSF1R inhibitors or antagonists. In some cases, the genetically modified CSF1R variant may be insensitive to one or more CSF1R inhibitors or antagonists used to deplete, suppress, or modulate host endogenous microglia cells within a MS subject. In some cases, the CSF1R variant may comprise a mutation at one or more of V647, W550, G669, T663, G795, M637, D796, C666, Y546. In some cases, the CSF1R variant may be selected from the group consisting of: V647I, W550F, W550L, G669A, G669V, T663I, G795A, M637L, D796A, C666A, and Y546F. In some cases, MCs or MLCs containing a genetically modified CSF1R variant may be introduced into a MS subject with or after introduction of one or more CSF1R inhibitors or antagonists. In some cases, MCs or MLCs containing a genetically modified CSF1R variant may repopulate the CNS of a MS subject in need thereof. Repopulation of the CNS by MCs or MLCs may be aided by the use of one or more CSF1R inhibitors or antagonists to deplete, suppress, or modulate host endogenous microglia cells, wherein the introduced MCs or MLCs containing a CSF1R variant are insensitive to the administered CSF1R inhibitors or antagonists. Similarly, control over the introduced MCs or MLCs repopulating the CNS of a MS subject may be achieved through the administration of one or more CSF1R inhibitors or antagonists for which the CSF1R variant is sensitive to.

MCs or MLCs administered into a MS subject may be further genetically modified beyond CSF1R. In some cases, MCs or MLCs may be further genetically modified for gene therapy against MS. In some cases, MCs or MLCs may be genetically modified to express endogenous or exogenous genes or proteins that provide therapeutic efficacy against MS.

Viral Infection

Microglia cells are implicated in viral infections including Herpes simplex virus (HSV) and human immunodeficiency virus (HIV). HSV infiltration into the CNS during infection can lead to encephalitis. Stimulation of microglia cells during infection leads to release of neuro-cytotoxic cytokines. HSV induced damage to the CNS can persist long term as the microglia cells remain activated for significant amounts of time post-infection. Alternatively, microglia cells are the main cell target for HIV-1 during infection and infiltration into the brain of a subject. HIV-1 establish intracellular residency within infected microglia cells. HIV particles enter into microglia cells through a variety of cell surface receptors. Infected microglia cells actively secrete endogenous neurotoxins such as TNF-α, IL-1β, CXCL8/IL-8, glutamate, quinolinic acid, platelet activating factor, eicosanoids, and nitric oxide. Infected microglia cells also release neurotoxic viral proteins including Tat, gp120, and gp41. These secreted factors stimulate other cells to secrete additional neurotoxic factors. As such, HIV infected microglia cells directly induce neuronal damage and dysfunction.

Compositions and methods of using MCs or MLCs, as described herein, may be used for the treatment of a viral infection in a subject in need thereof. MCs or MLCs may be used as a microglia replacement therapy for a viral infection within a subject in need thereof. In some cases, MCs or MLCs may be used to replace or supplement the activity of host endogenous microglia cells within a virus infected subject. In some cases, the host endogenous microglia cells of a virus infected subject are missing, inactive, or associated with a pathological state in a viral infection. In some cases, one or more CSF1R inhibitors or antagonists may be administered into a virus infected subject. The introduction of one or more CSF1R inhibitors or antagonists may be used to deplete, suppress, or modulate host endogenous microglia cells in a viral infected subject. In some instances, the introduction of one or more CSF1R inhibitors or antagonists may be transient or permanent in nature. In some instances, the introduction of one or more CSF1R inhibitors or antagonists may be to a specific region of the CNS of a virus infected subject. In some cases, MCs or MLCs which repopulate the CNS of a virus infected subject may demonstrate a gene expression signature (e.g., the microglia sensome/phenotypic profile) associated with healthy, normal microglia cells of a non-virally infected subject. In some cases, MCs or MLCs which repopulate the CNS of a virus infected subject may not demonstrate a gene expression signature (e.g., the microglia sensome/phenotypic profile) associated with diseased or unhealthy microglia cells of a virally infected subject.

Administration of one or more CSF1R inhibitors or antagonists may be used to open a niche environment within the CNS of a virus infected subject. In some cases, the opening of a niche environment within the CNS may allow for engraftment and residency of introduced MCs or MLCs. In some cases, MCs or MLCs are administered into a virus infected subject. Introduction of MCs or MLCs may lead to their relocation into the CNS of a virus infected subject. MC and/MLC introduction into or relocation into the CNS of a virus infected subject may lead to their repopulation of the host CNS with MCs or MLCs. In some cases, repopulation of the CNS of a virus infected subject with MCs or MLCs may restore normal, healthy CNS homeostasis. In some cases, restoration of normal, healthy CNS homeostasis by introduced MCs or MLCs can provide therapeutic benefits in treating a viral infection within a subject in need thereof. In some instances, the introduction of MCs or MLCs may be transient or permanent in nature. In some instances, the introduction of MCs or MLCs may be to a specific region of the CNS for a virus infected subject.

MCs or MLCs administered into a virus infected subject may be genetically modified. In some cases, genetically modified MC or MLCs may possess alterations that confer enhanced growth, survival or activity. MCs or MLCs may contain a genetically modified CSF1R variant. In some cases, the genetically modified CSF1R variant may contain increased or decreased sensitivity to one or more CSF1R inhibitors or antagonists. In some cases, the genetically modified CSF1R variant may be insensitive to one or more CSF1R inhibitors or antagonists used to deplete, suppress, or modulate host endogenous microglia cells within a virus infected subject. In some cases, the CSF1R variant may comprise a mutation at one or more of V647, W550, G669, T663, G795, M637, D796, C666, Y546. In some cases, the CSF1R variant may be selected from the group consisting of: V647I, W550F, W550L, G669A, G669V, T663I, G795A, M637L, D796A, C666A, and Y546F. In some cases, MCs or MLCs containing a genetically modified CSF1R variant may be introduced into a virus infected subject with or after introduction of one or more CSF1R inhibitors or antagonists. In some cases, MCs or MLCs containing a genetically modified CSF1R variant may repopulate the CNS of a virus infected subject in need thereof. Repopulation of the CNS by MCs or MLCs may be aided by the use of one or more CSF1R inhibitors or antagonists to deplete, suppress, or modulate host endogenous microglia cells, wherein the introduced MCs or MLCs containing a CSF1R variant are insensitive to the administered CSF1R inhibitors or antagonists. Similarly, control over the introduced MCs or MLCs repopulating the CNS of a virus infected subject may be achieved through the administration of one or more CSF1R inhibitors or antagonists for which the CSF1R variant is sensitive to.

MCs or MLCs administered into a virus infected subject may be further genetically modified beyond CSF1R. In some cases, MCs or MLCs may be further genetically modified for gene therapy against viral infection. In some cases, MCs or MLCs may be genetically modified to express endogenous or exogenous genes or proteins that provide therapeutic efficacy against viral infection.

Microbial Infection

Microglia cells have been implicated in contributing to neurotoxic inflammatory responses following microbial infections. Generally, microglia cells are stimulated by lipopolysaccharide, a component of the outer membrane of gram-negative bacteria, to produce cytokines, chemokines, and prostaglandins. Alternatively to LPS stimulation, microglia cells can directly interact with microbial cells via different cell surface receptors. Contact with microbial cells interaction can trigger microglia cell stimulation leading to the release of inflammatory molecules and compounds, such as nitric oxide. This inflammatory response can be neurotoxic.

Compositions and methods of using MCs or MLCs, as described herein, may be used for the treatment of a microbial infection in a subject in need thereof. MCs or MLCs may be used as a microglia replacement therapy for a microbial infection within a subject in need thereof. In some cases, MCs or MLCs may be used to replace or supplement the activity of host endogenous microglia cells within a microbial infected subject. In some cases, the host endogenous microglia cells of a microbial infected subject are missing, inactive, or in a pathological state associated with a microbial infection. In some cases, one or more CSF1R inhibitors or antagonists may be administered into a microbial infected subject. The introduction of one or more CSF1R inhibitors or antagonists may be used to deplete, suppress, or modulate host endogenous microglia cells in a microbial infected subject. In some instances, the introduction of one or more CSF1R inhibitors or antagonists may be transient or permanent in nature. In some instances, the introduction of one or more CSF1R inhibitors or antagonists may be to a specific region of the CNS of a microbial infected subject. In some cases, MCs or MLCs which repopulate the CNS of a microbial infected subject may demonstrate a gene expression signature (e.g., the microglia sensome/phenotypic profile) associated with healthy, normal microglia cells of a non-microbial infected subject. In some cases, MCs or MLCs which repopulate the CNS of a microbial infected subject may not demonstrate a gene expression signature (e.g., the microglia sensome/phenotypic profile) associated with diseased or unhealthy microglia cells of a microbial infected subject.

Administration of one or more CSF1R inhibitors or antagonists may be used to open a niche environment within the CNS of a microbial infected subject. In some cases, the opening of a niche environment within the CNS may allow for engraftment and residency of introduced MCs or MLCs. In some cases, MCs or MLCs are administered into a microbial infected subject. Introduction of MCs or MLCs may lead to their relocation into the CNS of a microbial infected subject. MC and/MLC introduction into or relocation into the CNS of a microbial infected subject may lead to their repopulation of the host CNS with MCs or MLCs. In some cases, repopulation of the CNS of a microbial infected subject with MCs or MLCs may restore normal, healthy CNS homeostasis. In some cases, restoration of normal, healthy CNS homeostasis by introduced MCs or MLCs can provide therapeutic benefits in treating a microbial infection within a subject in need thereof. In some instances, the introduction of MCs or MLCs may be transient or permanent in nature. In some instances, the introduction of MCs or MLCs may be to a specific region of the CNS for a microbial infected subject.

MCs or MLCs administered into a microbial infected subject may be genetically modified. In some cases, genetically modified MC or MLCs may possess alterations that confer enhanced growth, survival or activity. MCs or MLCs may contain a genetically modified CSF1R variant. In some cases, the genetically modified CSF1R variant may contain increased or decreased sensitivity to one or more CSF1R inhibitors or antagonists. In some cases, the genetically modified CSF1R variant may be insensitive to one or more CSF1R inhibitors or antagonists used to deplete, suppress, or modulate host endogenous microglia cells within a microbial infected subject. In some cases, the CSF1R variant may comprise a mutation at one or more of V647, W550, G669, T663, G795, M637, D796, C666, Y546. In some cases, the CSF1R variant may be selected from the group consisting of: V647I, W550F, W550L, G669A, G669V, T663I, G795A, M637L, D796A, C666A, and Y546F. In some cases, MCs or MLCs containing a genetically modified CSF1R variant may be introduced into a microbial infected subject with or after introduction of one or more CSF1R inhibitors or antagonists. In some cases, MCs or MLCs containing a genetically modified CSF1R variant may repopulate the CNS of a microbial infected subject in need thereof. Repopulation of the CNS by MCs or MLCs may be aided by the use of one or more CSF1R inhibitors or antagonists to deplete, suppress, or modulate host endogenous microglia cells, wherein the introduced MCs or MLCs containing a CSF1R variant are insensitive to the administered CSF1R inhibitors or antagonists. Similarly, control over the introduced MCs or MLCs repopulating the CNS of a microbial infected subject may be achieved through the administration of one or more CSF1R inhibitors or antagonists for which the CSF1R variant is sensitive to.

MCs or MLCs administered into a microbial infected subject may be further genetically modified beyond CSF1R. In some cases, MCs or MLCs may be further genetically modified for gene therapy against microbial infection. In some cases, MCs or MLCs may be genetically modified to express endogenous or exogenous genes or proteins that provide therapeutic efficacy against microbial infection. For example, MCs or MLCs may be modified to express and secrete antimicrobial agents.

Formulations

Pharmaceutical compositions or formulations containing MCs or MLCs, as well as one or more CSF1R inhibitors or antagonists, as described and provided herein, may be prepared with one or more optional pharmaceutically acceptable carriers, excipients/stabilizers, or any combination thereof. In some cases, pharmaceutical compositions or formulations of MCs or MLCs may be prepared as a lyophilized formulation or as an aqueous solution. Compositions described herein may comprise a liquid formulation, a semi-solid formulation, a solid formulation, or a combination thereof. In some cases, compositions or formulations of MCs or MLCs may be used with any applicator that is suitable for intravenous (IV) injection or intracerebroventricular injection (ICVI) into the blood or the cerebrospinal fluid of the CNS of a subject. Likewise, in some cases, compositions or formulations of MCs or MLCs may be used with any applicator that is suitable for intracerebral transplantation (ICT) or supratentorial injection into the CNS of a subject. Non-limiting examples of formulations may include a liquid, a liquid solution, a gel, a paste, a cream, an ointment, an emulsion, a nanoparticle solution, a colloidal mixture, or a suspension.

In some cases, compositions and formulations of MCs or MLCs may be generally tolerated by a subject upon administration without producing an allergic reaction or any other similar negative reaction. Compositions and formulations for administration into a subject may be sterilized prior to administration. For example, sterile filtration membranes may be used for sterilization. In some cases of the present invention, the compositions are formulated to be free of pyrogens or endotoxins such that they are acceptable for administration to a subject.

In some cases, MCs or MLCs, as well as one or more CSF1R inhibitors or antagonists of the present disclosure may be further formulated with any number of excipients. Excipients may include, but are not limited to, solvents, colorings, lubricants, preservatives, binders, diluents, stabilizers, or carriers. Excipients for use in the formulations may be compatible with the MCs or MLCs compositions provided herein. In some cases, the formulations may also contain minor amounts of non-toxic ancillary substances. Such ancillary substances may include, but are not limited to, wetting or emulsifying agents, pH buffering agents, sodium acetate, and triethanolamine. In some cases, the addition of such substances may improve the depletion, inactivation, and modulation of host endogenous microglia cells of a subject. In some cases, the addition of such substances may improve the engraftment and repopulation of the CNS of a subject by the administered MCs or MLCs In some cases, the pH of the formulation may be similar to the pH of the cerebrospinal fluid of the CNS. In some cases, the pH of the formulation may not cause adverse cytotoxic effects to the MCs or MLCs, CSF1R inhibitors or antagonists, or the CNS of the subject. In some instances, the pH of the formulation may be about 6.0, about 6.2, about 6.4, about 6.6, about 6.8, about 7.0, about 7.2, about 7.4, about 7.6, about 7.8, or about 8.0. In some instances, the pH of the formulation may be about 7.2, 7.3, 7.4, 7.5, or 7.6. In some cases, the pH of the formulation may not change upon administration. In some cases, the pH of the formulation may change upon administration. In some instances, the pH of the formulation may not change upon dilution. In some instances, the pH of the formulation may change upon dilution.

In some cases, the electrolyte concentration of any formulation may be similar to the electrolyte concentration of cerebrospinal fluid within the CNS. In some instances, any formulation may have higher chloride levels than plasma. In some instances, any formulation may have equivalent sodium levels as plasma. In some cases, the protein concentration of any formulation may be similar to the protein concentration of cerebrospinal fluid within the CNS. In some instances, any formulation may comprise about 0.3% plasma proteins. In some instances, the proteins within any formulation may be globular proteins or albumin. In some cases, any formulation may be free or nearly free of red blood cells. In some cases, any formulation may be free or nearly free of white blood cells.

Kits and Applicators

MCs or MLCs, as well as CSF1R inhibitors or antagonists of the disclosure may be prepared in a kit. In some cases, a kit may comprise one or more MCs or MLCs, and optionally, one or more kit instructions, any applicator suitable for IV injection, any applicator suitable for ICVI or ICT into the blood or the cerebrospinal fluid of the CNS of a subject, a tube, one or more tubes filled with one or more CSF1R inhibitors or antagonists suspended in bacteriostatic buffer or water, a vial, a vial filled with bacteriostatic media or buffer, a vial filled with a cleaning solution for the applicator, or any combination thereof. In some cases, kits provided herein may comprise genetically modified MCs or MLCs. Kits provided herein may comprise a tube or vial containing one or more doses of the MCs or MLCs. Kits provided herein may comprise a tube or vial containing one or more doses of one or more CSF1R inhibitors or antagonists.

In some cases, the genetically modified MCs or MLCs of a kit may comprise a genetically modified CSF1R variant. In such instances, the CSF1R variant may comprise increased or decreased sensitivity to one or more CSF1R inhibitors or antagonists. In some cases, the genetically modified MCs or MLC may comprise genetic alterations that improve cell growth, survival, engraftment, and repopulation of the CNS. In some cases, the genetically modified MCs or MLCs may comprise genetic alterations that improve the therapeutic efficacy of MCs or MLCs within the CNS of a subject with a neurological disease or disorder.

In some cases, a kit provided herein may comprise an applicator for IV or supratentorial injection. In some cases, the IV or supratentorial injection applicator may comprise a hypodermic needle or peripheral cannula of any suitable gauge size. In some cases, the IV or supratentorial injection applicator may be used for intermittent or continuous infusion. In some instances, intermittent infusion may be by secondary IV or an IV push. In some cases, the IV supratentorial injection applicator may be used for the administration of MCs or MLCs of the disclosure, as described herein. In some cases, the IV or supratentorial injection applicator may be used for the administration of one or more CSF1R inhibitors or antagonists of the disclosure, as described herein.

In some cases, a kit provided herein may comprise an applicator for ICVI injection or transplantation. In some cases, the ICVI or ICT applicator may comprise a hypodermic needle or peripheral cannula of any suitable gauge size. In some cases, the ICVI or ICT applicator may be used for intermittent or continuous infusion. In some cases, the ICVI or ICT applicator may be used for the administration of MCs or MLCs of the disclosure, as described herein. In some cases, the ICVI or ICT applicator may be used for the administration of one or more CSF1R inhibitors or antagonists of the disclosure, as described herein.

In some cases, a kit provided herein may comprise a formulation of MCs or MLCs as provided herein. In some cases, a kit provided herein may comprise a formulation of one or more CSF1R inhibitors or antagonists as provided herein. In some cases, the formulation comprises a carrier substance or an excipient. In some cases, the MCs or MLCs and the formulation are packaged separately and combined prior to administration. In some cases, the one or more CSF1R inhibitors or antagonists and the formulation are packaged separately and combined prior to administration. In some cases, the MCs or MLCs and one or more CSF1R inhibitors or antagonists are formulated and packaged separately and combined prior to administration. In some cases, the MCs or MLCs and one or more CSF1R inhibitors or antagonists are formulated together prior to administration.

Kits provided herein may comprise an applicator that is designed for IV, ICVI, ICT, OR supratentorial administration. In some cases, the applicator may be pre-filled with MCs or MLCs. In some cases, the applicator may be pre-filled with one or more CSF1R inhibitors or antagonists. In some cases, the applicator may be pre-filled with both MCs or MLCs and one or more CSF1R inhibitors or antagonists. In some cases, the applicator may be pre-filled with a single dose of MCs or MLCs, one or more CSF1R inhibitors or antagonists, or both. In some cases, the applicator may be pre-filled with multiple doses of MCs or MLCs, one or more CSF1R inhibitors or antagonists, or both.

In some cases, the kit comprises instructions for applying the MCs or MLCs, one or more CSF1R inhibitors or antagonists, or both to the CNS of a subject in need thereof. In some instances, the instructional information may recite medically necessary procedures for IV, ICVI, ICT, or supratentorial administration to the CNS of a subject. In some cases, the instructions may recite storage information, safety information, operational use information, dosage information, efficacy information, and/or regulatory information. In some cases, the instructions may recite information for sterile cleaning of the applicator. In some instances, the instructions may recite information for using a first vial filled with cleaning solution and a second vial filled with bacteriostatic water for cleaning the applicator.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. A Combination of Ontogeny and CNS Environment Establishes Microglia Identity Since our goal was to precisely measure how ontogeny and environment affect microglia identity, we aimed to create a system for transplantation of myeloid cells across development into the brain. We took advantage of Csf1r−/− mice, which lack microglia, and found that directly injected myeloid cells extensively engraft in the brain parenchyma, allowing study of donor populations with varied ontogeny. Transplantation into Csf1r−/− hosts offers several advantages. It can be used to study donor cells of diverse origin and developmental stage, and does not require conditioning irradiation or chemotherapy. It yields large numbers of donor derived microglia-like cells (MLCs) that have been conditioned by the brain parenchyma to express microglia genes in the absence of potentially confounding host macrophages, overcoming limitations of prior foundational approaches to understanding microglia identity.

By comparing multiple engrafted microglia types to MLCs from YS- and HSC-lineages, we found that microglia identity remains intact ex vivo, even following cell culture. We noted general similarity between MLCs derived from all donor lineages, but found striking ontogeny-dependent differences between HSC- and YS-derived populations, leading to discovery of durable markers of parenchymal macrophage ontogeny. We extended this approach to a humanized transplantation system and verified fundamental conclusions in human microglia and MLCs. In sum, we devised an experimental system to unravel the contributions of brain environment and ontogeny to macrophage identity in mouse and human.

The work also shows that although many kinds of macrophages can reside in the brain and resemble microglia, only those from the true developmental lineage of microglia are capable of attaining a normal microglia gene expression profile. Those from the adult hematopoietic system, which is not the normal source of microglia, likely cannot fully express microglia genes.

Results

Directly Transplanted Microglia Engraft and Ramify in the Csf1r–/– CNS

Figures 2A, 2B, 2C, 2D:
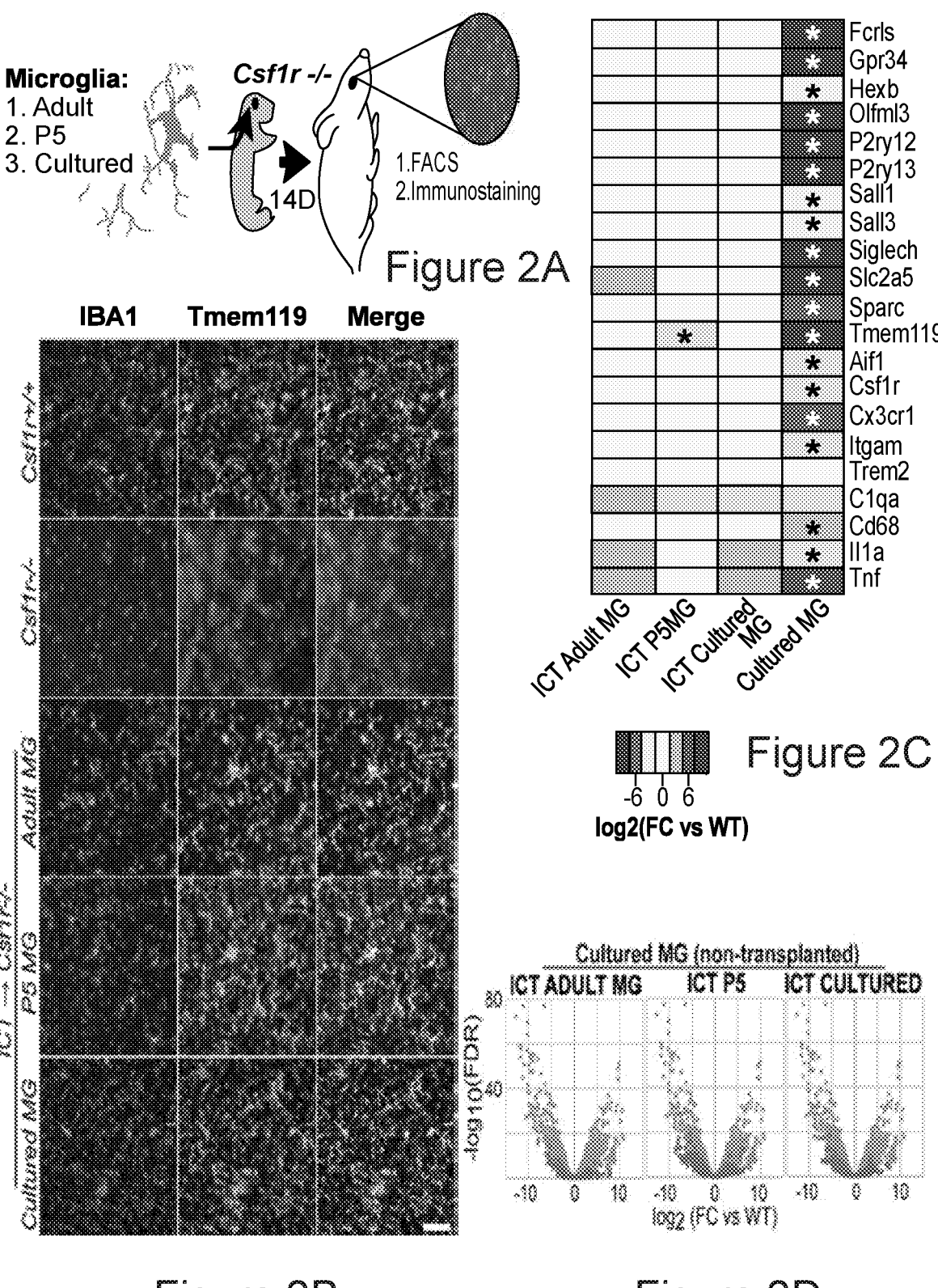
FIGS. 2A-D: Transplanted microglia engraft in the Csf1r−/− brain and express Tmem119.
Figure 3B:
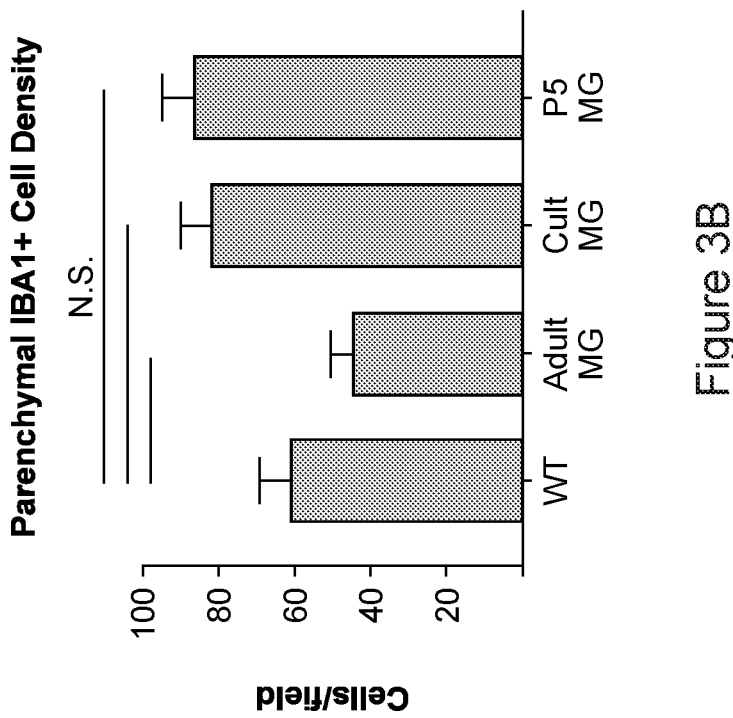
FIGS. 3A-G: Transplantation, sorting and recovery of donor derived WT Microglia.
Figure 3A:
Figure 3C:
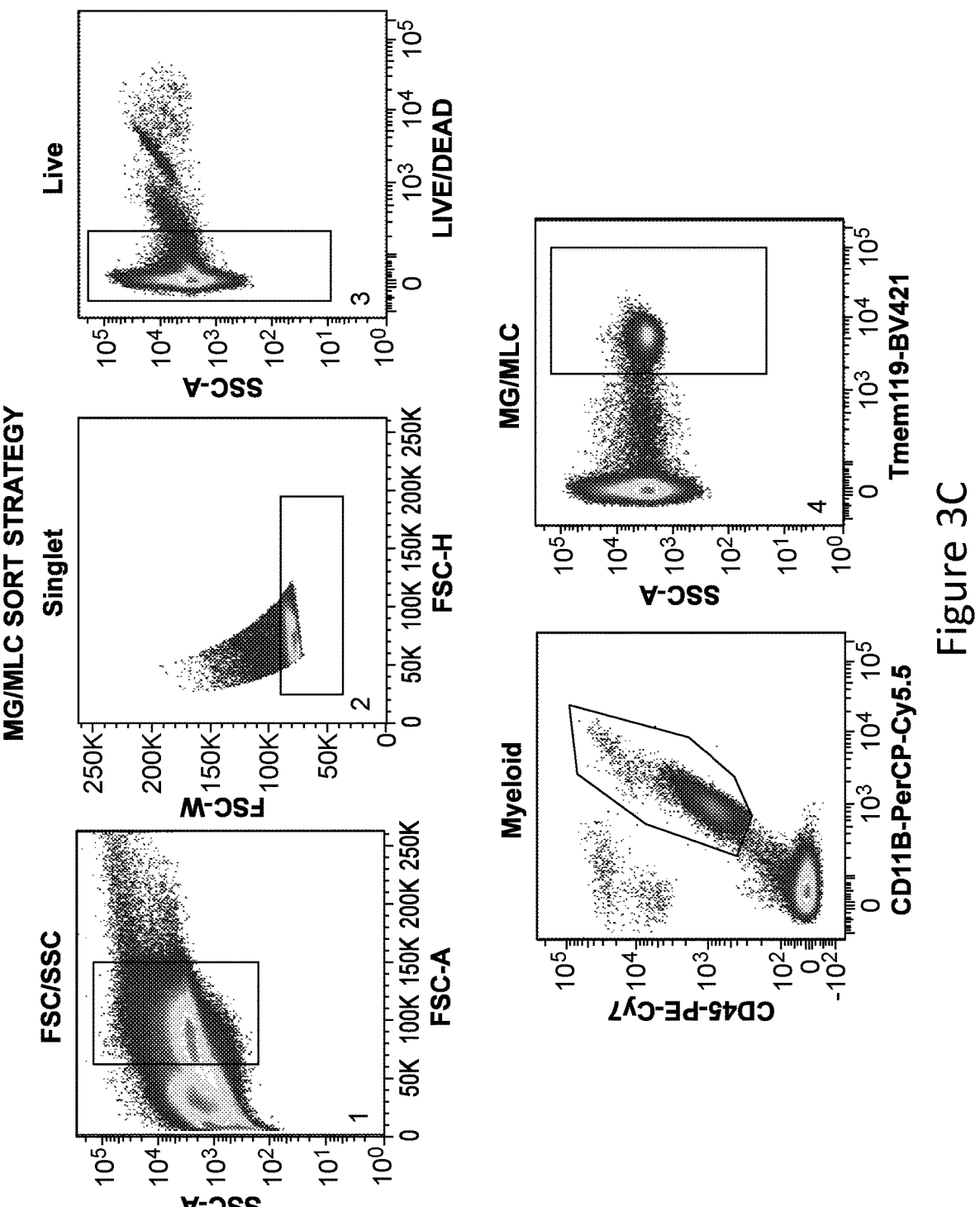
Figures 3D, 3E:
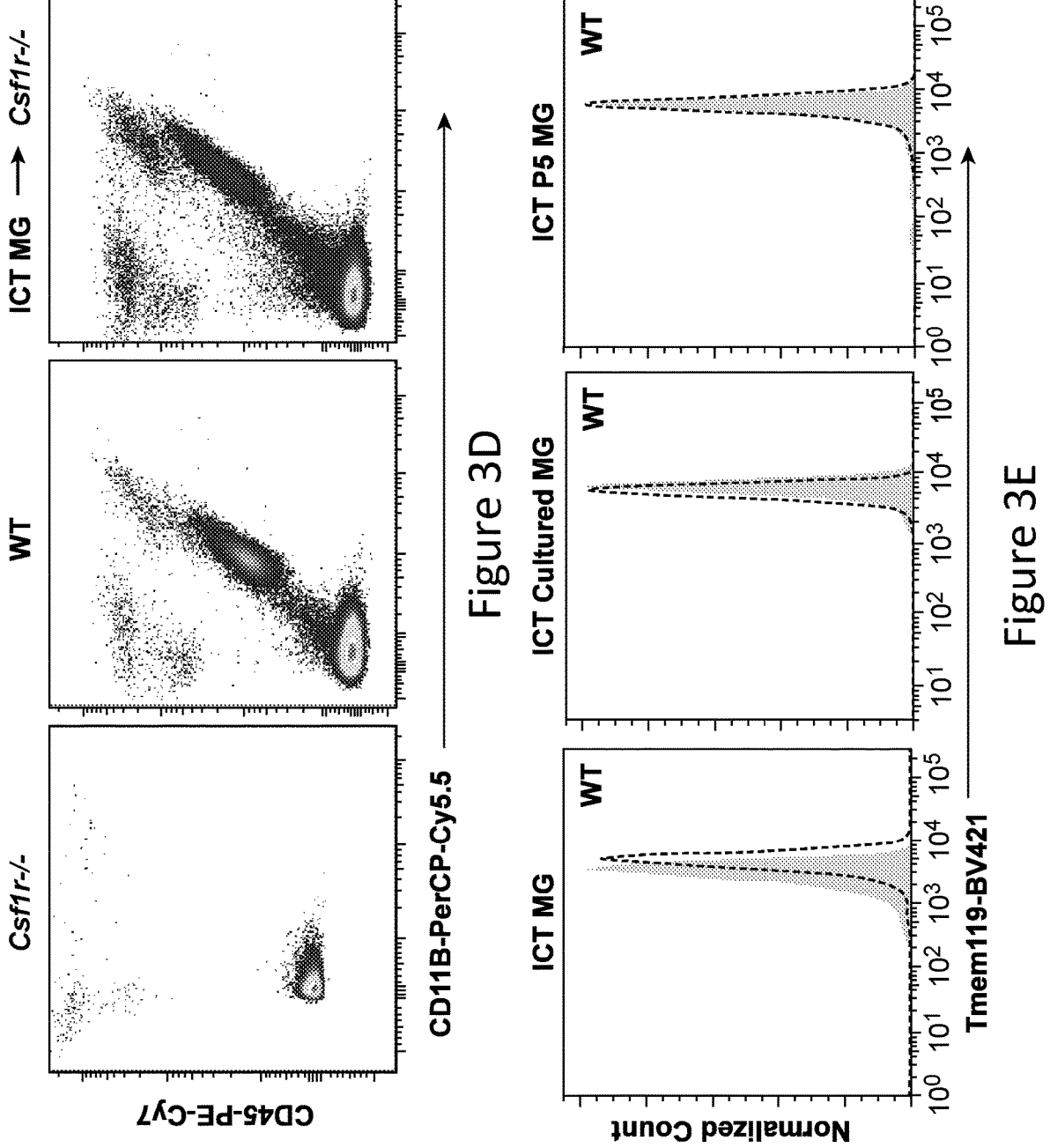
Figure 3G:
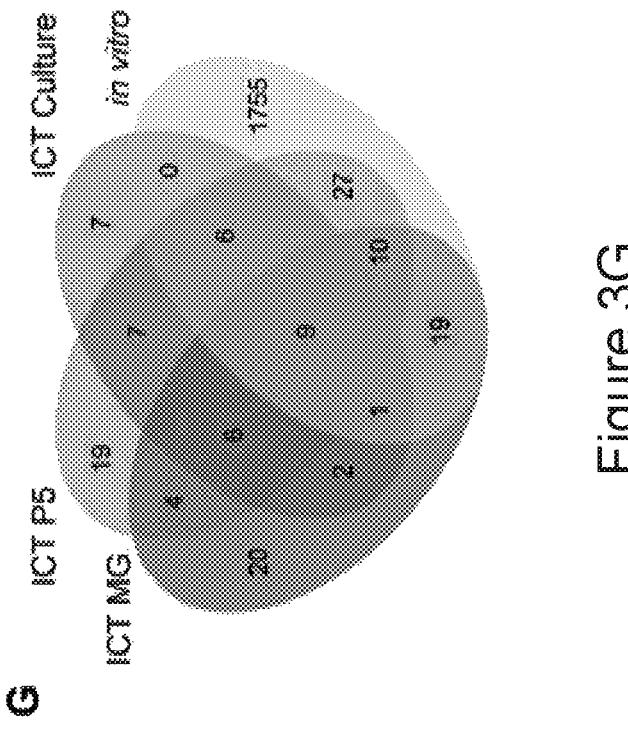
Figure 3F:
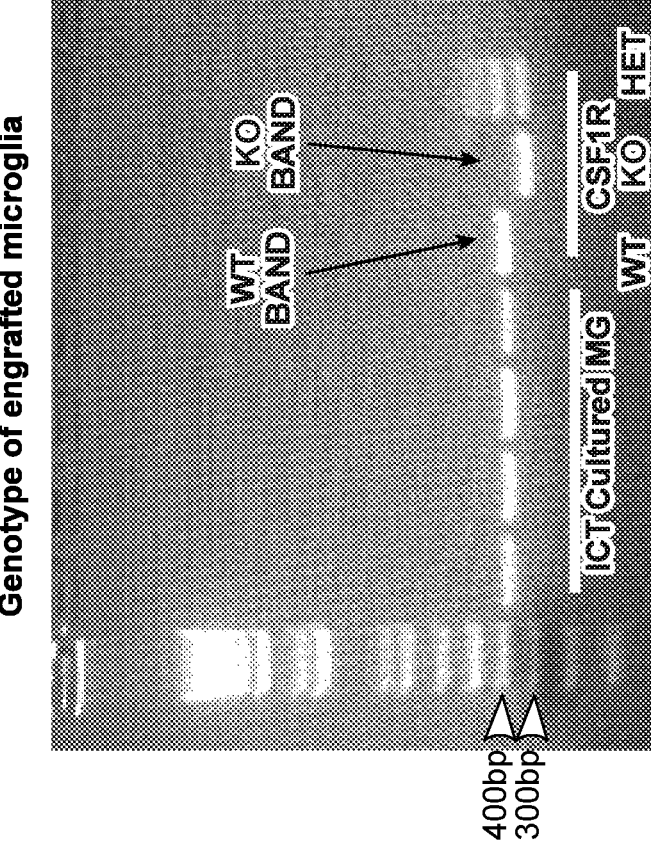

We recently demonstrated that cultured microglia have the capacity to engraft in the Csf1r–/– brain parenchyma, which otherwise lacks microglia, after intracerebral transplantation (ICT). To further study intrinsic versus acquired properties of microglia identity, we compared three distinct microglia populations after ICT into the CNS between postnatal day 0 to 4 (P0-4): 1) acutely isolated mature microglia (P21, "ICT MG") 2) developmentally immature microglia (P5, "ICT P5 MG"), which lack expression of the full microglia gene cassette, and 3) cultured microglia (P18-35, "ICT Cultured MG") that undergo dramatic transcriptional changes in vitro including loss of expression of the microglia signature cassette (FIG. 2A). By 14 days after intracerebral injection, all donor microglia types extensively engrafted and ramified in the brain parenchyma, often filling entire sagittal sections (FIG. 2B, FIG. 3A). When normalized to area of engraftment, transplanted microglia reached a similar density to endogenous microglia in a wildtype Csf1r+/+ (WT) host (FIG. 3B). By flow cytometric analysis, engrafted cells were CD45+CD11B+ and expressed WT levels of Tmem119 (FIGS. 3C-E). By immunostaining, 100% were Tmem119+ in sections from 4-7 biological and at least 5 technical replicates each across the brain. As in WT mice, we found no Tmem119 staining in the meninges and choroid plexus of ICT mice (not shown). Extent of donor cell engraftment varied—by FACS, we retrieved fewer microglia from transplanted hosts than WT controls, and occasionally observed minimal to no engraftment. Because the host strain for Csf1r–/– transplant experiments was FVB, for which no robustly expressed fluorescent reporters exist, we also verified that sorted engrafted microglia were WT at the Csf1r locus (FIG. 3F). These data show that microglia from multiple developmental stages can occupy the postnatal brain, ramify, and express Tmem119 only when engrafted in the parenchyma.

CNS Signals are Sufficient to Induce, Sustain, and Re-Induce Microglia Identity

To better understand relationships between microglia ontogeny, environment, and transcriptional phenotype, we used optimized techniques to isolate RNA from highly pure parenchymal microglia after ICT into Csf1r–/– hosts based on Tmem119 immunoreactivity. Transcriptomic profiling by RNAseq showed that by 14 days in vivo, microglia which had either lost expression of signature genes in vitro (ICT Cultured MG) or had not attained full maturity (ICT P5 MG), expressed mature microglia signature genes at nearly normal levels, including Tmem119, P2ry12, Olfml3, and Sall1 (FIG. 2C). More broadly, ICT cultured, P5, and adult microglia were highly similar to each other and to their WT counterparts. Of 1827 differentially expressed genes in in vitro microglia, all but 16 returned to within 2-fold of WT levels after re-engraftment of cultured microglia in the CNS (FIG. 3G). Volcano plot overlays demonstrate that differences between cultured WT microglia are largely restored after re-engraftment in the brain (FIG. 2D). While transplanted microglia have statistically meaningful differences in gene expression compared to untransplanted WT microglia, these changes likely represent an "engraftment signature" from donor cell isolation, culture, and the Csf1r–/– host environment. Gene expression changes were generally of small magnitude, included several chemokine genes, tetraspanins and G-protein coupled receptors but not a signature of reactivity or specific functional process (FIG. 4)). These experiments show that the Csf1r–/– CNS is sufficient to sustain, induce, and re-induce microglia identity, and that microglia identity potential persists despite dramatic transcriptional perturbations induced ex vivo.

Transplanted Cells of Diverse Ontogeny Engraft and Ramify in the Csf1r–/– CNS

Figure 5A:
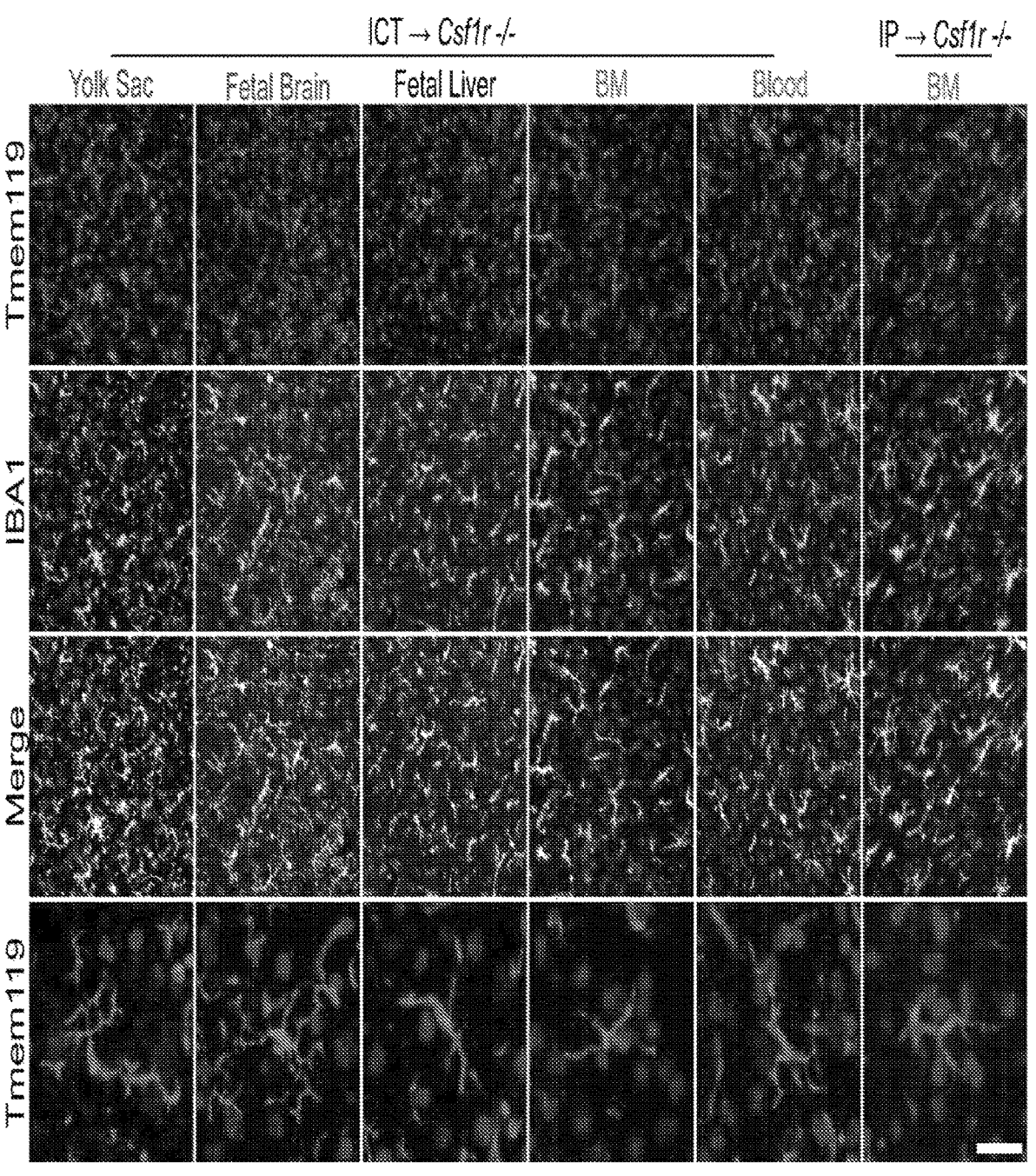
Figure 6A:
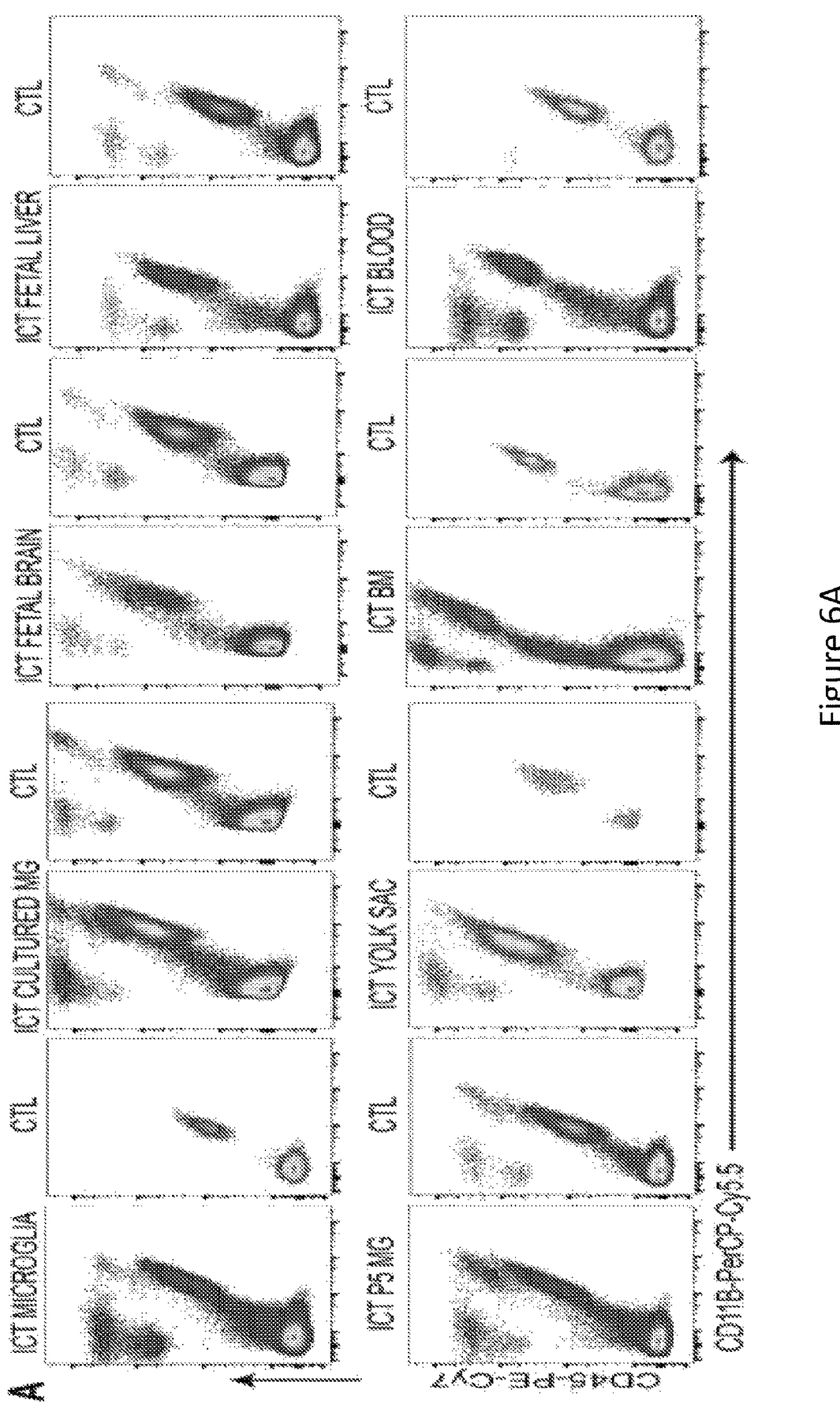

Given stable microglia identity despite highly plastic gene expression between adult, P5 and cultured microglia, we appreciated that ICT could clarify relationships between brain macrophage ontogeny and environment. In particular, we wondered whether HSC- or YS-derived macrophages originating outside the developed brain could become microglia in a permissive CNS environment capable of supporting homeostatic microglia. Therefore, we individually transplanted whole tissues and sorted myeloid cells into the Csf1r–/– CNS at P0-P4 including YS-derived cells from yolk sac and fetal brain, HSC-derived cells from blood and bone marrow (BM), and monocytes from the fetal liver which, at E13-14, contains a mix of HSC- and YS-derived cells. We observed extensive engraftment of ramified Iba1+/ Tmem119+ microglia-like cells (MLCs) using all tissue types tested across both embryonic and postnatal lineages (FIGS. 5A, 5B, 6A-6C, and 6F), though YS-derived MLCs (YS-MLCs) had a consistently more ramified morphology than HSC-derived (HSC-MLCs). We verified donor origin of MLCs using a GFP reporter after back crossing the Csf1r–/– allele to C57Bl/6 (FIG. 5B), and additionally noted extensive coverage of the spinal cord by donor cells delivered by supratentorial injection (FIG. 6D)

By flow cytometry, nearly all CD45+CD11B+ cells were Tmem119 immunoreactive, although HSC donor tissues consistently showed lower intensity staining than WT (FIG. 5C). Since we saw a small Tmem119-population in some cases, we again confirmed by immunostaining that, as with transplanted microglia, all parenchymal but no other Iba1+ MLCs were Tmem119+ (FIG. 6G). All donor tissues engrafted to similar densities as microglia in Csf1r–/– brains, except for fetal liver, which reached a significantly higher density (FIG. 6E). FACS plots, engraftment levels and percent Tmem119 positive values are further detailed in FIGS. 6A-6G to provide potential users a realistic assessment of the robustness of this system.

An inherent limitation of the Csf1r–/– model is poor host viability, which required us to measure the effects of CNS residence in ICT experiments after 14 days. To better study the trajectory of effects of longer incubation, we also created a chemotherapy- and irradiation-free peripheral bone marrow transplantation system that allows study of long term MLC engraftment. Whereas Csf1r–/– mice do not typically survive past weaning age, simple intraperitoneal injection (IP) of WT bone marrow "rescued" approximately 50% of pups, leading to prolonged survival, tooth eruption, occasional fertility, and engraftment of donor-derived myeloid cells in multiple tissues including the brain parenchyma and liver (FIGS. 7A-7D, 8A, 8B). By 1 month, the brain parenchyma of rescued mice showed complete, uniform coverage by donor-derived cells (FIG. 7A). We harvested well-appearing rescued mice up to 1 year after transplantation and observed stable occupancy of the brain parenchyma by MLCs (FIG. 7B). Taken together, these studies show that the CNS niche readily hosts macrophages from multiple donor tissues, including for long periods using bone marrow.

Figures 7E, 7F:
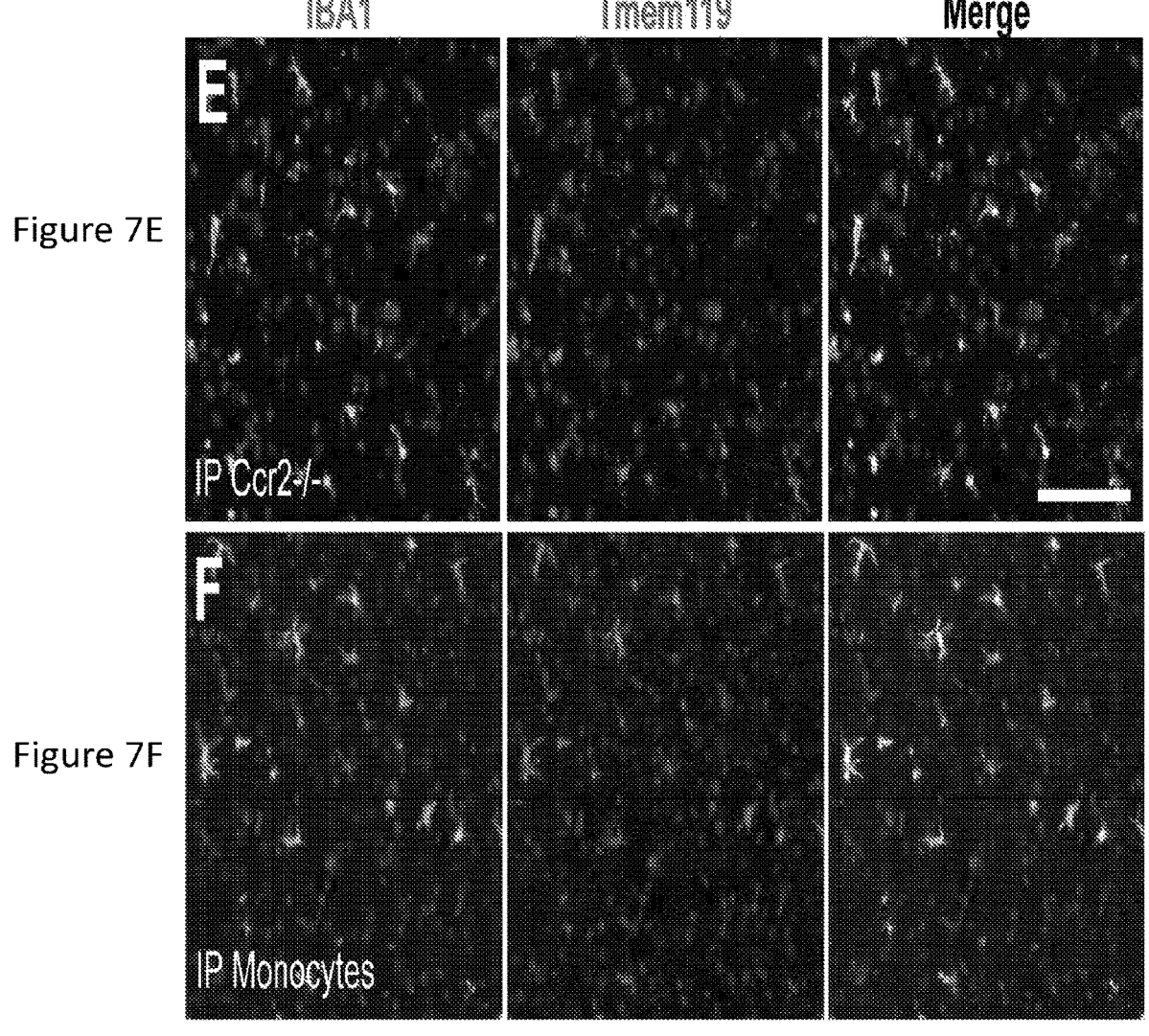
Figures 8A, 8B, 8C, 8D, 8E:
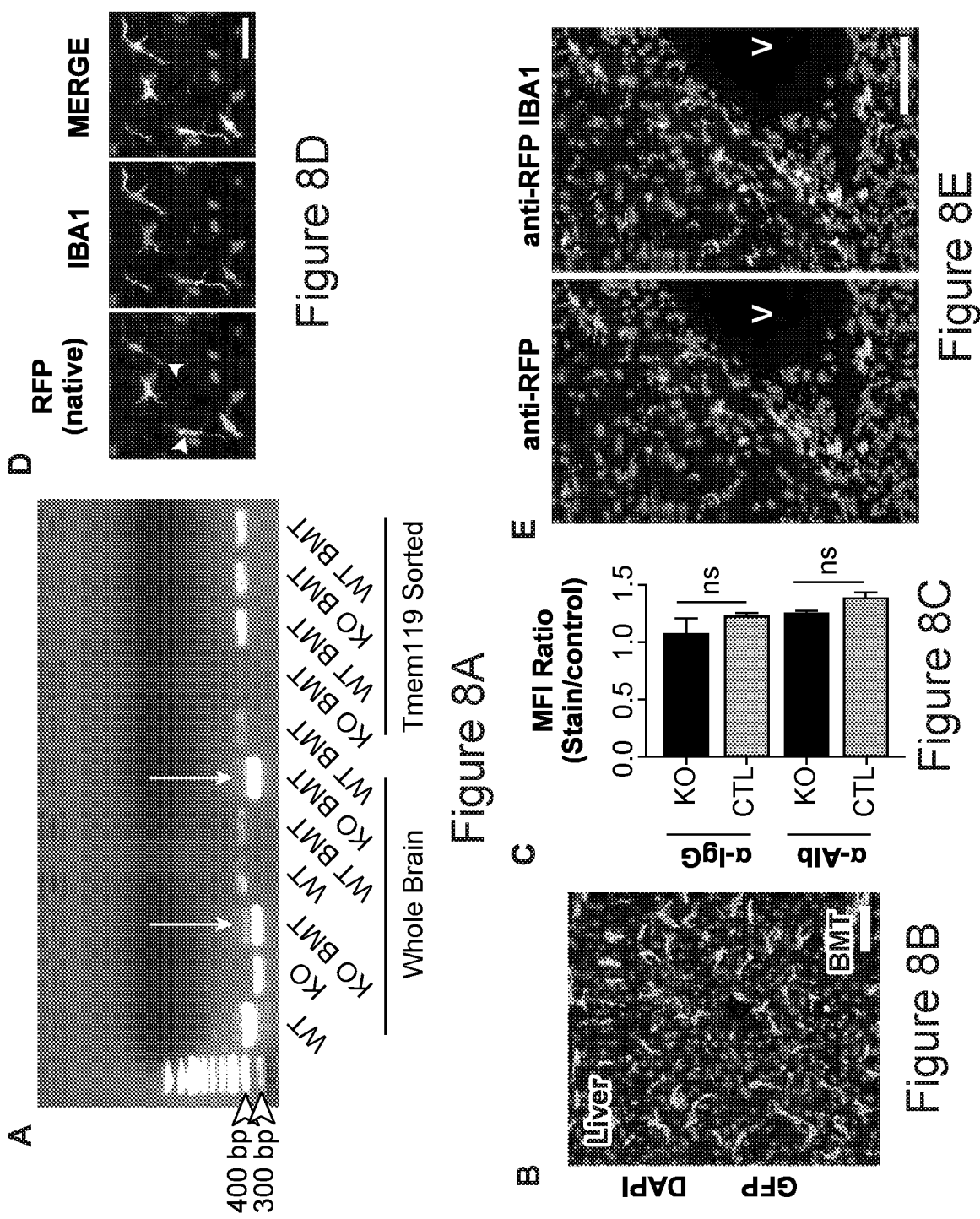
FIGS. 8A-F: Peripheral bone marrow transplantation leads to CCR2-independent engraftment of donor-derived cells in multiple tissues, and results in partial rescue of the Csf1r–/– phenotype.
Figure 8F:
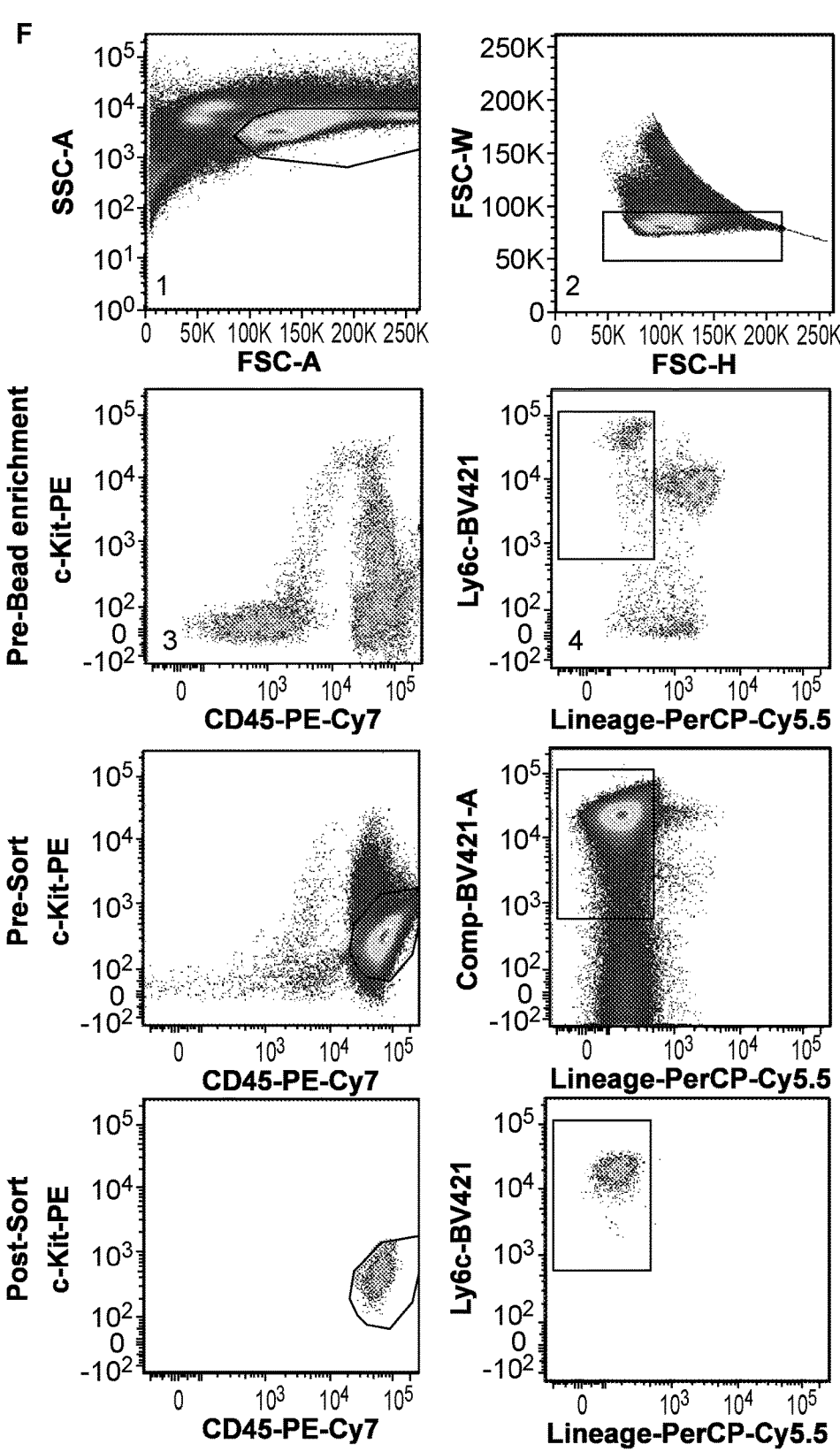

The surprising observation that IP injected bone marrow populated the Csf1r–/– brain without preconditioning led us to further characterize how donor cells might enter the brain. Since a prior study of macrophage repopulation by peripheral cells found evidence for increased blood brain barrier (BBB) permeability, we tested for the presence of increased levels of IgG and albumin in the brain, which are largely excluded from the parenchyma under homeostatic conditions. Quantitative ROI analysis of immunostained histological sections showed no evidence for increased albumin or IgG extravasation, and we did not observe focal areas of increased staining, suggesting "normal" BBB permeability (FIG. 8C). Since multiple studies suggest that monocyte infiltration into the diseased or injured CNS is facilitated by CCR2, we wondered whether engraftment of MLCs was similarly CCR2-dependent in Csf1r–/– hosts. We found that, as with WT bone marrow, IP injection of CCR2 Rfp/Rfp (Ccr2 knockout) bone marrow into Csf1r–/– mice leads to robust Tmem119+ MLC engraftment at 2 weeks, meaning that CCR2 is dispensable for Csf1r–/– IP BMT (FIG. 7E). Interestingly, we observed a range of RFP fluorescence levels in engrafted cells (FIG. 8D), suggesting that either brain signals suppress CCR2 expression, or that more than one population of bone marrow cells (as distinguished by CCR2 reporter expression) are capable of brain engraftment. We also noted a preponderance of RFP+ cells in a periventricular distribution (FIG. 8E). Finally, to determine whether myeloid progenitors or HSCs were strictly required to create MLCs, we also transplanted BM-monocytes that were stringently depleted of progenitor populations (FIG. 8F), and observed abundant Tmem119+ parenchymal MLCs by 2 weeks (FIG. 7F).

Figure 9B:
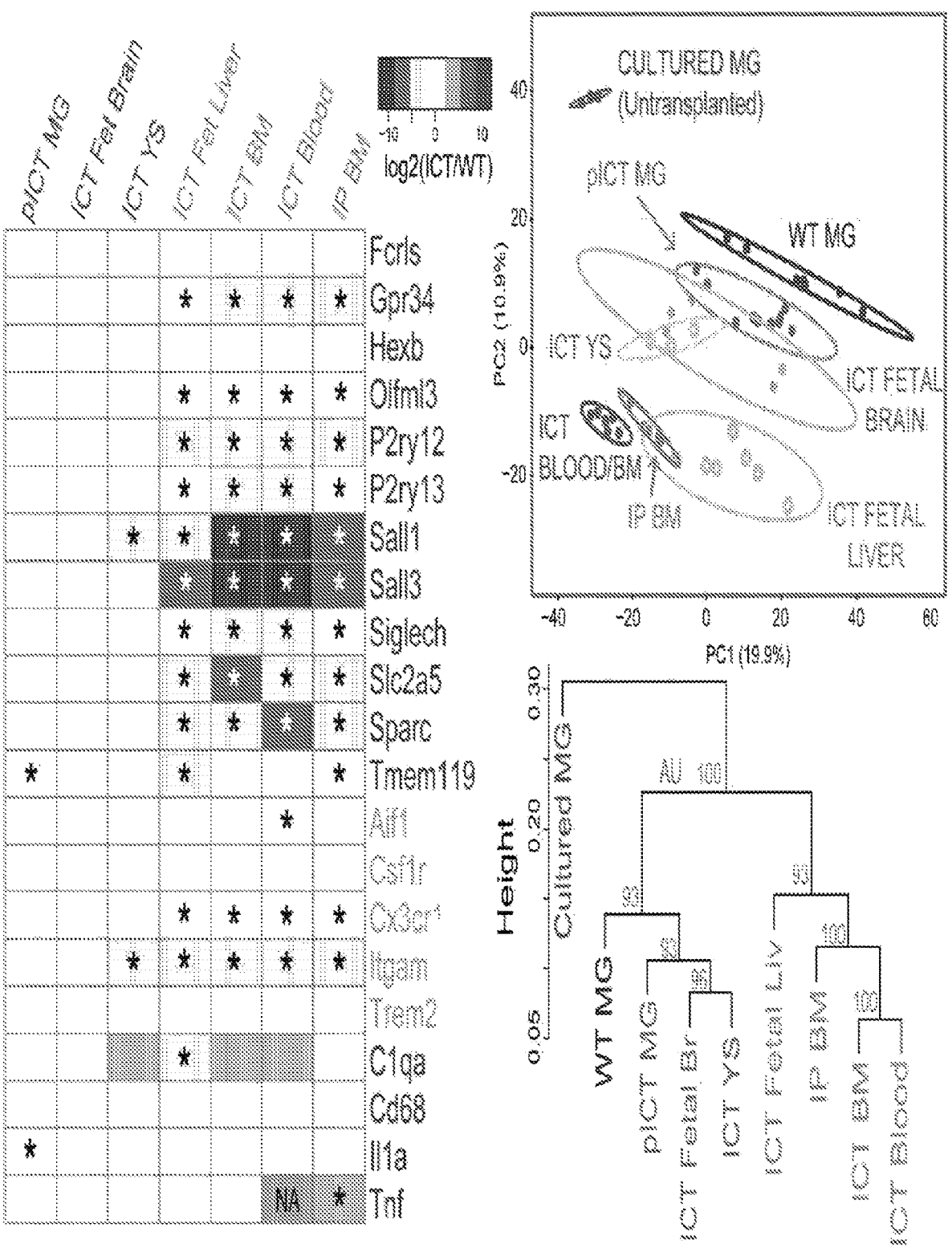
Figure 10A:
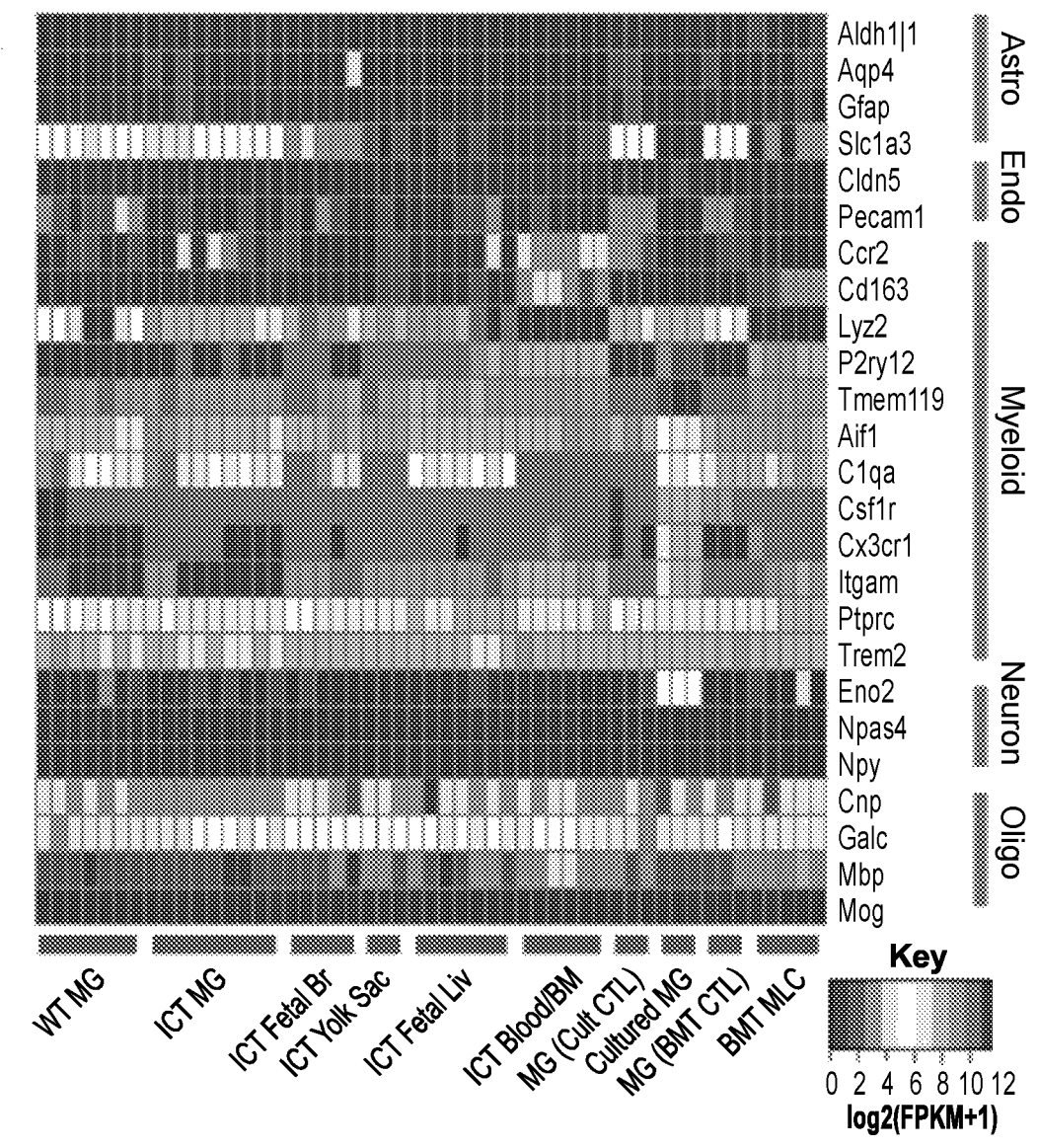
Figure 10B:
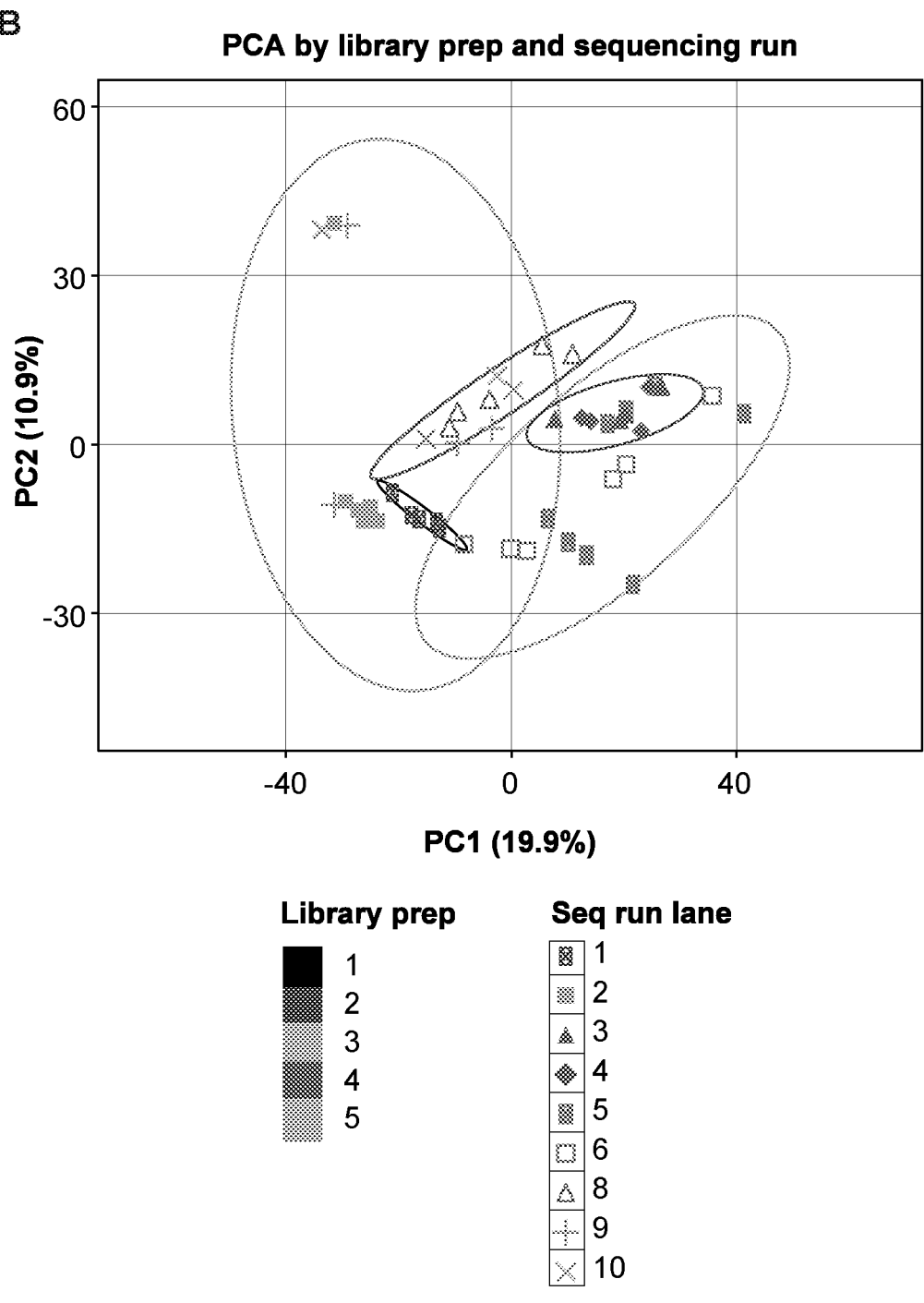
Figure 10C:
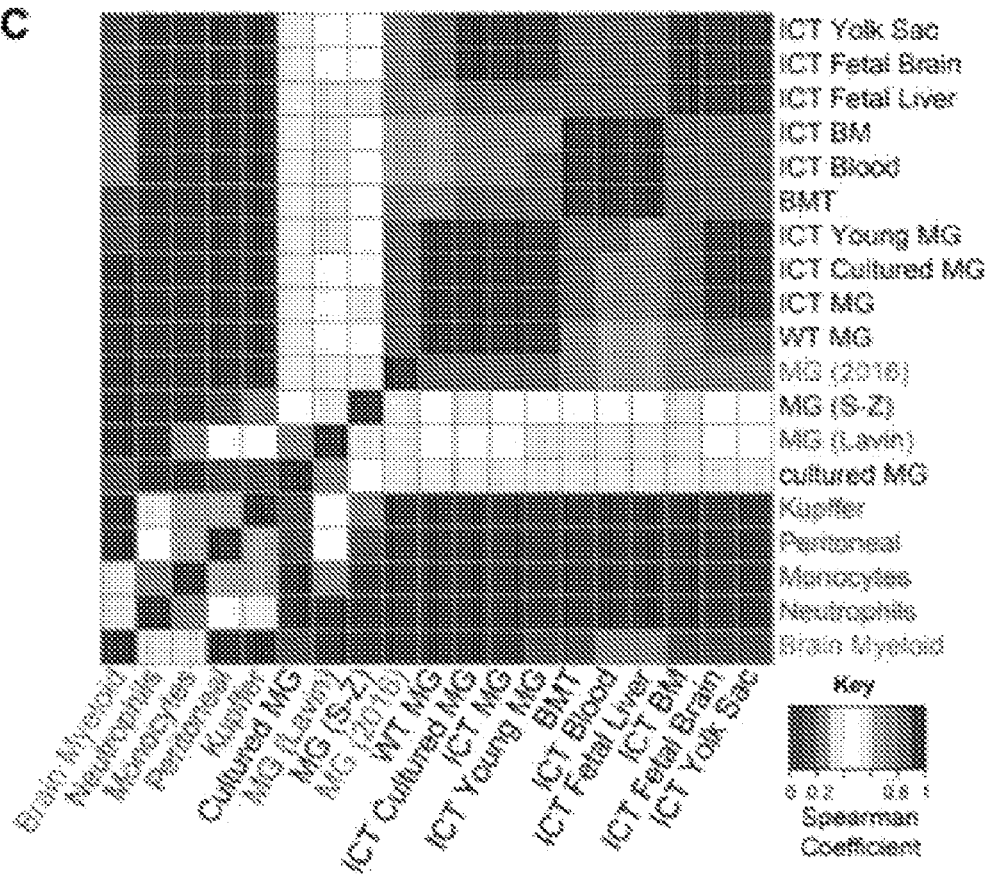

The CNS Environment Strongly and Rapidly Induces Microglia Gene Expression in CNS-Naive Cells The ability of both HSC- and YS-derived donor cells to engraft in the brain parenchyma and express Tmem119 only when engrafted attests to the potency of programming signals from the brain parenchyma. To comprehensively measure the ability of diverse transplanted cells to adopt a microglia transcriptional program, we purified parenchymal Tmem119+ MLCs using identical methods to transplanted microglia, allowing highly specific isolation of parenchymal macrophages. We transcriptionally profiled MLCs derived from E8 yolk sac, E12-13 fetal brain, E13-14 fetal liver, adult blood, and BM, comparing them to each other and to transplanted microglia. Among these highly purified transcriptomes, we observed a striking degree of similarity between engrafted cell types (FIGS. 9A, 10A-10C). MLCs, irrespective of ontogeny, expressed many microglia signature genes, including Tmem119, Fcrls, Hexb, and Olfml3, at near-microglia levels (FIG. 9A). Gene expression in all MLC types was well-correlated (Spearman coefficients >0.6-0.8), and in exploratory analyses combining published datasets, MLCs were more closely related to microglia than to other tissue macrophages, monocytes, or neutrophils (FIGS. 10C, 10D). These data confirm the strong programming effects of the brain parenchyma on macrophages, and the intrinsic ability of even CNS-alien macrophages to respond to programming signals by expressing microglia genes.

HSC Ontogeny Prevents Full Adoption of Microglia Identity

Although grossly similar, we found major ontogeny-dependent differences between HSC- and YS-MLCs. Principal component analysis showed that the transcriptomes of transplanted microglia, yolk sac MLCs, and fetal brain MLCs overlap with each other, distinct from blood, BM and fetal liver MLCs (FIG. 9B). Unsupervised hierarchical clustering similarly showed that YS-derived (YS, fetal brain) MLC gene expression is more closely related to transplanted microglia than HSC-derived (blood, BM) and mixed-origin MLCs (fetal liver) (FIG. 9C).

Figures 9D, 9E, 9F, 9G:
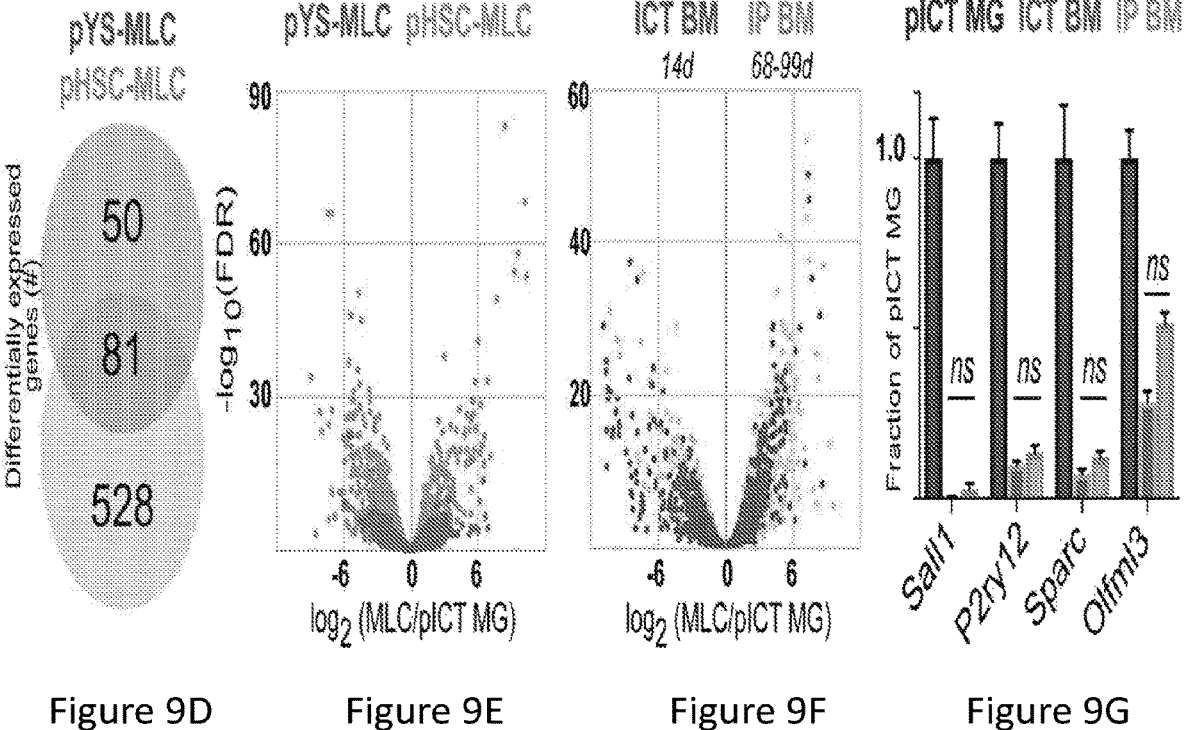
Figure 11:
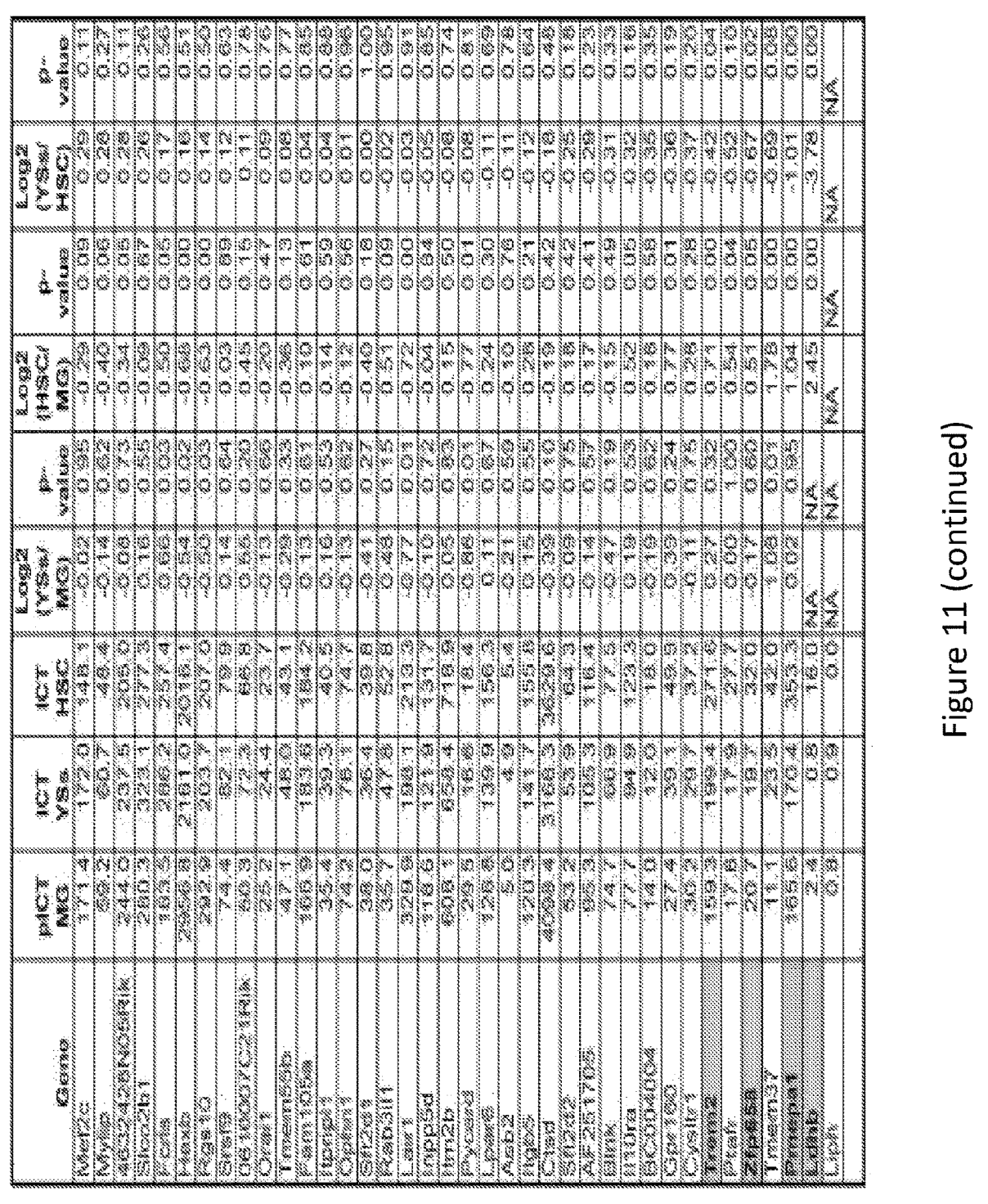
Figure 12:
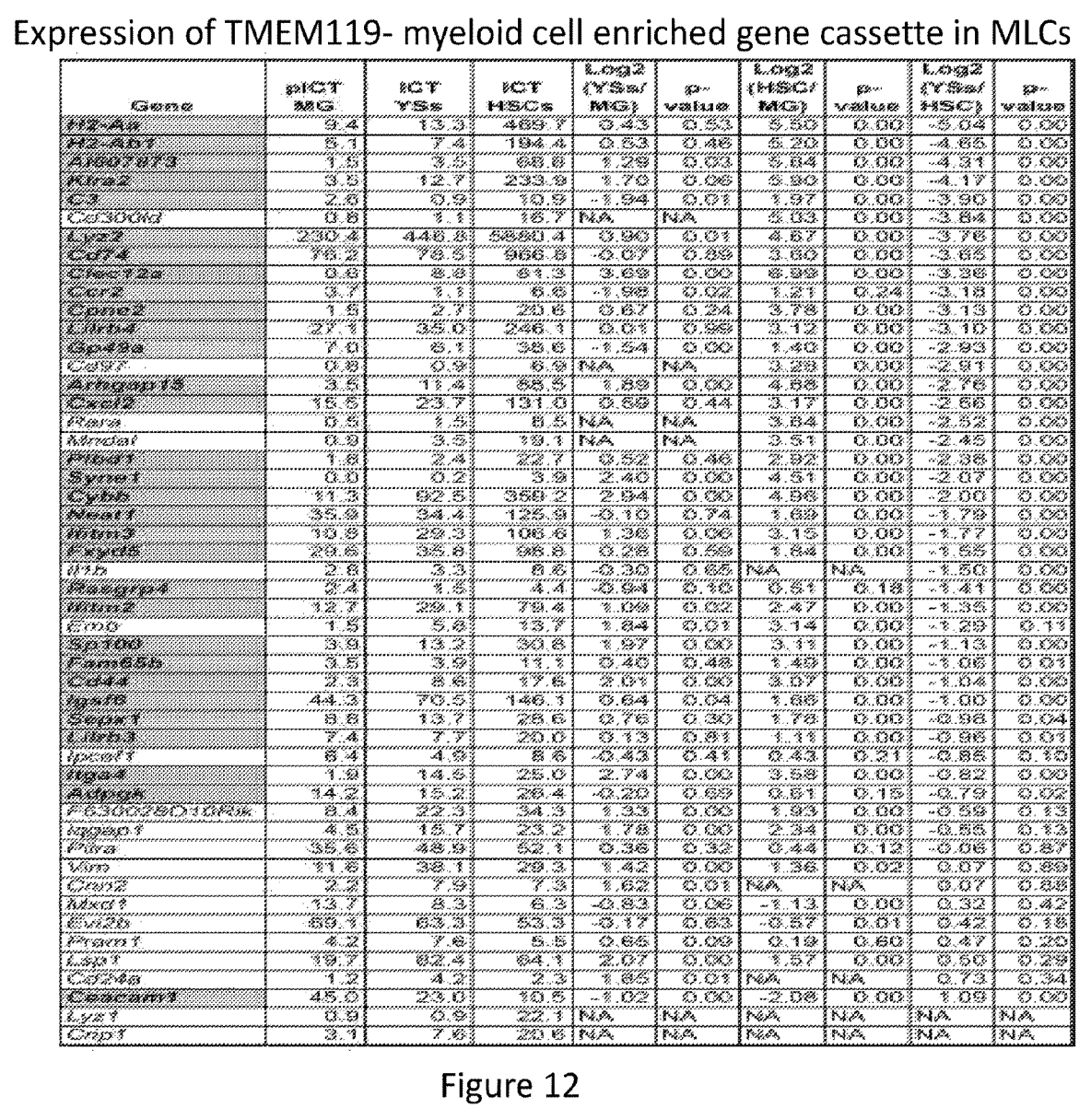
Figures 16A, 16B, 16C:
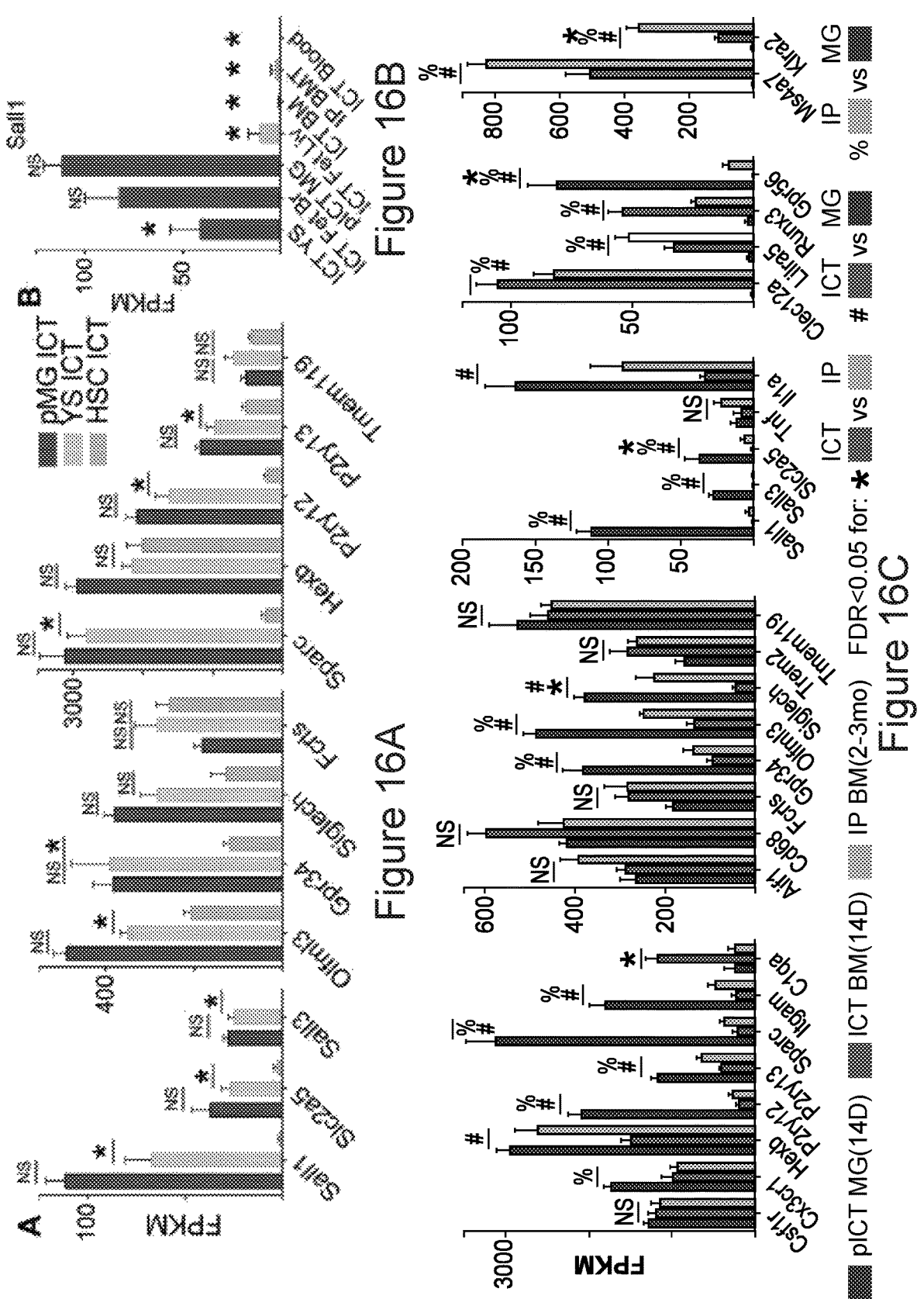
FIGS. 16A-D: Ontogeny but not prolonged CNS residence results in faithful expression of microglia genes.

To focus on ontogeny specific gene expression patterns, we pooled gene expression data from YS- and HSC-MLCs donor groups, excluding fetal liver-MLCs since E13-14 liver contains a mix of YS- and HSC-derived cells. As a group, YS-lineage MLCs had 131 differentially regulated genes compared to transplanted microglia, while HSC-derived MLCs had 609 (FIG. 9D). Volcano plot overlay further depicts the higher similarity of YS-MLCs to transplanted microglia at a whole-transcriptome level (FIG. 4E). At the gene level, YS-MLCs expressed microglia signature genes more faithfully than their HSC-derived counterparts, including Slc2a5, Olfml3, Gpr34, Sparc, and P2ry12 (FIG. 16A). Among microglia-enriched genes in Tmem119+ cells from a prior study, YS-MLCs were significantly closer to MG expression levels in 30 of 32 measured genes (FIG. 11). Similarly, among 31 genes enriched in non-microglia CNS myeloid cells, YS-MLCs were closer to microglia levels for 29 (FIG. 12). Of particular significance, HSC-MLCs did not express Sall1, a transcription factor recently implicated in microglia identity. Interestingly, the pattern of Sall1 expression by YS-MLCs correlated with its expression during microglia development, from low levels in yolk sac MLCs, intermediate levels in fetal brain MLCs, and highest in transplanted microglia (FIG. 16B).

While YS-MLCs were able to express all microglia signature genes by 2 weeks, HSC-MLCs were not. Based on prior studies using microglia repopulation systems, along with observations in other tissues we felt it was critical to address whether longer CNS engraftment was sufficient to better reprogram HSC-MLCs as microglia. If so, one would expect interval increases in the expression of microglia signature genes with prolonged brain engraftment, akin to observations in the liver between 15 and 30 days after engraftment. We therefore analyzed MLCs that were engrafted in the brain parenchyma of rescued mice for 2-3 months (mean 81 days) following peripheral bone marrow transplantation, and assessed for a trajectory of higher expression of microglia identity genes. We compared gene expression patterns to directly injected BM-MLCs harvested after 14 days and found almost no interval induction of microglia signature genes after prolonged CNS incubation. In particular, longer-term engrafted cells showed persistently low expression of Sall1, Sall3, Sparc, P2ry12, Gpr34 and Olfml3, none of which were statistically different from expression in short term engrafted cells (FIGS. 9A, 9G, 16C). By unbiased clustering, long term engrafted BM-MLCs were highly similar to short term engrafted BM and blood-MLCs (FIG. 9B, 9C). Volcano plot overlay does not show increased similarity of longer term engrafted cells to microglia (FIG. 9F). Longer-term engraftment was associated with differential gene expression (FIG. 13 and FIG. 14) though with no clear evidence of further reprogramming based on microglia signature genes (FIG. 16C). Taken together, these data show that when macrophages derived from HSCs engraft in the brain, they become similar to microglia by 14 days, but do not further increase expression of microglia identity genes when incubated in the brain at least four times longer. In contrast, YS-derived macrophages, which share a common ancestor with microglia, have the intrinsic potential to become highly similar to transplanted microglia by 14 days.

Figures 15A, 15B, 15C:
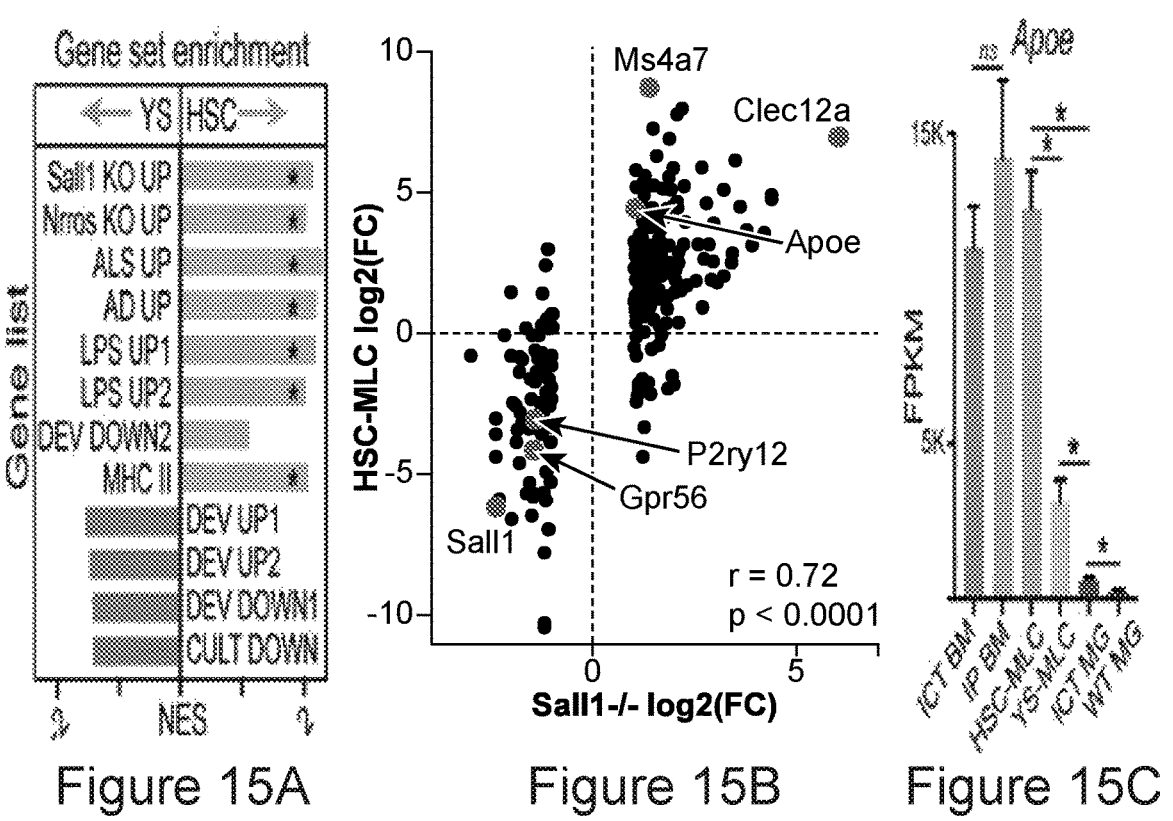
FIGS. 15A-D: HSC-MLCs resemble microglia lacking identity genes and in disease states.
Figure 16D:
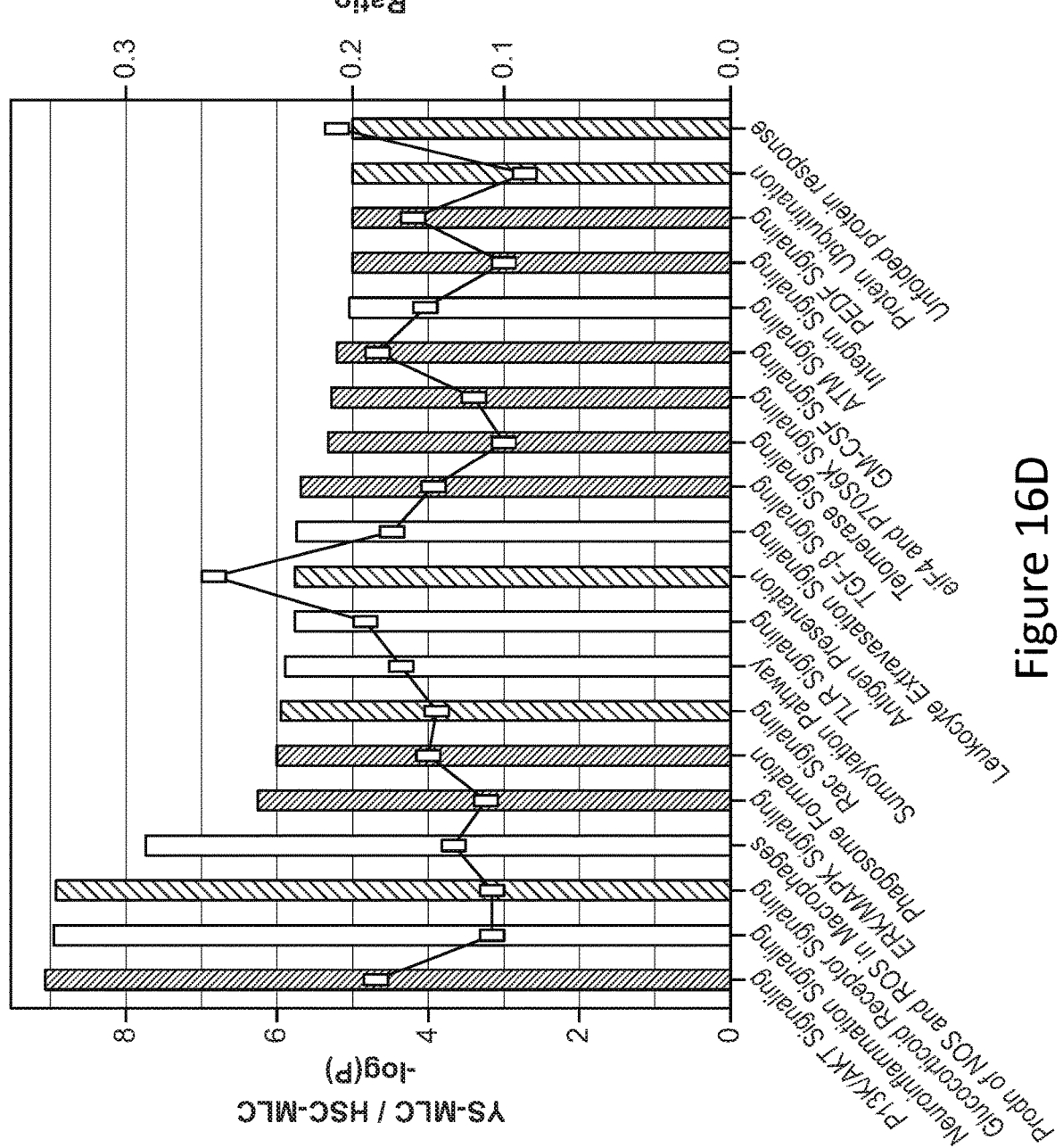

HSC-MLCs Share Transcriptional Signatures with Disease-Associated Microglia, Including Highly Elevated Apoe Expression To better understand transcriptomic differences between HSC- and YS-MLCs, we assessed transcriptional networks by multiple approaches. Pathway analysis (Ingenuity) suggested HSC-MLCs were enriched in pathways associated with CNS perturbation (neuroinflammatory signaling, NOS/ROS production, and TLR signaling, FIG. 16D). Recent studies of mouse and human microglia found significant overlap between transcriptional changes in cultured, Alzheimer's disease (AD), Amyotrophic Lateral Sclerosis (ALS), LPS exposed, and immature microglia, suggesting common downstream reactivity pathways. We wondered if the observed gene expression differences between HSC- and YS-MLCs overlapped with differences between brain myeloid cells in disease compared to health. Indeed, HSC-compared to YS-MLCs were significantly enriched in gene sets associated with ALS, AD, LPS treatment, immaturity, and in vitro culture from prior studies, along with major histocompatibility complex class II genes (FIG. 15A). YS-MLCs were relatively enriched in gene sets associated with homeostasis but these did not reach significance cutoff (FDR<0.05).

Since HSC-MLCs lack Sall1, we also tested for enrichment of genes that change with loss of microglia Sall1 and Nrros, which were recently found to cause similar shifts in transcriptional identity. We compared our datasets to published gene expression profiles of Sall1 and Nrros deficient microglia, and indeed HSC-MLCs showed significant enrichment for genes upregulated in both Sall1 and Nrros−/− microglia (FIG. 15A). In fact, gene expression in HSC-MLCs and Sall1−/− microglia were highly correlated (FIG. 15B), suggesting that lack of Sall1 could contribute to differential gene expression in HSC-MLCs.

Figure 15D:
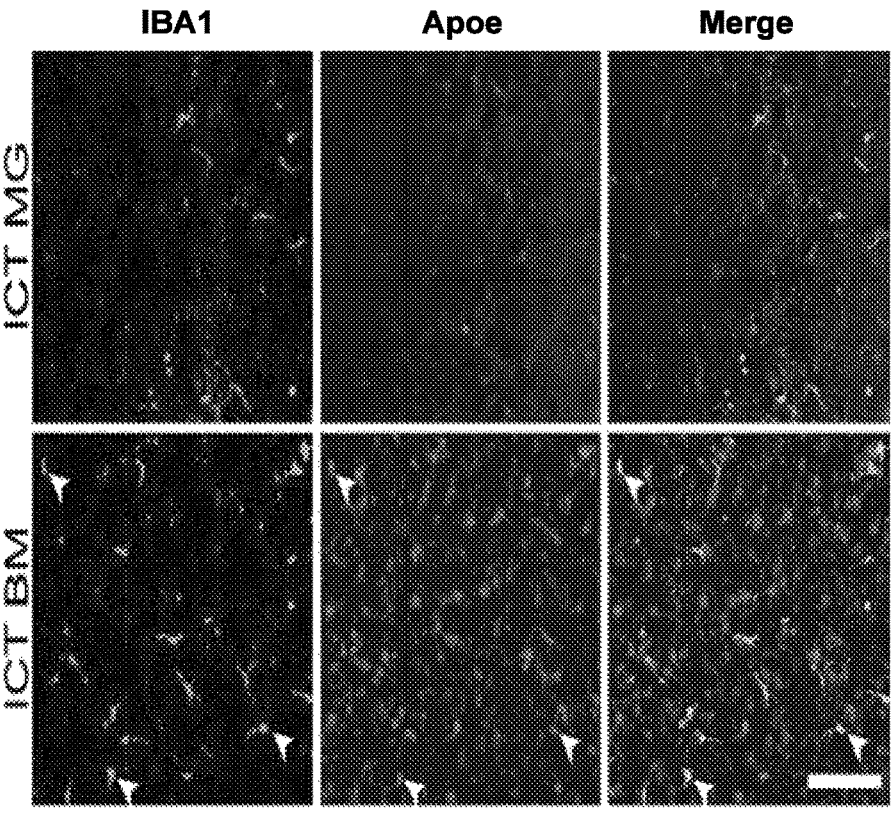

Among these dysregulated genes, Apoe stands out as the most highly expressed gene in HSC-MLCs, and does not decrease with longer engraftment (FIG. 15C). To validate high Apoe expression observed in HSC-MLCs, we performed RNA in situ hybridization. As anticipated, we found high intensity signal in many brain macrophages after BM but not MG ICT. Surprisingly, we also found increased probe signal throughout the brain parenchyma in Iba1 negative cells of BM-ICT animals, which may reflect increased expression by astrocytes in the presence of HSC-MLCs (FIG. 15D). Taken together, these results show that HSC-but not YS-MLCs nor transplanted microglia share gene expression signatures with microglia in disease states or after loss of identity genes.

HSC-MLCs Express Markers Distinct from YS-MLCs and Microglia

Figures 17A, 17B, 17C:
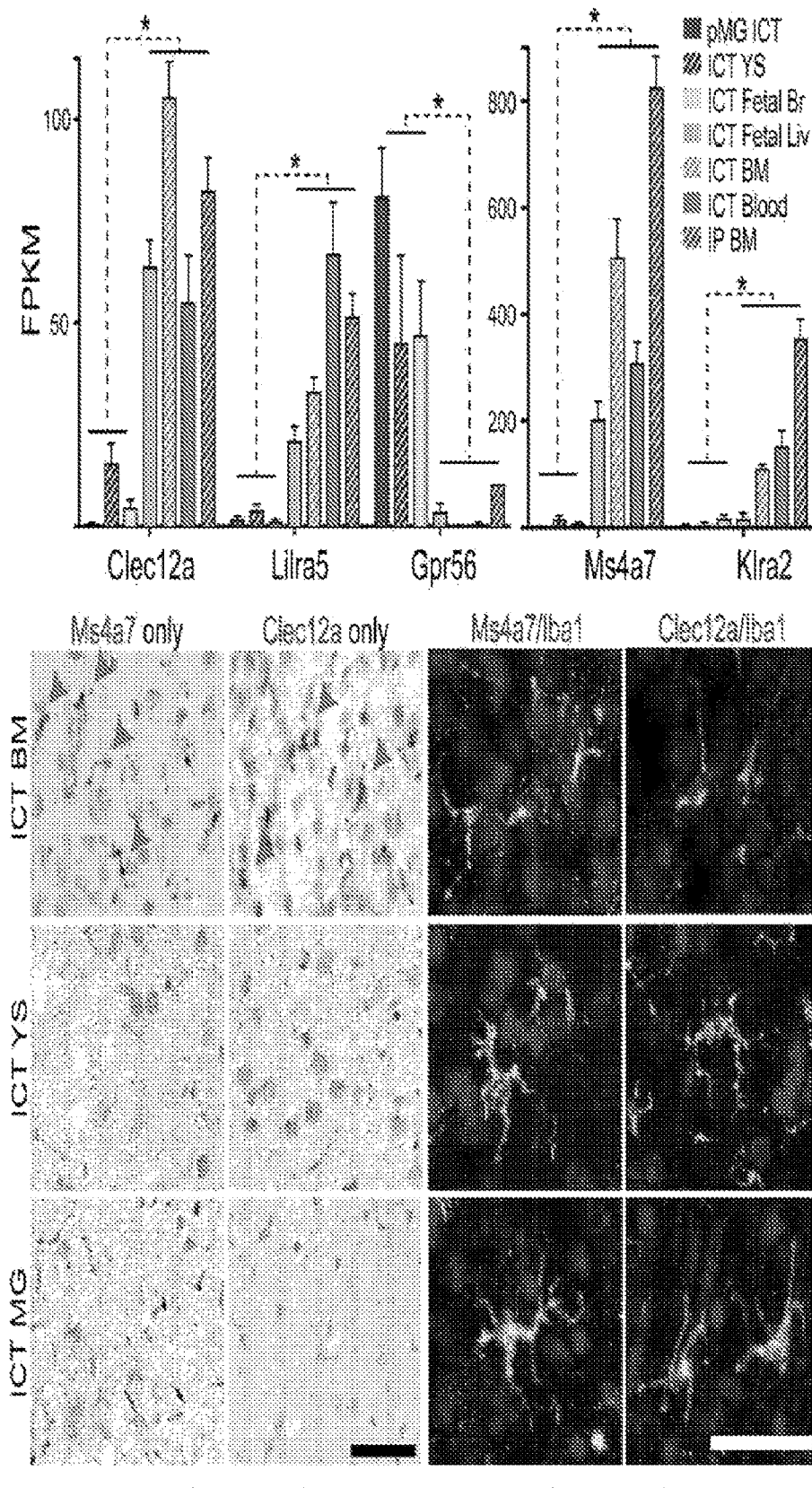
FIGS. 17A-D: Ontogeny markers discriminate HSC- from YS-MLCs and microglia.
Figure 17D:
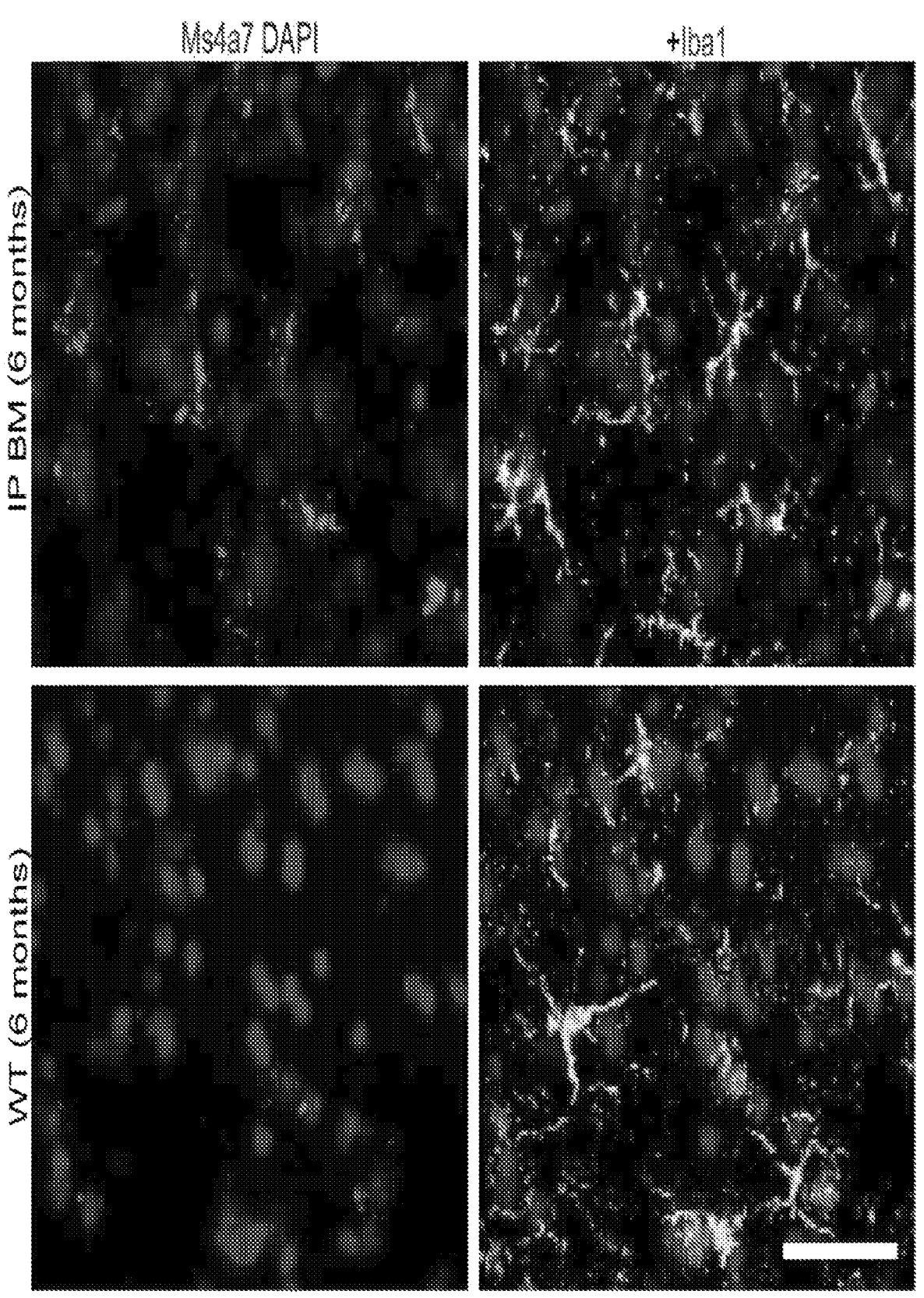
Figures 18A, 18B, 18C:
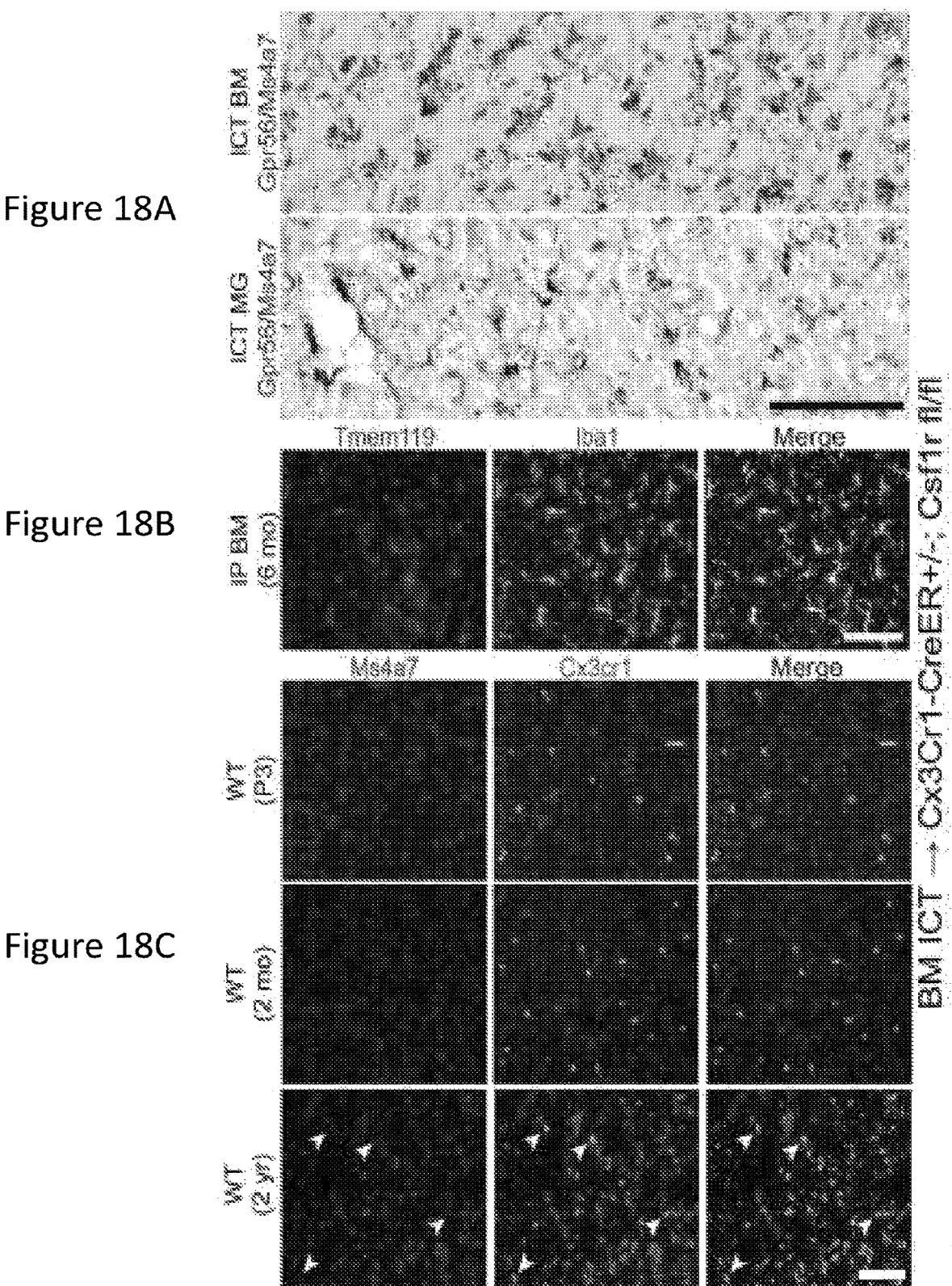
FIGS. 18A-G: HSC-MLCs persist in the brain for long periods, and show distinct expression of origin markers in multiple transplantation systems.
Figures 18D, 18E, 18F, 18G:
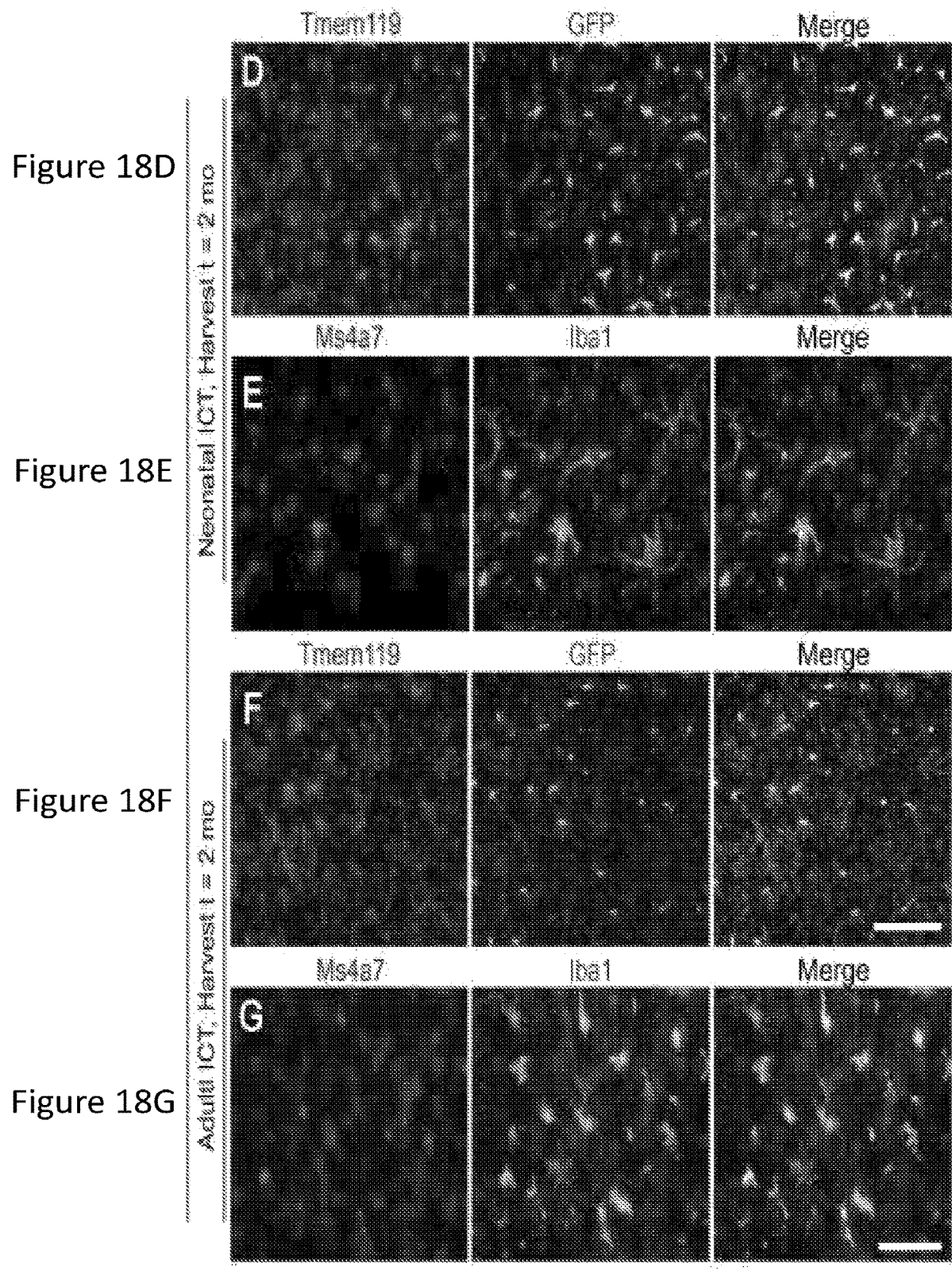

The Csf1r−/− transplantation approach demonstrates that many macrophage types have the intrinsic potential to masquerade as microglia by expressing signature genes and TMEM119 protein in the brain. This does not occur following conventional BMT and complicates the use of microglia signature genes to distinguish microglia from HSC-MLCs in complex disease models, which now requires creation of new tools. To identify stable markers of brain parenchymal macrophage ontogeny, we screened our dataset for genes 1) highly expressed across HSC-MLC types, but lowly expressed in YS-MLCs and microglia or 2) highly expressed in YS-MLCs and microglia but not HSC-MLCs. We then eliminated genes dysregulated in microglia in AD and after LPS stimulation, yielding five candidate ontogeny markers: Clec12a, Ms4a7, Lilra5, Klra2, and Gpr56 (FIG. 17A). We performed RNA in situ hybridization to validate the localization of Ms4a7, Clec12a, and Gpr56 in engrafted brain tissues (FIGS. 17B-17D; 18A). As predicted by transcriptomic data, virtually all HSC-MLCs but no microglia nor YS-MLCs were Ms4a7+ and Clec12a+. Meanwhile, no HSC lineage cells were Gpr56+, a gene recently associated with microglia ontogeny in transcriptomic studies and also expressed by other glia, such as astrocytes. Importantly, we probed healthy postnatal CNS tissue and did not find Ms4a7 expression by microglia across the lifespan (FIG. 18C). We also tested whether these HSC ontogeny markers were unique to the Csf1r−/− system. We transplanted GFP+BM directly into the CNS of neonatal and adult Cx3cr1-CreER+/−; Csf1r fl/fl mice, treated with tamoxifen, to partially and transiently deplete microglia. At 2 months, we observed abundant GFP+Tmem119+ cells in the brain parenchyma, and concordant clusters of Ms4a7+ cells by RNA in situ (FIGS. 18D-18G), suggesting that HSC ontogeny marker induction is neither unique to the Csf1r−/− mouse system nor the neonatal CNS.

Since ICT transplanted Csf1r−/− animals do not survive long enough to test prolonged time points, we also tested whether HSC-MLCs in animals rescued by IP BMT were able to downregulate Ms4a7 six months after transplantation, as would be expected if environmental signals superseded the limits of ontogeny. We found that all HSC-MLCs remained TMEM119+ and Ms4a7+ after 6 month incubation (FIGS. 17D; 18B). This is consistent with our transcriptomic observations at 2-3 months, when HSC-MLCs sustained expression of ontogeny markers, and in fact increased expression of one such ontogeny marker, Klra2 (FIG. 16C). In sum, we capitalized on transcriptomic data from transplanted brain macrophages to validate ontogeny markers that are stable despite the high plasticity of brain macrophage gene expression in response to the CNS environment.

Figure 19A:
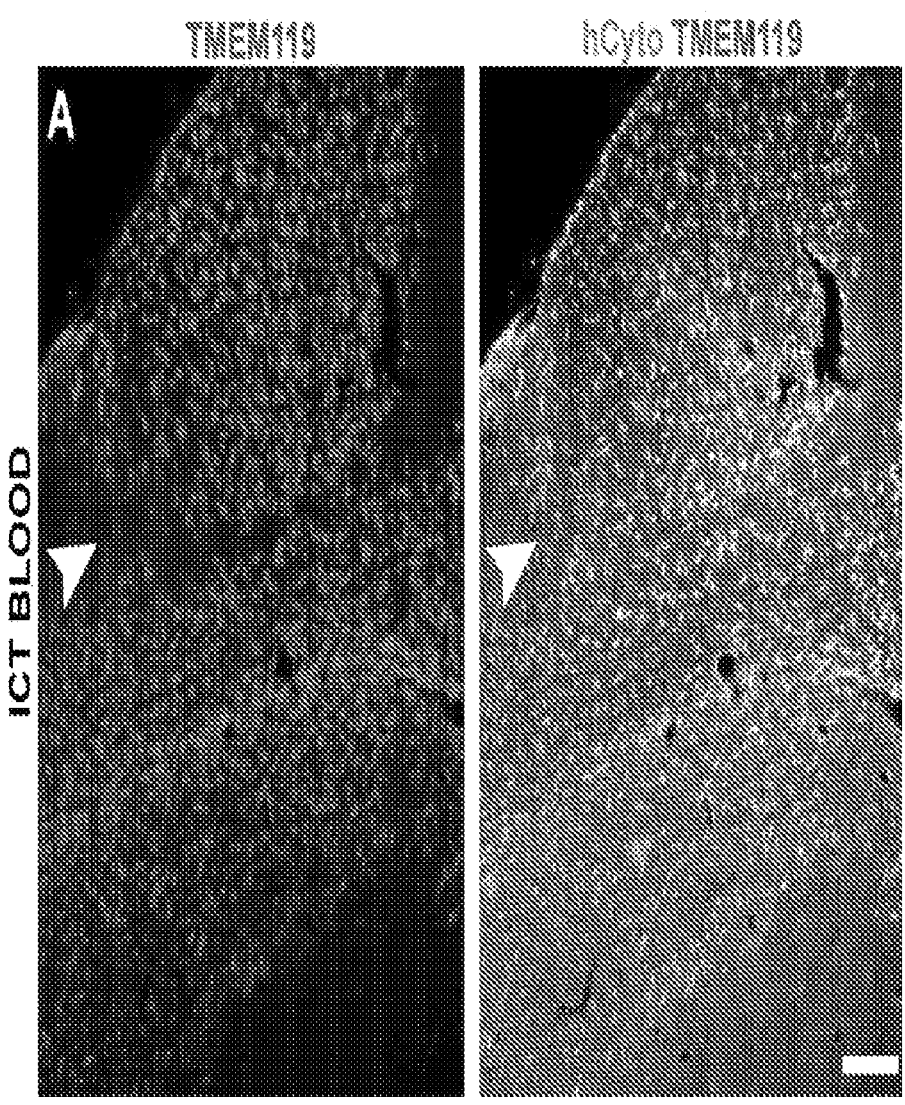
FIGS. 19A-K: Macrophage transplantation, origin markers, and anti-TMEM119 monoclonal antibodies for the study of primary human macrophages in vivo.
Figures 19B, 19C, 19D:
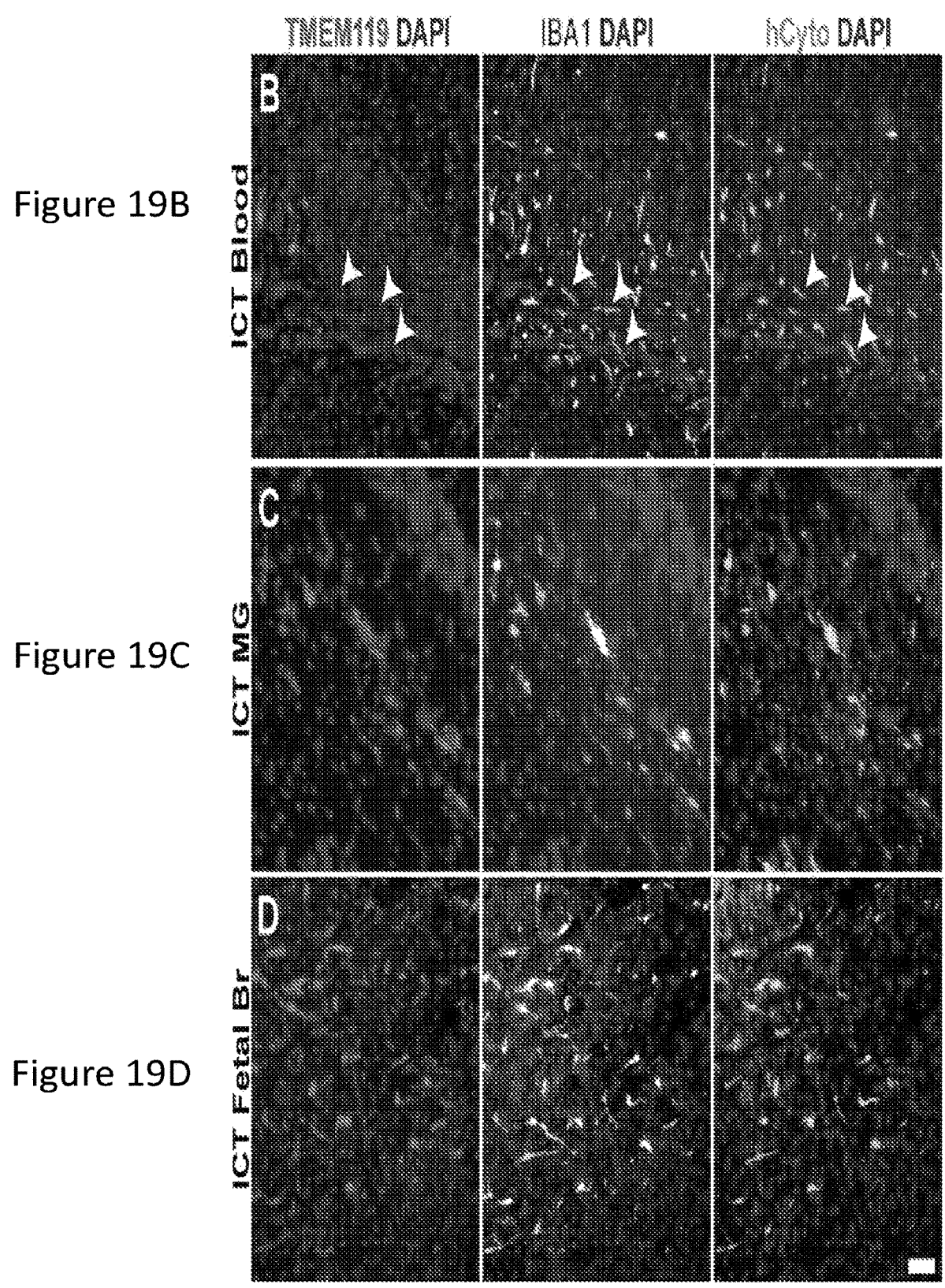

Human Primary Cells Engraft, Ramify and Express Tmem119 in Humanized Csf1r−/− Mice, but Only HSC-MLCs are Ms4a7 Immunoreactive To explore the utility of this transplantation system for human brain macrophage study, we crossed Csf1r+/− mice into an immunodeficient strain expressing the human form of MCSF, based on our observations that murine MCSF does not promote human microglia survival (unpublished observations), creating a Rag2−/− IL2rg−/− hMCSF Csf1r−/− mouse. We transplanted human blood, fetal brain macrophages, and postnatal microglia from neurosurgical cases directly into the mouse CNS. We observed engraftment, survival and ramification of all cell types, often over large territories of the mouse brain parenchyma (FIGS. 19A-19D). Most all transplanted human fetal and postnatal brain parenchymal macrophages were Tmem119 immunoreactive (FIGS. 19C, 19D), whereas engrafted peripheral blood cells showed variable staining: in some animals, nearly all engrafted blood-derived cells were Tmem119+ (FIG. 19A), while in others, expression was restricted to a fraction (FIG. 19B).

Figure 19E:
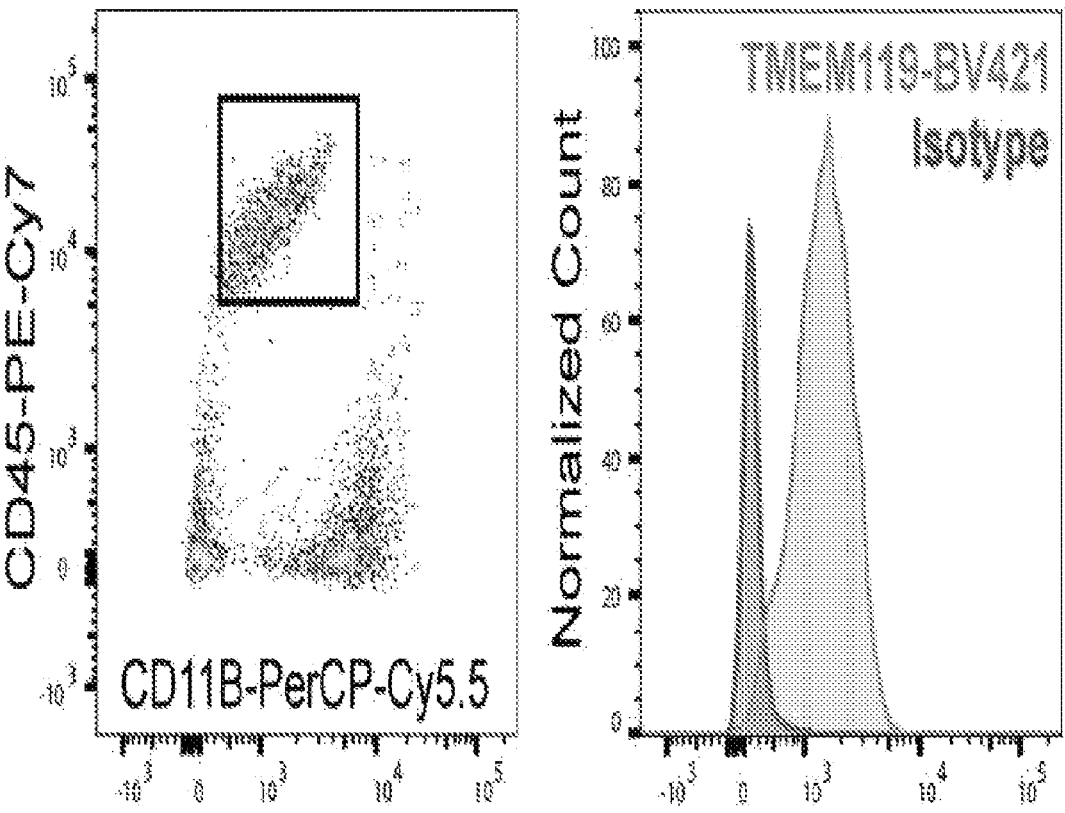
Figure 20A:
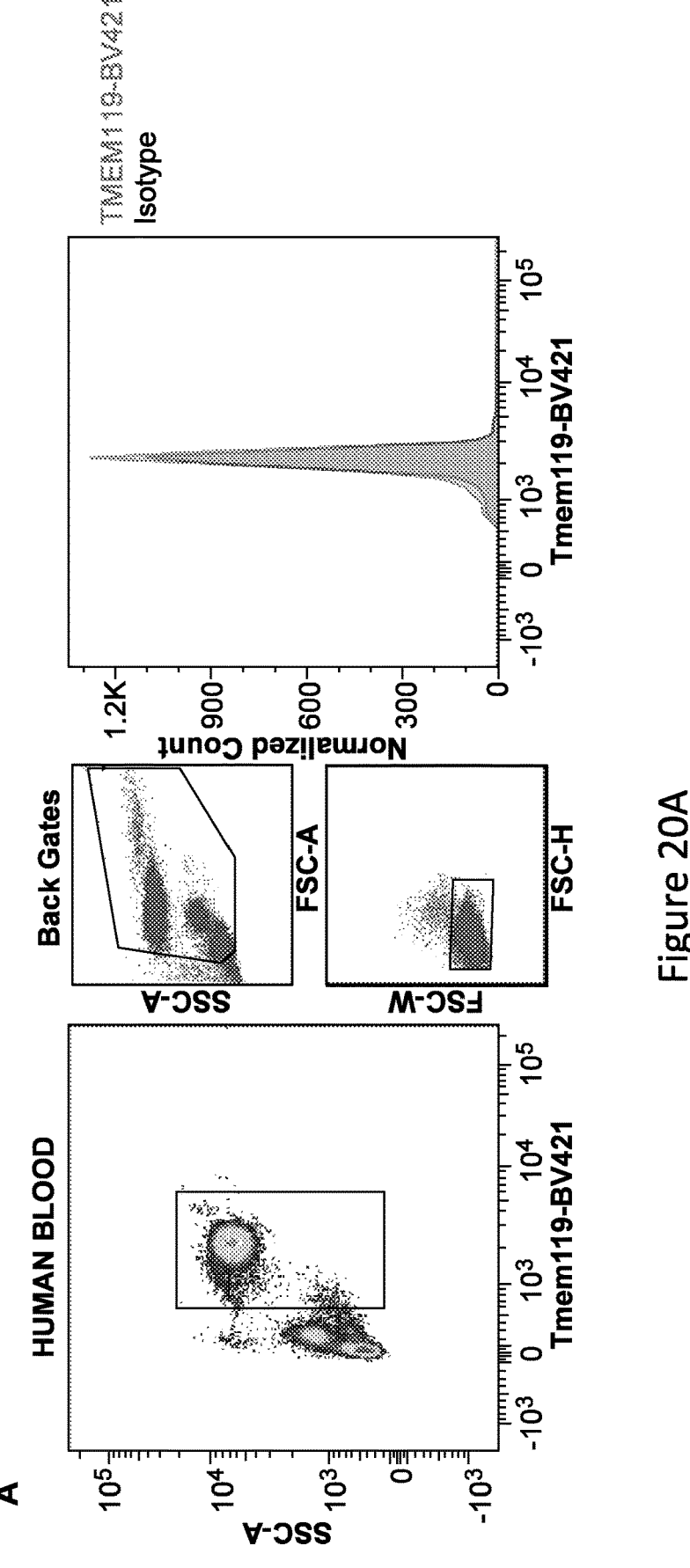
FIGS. 20A-I: Validation of human TMEM119 monoclonal antibody and MS4A7 antibody specificity.
Figure 20B:
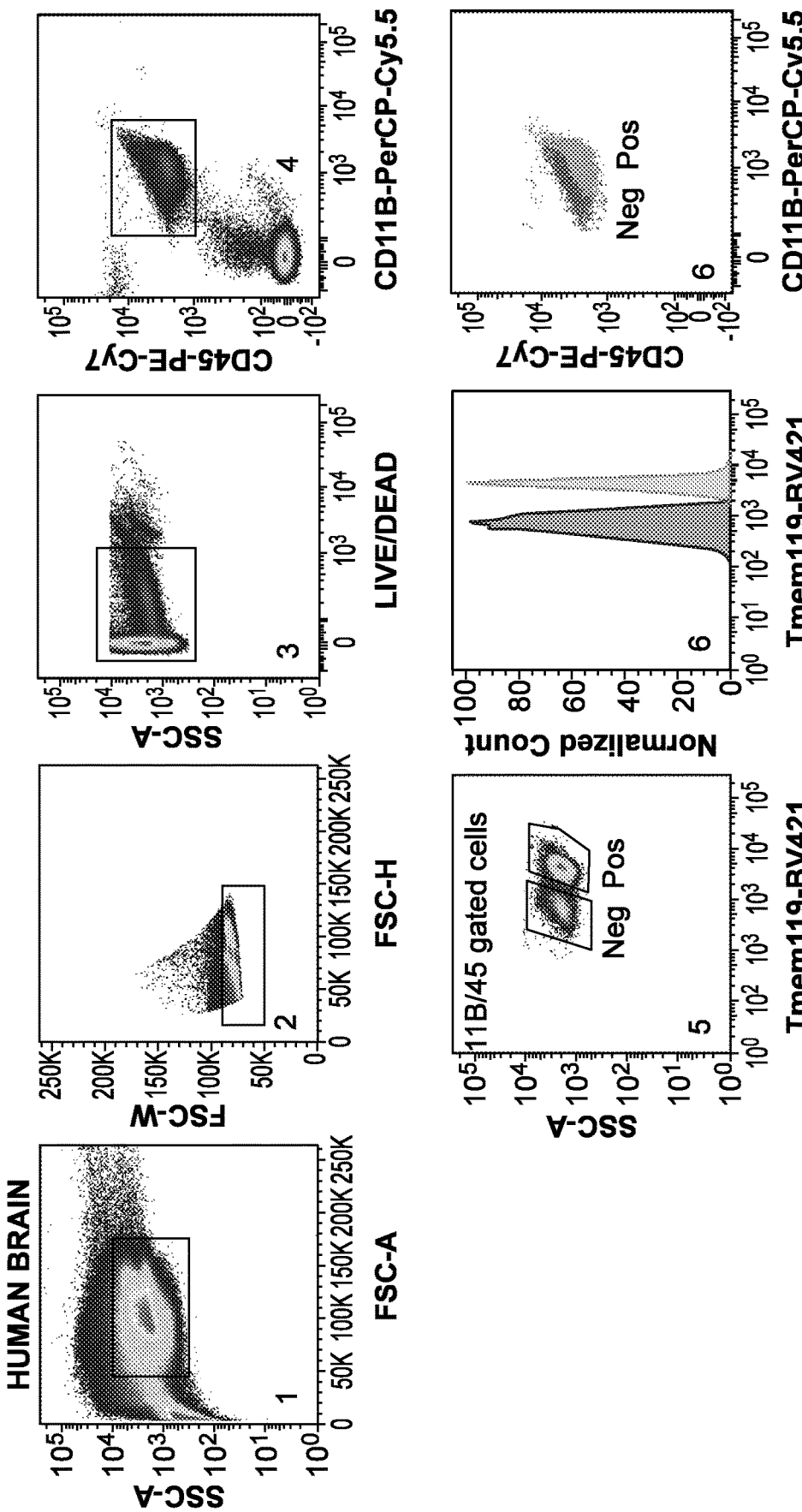
Figure 20C:
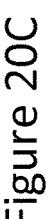
Figures 20D, 20E, 20F:
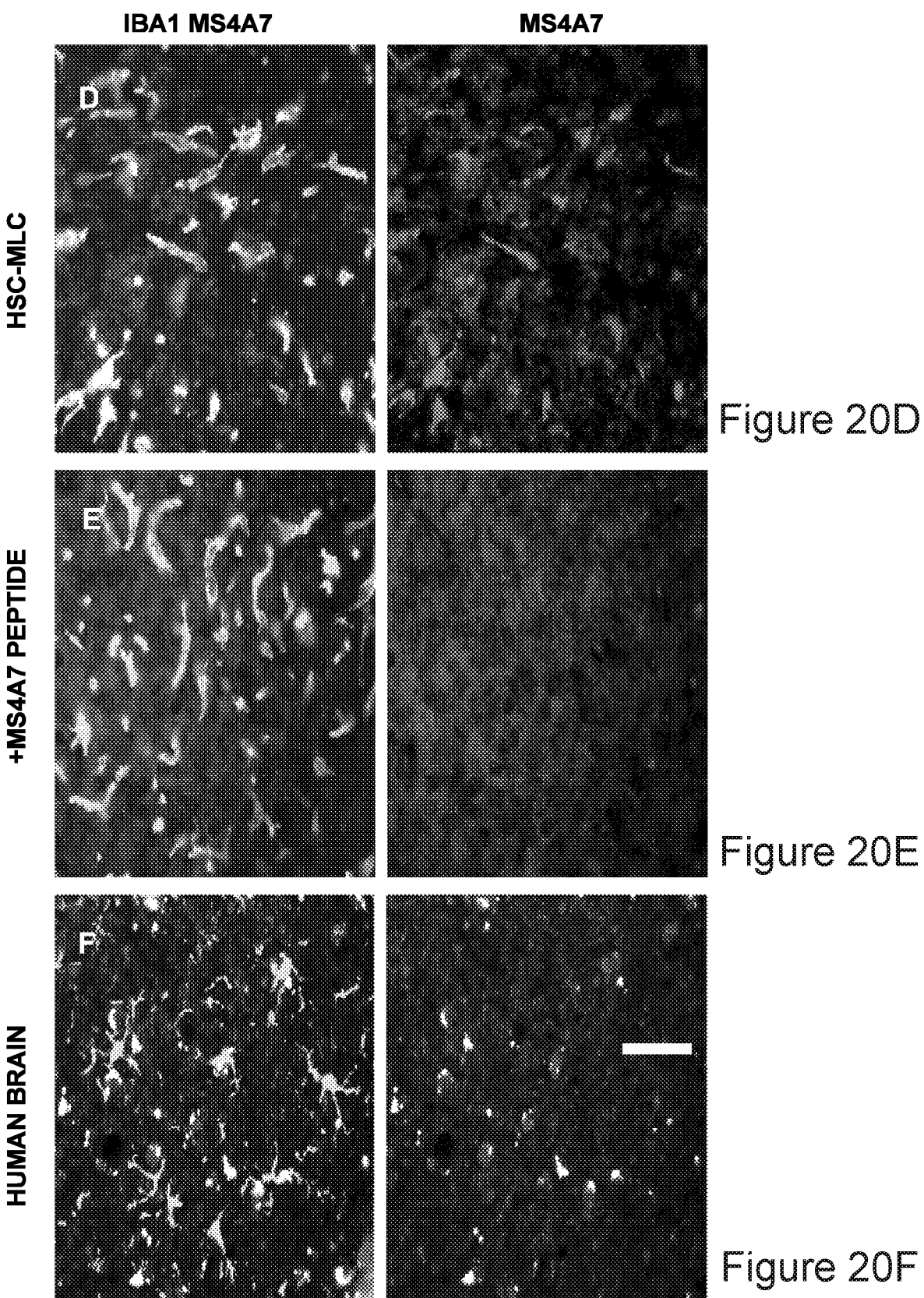

To better study human microglia, we generated a mouse monoclonal antibody against the extracellular domain of human TMEM119 using the same approach we recently used for mouse TMEM119. This custom antibody does not stain human blood (FIG. 20A), but does identify a distinct subpopulation of CD45+/CD11B+ cells in human brain cell suspensions (FIG. 20B), as well as human fetal brain macrophages engrafted in the mouse brain (FIGS. 19E, 20C). This tool will allow specific purification of human microglia in the future.

Figures 19F, 19G, 19H, 19I, 19J, 19K:
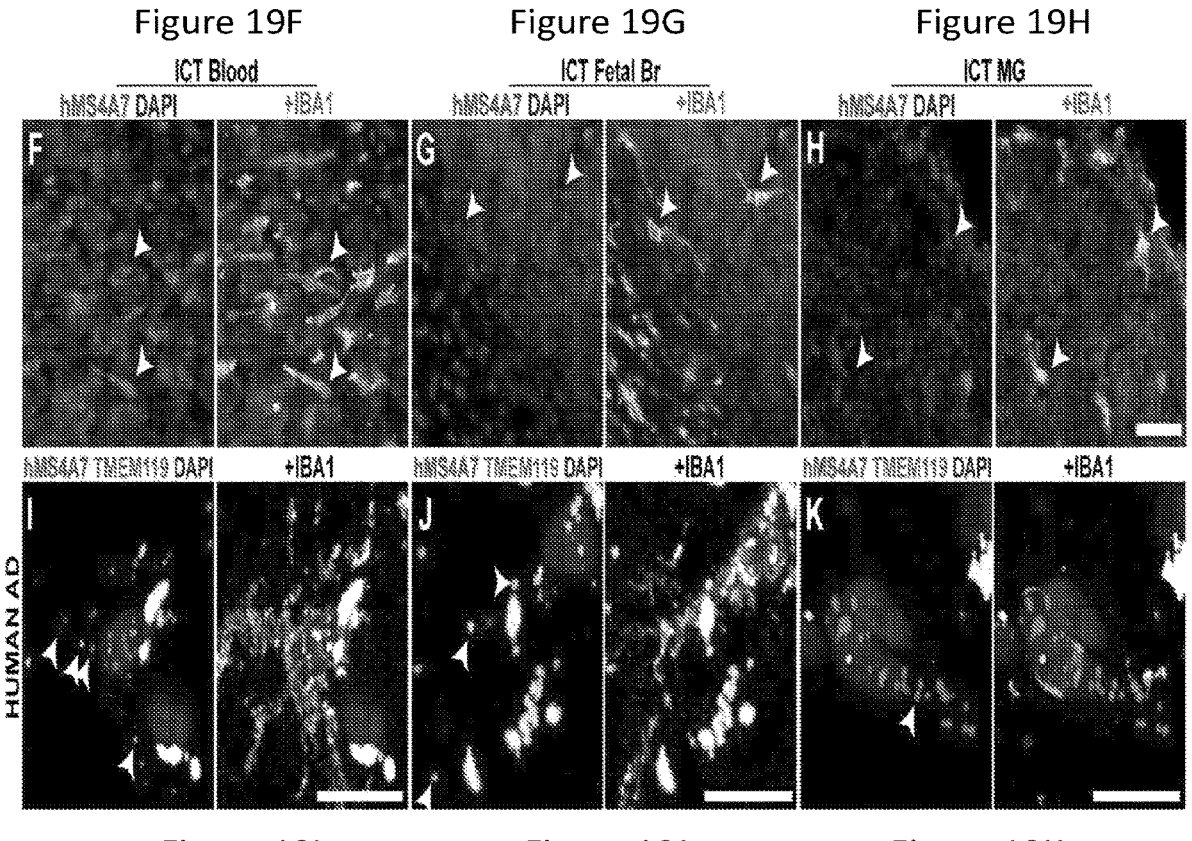
Figures 20G, 20H, 20I:
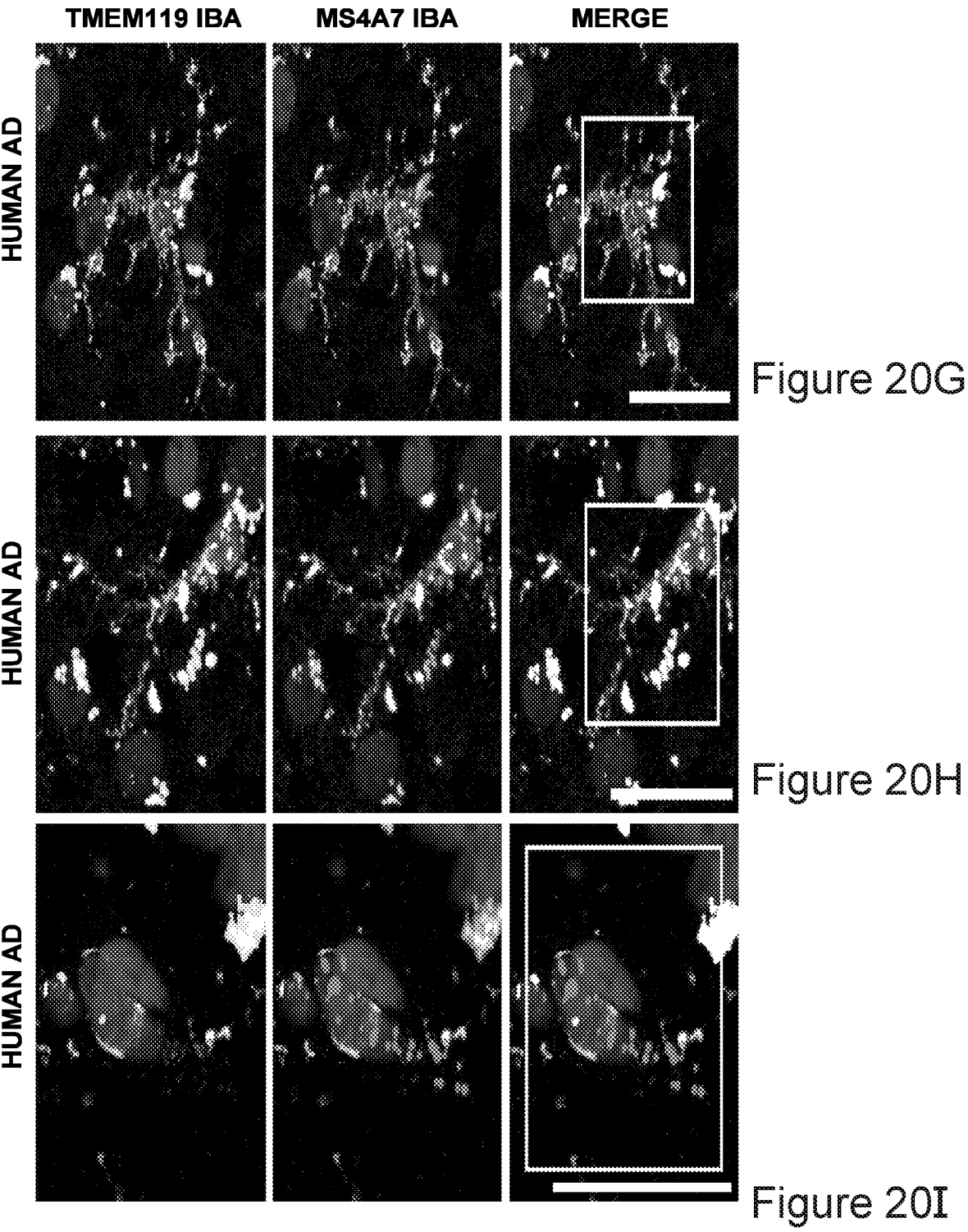

Finally, we wondered whether MS4A7 has potential for use as an ontogeny marker for human brain macrophages. We found that xenograft, blood-derived human HSC-MLCs, but not microglia were MS4A7 immunoreactive (FIGS. 19F-19H, 20D-20F). Having demonstrated that MS4A7 can identify human HSC-MLCs, we next tested if we could detect putative HSC-MLCs in a complex human disease. In post-mortem samples from cases of Alzheimer's and severe cerebrovascular disease, we observed rare ramified TMEM119+/MS4A 7+/IBA1+ cells, which we could not detect in healthy controls (FIGS. 19I, 19J, 20G, 20H). Interestingly, we also found frequent MS4A 7+/Iba1+ cells in a perivascular distribution that were not associated with disease (FIGS. 19K, 20I). Together, these findings demonstrate that MS4A7 is a conserved ontogeny marker, and that the presence of HSC-MLCs may be associated with human neurological disease.

Discussion

Direct CNS Transplantation Reveals Fundamental Principles of Microglia Identity and Plasticity Ex vivo manipulations cause dramatic shifts in microglia gene expression that resemble patterns found during disease and in immature embryonic microglia. Using a cell transplantation system we found that upon return to the CNS, microglia readily inhabit the Csf1r-/- brain, adopt a ramified morphology, and revert to a normal transcriptional program despite profound ex vivo derangement. Our findings demonstrate that though remarkably sensitive to environment, microglia robustly retain the potential to return to a homeostatic state. Comparison between transplanted mature, young, and cultured microglia clarifies that the brain is replete with necessary factors to sustain, induce and re-induce homeostatic microglia gene expression. These findings have direct relevance to microglia reactivity, and development of myeloid cell therapies for brain disease. They suggest that microglia themselves could be cultured, modified, and used translationally for CNS cell therapies, and further, identify the parenchymal macrophage niche as a valid "in vivo culture system" for transplanted microglia. Our findings also encourage continued efforts to develop an in vitro culture system that better sustains microglia identity.

The CNS Induces Microglia Gene Expression in Diverse Myeloid Populations

Cell depletion and bone marrow transplantation studies demonstrate the brain's ability to host peripheral myeloid cells. Here, we show that the Csf1r-/- brain readily and durably hosts myeloid cells from blood, bone marrow, fetal liver, fetal brain, and yolk sac. We found strong induction of microglia signature genes and TMEM119 protein within 14 days, by as yet unknown CNS environmental cues. Based on observations using BMT or genetic microglia ablation with our study, macrophages likely also need access to an open parenchymal macrophage niche. Here, without conditioning irradiation or chemotherapy, we were able to directly compare multiple engrafted TMEM119+ populations from the YS and HSC lineages at multiple stages of development, to clearly delineate the consequences of ontogeny on gene expression in brain resident macrophages.

Peripheral Bone Marrow Injection Rescues Csf1r-/- Animals and Results in Pervasive Engraftment of Brain Macrophages without Irradiation or Chemotherapy Intraperitoneal injection of whole BM with no preconditioning prolongs the survival of Csf1r-/- mice, which typically succumb around 2 weeks of life. In rescued animals, we observed pervasive engraftment of donor cells in all tissues examined, including the brain and spinal cord. Surprisingly, although classic studies identify CCR2 as critical for CNS entry in the setting of inflammation, we find that MLC engraftment did not depend on CCR2, nor did the Csf1r-/- host show evidence for frank BBB breakdown. These data suggest the existence of an alternative mechanism for cell entry into the brain, which we hope to address in future studies. Furthermore, we found that isolated bone marrow monocytes themselves can become TMEM119+ MLCs, consistent with recent results using conditional Csf1r deletion to deplete microglia. Though this does not exclude the possibility that myeloid progenitors or HSCs also contribute to MLC formation, it suggests monocytes as a candidate donor population for cell-based therapies. Provocatively, circulating cells do not contribute to repopulation following pharmacologic depletion of microglia, suggesting that surviving host microglia, which are absent in Csf1r-/- hosts, may be advantaged colonizers or limit parenchymal macrophage niche access.

Ontogeny Regulates Adoption of Microglia Identity, and is Revealed by Stable Markers Direct CNS injection allowed detailed and controlled exploration of fundamental differences between microglia and MLCs from multiple ontogenies across development. Although all MLC types shared similarities with microglia, we observed major effects of ontogeny on transcriptomic identity. YS-MLCs, which share a common progenitor with microglia, became more microglia-like than HSC-MLCs, notably in their expression of microglia signature genes. These findings contrast observations in lung, where engrafted yolk sac, fetal liver and bone marrow monocytes were reported to be near-identical to alveolar macrophages.

Since Tmem119 and other microglia markers may be expressed by HSC-MLCs, their presence does not assure microglia ontogeny. Here, we validated a panel of HSC ontogeny markers that are homogenously expressed among engrafted cells. Despite exposure to the same CNS signals, HSC-MLCs but not YS-MLCs/microglia express Ms4a7, Clec12a, Klra2, Lilra5. In contrast, HSC-MLCs do not express Gpr56, which is expressed by most if not all YS-MLCs/microglia. These ontogeny markers may augment current origin-mapping approaches such as parabiosis and genetic fate labeling. Interestingly, while Clec12a, Lilra5, and Klra2 are broadly expressed by circulating and tissue myeloid cells, Ms4a7 expression is restricted to macrophages. It is highly expressed by intestinal macrophages, which increasingly arise from HSCs in adulthood, raising the possibility that ontogeny markers may be valid outside of the CNS.

YS-MLCs were able to express the full complement of known microglia identity genes by 14 days, but HSC-MLCs were not. An important caveat to the Csf1r-/- system is the limited ability to study MLCs at long time points after transplantation due to host viability. Peripheral BM injection permitted comparison of long- to short-term resident HSC-MLCs to determine whether prolonged CNS residence further promoted microglia gene expression. We found surprisingly little difference between HSC-MLCs at 14 days versus 2-3 months using both unbiased and targeted analyses. In particular, HSC-MLCs remained unable to express Sall1/Sall3, did not further increase expression of signature genes such as Tmem119, P2ry12, Olfml3, and continued to express HSC ontogeny markers, some at increased levels. After 6 months of brain residence, HSC-MLCs continued to express Ms4a7, which also marked HSC-MLCs in both neonatal and adult tamoxifen-treated Cx3cr1-CreER; Csf1r fl/fl hosts after 2 months. Taken together, these observations suggest that prolonged CNS incubation is not sufficient to completely over-ride cell-intrinsic properties associated with ontogeny, an important consideration for the development of myeloid cell therapies for brain disease. The limitations of the Csf1r−/− model, or in fact any mouse model, call for future studies to determine if years-long incubation relevant for human lifespan is sufficient to fully induce microglia identity in HSC-derived cells.

HSC-MLCs Resemble Microglia in Disease States

Sall1 and Nrros are central to microglia identity and when absent, microglia adopt an abnormal phenotype characterized by reduced expression of microglia signature genes and increased expression of macrophage markers associated with inflammation. HSC-MLCs are unable to express Sall1 in Csf1r−/− hosts and resemble microglia from multiple disease states. Of particular interest, Apoe is the most highly expressed gene in HSC-MLCs—4-20 times higher than in transplanted microglia or YS-MLCs. By in situ hybridization, HSC-MLC engrafted brains also showed increased Apoe levels in other brain cell types in addition to microglia. Apoe genotype remains one of the most important risk factors in Alzheimer disease (AD), and may directly drive microglia dyshomeostasis during neurodegeneration.

Intriguingly, HSC-MLC ontogeny markers from our study have previously been implicated in neurological processes. The Ms4a family of genes is associated with AD risk in large human studies. In addition, Clec12a blockade attenuated a mouse model of multiple sclerosis. Associations between HSC transcriptomes, ontogeny markers, and brain disease raise the tantalizing hypothesis that infiltrating cells could masquerade as microglia and contribute to brain malfunction. The future study of the functional consequences of HSC-MLCs and different ontogeny markers may be critical to understanding brain function in health and disease.

Transplantation of Primary Human Cells and a Custom Anti-Human Tmem119 Antibody Facilitate Study of Human Microglia and MLCs In vitro studies of human microglia are limited by loss of microglia identity in culture. Here, we found that cultured and acutely isolated primary cells from human blood and brain engraft, ramify, and express TMEM119 in humanized Csf1r−/− rodent brains. This shows that the murine brain is replete with factors to support survival of primary human macrophages and expression of a microglia protein not reliably detectable in culture. It also offers a new approach to studying human microglia in a living and highly controllable CNS environment that we hope will facilitate future studies of disease. Since blood from patients with brain diseases is relatively accessible, direct CNS transplantation may be used to compare MLCs from healthy and disease states, complementing analogous approaches limited by lack of microglia gene expression in vitro. We also validated a custom anti-human TMEM119 antibody for FACS sorting of pure human microglia from human and xenograft samples, for use by the microglia community.

Of equal importance, we confirmed that MS4A7 marks human HSC-MLCs but not microglia, suggesting that it is an ontogeny marker across species. The relevance of infiltrating myeloid cells to human brain disease is unresolved but of great consequence to the development of novel therapies. Since parabiosis and fate-labeling are not possible in human, MS4A7 may offer a feasible approach to detecting long term resident HSC-MLCs in the CNS. Importantly, we found MS4A7+/TMEM119+ cells in brains of neurological disease patients but not healthy controls, demonstrating the feasibility of this method and supporting the possibility that infiltrating myeloid cells may reside in the degenerating human brain.

Relevance of Ontogeny and Environment to Microglia Replacement Therapy

Here, we provided new tools to study transplanted mouse and human brain macrophages, and applied them to relationships between environment, ontogeny, and tissue macrophage identity. In addition to the future studies discussed above, direct myeloid cell transplantation holds potential as a form of treatment for diverse neurological and psychiatric diseases. Our results reveal the importance of both ontogeny and CNS environmental cues to brain resident macrophage identity, as well as potential future avenues for understanding the CNS macrophage niche. These findings warrant future studies to reveal the functional and phenotypic consequences of these important differences, in order to make robust human microglia replacement therapies a reality.

Methods

Experimental Model and Subject Details

Mouse Models

All animal studies were performed with approval from the Stanford Administrative panel on Laboratory Animal Care in accordance with institutional and national regulations.

Csf1r−/− (FVB.129X1-Csf1r$^{tm1Ers}$) and Csf1r+/+ littermate animals on the FVB background were a generous gift from Dr. Richard Stanley, Albert Einstein College of Medicine, New York, USA. Adult WT FVB donor animals were bred from the identical starting strain. Timed FVB embryonic tissues were obtained from Charles River (Hollister, CA). For experiments using GFP-expressing donor cells, we back crossed the Csf1r KO allele onto the C57BL/6 strain using MaxBax speed congenics (Charles River) for 5 generations to >99.7% C57BL/6, then crossed 1 further generation. We generated a Cx3Cr1$^{CreER}$; Csf1r$^{fl/fl}$ line by intercrossing Jax 021212 and 021160. For experiments, we crossed Cx3Cr1$^{CreER}$+/−; Csf1r$^{fl/fl}$ to Csf1r$^{fl/fl}$ animals. To test whether engraftment required CCR2, we use Ccr2 Rfp/Rfp homozygous donors (Jax 017586). We also used C57BL/6-Tg(CAG-EGFP)131Osb/LeySopJ ("Osb-GFP," Jax 006567) as a source for GFP-tagged donor cells. To generate the Rag2−/− IL2rg−/− hMCSF+/+ Csf1r−/− mouse we crossed the Csf1r$^{tm1Ers}$ allele into C; 129S4-Rag2$^{tm1}$.1Flv Csf1$^{tm1(CSF1)Flv}$ Il2rg$^{tm1.1Flv/J}$ (Jax 017708). Animal lines were genotyped by Transnetyx (Cordova, TN) except pan-GFP animals which were genotyped by green florescence upon blue light exposure. We sometimes genotyped for Csf1r with in-house PCR (F1 5'-AGACTCATTCCAGAACCAGAGC-3' (SEQ ID NO: 15), F2 5'-CCGGTAGAATTCCTCGAGTCTA-3' (SEQ ID NO: 16), R1 5'-GAATTTGGAGTCCTCACCTTTG-3' (SEQ ID NO: 17)). We verified Csf1r genotypes with second genotyping post-mortem.

Human Tissue Samples

Human studies were approved by the Stanford Research Compliance Office and included IRB approval. Informed consent was obtained from all subjects. Postnatal brain macrophages used in transplantation experiments were obtained from n=4 pediatric and adult neurosurgical cases for temporal lobe epilepsy. We used pieces of temporal cortex outside the epileptic focus; these were described as normal on MRI and by the operating surgeon. Fetal brain tissue (n=2, 16-20 wk gestational age) was obtained from Stemexpress (Folsom, CA). Adult peripheral blood (n=6) was obtained from the Stanford Blood Center (Palo Alto, CA). All donor information was anonymized prior to investigator acquisition of samples. For human in situ hybridizations, flash frozen post-mortem brain tissue was obtained from the Stanford Brain Bank and diagnosed by E.P., a board-certified neuropathologist, thawed and fixed overnight in 4% PFA, then cryoprotected in 30% sucrose prior to frozen sectioning. We assessed N=3 cases of severe AD pathology (one of which also showed Lewy Body disease and cerebral amyloid angiopathy) and N=1 case of severe cerebrovascular disease, comparing to N=2 controls from temporal lobe epilepsy surgeries.

Method Details

Microglia/MLC Transplantation

For ICTs, P0-P4 Csf1r−/− pups and +/+ controls were injected as described previously (Bohlen et al., 2017) by hand using a pulled glass microcapillary tube in an electrode holder connected by silicon tubing to a syringe. One microliter containing a single cell suspension of donor cells in PBS was slowly injected bilaterally into cortex, 1-2 mm anterior and 2-3 mm lateral to lambda at a depth of 0.5-1 mm. Host animals were harvested after 14 days. Due to the constitutional fragility of Csf1r−/− animals, we harvested surviving animals of both sexes and pooled them for analyses. IP bone marrow injections were performed in P0-4 pups using an insulin syringe containing 20 µl of a single cell suspension in PBS. For adult CX3CR1-CreERT+/−; Csf1r fl/fl×Csf1r fl/fl ICTs, 5 month old mice were injected with 150 mg/kg 4-hydroxy tamoxifen for two days. On day one, host animals were anesthetized with isofluorane, and five million bone marrow cells from Osb-GFP mouse donors were injected per hemisphere through two small burr holes bilaterally, approximately 1 mm behind Bregma. The incision was closed using 4-0 vicryl sutures. Mice were treated with 5 mg/kg subcutaneous carprofen analgesia and monitored closely post-operatively. Neonatal pups of CX3CR1-CreERT+/−; Csf1r fl/fl×Csf1r fl/fl mice were injected daily between P1-P4 with 200 mg/kg 4-hydroxytamoxifen subcutaneously. These hosts were then transplanted via direct intracerebral injection on day 5.

Donor Tissue Preparation

Microglia

Microglia were isolated as previously described (Bennett et al., 2016) with the following substitutions: Mice were euthanized by $CO_2$ asphyxiation and intravascularly perfused with 10 mL cold PBS, except for P5 animal brains which were carefully rinsed in PBS after dissection of the meninges. After myelin depletion using MACS beads, cell suspensions were positively selected for CD11b expression by magnetic bead separation using the MACS system (Miltenyi). Where applicable, mouse microglia were then cultured in TIC medium (described in (Bohlen et al., 2017)) supplemented with 10% heat inactivated FCS for 16-20 hours at 37° C. and 10% $CO_2$, and subsequently harvested for RNA isolation or intracranial transplantation. Cells were cultured on tissue culture plastic, and harvested by incubation on ice for 5-10 minutes, followed by 3-5 washes with ice cold FACS buffer (PBS, 25 mM HEPES, 2 mM EDTA, and 2% FCS) and repeated pipetting. 20-100×10³ cells were injected per host based on cell yields. For injection of human brain macrophages, we used identical methods, except that for 2 of the adult brain samples we omitted CD11B+ selection due to limited sample size. For postnatal samples, we injected 2-40×10³ cells, and for fetal, 5×10³. Where applicable, we cultured human fetal brain macrophages identically to mouse, with the exception of using human MCSF (Peprotech) instead of mouse, at identical concentration.

Yolk Sac

We manually dissected the yolk sac from 4-6 pregnant females at E8 (Charles River) into cold PBS (counting plug date as E0), yielding approximately 30 yolk sacs per prep. We then gently homogenized with 5 slow triturations each across successively smaller outlets (p1000 tip→p200 tip→18 g needle→27 g), and passed the homogenate over a 70 µm cell strainer. We next centrifuged for 5 min at 175 g, resuspended in 40 µl cold PBS, and injected 1 µL per pup (~0.75 yolk sacs per mice) into 30-40 pups across 5-7 litters.

Fetal Brain

We manually dissected fetal brain tissue from E12-13 embryos into cold PBS, dissociated by 20 gentle triturations using a p1000 tip, and passed over a 40 µm cell strainer. To enrich for macrophages, we either used CD11B+ MACS positive selection as described for microglia or FACS, using the sort strategy shown in FIG. 6B. We injected 2.5-8.5×10³ cells per host as limited by cell yield.

Fetal Liver

Figure 6C:
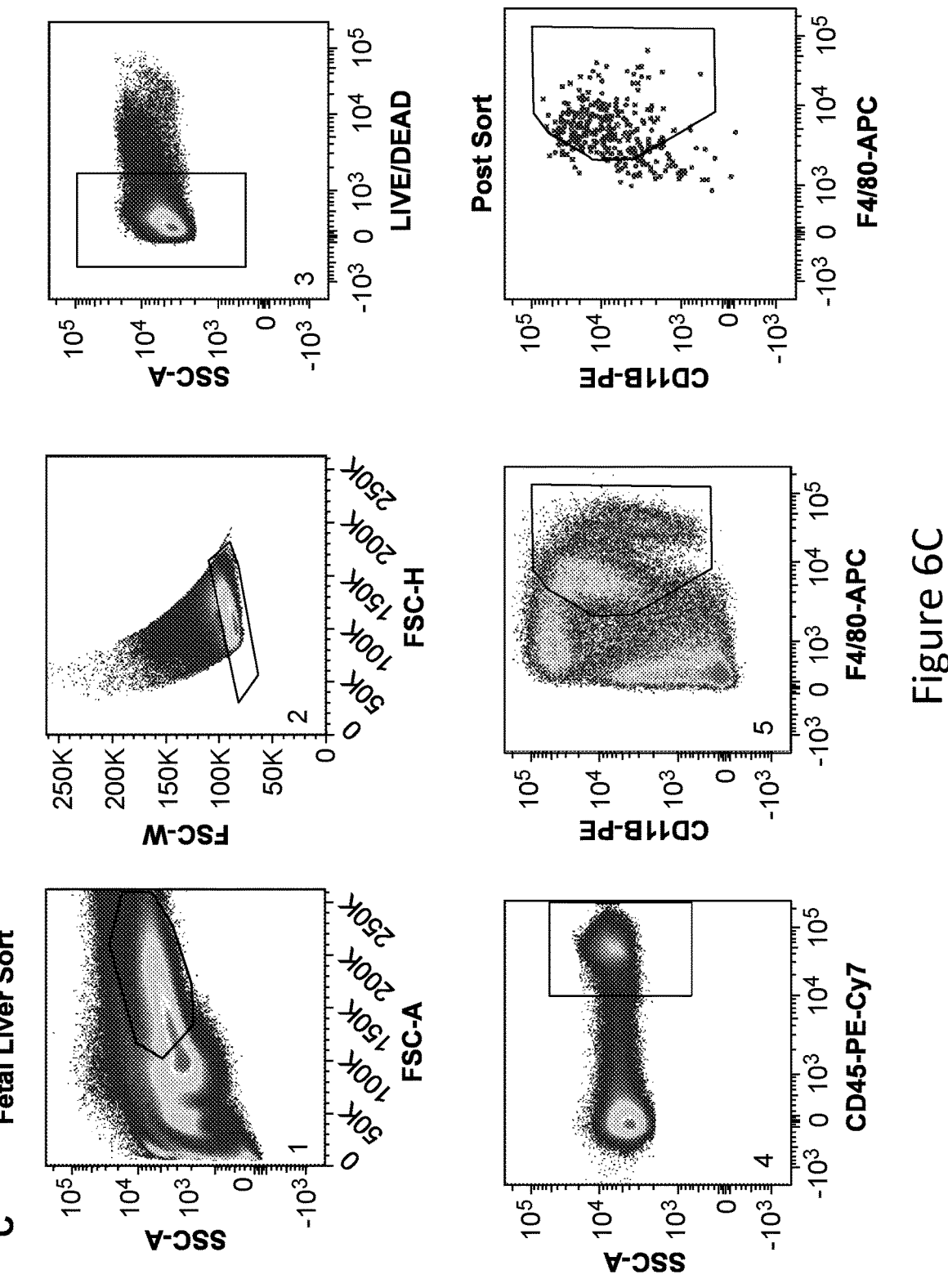
Figures 6D, 6E, 6F:
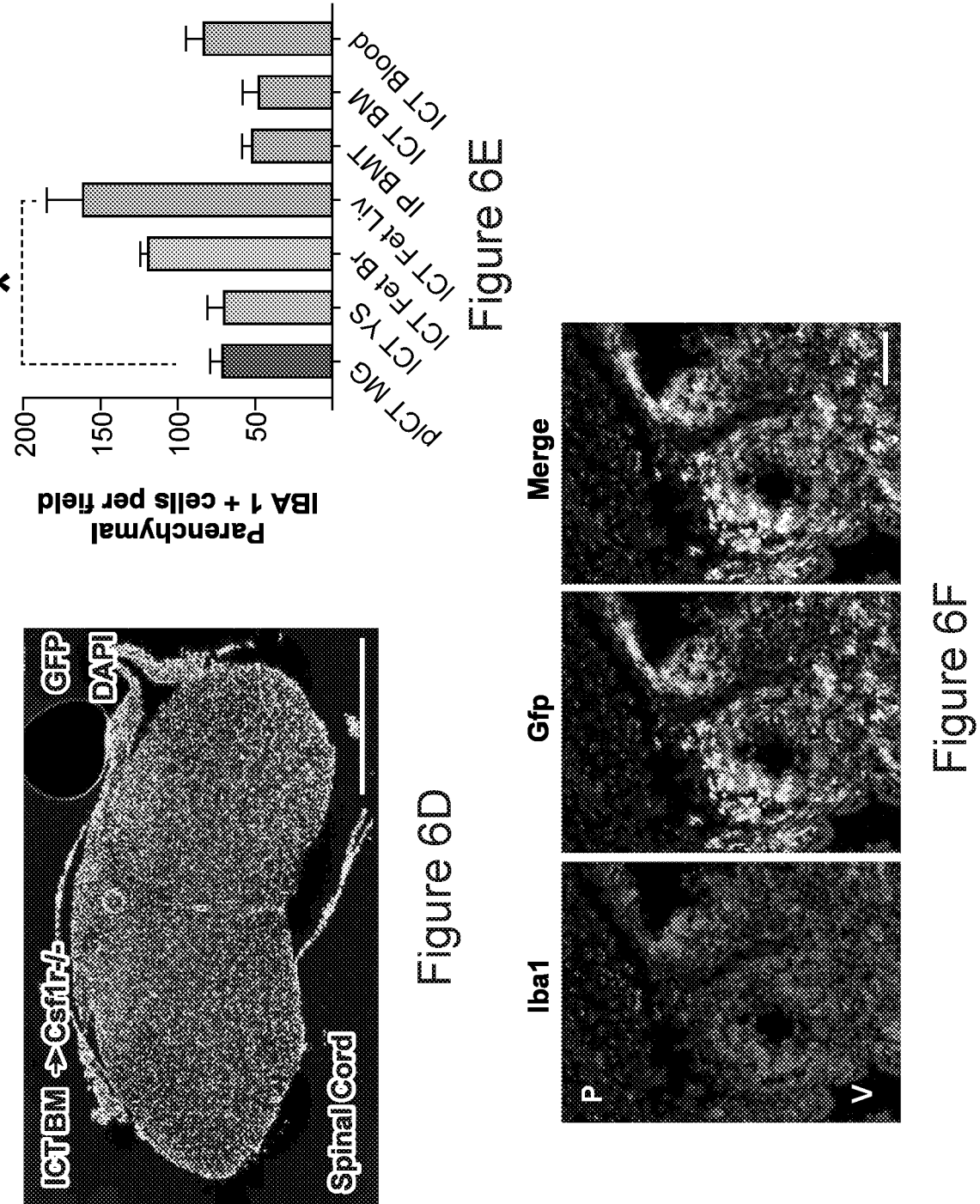

We manually dissected fetal liver from E13-14 embryos, homogenized by gentle trituration using a p1000, passed over a 40 µm strainer, and stained cells for FACS, using the sort strategy shown in FIG. 6C. We injected 5-20×10³ cells per host as limited by cell yield.

Bone Marrow

We dissected femurs and tibia from 4-8 week old FVB WT, Osb-GFP and Ccr2 KO (Rfp/Rfp) animals of mixed sex, isolated whole bone marrow by flushing bones with PBS, and lysed RBCs using ACK as previously described (Bennett et al., 2016). For ICTs, we injected 100-200×10³ cells per host. For IP BMTs we injected 2-5×10⁶ cells per animal.

Bone Marrow Monocytes

We isolated bone marrow as described above, then enriched for bone marrow monocytes using the bone marrow monocyte isolation kit (Miltenyi), which enriches for monocytes by depletion of other cell types. We then stained this enriched population for CD45, c-kit, Lytic, NK1.1, CD3, B220, Il7ra, Siglecf, Ly6g using antibodies and dilutions shown in the key resources table, and sorted for monocytes using the sort strategy in FIG. 8F. We injected 0.5-2×10⁶ cells per mouse by the intraperitoneal route.

Blood

We collected whole blood from 6-8 week old FVB WT animals of mixed sex in 0.5M EDTA coated syringes by cardiac puncture, pooled blood from all animals in 0.05M final concentration of EDTA, and centrifuged at 1000 RPM for 12 minutes at RT. We then collected the buffy coat layer, lysed RBCs in 10-20 volumes ACK buffer (Gibco) for 10 min at RT, centrifuged for 5 min at 200 g, washed ×1 and then resuspended in PBS. We injected 100-200×10³ cells per host.

Flow Cytometry

MG/MLC Isolation

We generated single cell suspensions of MG/MLCs using dounce homogenization and MACS myelin depletion as described above, then followed methods described in (Bennett et al., 2016). Briefly, we stained with a vital dye to exclude dead cells (Thermo Fisher), then for CD45, CD11b, and Tmem119 at dilutions shown in key resources table, adding RNAsin (Promega) and DNAse (Worthington) to our sort tubes, following the sort strategy shown in FIG. 3C.

Donor Tissue Isolation and Analysis by FACS

For FACS sorting of donor tissues described above, we used identical staining protocols except performed centrifugation steps at 300 g for 5 minutes, and stained for different markers as described above. We performed all flow cytometry experiments using a large diameter (100 μm) nozzle at rates of 1-2.5 on BD FACSAria instruments in the Stanford Shared FACS Facility core. We sorted into FACS buffer for transplantation experiments. We used Flowjo software (Treestar) to analyze and visualize data. Gating strategies are shown wherever applicable in FIGS. 3, 6 and 20.

RNA and DNA Extraction

We sorted engrafted cells directly into RNA extraction buffer. For BMT experiments we used Trizol LS (Sigma) according to manufacturer's protocols, collecting RNA and sometimes genomic DNA for genotyping of sorted cells. For one MG ICT experiment we sorted into RLT Plus (Qiagen) and isolated both RNA and genomic DNA using the Allprep Micro kit. For remaining experiments we sorted into RLT buffer (Qiagen) and isolated RNA using the RNAeasy micro kit with on column DNAse digestion. We measured RNA quality by Agilent Bioanalyzer, and only processed samples with RIN>7. We found that in order to reliably obtain adequate quantity and quality of RNA, we required $30\times10^3$ sorted cells.

RNAseq Library Construction and Sequencing

We constructed and quality controlled libraries as described previously (Bennett et al., 2016), using the Nugen Ovation RNA-seq system V2, and the NEB Next Ultra RNAseq kit for Illumina, with 9-10 cycles of PCR enrichment. High quality libraries were sequenced by Miseq (Illumina), using 75 bp paired end reads. Aside from one WT control sample with $0.9\times10^6$, we obtained at least $1\times10^6$ paired reads per sample, with a range of $1$-$6\times10^6$. At least 70% of reads were mapped in all samples.

Anti-Human Tmem119 Antibody Generation

To generate mouse anti-human TMEM119 FACS antibodies, we cloned the extracellular domain (ECD) after the signal peptide for human Tmem119 (corresponding residues: 26-95) into a custom pMAL vector for periplasmic MBP-ECD-8×His fusion expression (gift from A. Ring, Yale University, New Haven, CT). We purified recombinant fusion proteins by Ni-NTA columns. BioLegend (San Diego, CA) immunized mice with the recombinant ECD proteins and screened positive multi-clone supernatants by ELISA. We tested multi- and then single-clone supernatants first by staining HEK cells transfected with His-tagged human Tmem119 expressed in pCMV-SPORT6 mammalian expression vector. For promising clones we verified that staining was blocked by pre-incubation with immunizing peptide, and tested them on primary human brain and blood tissue samples. We found that clone A16075D stained 70-98% of CD45+/CD11B+ human brain cells with the highest signal to noise ratio; public release of clone A16075D by Biolegend is forthcoming.

Tissue Immunostaining

We performed immunostaining on 4% PFA perfusion- or immersion-fixed samples depending on whether whole animals or brain pieces were processed. Samples were cryoprotected in 30% sucrose-PBS, embedded in OCT (Fisher), cryosectioned (12-16 μm), mounted on Superfrost Plus slides (Fisher) and stored at −80 until use. For mouse TMEM119 and IBA1 staining, we dried slides at 60° C., rehydrated in PBS, blocked for 1 hour at room temperature (RT) in PBSTx (PBS with 0.3-0.5% Triton X-100) with 10% serum. We then incubated with primary antibodies in PBSTx/1% serum (staining buffer) overnight at 4° C. After washing, we incubated slides in staining buffer with Alexa-conjugated secondary antibodies (Life Technologies) for 2 hr at RT, washed, Antibodies for MS4A7 (Atlas) and human TMEM119 (Abcam) required antigen retrieval prior to blocking. After rehydration, we boiled samples for 4 minutes in 10 mM sodium citrate/0.05% Tween 20, pH 6, then incubated for 15 more minutes at RT in hot buffer. For MS4A7 peptide blocking studies, we obtained immunizing peptide from the antibody manufacturer (Atlas). We preincubated primary antibody with 40 molar excess of blocking peptide in 31.5 μl PBS overnight at 4° C. prior to staining. To measure percent of parenchymal IBA1+ cells that were also TMEM119+, we provided numerically coded images obtained by FCB to FY, who also was not told the purpose of the experiment, but was instructed to mark all green cells (IBA1 channel), and then the number of these that had any co-localized red (TMEM119 channel) staining. To measure cell density, we counted the number of nucleated TMEM119 positive cells in the same dataset, expressed as cells per unit area. To measure albumin and IgG accumulation in the brain parenchyma, we stained 30 micron sections from animals perfused at approximately 70% of cardiac output (0.07× mass in grams) for albumin (Abcam) or IgG (Life Technologies), and compared to unstained tissue (IgG) or secondary only (albumin) controls processed in parallel for each sample. We examined all samples for qualitative evidence of local staining, and quantified mean florescence intensity in identical ROIs from the cortex. We expressed positive staining as a fold change over the MFI from negative control samples, propagating error accordingly.

RNA In Situ Hybridization

We performed in situ hybridizations on fixed frozen samples using the RNAscope system (ACDbio) with RNAscope 2.5 HD Duplex Reagent kit for colorimetric and Fluorescent Multiplex Reagent kit V2 for fluorescent development, according to manufacturer's protocols using TSA reagents (Perkin Elmer). When staining concurrently for IBA1 protein, we used our standard immunostaining protocol, omitting Triton-x100, with fluorescent secondary antibodies or HRP-conjugated secondary antibodies (Jackson Immuno-research) and DAB development kit (Thermo Scientific). Sections were counterstained with hematoxylin (colorimetric) or DAPI (fluorescent) for nuclei.

Image Acquisition and Processing

We acquired epifluorescence images using an Axio Imager M1 (Zeiss), except for stitched images in FIGS. 5, 7, and 6 for which we used a BZ-X700 Fluorescent Microscope (Keyence), confocal images for which we used an LSM710 (Zeiss) and DNA gels for which we used an Alpha Imager (Innotech). We acquired color images using an Axio Imager A2 (Zeiss). We analyzed images in Fiji (https://imagej.net/Fiji) or ICY (icy.bioimageanalysis.org), adjusting for brightness and black values (notes and raw images available upon request). We performed no other image math or processing.

Analysis of RNAseq Data

We mapped, assembled transcripts, estimated FPKM, and analyzed differential gene expression as described previously (Bennett et al., 2016), using the tuxedo pipeline and edgeR, and identical reference genome. To avoid misinterpretation of expression differences in lowly expressed genes, we focused most analyses on genes with moderate or high expression (FPKM>20), and only interpreted gene expression differences with log 2 (FC)>1 and FDR<0.05. To generate a correlation heatmap, we selected the top 1000 most variant genes across the datasets studied and used the R package gplots cor function to generate a map of Spearman coefficients for each comparison. When other published datasets were used, we normalized their reads to the average by a simple scalar. To make heatmaps, we used gplots heatmap.2 function. For PCAs, we used Clustvis. We ran analyses on the top 2500 most variant genes based on log 2 (FPKM+1 values), applying unit variance scaling to rows, and using SVD with imputation to calculate principal components. In PCA plots, ellipses predict cluster boundaries with probability 0.95. We used JVenn to create Venn diagrams showing shared and distinct differential gene expression. GSEA was performed using GSEA software V3, running 1000 permutations by phenotype, calculating weight enrichment and ranking genes by Signal2Noise. ALS UP, AD UP, LPS UP 1/2, DEV UP 1/2, CULTURE UP, and CULTURE DOWN were obtained from (Bohlen et al., 2017). The Sall1 UP gene list represents the top 49 most upregulated genes in Sall1 KO microglia by fold change with FDR<0.05 from (Buttgereit et al., 2016), downloaded from https://www.ebi.ac.uk/arrayexpress/experiments/E-MTAB-5077/. The NRROS UP gene list contains genes with log 2 (NRROSKO/WT)>1.5 in sorted microglia/macrophages and adjusted p-value <0.05 from (Wong et al., 2017). For the correlation plot in panel 5B, we merged gene lists from Sall−/− microglia (log 2 (FC/WT)>1 or <−1) with those from HSC-MLCs, omitting genes for which edgeR was unable to obtain Log 2FC values or did not appear in 1 of the 2 datasets.

Replicates

Number of biological replicates used in immunostaining and RNAseq experiments are specified below:

Adult microglia; Immunostaining: 6, RNAseq: 2
P5 microglia; Immunostaining: 5, RNAseq: 2
Cultured microglia; Immunostaining: 7, RNAseq: 4
Yolk sac; Immunostaining: 6, RNAseq: 3
Fetal Brain; Immunostaining: 3, RNAseq: 5
Bone marrow ICT; Immunostaining: 7, RNAseq: 7
Blood; Immunostaining; 9, RNAseq: 3
Bone marrow IP; Immunostaining; 9 RNAseq: 5
WT control; Immunostaining; 7, RNAseq: 7

Quantification and Statistical Analysis

For all plots not elsewhere described, we used Graphpad Prism or Microsoft Excel. For statistical analyses of differential gene expression, we used the false discovery rate (FDR) calculated in edgeR. We performed Dunnett's test for multiple comparisons, ANOVA, and linear regression in Graphpad.

Figure 21:
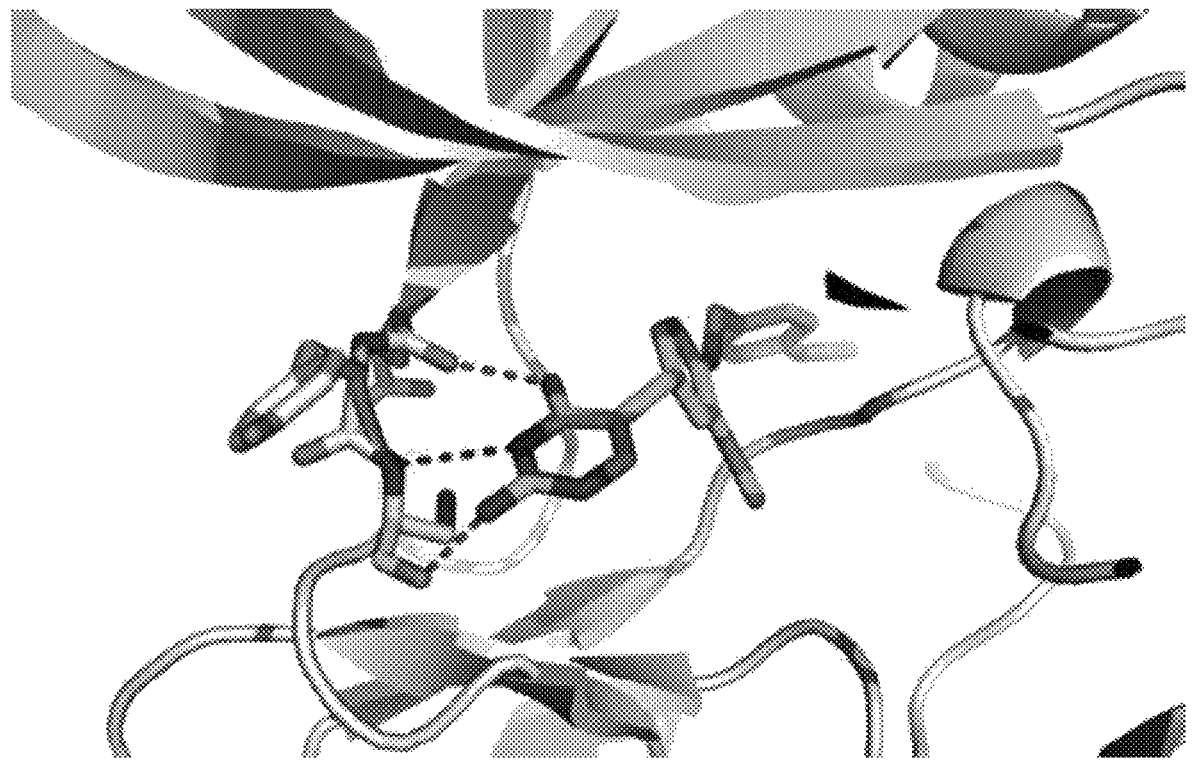
FIG. 21: Crystallographic structure of CSF1R bound to the CSF1R inhibitor, GW-2580.
Figure 22:
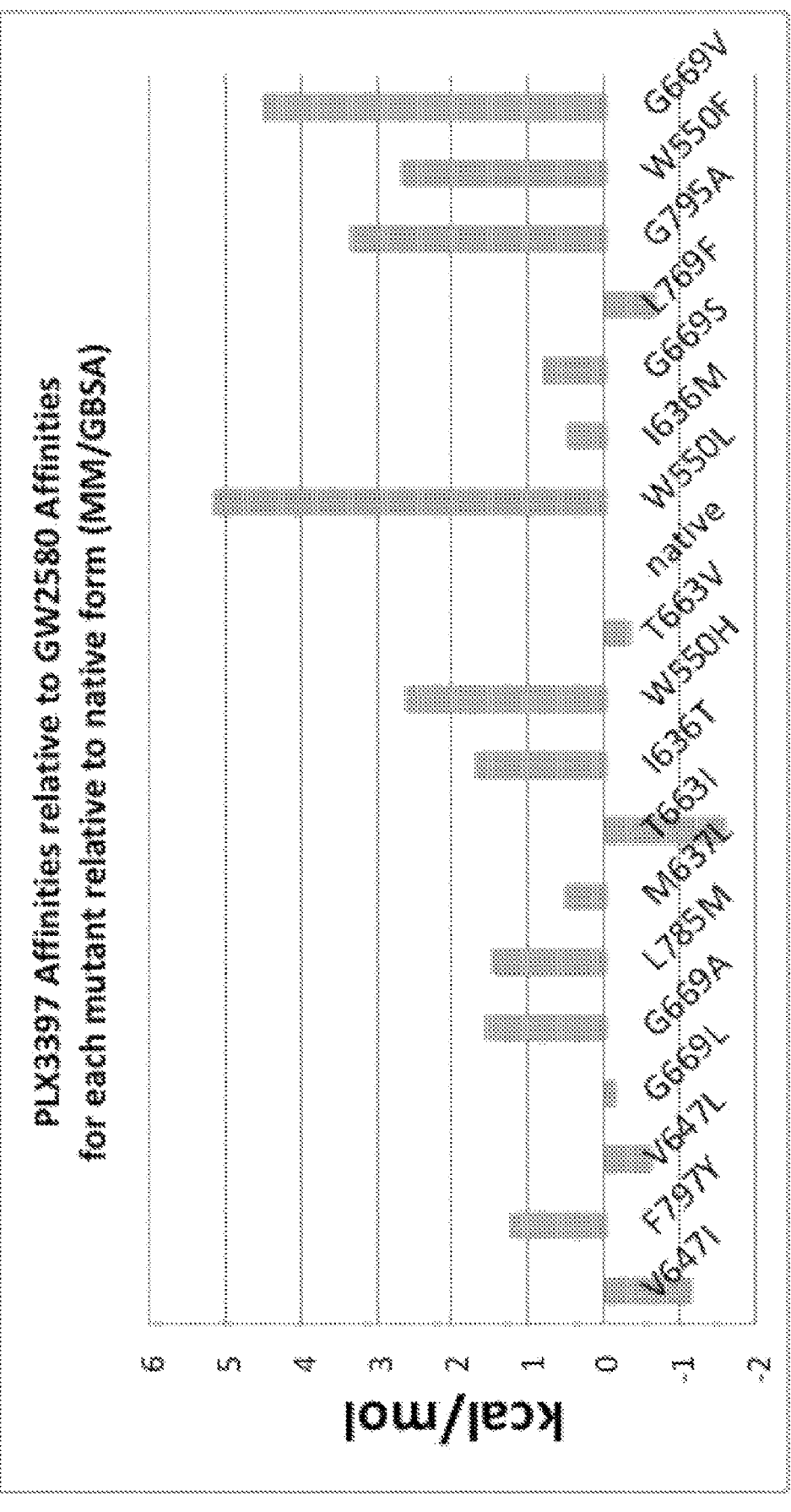
FIG. 22: Non-limiting example of a plot of the difference in interaction energy for CSF1R inhibitors PXL-3397 and GW-2580 with various CSF1R muteins.

Example 2. Computational Modeling of CSF1R Muteins and Interactions with Small Molecule CSF1R Inhibitors A model of the CSF1R inhibitor, GW-2580, bound to CSF1R was constructed as follows. First, of all the published CSF1R structures in the RCSB Protein DataBank (PDB) available at the time of this work, it was determined that the structure with PDB code 3LCO was the best starting point for the model building. The information contained in the published crystal structure of TrkB kinase domain in complex with GW-2580 (PDB code: 4AT5) was combined with 3LCO in order to produce an initial model. This initial model was protonated, partial charges applied, and molecular mechanics used to produce an energy-refined model. Visual analysis of the PLX3397-bound CSF1R crystal structure (PDB code: 4R7H; FIGS. 1B, 1C), and of the GW-2580-bound homology model of CSF1R (FIG. 21), identified amino acids that would be suitable as candidate muteins. These amino acids were computationally mutated to a range of alternatives and these 3-dimensional models were subjected to molecular mechanics and molecular dynamics (with both explicit and implicit solvation). In order to conduct these simulations, the NAMD software suite and AMBER ff14SB forcefield were utilized. The MMPBSA.py approach within the ambertools suite was used to compute the interaction energies for both PLX3397 and GW-2580 to each of the muteins and the native form of human CSF1R. The difference in interaction energy for each inhibitor with each mutein (FIG. 22) was used to guide the selection of a number of muteins for further work.

Example 3. Screening Approaches

Candidate mutations can be generated that are likely to reduce stability of PLX3397-CSF1R interactions, and thus confer relative resistance to inhibition. These candidates may be screened in vitro using well-established survival assays with transduced primary BMDMs and BAC1.2F5 macrophages (a CSF1 dependent cell line) for ligand dependent resistance to PLX3397-mediated killing, using retroviral expression vectors. Candidates may then be tested that show relative resistance to inhibitor for normal ligand dependent proliferation, auto-/trans-phosphorylation of receptor tyrosine residues, and responses to IL34, an alternative CSF1R ligand. Promising candidates may be tested in vivo for resistance to depletion after transplantation of transduced BMDMs, and finally, a transgenic mouse may be made with knock-in mutation conferring resistance, as a source of inhibitor resistant donor tissues. This may allow comprehensive optimization of microglial replacement in mouse disease models without use of genetic tools, irradiation or chemotherapy, and rigorous testing for potential negative effects of receptor mutation in long term studies in vivo. Once available, it can also be used in place of Cx3cr1$^{CreER}$; Csf1r$^{F/F}$.

Though carefully chosen using structural and genomic data, candidate mutations may not confer an acceptable balance of inhibitor resistance and normal ligand dependent signaling. Fortunately, CSF1-dependent survival of BMDMs is a simple and scalable approach. Having already established a validation pipeline, one may screen for surviving BMDM clones transduced with a saturating receptor variant library at critical residues and treated concurrently with CSF1 and PLX3397, or a reportedly more specific and CNS-penetrant variant, PLX5622. The use of a downstream signaling reporter (such as SRE-luciferase) may also enhance sensitivity and throughput. A receptor variant library can also be used more broadly to screen for any desired macrophage phenotype resulting from nuanced modulation of CSF1R signaling. Lastly, a recent but non-quantitative study suggests that intranasal PLX3397 administration may permit engraftment of transplanted microglia, offering a completely alternative delivery approach.

In all described experiments, sex may be measured as a biological variable and tested for evidence of sex-specific effects. Screen hits in both sexes may be validated. Transplantation also offers the opportunity to deeply explore intrinsic sex differences in future studies.

Example 4. Generation of Bone Marrow Derived Macrophages, Retroviral Transduction, and In Vitro Survival Assay Bone marrow derived macrophages (BMDMs) from adult wild-type FVB/NJ mice were generated in vitro by MCSF stimulation. Briefly, whole bone marrow was cultured in a petri dish with BMDM media (DMEM, supplemented with 10% FBS and 10 ng/ml Recombinant Human M-CSF). After 6 hours of incubation at 37° C., 5% CO2, non-adherent cells were collected and transferred to 96 well tissue culture plates at $4 \times 10^4$ cells/well in 50 μl. BMDMs were virally transduced using a gamma retrovirus containing the wild-type full-length human CSF1R cDNA or mutant variants of human CSF1R cDNA. Retroviral supernatant was supplemented with 10 ng/ml of M-CSF1 and 50 μl was added to wells containing BMDMs. 24 hours later, media was changed to fresh BMDM media and cells were maintained for 48 hours before starting inhibitor insensitive screening. PLX3397 was added to BMDM media at 100 nM. Cells cultured in BMDM media and media without M-CSF1 served as controls. 48 hours after addition of PLX3397, cell numbers were determined using the CellTiter-Glo 2 Luminescent Cell Viability Assay, as described by the manufacturer.

Figure 23:
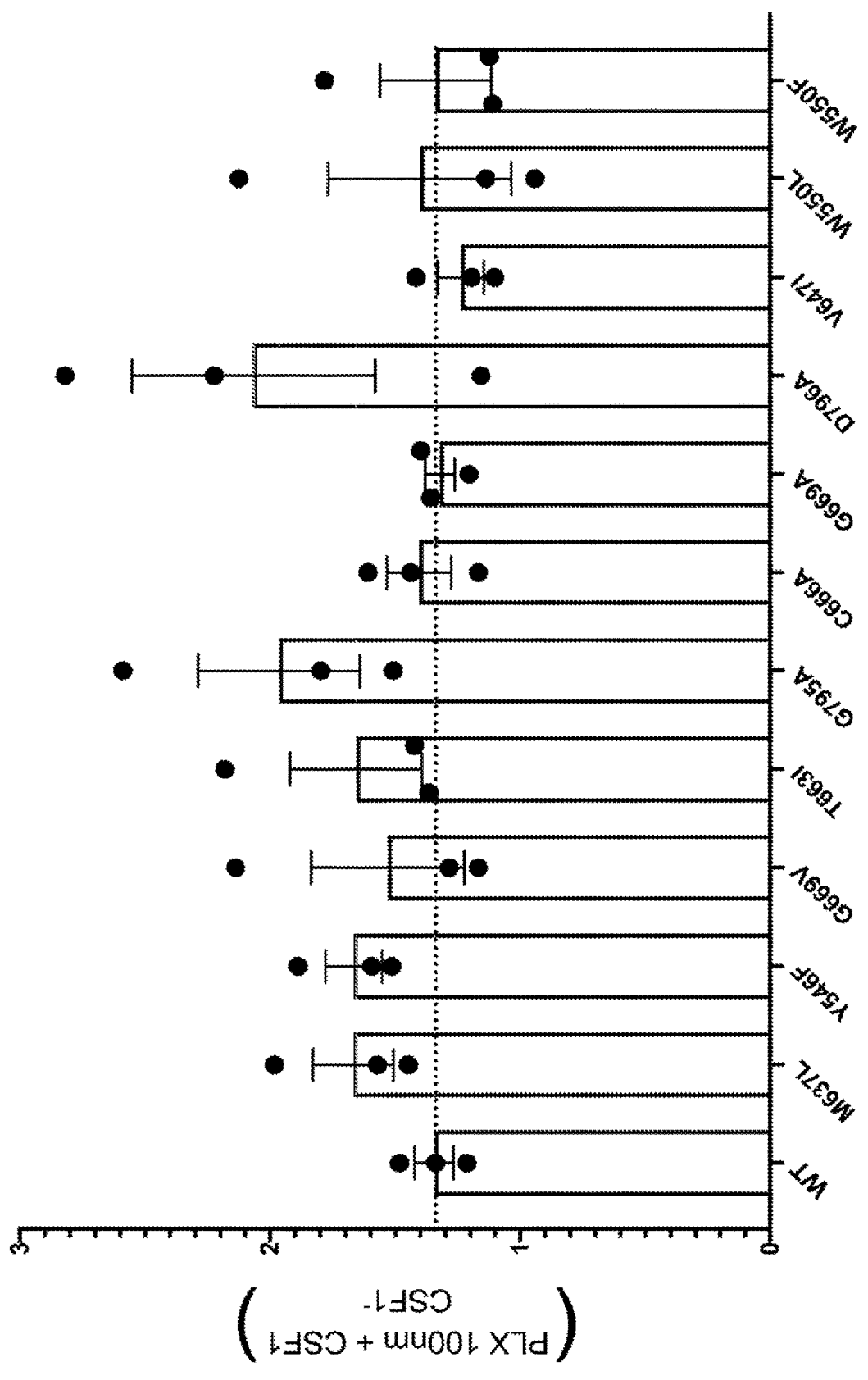
FIG. 23 depicts a non-limiting example of an in vitro survival assay demonstrating resistance of bone marrow-derived macrophages expressing various CSF1R variants to the CSF1R inhibitor, PLX-3397.

The data depicted in FIG. 23 shows the ratio between the number of cells following treatment with CSF1R inhibitor (PLX-3397)+ CSF1R ligand (i.e., CSF1), and the number of cells following complete deprivation CSF1R ligand (i.e., CSF1). The data demonstrates that cells expressing several CSF1R variants (e.g., M637L, Y546F, G795A, D796A) have a higher ratio than cells expressing WT CSF1R. This demonstrates that these cell populations are relatively resistant to killing by inhibitor compared to the WT expressing cells, and further suggests that this resistance may be due to expression of an inhibitor insensitive CSF1R variant. There was variability across the different receptor variants in the amount of growth seen in the absence of inhibitor (data not shown), which may be due to the effects of viral transduction or the effect of CSF1R expression on the cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a genetically modified human myeloid cell, wherein the genetically modified human myeloid cell comprises a nucleic acid encoding a modified human Colony-Stimulating Factor 1 Receptor (CSF1R) protein comprising an amino acid substitution selected from the group consisting of:
   (i) a glycine-to-alanine substitution at an amino acid residue corresponding to an amino acid at position 795 (G795A) of SEQ ID NO: 3;
   ii) an aspartate-to-alanine substitution at an amino acid residue corresponding to an amino acid at position 796 (D796A) of SEQ ID NO: 3;
   (iii) a threonine-to-isoleucine substitution at an amino acid residue corresponding to an amino acid at position 663 (T663I) of SEQ ID NO: 3;
   (iv) a methionine-to-leucine substitution at an amino acid residue corresponding to an amino acid at position 637 (M637L) of SEQ ID NO: 3; and
   (v) a glycine-to-valine substitution at an amino acid residue corresponding to an amino acid at position 669 (G669V) of SEQ ID NO: 3.

2. The composition of claim 1, wherein the genetically modified human myeloid cell is a myeloid precursor cell, a myeloid progenitor cell, an erythro-myeloid precursor cell, an erythro-myeloid progenitor cell, a myeloid-derived macrophage, a myeloid-derived monocyte, a myeloid-derived fetal macrophage, a non-hematopoietic stem cell (HSC)-derived myeloid cell, a hematopoietic stem cell (HSC)-derived myeloid cell, or a yolk-sac-derived myeloid cell.

3. The composition of claim 1, wherein the genetically modified human myeloid cell is a microglia-like cell.

4. The composition of claim 1, wherein the genetically modified human myeloid cell is derived from a natural myeloid cell.

5. The composition of claim 1, wherein the genetically modified human myeloid cell is derived from a non-natural myeloid cell.

6. The composition of claim 1, wherein the genetically modified human myeloid cell is generated or differentiated in vitro.

7. The composition of claim 1, wherein the genetically modified human myeloid cell is generated or differentiated ex vivo.

8. The composition of claim 1, wherein the genetically modified human myeloid cell is from an individual that is healthy or afflicted with a neurological disease or disorder.

9. The composition of claim 1, wherein the genetically modified human myeloid cell is from an individual that does not have a peripheral blood disorder or blood cancer.

10. A modified human Colony-Stimulating Factor 1 Receptor (CSF1R) polypeptide comprising an amino acid substitution selected from the group consisting of:
   (i) a glycine-to-alanine substitution at an amino acid residue corresponding to an amino acid at position 795 of SEQ ID NO: 3;
   (ii) an aspartate-to-alanine substitution at an amino acid residue corresponding to an amino acid at position 796 of SEQ ID NO: 3;
   (iii) a threonine-to-isoleucine substitution at an amino acid residue corresponding to an amino acid at position 663 of SEQ ID NO: 3;
   (iv) a methionine-to-leucine substitution at an amino acid residue corresponding to an amino acid at position 637 of SEQ ID NO: 3; and
   (v) a glycine-to-valine substitution at an amino acid residue corresponding to an amino acid at position 669 of SEQ ID NO: 3.

11. The composition of claim 1, wherein the genetically modified human myeloid cell is a myeloid precursor cell.

12. The composition of claim 1, wherein the genetically modified human myeloid cell is a microglia-like cell that expresses at least one gene selected from the group consisting of TMEM119, P2RY12, TREM2, MS4A7, HEXB, SIGLECH, SPARC, CX3CR1, P2RY13, ITGAM, OLFML3, SALL1, GPR34, GPR84, CD11B, IBA1, LILRA5, and CD45.

13. The composition of claim 1, wherein the amino acid substitution comprises the glycine-to-alanine substitution at the amino acid residue corresponding to the amino acid at position 795 of SEQ ID NO: 3.

14. The composition of claim 1, wherein the amino acid substitution comprises the aspartate-to-alanine substitution at the amino acid residue corresponding to the amino acid at position 796 of SEQ ID NO: 3.

15. The composition of claim 1, wherein the amino acid substitution comprises the threonine-to-isoleucine substitution at the amino acid residue corresponding to the amino acid at position 663 of SEQ ID NO: 3.

16. The composition of claim 1, wherein the amino acid substitution comprises a methionine-to-leucine substitution at the amino acid residue corresponding to the amino acid at position 637 of SEQ ID NO: 3.

17. The composition of claim 1, wherein the amino acid substitution comprises a glycine-to-valine substitution at the amino acid residue corresponding to the amino acid at position 669 of SEQ ID NO: 3.

* * * * *